US011141460B2

(12) United States Patent
Depaoli et al.

(10) Patent No.: US 11,141,460 B2
(45) Date of Patent: *Oct. 12, 2021

(54) METHODS FOR TREATMENT OF BILE ACID-RELATED DISORDERS AND PREDICTION OF CLINICAL SENSITIVITY TO TREATMENT OF BILE ACID-RELATED DISORDERS

(71) Applicant: NGM Biopharmaceuticals, Inc., South San Francisco, CA (US)

(72) Inventors: Alexander Mark Depaoli, Santa Barbara, CA (US); Jian Luo, Albany, CA (US); Hui Tian, Foster City, CA (US)

(73) Assignee: NGM BIOPHARMACEUTICALS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/562,150

(22) Filed: Sep. 5, 2019

(65) Prior Publication Data
US 2020/0164036 A1 May 28, 2020

Related U.S. Application Data

(62) Division of application No. 15/524,896, filed as application No. PCT/US2015/059474 on Nov. 6, 2015, now Pat. No. 10,434,144.

(60) Provisional application No. 62/077,060, filed on Nov. 7, 2014.

(51) Int. Cl.
A61K 38/18 (2006.01)
G01N 33/92 (2006.01)
G01N 33/68 (2006.01)
A61P 1/00 (2006.01)
G01N 33/50 (2006.01)

(52) U.S. Cl.
CPC ............ *A61K 38/1825* (2013.01); *A61P 1/00* (2018.01); *G01N 33/5088* (2013.01); *G01N 33/6848* (2013.01); *G01N 33/92* (2013.01); *G01N 2405/00* (2013.01); *G01N 2800/08* (2013.01); *G01N 2800/52* (2013.01)

(58) Field of Classification Search
CPC .......................... A61K 38/1825; G01N 33/92
See application file for complete search history.

(56) References Cited

U.S. PATENT DOCUMENTS

| | | |
|---|---|---|
| 4,235,871 A | 11/1980 | Papahadjopoulos |
| 4,501,728 A | 2/1985 | Geho |
| 4,837,028 A | 6/1989 | Allen |
| 6,635,468 B2 | 10/2003 | Ashkenazi |
| 6,716,626 B1 | 4/2004 | Itoh |
| 6,806,352 B2 | 10/2004 | Desnoyers |
| 6,812,339 B1 | 11/2004 | Venter |
| 6,987,121 B2 | 1/2006 | Kliewer |
| 7,115,415 B2 | 10/2006 | Goddard |
| 7,129,072 B1 | 10/2006 | Schlessinger |
| 7,208,312 B1 | 4/2007 | Desnoyers |
| 7,259,248 B2 | 8/2007 | Itoh |
| 7,288,406 B2 | 10/2007 | Bogin |
| 7,390,879 B2 | 6/2008 | Ashkenazi |
| 7,459,540 B1 | 12/2008 | Thomason |
| 7,491,697 B2 | 2/2009 | Beals |
| 7,576,190 B2 | 8/2009 | Glaesner |
| 7,582,607 B2 | 9/2009 | Frye |
| 7,622,445 B2 | 11/2009 | Frye |
| 7,655,627 B2 | 2/2010 | Frye |
| 7,667,008 B2 | 2/2010 | Thomason |
| 7,705,195 B2 | 4/2010 | French |
| 7,723,297 B2 | 5/2010 | Itoh |
| 7,947,866 B2 | 5/2011 | Sparks |
| 8,012,931 B2 | 9/2011 | Cujec |
| 8,034,770 B2 | 10/2011 | Belouski |
| 8,188,040 B2 | 5/2012 | Belouski |
| 8,324,160 B2 | 12/2012 | Li |
| 8,361,963 B2 | 1/2013 | Belouski |
| 8,383,365 B2 | 2/2013 | Cujec |
| 8,410,051 B2 | 4/2013 | Belouski |
| 8,420,088 B2 | 4/2013 | Glass |
| 8,481,031 B2 | 7/2013 | Glass |

(Continued)

FOREIGN PATENT DOCUMENTS

| | | |
|---|---|---|
| CN | 101591653 A | 12/2009 |
| CN | 102656266 A | 9/2012 |

(Continued)

OTHER PUBLICATIONS

Schreuder et al., 2010, The hepatic response to FGF19 is impaired in patients with nonalcoholic fatty liver disease and insulin resistance, Am J Physiol Gastrointest Liver Physiol, 298: G440-G445.*

Johnston et al., 2011, New Insights into Bile Acid Malabsorption, Curr Gastroenterol Rep, 13: 418-425.*

Walters et al., 2015 (online 2014), The response of patients with bile acid diarrhea to the farnesoid X receptor agonist obeticholic acid, Aliment Pharmacol Ther, 41: 54-64.*

Ilchenko, "Bile acids in norm and pathology," *Experimental and Clinical Gastroenterology*, 4:3-13 (2010). (English translation of abstract attached).

(Continued)

*Primary Examiner* — Amber D Steele
(74) *Attorney, Agent, or Firm* — Jones Day

(57) ABSTRACT

Provided herein are methods of using 7α-hydroxy-4-cholesten-3-one (C4) in predicting the clinical sensitivity to treatment of bile acid-related and associated disorders with treatment peptides, such as variants of fibroblast growth factor 19 (FGF19) proteins and peptide sequences (and peptidomimetics) and fusions of FGF19 and/or fibroblast growth factor 21 (FGF21) proteins and peptide sequences (and peptidomimetics), and variants of fusions of FGF19 and/or FGF21 proteins and peptide sequences (and peptidomimetics).

10 Claims, No Drawings
Specification includes a Sequence Listing.

(56) References Cited

U.S. PATENT DOCUMENTS

| | | |
|---|---|---|
| 8,535,912 B2 | 9/2013 | Sonoda |
| 8,541,369 B2 | 9/2013 | Dickinson |
| 8,580,936 B2 | 11/2013 | Williams |
| 8,618,053 B2 | 12/2013 | Belouski |
| 8,642,546 B2 | 2/2014 | Belouski |
| 8,673,860 B2 | 3/2014 | Schellenberger |
| 8,741,841 B2 | 6/2014 | Darling |
| 8,795,985 B2 | 8/2014 | Belouski |
| 8,802,697 B2 | 8/2014 | Bifulco |
| 8,809,499 B2 | 8/2014 | Fan |
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,023,791 B2 | 5/2015 | Boettcher et al. |
| 9,085,626 B2 | 7/2015 | Sonoda et al. |
| 9,089,525 B1 | 7/2015 | Ling |
| 9,273,107 B2 | 3/2016 | Ling |
| 9,290,557 B2 | 3/2016 | Ling |
| 9,474,785 B2 | 10/2016 | Mohammadi et al. |
| 9,475,856 B2 | 10/2016 | Mohammadi et al. |
| 9,550,820 B2 | 1/2017 | Mohammadi et al. |
| 9,580,483 B2 | 2/2017 | Ling |
| 9,670,260 B2 | 6/2017 | Ling |
| 9,751,924 B2 | 9/2017 | Ling |
| 9,789,160 B2 | 10/2017 | Wellstein |
| 9,878,008 B2 | 1/2018 | Ling |
| 9,878,009 B2 | 1/2018 | Ling |
| 9,889,177 B2 | 2/2018 | Ling |
| 9,889,178 B2 | 2/2018 | Ling |
| 9,895,416 B2 | 2/2018 | Ling |
| 9,925,242 B2 | 3/2018 | Ling |
| 9,926,356 B2 | 3/2018 | Mohammadi et al. |
| 9,963,494 B2 | 5/2018 | Ling |
| 9,974,833 B2 | 5/2018 | Ling |
| 10,174,090 B2 | 1/2019 | Mohammadi et al. |
| 10,369,199 B2 | 8/2019 | Ling |
| 10,398,758 B2 | 9/2019 | Ling et al. |
| 10,413,590 B2 | 9/2019 | Ling et al. |
| 10,434,144 B2 * | 10/2019 | Depaoli .......... A61P 1/00 |
| 10,456,449 B2 | 10/2019 | Ling et al. |
| 10,517,929 B2 | 12/2019 | Lindhout et al. |
| 10,744,185 B2 | 8/2020 | Ling et al. |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2005/0250684 A1 | 11/2005 | Heuer |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0055730 A1 | 3/2010 | Usheva-Simidjiyska |
| 2010/0215657 A1 | 8/2010 | Glass |
| 2010/0239554 A1 | 9/2010 | Schellenberger |
| 2010/0240587 A1 | 9/2010 | Schlein |
| 2010/0323954 A1 | 12/2010 | Li |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Baurin |
| 2011/0195077 A1 | 8/2011 | Glass |
| 2011/0195895 A1 | 8/2011 | Walker |
| 2011/0207912 A1 | 8/2011 | Botstein |
| 2011/0268794 A1 | 11/2011 | Camilleri |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2012/0157397 A1 | 6/2012 | Hazen |
| 2013/0004492 A1 | 1/2013 | Marshall |
| 2013/0023474 A1 * | 1/2013 | Ling .......... A61K 38/1825 514/9.1 |
| 2013/0116171 A1 | 5/2013 | Jonker |
| 2013/0122004 A1 | 5/2013 | Glass |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194352 A1 | 7/2014 | Ling |
| 2014/0243260 A1 | 8/2014 | Mohammadi |
| 2014/0243266 A1 | 8/2014 | Ling |
| 2014/0294820 A1 | 10/2014 | Faul et al. |
| 2015/0079065 A1 | 3/2015 | Wolf |
| 2015/0111821 A1 | 4/2015 | Suh |
| 2015/0132309 A1 | 5/2015 | Desnoyers |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |

(56) References Cited

U.S. PATENT DOCUMENTS

| | | | |
|---|---|---|---|
| 2016/0223568 A1 | 8/2016 | Genovese et al. |
| 2016/0252497 A1 | 9/2016 | Ling |
| 2017/0173114 A1 | 6/2017 | Kahn et al. |
| 2017/0182122 A1 | 6/2017 | Ling |
| 2017/0182123 A1 | 6/2017 | Ling |
| 2017/0232067 A1 | 8/2017 | Lindhout |
| 2017/0327551 A1 | 11/2017 | Ling |
| 2018/0079806 A1 | 3/2018 | Sonoda |
| 2018/0100018 A1 | 4/2018 | Sonoda et al. |
| 2018/0110834 A1 | 4/2018 | DePaoli |
| 2018/0177846 A1 | 6/2018 | Ling |
| 2018/0186850 A1 | 7/2018 | Mohammadi et al. |
| 2018/0208677 A1 | 7/2018 | Desnoyers |
| 2018/0280479 A1 | 10/2018 | Choi et al. |
| 2018/0318390 A1 | 11/2018 | Ling |
| 2018/0340028 A1 | 11/2018 | Rajan |
| 2018/0355007 A1 | 12/2018 | Ling |
| 2018/0362605 A1 | 12/2018 | Ling |
| 2018/0369331 A1 | 12/2018 | Fouillous-Meugnier et al. |
| 2019/0060403 A1 | 2/2019 | Ling |
| 2019/0175692 A1 | 6/2019 | Ling |
| 2019/0175693 A1 | 6/2019 | Ling |
| 2019/0175694 A1 | 6/2019 | Ling |
| 2019/0175695 A1 | 6/2019 | Ling |
| 2019/0175696 A1 | 6/2019 | Ling |
| 2019/0175697 A1 | 6/2019 | Ling |
| 2019/0177384 A1 | 6/2019 | Ling et al. |
| 2019/0194337 A1 | 6/2019 | Ling et al. |
| 2019/0307847 A1 | 10/2019 | Ling |
| 2020/0054714 A1 | 2/2020 | Ling et al. |
| 2020/0164035 A1 | 5/2020 | Ling |
| 2020/0197489 A1 | 6/2020 | Ling et al. |
| 2020/0197490 A1 | 6/2020 | Lindhout et al. |
| 2020/0330555 A1 | 10/2020 | Rossi et al. |

FOREIGN PATENT DOCUMENTS

| | | |
|---|---|---|
| CN | 103127503 A | 6/2013 |
| DE | 10100588 | 7/2002 |
| DE | 10100587 | 11/2002 |
| EA | 201001204 A1 | 2/2011 |
| EA | 015363 B1 | 6/2011 |
| EP | 2163626 | 3/2010 |
| JP | 2002112772 | 4/2002 |
| JP | 2009039117 | 2/2009 |
| JP | 2012530493 | 12/2012 |
| JP | 2013194049 | 9/2013 |
| KR | 10-2012-0095392 A | 8/2012 |
| NZ | 602702 | 3/2014 |
| WO | WO 2000/060085 | 10/2000 |
| WO | WO 2001/018209 | 3/2001 |
| WO | WO 2001/049740 | 7/2001 |
| WO | WO 2001/049849 | 7/2001 |
| WO | WO 2001/061007 | 8/2001 |
| WO | WO 2002/036732 | 5/2002 |
| WO | WO 2002/041911 | 5/2002 |
| WO | WO 2002/055693 | 7/2002 |
| WO | WO 2003/080803 | 10/2003 |
| WO | WO 2004/026228 | 4/2004 |
| WO | WO 2004/063355 | 7/2004 |
| WO | WO 2006/004076 | 1/2006 |
| WO | WO 2006/048291 | 5/2006 |
| WO | WO 2006/049854 | 5/2006 |
| WO | WO 2008/021196 | 2/2008 |
| WO | WO 2008/030273 | 3/2008 |
| WO | WO 2009/076478 | 6/2009 |
| WO | WO 2009/090553 | 7/2009 |
| WO | WO 2009/095372 | 8/2009 |
| WO | WO 2009/116861 | 9/2009 |
| WO | WO 2009/155381 | 12/2009 |
| WO | WO 2010/004204 | 1/2010 |
| WO | WO 2010/006214 | 1/2010 |
| WO | WO 2010/042747 | 4/2010 |
| WO | WO 2010/065439 | 6/2010 |
| WO | WO 2010/080976 | 7/2010 |
| WO | WO 2010/083051 | 7/2010 |
| WO | WO 2010/129600 | 11/2010 |
| WO | WO 2010/139741 | 12/2010 |
| WO | WO 2010/142665 | 12/2010 |
| WO | WO 2010/148142 | 12/2010 |
| WO | WO 2011/047267 | 4/2011 |
| WO | WO 2011/071783 | 6/2011 |
| WO | WO 2011/084808 | 7/2011 |
| WO | WO 2011/089203 | 7/2011 |
| WO | WO 2011/092234 | 8/2011 |
| WO | WO 2011/130417 | 10/2011 |
| WO | WO 2011/130729 | 10/2011 |
| WO | WO 2011/154349 | 12/2011 |
| WO | WO 2012/010553 | 1/2012 |
| WO | WO 2012/031603 | 3/2012 |
| WO | WO 2012/062078 | 5/2012 |
| WO | WO 2012/066075 | 5/2012 |
| WO | WO 2012/086809 | 6/2012 |
| WO | WO 2012/138919 | 10/2012 |
| WO | WO 2012/140650 | 10/2012 |
| WO | WO 2012/154263 | 11/2012 |
| WO | WO 2012/158704 | 11/2012 |
| WO | WO 2012/170438 | 12/2012 |
| WO | WO 2012/170704 | 12/2012 |
| WO | WO 2012/177481 | 12/2012 |
| WO | WO 2013/006486 | 1/2013 |
| WO | WO 2013/010780 | 1/2013 |
| WO | WO 2013/027191 | 2/2013 |
| WO | WO 2013/033452 | 3/2013 |
| WO | WO 2013/049234 | 4/2013 |
| WO | WO 2013/109856 | 7/2013 |
| WO | WO 2013/131091 | 9/2013 |
| WO | WO 2013/151671 | 10/2013 |
| WO | WO 2013/173158 | 11/2013 |
| WO | WO 2013/184958 | 12/2013 |
| WO | WO 2013/184960 | 12/2013 |
| WO | WO 2013/184962 | 12/2013 |
| WO | WO 2013/188182 | 12/2013 |
| WO | WO 2014/031420 | 2/2014 |
| WO | WO 2014/037373 | 3/2014 |
| WO | WO 2014/085365 | 6/2014 |
| WO | WO 2014/105939 | 7/2014 |
| WO | WO 2014/130659 | 8/2014 |
| WO | WO 2014/149699 | 9/2014 |
| WO | WO 2014/152089 | 9/2014 |
| WO | WO 2014/152090 | 9/2014 |
| WO | WO 2015/065897 | 5/2015 |
| WO | WO 2015/112886 | 7/2015 |
| WO | WO 2015/183890 | 12/2015 |
| WO | WO 2015/195509 | 12/2015 |
| WO | WO 2016/048995 | 3/2016 |
| WO | WO 2016/065106 | 4/2016 |
| WO | WO 2016/073855 | 5/2016 |
| WO | WO 2017/083276 | 5/2017 |
| WO | WO 2018/039557 | 3/2018 |
| WO | WO 2018/044778 | 3/2018 |
| WO | WO 2018/171557 | 9/2018 |
| WO | WO 2018/195390 | 10/2018 |
| WO | WO 2019/010314 | 1/2019 |
| WO | WO 2020/176703 | 9/2020 |
| WO | WO 2020/214753 | 10/2020 |

OTHER PUBLICATIONS

"TaqMan SNP Genotyping Assays," Life Technologies Corporation (2012).
Angulo et al., "Liver Fibrosis, but No Other Histologic Features, Is Associated With Long-term Outcomes of Patients With Nonalcoholic Fatty Liver Disease," *Gastroenterology*, 149:389-397 (2015).
Aranha et al., "Bile acid levels are increased in the liver of patients with steatohepatitis," *Eur. J. Gastroenterol. Hepatol.*, 20(6):519-525 (2008).
Beenken et al, "The FGF family: biology, pathophysiology and therapy," *Nat. Rev. Drug Discov.*, 8:235-253 (2009).
Beuers et al., "Medical treatment of primary sclerosing cholangitis: a role for novel bile acids and other (post-) transcriptional modulators?," *Clin. Rev. Allergy Immunol.*, 36(1):52-61 (2009).

(56) References Cited

OTHER PUBLICATIONS

Bromberg et al., "Stat3 as an oncogene," *Cell*, 98:295-303 (1999).
Calvisi et al., "Ubiquitous activation of Ras and Jak/Stat pathways in human HCC," *Gastroenterol.*, 130:1117-1128 (2006).
Camilleri et al., "Effect of increased bile acid synthesis or fecal excretion in irritable bowel syndrome-diarrhea," *Am. J. Gastroenterol.*, 109:1621-1630 (2014).
Camilleri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandom Mass Spectrometry," *Neurogastroenterol Motil.*, 21(7):734-e43 (2009).
Chazouilleres, "Primary sclerosing cholangitis and bile acids," *Clinics and Research in Hepatology and Gastroenterology*, 36:S21-S25 (2012).
Chen et al., "Soluble FGFR4 extracellular domain inhibits FGF19-induced activation of FGFR4 signaling and prevents nonalcoholic fatty liver disease," *Biochem. Biophys. Res. Comm.*, 409:651-656 (2011).
Chen et al., "Sorafenib overcomes TRAIL resistance of hepatocellular carcinoma cells through the inhibition of STAT3," *Clin. Cancer Res.*, 16:5189-5199 (2010).
Claudel et al., "Role of Nuclear Receptors for Ble Acid Metabolism, Bile Secretion, Cholestasis, and Gallstone Disease," *Biochim. Biophys. Acta*, 1812:867-878 (2011).
Desnoyers et al., "Targeting FGF19 inhibits tumor growth in colon cancer xenograft and FGF19 transgenic hepatocellular carcinoma models," *Oncogene*, 27:85-97 (2008).
Dichenko et al., "Sat-374: Steroid 7 Alpha-Hydroxylases: Neurosteroids Activation and Cholesterol Catabolism," The Endocrine Society's 95th Annual Meeting and Expo, San Francisco, Abstract, Jun. 15-18, 2013.
Ďurovcová et al., "Plasma Concentration of Fibroblast Growth Factors 21 and 19 in Patients with Cushing's Syndrome," *Physiol. Res.*, 59:415-422 (2010).
Foltz et al., "Supplementary Materials for: Treating Diabetes and Obesity with an FGF21-Mimetic Antibody Activating the βKlotho/FGFR1c Receptor Complex," *Sci. Transl. Med.*, 4:162ra153, pp. 1-13 (2012).
Foltz et al., "Treating Diabetes and Obesity with an FGF21-Mimetic Antibody Activating the βKlotho/FGFR1c Receptor Complex," *Sci. Transl. Med.*, 4:162ra153, pp. 1-10 (2012).
Frankel et al., "Characterization of diphtheria fusion proteins targeted to the human interleukin-3 receptor," *Protein Eng.*, 13(8):575-581 (2000).
French et al., "Targeting FGFR4 Inhibits Hepatocellular Carcinoma in Preclinical Mouse Models," *PLoS One*, 7(5):e36713 (2012).
Galman et al., "Monitoring hepatic cholesterol 7α-hydroxylase activity by assay of the stable bile acid intermediate 7α-hydroxy-4-cholesten-3-one in peripheral blood," *J. Lipid Res.*, 44:859-866 (2003).
Ge et al., "Characterization of a FGF19 Variant with Altered Receptor Specificity Revealed a Central Role for FGFR1c in the Regulation of Glucose Metabolism," *PLoS One*, 7(3):e33603 (2012).
Harmer et al., "The Crystal Structure of Fibroblast Growth Factor (FGF) 19 Reveals Novel Features of the FGF Family and Offers a Structural Basis for Its Unusual Receptor Affinity," *Biochemistry*, 43:629-640 (2004).
Hasegawa, "The expansion of PROMININ-1-positive epithelial-mesenchymal cells within periportal fibrosis of rotavirusinduced biliary atresia," *Hepatol.*, 58:802A (2013).
He et al., "Hepatocyte IKKbeta/NF-kappaB inhibits tumor promotion and progression by preventing oxidative stress-driven STAT3 activation," *Cancer Cell*, 17:286-297 (2010).
He et al., "Identification of liver cancer progenitors whose malignant progression depends on autocrine IL-6 signaling," *Cell*, 155:384-396 (2013).
He et al., "NF-κB and STAT3—key players in liver inflammation and cancer," *Cell Res.*, 21:159-168 (2011).

Hofmann et al., "Chronic diarrhea due to excessive bile acid synthesis and not defective ileal transport: A new syndrome of defective FGF19 release," *Clin Gastroenterol Hepatol.*, 7(11):1151-1154 (2009).
Holt et al., "Definition of a novel growth factor-dependent signal cascade for the suppression of bile acid biosynthesis," *Genes Dev.*, 17:1581-1591 (2003).
Ikeda et al., "Leptin receptor somatic mutations are frequent in HCV-infected cirrhotic liver and associated with hepatocellular carcinoma," *Gastroenterol.*, 146:222-232 (2014).
Inagaki et al., "Fibroblast Growth Factor 15 Functions as an Enterohepatic Signal to Regulate Bile Acid Homeostasis," *Cell Metabolism*, 2:217-225 (2005).
Islam et al., "Bile Acids: An Underrecognized and Underappreciated Cause of Chronic Diarrhea," *Pract. Gastroenterol.*, 110:32-44 (2012).
Kakumu et al., "Interleukin 6 production by peripheral blood mononuclear cells in patients with chronic hepatitis B virus infection and primary biliary cirrhosis," *Gastroenterologia Japonica*, 28:18-24 (1993).
Karras et al., "STAT3 regulates the growth and immunoglobulin production of BCL(1) B cell lymphoma through control of cell cycle progression," *Cellular immunol.*, 202:124-135 (2000).
Kaushik et al., "Why is Trehalose an Exceptional Protein Stabilizer?," *J. Biol. Chem.*, 278(29):26458-26465 (2003).
Kenakin et al., "Signalling bias in new drug discovery: detection, quantification and therapeutic impact," *Nat. Rev. Drug Discov.*, 12:205-216 (2013).
Kir et al., "Roles of FGF19 in Liver Metabolism," *Cold Spring Harb. Symp. Quant. Biol.*, 76:139-144 (2011).
Kovar et al., "Regulation of Diurnal Variation of Cholesterol 7α-hydroxylase (CYP7A1) Activity in Healthy Subjects," *Physiol. Res.*, 59:233-238 (2010).
Kurosu et al., "Supplemental Data for: Tissue-specific Expression of βKlotho and Fibroblast Growth Factor (FGF) Receptor Isoforms Determines Metabolic Activity of FGF19 and FGF21," *J. Biol. Chem.*, (2007) (available at: http://www.jbc.org/content/suppl/2007/07/11/M704165200.DC1/Kurosu_Suppl_Data.pdf (last visited Jul. 23, 2014).
Kurosu et al., "Tissue-specific Expression of βKlotho and Fibroblast Growth Factor (FGF) Receptor Isoforms Determines Metabolic Activity of FGF19 and FGF21," *J. Biol. Chem.*, 282(37):26687-26695 (2007).
Le et al., "Management of non-alcoholic fatty liver disease and steatohepatitis," *J. Clin. Exp. Hepatol.*, 2:156-173 (2012).
Lin et al., "Adiponectin mediates the metabolic effects of FGF21 on glucose homeostasis and insulin sensitivity in mice," *Cell. Metab.*, 17:779-789 (2013).
Lin et al., "The STAT3 inhibitor NSC 74859 is effective in hepatocellular cancers with disrupted TGF-beta signaling," *Oncogene*, 28:961-972 (2009).
Lindor, "Ursodeoxycholic acid for the treatment of primary biliary cirrhosis," *New Engl. J. Med.*, 11(357; 15) 1524-1529 (2007).
Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.
Ling et al., NGM Biopharmaceuticals, Identification of Gut Factors that Mimic the Metabolic Benefits of Gastric Bypass Surgery, p. 1, Jun. 8-12 (2012) Abstract.
Luo et al., "A nontumorigenic variant of FGF19 treats cholestatic liver diseases," *Sci. Transl. Med.*, 6: 247ra100 (2014).
Micanovic et al., "Different roles of N- and C-termini in the functional activity of FGF21," *J. Cell. Physiol.*, 219:227-234 (2009).
Miyata et al., "Involvement of Multiple Elements in FXR-mediated Transcriptional Activation of FGF19," *J. Steroid Biochm. Mol. Biol.*, 132:41-47 (2012).
Mudaliar et al., "Efficacy and safety of the farnesoid X receptor agonist obeticholic acid in patients with type 2 diabetes and non-alcoholic fatty liver disease," *Gastroenterology*, 145:574-582 (2013).
Nguyen et al., "Purification of cholesterol 7 alpha-hydroxylase from human and rat liver and production of inhibiting polyclonal antibodies," *J. Biol. Chem.*, 265:4541-4546 (1990).

(56) References Cited

OTHER PUBLICATIONS

Nicholes et al., "A Mouse Model of Hepatocellular Carcinoma: Ectopic Expression of Fibroblast Growth Factor in Skeletal Muscle of Transgenic Mice," *Amer. J. Pathol.*, 160:2295-2307 (2002).
Noguchi et al., "PDX-1 protein containing its own antennapedia-like protein transduction domain can transduce pancreatic duct and islet cells," *Diabetes*, 52(7):1732-1737 (2003).
Oduyebi et al., "Effects of NGM282, an FGF19 variant, on colonic transit and bowel function in functional constipation: a randomized phase 2 trial," *Am. J. Gastoenterol.*, 113:725-734 (2018).
Ogawa et al., "BetaKlotho is Required for Metabolic Activity of Fibroblast Growth Factor 21," *Proc. Natl. Acad. Sci. USA.*, 104:7432-7437 (2007).
Pai et al., "Antibody-Mediated Inhibition of Fibroblast Growth Factor 19 Results in Increased Bile Acids Synthesis and Ileal Malabsorption of Bile Acids in Cynomolgus Monkeys," *Toxicological Sciences*, 126(2):446-456 (2012).
Pattni et al., "Fibroblast Growth Factor 19 and 7α-Hydroxy-4-Cholesten-3-one in the Diagnosis of Patients With Possible Bile Acid Diarrhea," *Clinical and Translational Gastroenterology*, 3:e18 (2012).
Potthoff et al., "Endocrine Fibroblast Growth Factors 15/19 and 21: From Feast to Famine," *Genes Dev.*, 26:312-324 (2012).
Pusl et al., "Intrahepatic cholestasis of pregnancy," *Orphanet J. Rare Diseases*, 2:26 (2007).
Rivera et al., "Long-term regulated expression of growth hormone in mice after intramuscular gene transfer," *Proc. Natl. Acad. Sci. USA*, 96:8657-8662 (1999).
Rose et al., "Molecular Control of Systemic Bile Acid Homeostasis by the Liver Glucocorticoid Receptor," *Cell Metabolism*, 14:123-130 (2011).
Rossi et al., "P1313 Ngm282, a Novel Specific Inhibitor of Cyp7a1-Mediated Bile Acid Synthesis, is Safe and Well Tolerated with Predictable Pharmacokinetics in Healthy Human Subjects," *J. Hepatology*, 60(1):S533 (2014).
Ryan et al., "FXR is a Molecular Target for the Effects of Vertical Sleeve Gastroectomy," *Nature*, 509(7499):183-188 (2014); epub ahead of print Mar. 26, 2014.
Sawey et al., "Identification of a Therapeutic Strategy Targeting Amplified FGF19 in Liver Cancer by Oncogenomic Screening," *Cancer Cell*, 19(3):347-358 (2011).
Schaap et al., "High expression of the bile salt-homeostatic hormone fibroblast growth factor 19 in the liver of patients with extrahepatic cholestasis," *Hepatol.*, 49:1228-1235 (2009).
Schaap, "Role of Fibroblast Growth Factor 19 in the Control of Glucose Homeostasis," *Curr. Opin. Clin. Nutr. Metab. Care*, 15(4):386-391 (2012).
Storer et al., "An industry perspective on the utility of short-term carcinogenicity testing in transgenic mice in pharmaceutical development," *Toxicologic Pathol.*, 38:51-61 (2010).
Tartaglia et al., "Identification and expression cloning of a leptin receptor, OB-R," *Cell*, 83:1263-1271 (1995).
Tokuriki et al., "Stability effects of mutations and protein evolvability," *Curr. Opin. Struct. Biol.*, 19(5):596-604 (2009).
Tomlinson et al., "Transgenic Mice Expressing Human Fibroblast Growth Factor-19 Display Increased Metabolic Rate and Decreased Adiposity," *Endocrinology*, 143(5):1741-1747 (2002).
Trehin et al., "Cellular uptake but low permeation of human calcitonin-derived cell penetrating peptides and Tat(47-57) through well-differentiated epithelial models," *Pharm. Research*, 21:1248-1256 (2004).
Vijayvargiya et al., "Diagnostic Methods for Bile Acid Malabsorption in Clinical Practice," *Clin. Gastroenterol. Hepatol.*, 11(10):1232-1239 (2013).
Walters et al., "Managing bile acid diarrhoea," *Ther. Adv. Gastroenterol.*, 3(6):349-357 (2010).
Walters, "A variant of FGF19 for treatment of disorders of cholestasis and bile acid metabolism," *Ann. Transl. Med.*, 3(S1):S7 (2015).
Walters, "Bile acid diarrhoea and FGF19: new views on diagnosis, pathogenesis and therapy," *Nat. Rev. Gastroenterol. Hepatol.*, 11(7):426-434 (2014).
Wang et al., "Leptin in hepatocellular carcinoma," *World J. Gastroenterol.*, 16:5801-5809 (2010).
Wender et al., "The design, synthesis, and evaluation of molecules that enable or enhance cellular uptake: peptoid molecular transporters," *Proc. Natl. Acad. Sci. USA*, 97:13003-13008 (2000).
Wong et al, "Pharmacogenetics of the effects of colesevelam on colonic transit in irritable bowel syndrome with diarrhea," *Dig. Dis. Sci.*, 57(5):1222-1226 (2012).
Wu et al., "FGF19 Regulates Cell Proliferation, Glucose and Bile Acid Metabolism via FGFR4-Dependent and Independent Pathways," *PLoS One*, 6(3):e17868 (2011).
Wu et al., "C-terminal Tail of FGF19 Determines Its Specificity toward Klotho C-receptors," *J. Biol. Chem.*, 283(48):33304-33309 (2008).
Wu et al., "FGF19-induced Hepatocyte Proliferation is Mediated Through FGFR4 Activation," *J. Biol. Chem.*, 285(8):5165-5170 (2010).
Wu et al., "Role of FGF19 Induced FGFR4 Activation in the Regulation of Glucose Homeostasis," *Aging*, 1(12):1023-1027 (2009).
Wu et al., "Selective Activation of FGFR4 by an FGF19 Variant Does Not Improve Glucose Metabolism in ob/ob Mice," *Proc. Natl. Acad. Sci. USA*, 106(34):14379-14384 (2009).
Wu et al., "Separating Mitogenic and Metabolic Activities of Fibroblast Growth Factor 19 (FGF19)," *Proc. Natl. Acad. Sci. USA*, 107(32):14158-14163 (2010).
Wu et al., "Therapeutic Utilities of Fibroblast Growth Factor 19," *Expert Opin. Ther. Targets*, 15(11):1307-1316 (2011).
Xie et al., "FGF-19, A Novel Fibroblast Growth Factor with Unique Specificity for FGFR4," *Cytokine*, 11(10):729-735 (1999).
Zaiss et al., "Differential activation of innate immune responses by adenovirus and adeno-associated virus vectors," *J. Virol.*, 76:4580-4590 (2002).
Zender et al., "VP22-mediated intercellular transport of p53 in hepatoma cells in vitro and in vivo," *Cancer Gene Ther.*, 9(6):489-496 (2002).
Zhang et al., "Adenovirus-adeno-associated virus hybrid for large-scale recombinant adeno-associated virus production," *Hum. Gene Ther.*, 20:922-929 (2009).
Zhou et al., "Serum tumor markers for detection of hepatocellular carcinoma," *World J. Gastroenterol.*, 12(8):1175-1181 (2006).
Zhou et al., "Engineered fibroblast growth factor 19 reduces liver injury and resolves sclerosing cholangitis in Mdr2-deficient mice," *Hepatology*, 63(3):914-929 (2016).
Zhou et al., "Separating Tumorigenicity from Bile Acid Regulatory Activity for Endocrine Hormone FGF19," *Cancer Res.*, 74(12):3306-3316 (2014).
Zincarelli et al., "Analysis of AAV serotypes 1-9 mediated gene expression and tropism in mice after systemic injection," *Mol. Ther.*, 16:1073-1080 (2008).
Bergasa, "Pruritus of Cholestasis," *Itch: Mechanisms and Treatment*, Carstens et al. eds., CRC Press/Taylor & Francis, Boca Raton, FL, Chapter 6, 24 pages (2014).
Depaoli et al., "NGM313, a novel activator of beta-Klotho/ FGFR1c: A single dose significantly reduces steatosis (liver fat by MRI-PDFF), inflammation (ALT, AST) and fibrogenic activity (Pro-C3) in NAFLD subjects," Presentation at EASL International Liver Congress, Vienna, Austria, Apr. 12, 2019, 16 pages.
Depaoli et al., "NGM313, a novel activator of beta-Klotho/ FGFR1c: A single dose significantly reduces steatosis (liver fat by MRI-PDFF), inflammation (ALT, AST) and fibrogenic activity (Pro-C3) in NAFLD subjects," Abstract 4579, EASL International Liver Congress, Vienna, Austria, Apr. 12, 2019, 3 pages.
Harrison et al., "NGM282 Improves Liver Fibrosis and Histology in 12 Weeks in Patients With Nonalcoholic Steatohepatitis," *Hepatology*, 1-15 (2019).
Harrison et al., "NGM282 in NASH: 3 mg vs 6 mg QD (phase 2)," *Lancet*, 391:1174-1185 (2018).
Hirschfield et al., "Effect of NGM282, an FGF19 analogue, in primary sclerosing cholangitis: A multicenter, randomized, double-

(56) References Cited

OTHER PUBLICATIONS blind, placebo-controlled phase II trial," *J. Hepatology*, European Association for the Study of the Liver, pp. 1-12, 2018.
Hirschfield et al., "Serum Bile Acids Significantly Associate with the Fibrogenesis Biomarker Pro-C3: Analysis of a Randomized, Placebo-Controlled Trial of NGM282 in Patients with Primary Sclerosing Cholangitis (PSC)," NGM Biopharmaceuticals Inc. Poster, European Association for the Study of the Liver (EASL), International Liver Congress, Apr. 11, 2019.
Hirschfield et al., "A long term safety extension trial of the farnesoid X receptor (FXR) agonist obeticholic acid (OCA) and UDCA in primary biliary cirrhosis (PBC)," *Hepatol.*, 54(4):429A (2011).
Kremer et al., "High serum autotaxin activity predisposes to sever pruritus during treatment with obeticholic acid in primary biliary cirrhosis," *J. Hepatol.*, 54:2, 1 page (2011).
Ling et al., "NGM282 Promotes HDL Biogenesis and Transhepatic Cholesterol Efflux to Prevent Atherosclerosis in Mice," NGM Biopharmaceuticals Inc. Poster, European Association for the Study of the Liver (EASL), International Liver Congress, Apr. 11, 2019.
Mason et al., "Farnesoid-X receptor agonists: A new class of drugs for the treatment of PBC? An international study evaluating the addition of INT-747 to ursodeoxycholic acid," *J. Hepatol.*, 52:2, 1 page (2010).
Mayo et al., "Effect of NGM282, an FGF19 Analogue, on Pruritus in Patients with Primary Sclerosing Cholangitis: Analysis of a Phase 2, Multicenter, Randomized, Double-Blind, Placebo-Controlled Trial," NGM Biopharmaceuticals Inc. Poster, European Association for the Study of the Liver (EASL), International Liver Congress, Apr. 11, 2019.
"NGM Bio Announces Results From Phase 2 Study of NGM282 in NASH Patients Demonstrating Clinically Significant Improvements in Liver Histology After 12 Weeks," PipielineReview.com, pp. 1-5 (Apr. 15, 2018). Retrieved from the Internet: https://pipelinereview.com/ ...NASH-Patients-Demonstrating-Clinically-Significant-Improvements-In-Liver-Histology-After-12-Weeks.html, on Feb. 12, 2019.
Paredes et al., "NGM282 Maintains a Durable Off-Treatment Response on Hepatic Steatosis, Inflammation and Fibrogenesis in Patients with Biopsy-Confirmed Nonalcoholic Steatohepatitis: Results of a Multi-Center Phase 2 Dose-Finding Study," Aasld Abstracts, Hepatology, 68(1):1459A-1460A (2018).
Paredes et al., "NGM282 Maintains a Durable Off-Treatment Response on Hepatic Steatosis, Inflammation and Fibrogenesis in Patients with Biopsy-Confirmed Nonalcoholic Steatohepatitis: Results of a Multi-Center Phase 2 Dose-Finding Study," NGM Biopharmaceuticals Inc. Poster, American Association for the Study of Liver Diseases (AASLD), Liver Meeting, Nov. 12, 2018.
Sanyal et al., "Changes in Serum Bile Acids Correlate with 7alpha-Hydroxy-4-Cholesten-One and Fibrogenesis Biomarker Pro-C3 with NGM282 Therapy in Patients with Nonalcoholic Steatohepatitis," NGM Biopharmaceuticals, Inc. Poster, European Association for the Study of the Liver (EASL), International Liver Congress, Apr. 11, 2019.
United States Securities and Exchange Commission, *Form S-1 Registration Statement: NGM Biopharmaceuticals, Inc.*, Sep. 28, 2018, pp. 1-282.
Zhou et al., "Non-cell-autonomous activation of IL-6/STAT3 signaling mediates FGF19-driven hepatocarcinogenesis," *Nat. Commun.*, 8:15433 (2017).
Zhou et al, "Therapeutic FGF19 promotes HDL biogenesis and transhepatic cholesterol efflux to prevent atherosclerosis," *J. Lipid Res.*, 60:550-565 (2019).
Paumgartner, et al. "Gallstones: pathogenesis," Lancet, 338(8775):1117-1121 (1991).
Penz-Osterreicher et al., "Fibrosis in autoimmune and cholestatic liver disease," Best Pract Res Clin Gastroenterol., 25(2):245-258, 2011.
Yoneda et al., "Noninvasive assessment of liver fibrosis by measurement of stiffness in patients with nonalcoholic fatty liver disease (NAFLD)," *Digestive Liver Disease*, 40:371-378 (2008).

* cited by examiner

METHODS FOR TREATMENT OF BILE ACID-RELATED DISORDERS AND PREDICTION OF CLINICAL SENSITIVITY TO TREATMENT OF BILE ACID-RELATED DISORDERS

CROSS-REFERENCE TO RELATED APPLICATIONS

This application is a division of U.S. Ser. No. 15/524,896, now U.S. Pat. No. 10,434,144, filed May 5, 2017, which is a 371 national stage application of international application Serial No. PCT/US2015/059474 filed Nov. 6, 2015, which claims the benefit of priority to U.S. Ser. No. 62/077,060 filed Nov. 7, 2014, the contents of each of which is incorporated herein by reference in its entirety.

1. FIELD

Provided herein are methods of using 7α-hydroxy-4-cholesten-3-one (C4) in predicting the clinical sensitivity to treatment of bile acid-related and associated disorders with treatment peptides, such as variants of fibroblast growth factor 19 (FGF19) proteins and peptide sequences (and peptidomimetics) and fusions of FGF19 and/or fibroblast growth factor 21 (FGF21) proteins and peptide sequences (and peptidomimetics), and variants of fusions of FGF19 and/or FGF21 proteins and peptide sequences (and peptidomimetics).

2. BACKGROUND

Bile acids, steroid acids that are found predominantly in the bile of mammals, regulate cholesterol, triglyceride, glucose and energy homeostasis, and facilitate digestion and absorption of lipids in the small intestine. In humans, bile acid production occurs primarily in the perivenous hepatocytes through a series of enzymatic reactions that convert cholesterol into the two primary bile acids, cholic acid and chenodeoxycholic acid.

The primary bile acids are synthesized by two distinct pathways. In the "classic" or "neutral" pathway, the primary bile acids are produced by hydroxylation of cholesterol through catalysis by the cytochrome P450 enzyme cholesterol 7α-hydroxylase (CYP7A1), which catalyzes the first and rate-limiting step. The conversion of cholesterol to bile acids is primarily effected by this pathway. See, e.g., Inagaki et at, Cell Metabolism 2:217-25 (October 2005). CYP7A1 activity is down-regulated by cholic acid and up-regulated by cholesterol; thus, CYP7A1 is regulated by bile acids themselves. Thus, repression of CYP7A1 results in the decreased synthesis of bile acids from intrahepatic cholesterol in response to the daily feeding-fasting cycle. In addition, in most individuals approximately 6% of bile acids are synthesized by an "alternative" or "acidic" pathway. This pathway is regulated by the enzyme CYP27A1, which converts oxysterols to bile acids. In contrast to CYP7A1, CYP27A1 is not regulated by bile acids.

When cholic acid and chenodeoxycholic acid are secreted into the lumen of the intestine, intestinal bacteria dehydroxylate a portion of each to form the secondary bile acids, deoxycholic acid (derived from cholic acid) and lithocholic acid (derived from chenodeoxycholic acid). Enterohepatic circulation enables ~90-95% of all four bile acids to be reabsorbed from the distal ileum and transported back to the liver. The approximately 5% of bile acids that are not reabsorbed are eliminated in the feces, and that amount of loss is subsequently replaced by de novo bile acid synthesis in the liver See, e.g., Rose et al, Cell Metabolism, 14:1, pp 123-130 (6 Jul. 2011).

As surfactants or detergents, bile acids are potentially toxic to cells, and the size of the bile acid pool is tightly regulated within the liver and intestine to prevent cytotoxic accumulation. When the bile acid pool size increases, a feedback mechanism involving the interplay of several nuclear receptors, including FXR, is activated to inhibit de novo bile acid synthesis. See, e.g., Fiorucci et al., Prog Lipid Res. 2010 April; 49(2):171-85. Epub 2009 Dec. 2. In one signaling pathway, intestinal FXR activation due to transintestinal bile acid flux after a meal induces the expression of the hormone FGF19, which is released by small intestinal epithelial cells and circulates to bind to hepatocyte FGF receptor 4 (FGFR4) receptors. The FGFR4 receptors signal a reduction in bile acid synthesis via c-Jun $NH_2$-terminal kinase (JNK) pathway activation.

Cholestasis, one of the most common bile acid-related disorders, is a condition characterized by a reduction or cessation of bile flow from the liver to the small intestine (principally the duodenum). Primary biliary cirrhosis (PBC) is the most common cholestatic liver disease and is the fifth most common cause of liver transplant in the United States. PBC is a progressive hepatic disease that primarily results from autoimmune destruction of the bile ducts that transport bile acids out of the liver. As the disease progresses, persistent toxic build-up of bile acids causes progressive liver damage marked by chronic inflammation and fibrosis. A majority of PBC patients are asymptomatic at the time of initial diagnosis, but most develop symptoms, such as fatigue and pruritus, over time. Jaundice may result from advanced disease.

While several therapeutic modalities exist for the treatment and prevention of bile acid-related disorders in general, and primary biliary cirrhosis in particular, there remains a need for methods of predicting and/or monitoring the responsiveness of a subject having or suspected of having a bile acid-related or associated disorder to a treatment. Such methods are useful in the treatment of bile acid disorders, such as the foregoing disorders and including, but not limited to: metabolic syndrome; a lipid or glucose disorder; cholesterol or triglyceride metabolism; type 2 diabetes; cholestasis, including, for example diseases of intrahepatic cholestasis (e.g., primary biliary cirrhosis (PBC), primary familial intrahepatic cholestasis (PFIC) (e.g., progressive PFIC), primary sclerosing choangitis (PSC), pregnancy intrahepatic cholestasis (PIC), neonatal cholestasis, and drug induced cholestasis (e.g., estrogen)), and diseases of extrahepatic cholestasis (e.g., bile duct compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., bile acid diarrhea (BAD)) and GI symptoms, and GI, liver, and/or biliary cancers (e.g., colon cancer and hepatocellular cancer); and/or bile acid synthesis abnormalities, such as those contributing to non-alcoholic steatohepatitis (NASH), cirrhosis and portal hypertension. The invention satisfies this need and provides related benefits.

3. SUMMARY

In one aspect, provided herein is a method of identifying a subject having or suspected of having a bile acid-related or associated disorder who is likely to be responsive to a treatment peptide, comprising: (a) administering the treatment peptide to a subject having a bile acid-related or associated disorder; (b) obtaining a test sample from the subject; (c) determining the level of 7α-hydroxy-4-cholesten-3-one (C4) in the test sample; and (d) identifying the subject as being likely to be responsive to the treatment peptide if the level of C4 in the test sample of the subject decreases as compared to a reference level of C4. In certain embodiments, the method further comprises administering a therapeutically effective amount of the treatment peptide to the subject identified to be likely to be responsive to the treatment peptide.

In another aspect, provided herein is a method of predicting the responsiveness of a subject having or suspected of having a bile acid-related or associated disorder to a treatment peptide, comprising: (a) administering the treatment peptide to a subject having a bile acid-related or associated disorder; (b) obtaining a test sample from the subject; (c) determining the level of C4 in the test sample; and (d) identifying the subject as being likely to be responsive to a treatment of the bile acid-related or associated disorder with the treatment peptide if the level of C4 in the test sample decreases as compared to a reference level of C4. In certain embodiments, the method further comprises administering a therapeutically effective amount of the treatment peptide to the subject identified to be likely to be responsive to the treatment peptide.

In another aspect, provided herein is a method of monitoring the efficacy of a treatment of a bile acid-related or associated disorder in a subject with a treatment peptide, comprising: (a) administering the treatment peptide to a subject having a bile acid-related or associated disorder; (b) obtaining a test sample from the subject; (c) determining the level of C4 in the test sample; and (d) comparing the level of C4 in the test sample with a reference level of C4, wherein a decrease in the level in the test sample as compared to the reference level is indicative of the efficacy of the treatment peptide in treating the bile acid-related or associated disorder in the subject. In certain embodiments, the method further comprises administering a therapeutically effective amount of the treatment peptide to the subject identified to be likely to be responsive to the treatment peptide.

In yet another aspect, provided herein is a method of treating a bile acid-related or associated disorder, comprising: (a) obtaining a test sample from the subject; (b) determining the level of C4 in the test sample; (c) identifying the subject as being likely to be responsive to a treatment peptide if the level of C4 in the test sample of the subject is higher than a reference level of C4; and (d) administering a therapeutically effective amount of the treatment peptide to the subject identified to be likely to be responsive to the treatment peptide.

In some embodiments, the methods provided herein further comprise administering the treatment peptide to a subject having a bile acid-related or associated disorder prior to the step (a); comparing the level of C4 in the test sample after the administration with the treatment peptide with a reference level of C4, wherein a higher level of C4 in the test sample after the administration than the reference level is indicative that the patient is in need of an additional amount of treatment peptide in treating the bile acid-related or associated disorder in the subject; and administering the additional amount of the treatment peptide to the subject. In some embodiments, the reference is prepared by using a control sample obtained from a control subject without a bile acid-related or associated disorder.

In some embodiments, C4 is quantified using liquid chromatography-tandem mass spectrometry (LCMS/MS).

In certain embodiments, the treatment peptide is chimeric peptide sequence provided herein.

In some embodiments of the various methods provided herein, the treatment peptide is selected from a group consisting of variants of FGF19 peptide sequences, fusions of FGF19 and/or FGF21 peptide sequences and variants of fusions (chimeras) of FGF19 and/or FGF21 peptide sequences having one or more activities, such as bile acid homeostasis modulating activity. Such variants and fusions (chimeras) of FGF19 and/or FGF21 peptide sequences include sequences that are used for treating a bile acid-related or associated disorder. Such variants and fusions (chimeras) of FGF19 and/or FGF21 peptide sequences also include sequences that do not substantially or significantly increase or induce hepatocellular carcinoma (HCC) formation or HCC tumorigenesis. Such variants and fusions (chimeras) of FGF19 and/or FGF21 peptide sequences further include sequences that do not induce a substantial elevation or increase in lipid profile.

In one embodiment, the treatment peptide provided herein is a chimeric peptide comprising: a) an N-terminal region comprising at least seven amino acid residues, the N-terminal region having a first amino acid position and a last amino acid position, wherein the N-terminal region comprises DSSPL (SEQ ID NO:121) or DASPH (SEQ ID NOL122); and b) a C-terminal region comprising a portion of SEQ ID NO:99 (FGF19), the C-terminal region having a first amino acid position and a last amino acid position, wherein the C-terminal region comprises amino acid residues 16-29 of SEQ ID NO:99 (FGF19) (WGDPIRLRHLYTSG; SEQ ID NO:169), wherein the W residue corresponds to the first amino acid position of the C-terminal region, to modulate bile acid homeostasis or treat the bile acid-related or associated disorder.

In another embodiment, the treatment peptide, comprises: a) an N-terminal region comprising at least seven amino acid residues, the N-terminal region having a first amino acid position and a last amino acid position, wherein the N-terminal region comprises DSSPL (SEQ ID NO:121) or DASPH (SEQ ID NO:122); and b) a C-terminal region comprising a portion of SEQ ID NO:99 [FGF19], the C-terminal region having a first amino acid position and a last amino acid position, wherein the C-terminal region comprises (i) a first C-terminal region sequence comprising WGDPIRLRHLYTSG (amino acids 16 to 29 of SEQ ID NO:99 [FGF19]), wherein the W residue corresponds to the first amino acid position of the C-terminal region; and (ii) a second C-terminal region sequence comprising

```
PHGLSSCFLRIRADGVVDCARGQSAHSLLEIKAVALRTVAIKGVHSVRYL

CMGADGKMQGLLQYSEEDCAFEEEIRPDGYNVYRSEKHRLPVSLSSAKQR

QLYKNRGFLPLSHFLPMLPMVPEEPEDLRGHLESDMFSSPLETDSMDPFG

LVTGLEAVRSPSFEK
(amino acid residues 30 to 194 of SEQ ID NO: 99
[FGF19]).
```

In certain embodiments, the peptide (i) binds to fibroblast growth factor receptor 4 (FGFR4) with an affinity equal to or greater than FGF19 binding affinity for FGFR4; (ii) activates FGFR4 to an extent or amount equal to or greater than FGF19 activates FGFR4; (iii) has at least one of reduced hepatocellular carcinoma (HCC) formation; greater glucose lowering activity, less lipid increasing activity, less triglyceride activity, less cholesterol activity, less non-HDL activity or less HDL increasing activity, as compared to FGF19, or as compared to an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19 (SEQ ID NO:99); and/or (iv) has less lean mass reducing activity as compared to FGF21.

In some embodiments, the second C-terminal region sequence of the treatment peptide comprises from 1 to 5 amino acid substitutions, deletions or insertions. In some embodiments, the treatment peptide is less than about 250 amino acids in length.

In one embodiment, the treatment peptide has an amino acid sequence comprising or consisting of MRDSSPLVHYGWGDPIRLRHLYTSGPHGLSSCFLRI-RADGVVDCARGQSAHSLLEIKAVALR TVAI-KGVHSVRYLCMGADGKMQGLLQYSEEDCAFEEE-IRPDGYNVYRSEKHRLPVSLSSAK QRQLYKNRGFLPLSHFLPMLPMVPEEPEDLRGHL-ESDMFSSPLETDSMDPFGLVTGLEAVRS PSFEK (SEQ ID NO:70). In certain embodiments, the treatment peptide has an amino acid sequence comprising SEQ ID NO:70. In other embodiments, the treatment peptide has an amino acid sequence consisting of SEQ ID NO:70. In some embodiments, the treatment peptide is fused with an immunoglobulin Fc region.

In another embodiment, the treatment peptide has an amino acid sequence comprising or consisting of RDSSPLVHYGWGDPIRLRHLYTSGPHGLSSCFLRI-RADGVVDCARGQSAHSLLEIKAVALRT VAI-KGVHSVRYLCMGADGKMQGLLQYSEEDCAFEEE-IRPDGYNVYRSEKHRLPVSLSSAKQ RQLYKNRGFLPLSHFLPMLPMVPEEPEDLRGHL-ESDMFSSPLETDSMDPFGLVTGLEAVRSP SFEK (SEQ ID NO:69). In certain embodiments, the treatment peptide has an amino acid sequence comprising SEQ ID NO:69. In other embodiments, the treatment peptide has an amino acid sequence consisting of SEQ ID NO:69. In some embodiments, the treatment peptide is fused with an immunoglobulin Fc region.

In another embodiment, the treatment peptide provided herein is a chimeric peptide comprising: a) an N-terminal region comprising a portion of SEQ ID NO:100 (FGF21), the N-terminal region having a first amino acid position and a last amino acid position, wherein the N-terminal region comprises amino acid residues GQV, and wherein the V residue corresponds to the last amino acid position of the N-terminal region; and b) a C-terminal region comprising a portion of SEQ ID NO:99 (FGF19), the C-terminal region having a first amino acid position and a last amino acid position, wherein the C-terminal region comprises amino acid residues 21-29 of SEQ ID NO:99 (FGF19), RLRHLYTSG (SEQ ID NO:185), and wherein the R residue corresponds to the first position of the C-terminal region, to modulate bile acid homeostasis or treat the bile acid-related or associated disorder.

In a further embodiment, the treatment peptide provided herein is a chimeric peptide comprising: a) an N-terminal region comprising a portion of SEQ ID NO:100 (FGF21), the N-terminal region having a first amino acid position and a last amino acid position, wherein the N-terminal region comprises at least 5 contiguous amino acids of SEQ ID NO:100 (FGF21) including the amino acid residues GQV, and wherein the V residue corresponds to the last amino acid position of the N-terminal region; and b) a C-terminal region comprising a portion of SEQ ID NO:99 (FGF19), the C-terminal region having a first amino acid position and a last amino acid position, wherein the C-terminal region comprises amino acid residues 21-29 of SEQ ID NO:99 (FGF19), RLRHLYTSG (SEQ ID NO:185), and wherein the R residue corresponds to the first position of the C-terminal region, to modulate bile acid homeostasis or treat the bile acid-related or associated disorder.

In an additional embodiment, the treatment peptide is a peptide comprising or consisting of any of: a) a FGF19 sequence variant having one or more amino acid substitutions, insertions or deletions compared to a reference or wild type FGF19; b) a FGF21 sequence variant having one or more amino acid substitutions, insertions or deletions compared to a reference or wild type FGF21; c) a portion of a FGF19 sequence fused to a portion of a FGF21 sequence; or d) a portion of a FGF19 sequence fused to a portion of a FGF21 sequence, wherein the FGF19 and/or FGF21 sequence portion(s) have one or more amino acid substitutions, insertions or deletions compared to a reference or wild type FGF19 and/or FGF21, to modulate bile acid homeostasis or treat the bile acid-related or associated disorder.

In various particular embodiments, a chimeric peptide sequence has an N-terminal region with at least 6 contiguous amino acids of SEQ ID NO:100 (FGF21) including the amino acid residues GQ; or has an N-terminal region with at least 7 contiguous amino acids of SEQ ID NO:100 (FGF21) including the amino acid residues GQV.

In various additional embodiments, a peptide sequence has amino-terminal amino acids 1-16 of SEQ ID NO:100 (FGF21) fused to carboxy-terminal amino acids 21-194 of SEQ ID NO:99 (FGF19), or the peptide sequence has amino-terminal amino acids 1-147 of SEQ ID NO:99 (FGF19) fused to carboxy-terminal amino acids 147-181 of SEQ ID NO:100 (FGF21) (M41), or the peptide sequence has amino-terminal amino acids 1-20 of SEQ ID NO:99 (FGF19) fused to carboxy-terminal amino acids 17-181 of SEQ ID NO:100 (FGF21) (M44), or the peptide sequence has amino-terminal amino acids 1-146 of SEQ ID NO:100 (FGF21) fused to carboxy-terminal amino acids 148-194 of SEQ ID NO:99 (FGF19) (M45), or the peptide sequence has amino-terminal amino acids 1-20 of SEQ ID NO:99 (FGF19) fused to internal amino acids 17-146 of SEQ ID NO:100 (FGF21) or fused to carboxy-terminal amino acids 148-194 of SEQ ID NO:99 (FGF19) (M46).

In various further embodiments, a peptide sequence has at least one amino acid substitution to amino acid residues 125-129 of SEQ ID NO:99 (FGF19), EIRPD; at least one amino acid substitution to amino acid residues 126-128 of SEQ ID NO:99 (FGF19), IRP; or at least one amino acid substitution to amino acid residues 127-128 of SEQ ID NO:99 (FGF19), RP, or at least one amino acid substitution to amino acid residues 1-124 of SEQ ID NO:99 (FGF19) and/or to amino acid residues 130-194 of SEQ ID NO:99 (FGF19). More specifically, for example, a peptide sequence with a substitution to one of amino acid residues 127-128 of SEQ ID NO:99 (FGF19), IRP, wherein at least one amino acid substitution is R127L or P128E. Said substitutions within a corresponding FGF19 sequence (e.g., EIRPD (amino acids 2-6 of SEQ ID NO:190), IRP or RP) of a peptide variant provided herein is also contemplated. In certain embodiments, the peptide comprises both a R127L and P128E substitution to amino acid residues 127-128 of SEQ ID NO:99 (FGF19), RP, or the corresponding FGF19 sequence thereof in a variant peptide provided herein. In certain embodiments, the amino acid sequence of the peptide comprises at least one amino acid substitution in the Loop-8 region of FGF19, or the corresponding FGF19 sequence thereof in a variant peptide provided herein. In certain embodiments, the amino acid sequence of the peptide comprises one amino acid substitution to the EIRPD (amino acids 2-6 of SEQ ID NO:190) amino acid sequence in the Loop-8 region of FGF19. In some embodiments, the amino acid sequence of the peptide comprises two amino acid substitutions to the EIRPD (amino acids 2-6 of SEQ ID NO:190) amino acid sequence in the Loop-8 region of FGF19. In other embodiments, the amino acid sequence of the peptide comprises three amino acid substitutions to the EIRPD (amino acids 2-6 of SEQ ID NO:190) amino acid sequence in the Loop-8 region of FGF19. In certain embodiments, the amino acid sequence of the peptide comprises four amino acid substitutions to the EIRPD (amino acids 2-6 of SEQ ID NO:190) amino acid sequence in the Loop-8 region of FGF19. In some embodiments, the amino acid sequence of the peptide comprises five amino acid substitutions to the EIRPD (amino acids 2-6 of SEQ ID NO:190) amino acid sequence in the Loop-8 region of FGF19. In certain embodiments, the amino acid sequence of the peptide comprises one amino acid substitution to the IRP (amino acids 3-5 of SEQ ID NO:190) amino acid sequence in the Loop-8 region of FGF19. In some embodiments, the amino acid sequence of the peptide comprises two amino acid substitutions to the IRP (amino acids 3-5 of SEQ ID NO:190) amino acid sequence in the Loop-8 region of FGF19. In other embodiments, the amino acid sequence of the peptide comprises three amino acid substitutions to the IRP (amino acids 3-5 of SEQ ID NO:190) amino acid sequence in the Loop-8 region of FGF19. In certain embodiments, the amino acid sequence of the peptide comprises one amino acid substitution to the RP (amino acids 4-5 of SEQ ID NO:190) amino acid sequence in the Loop-8 region of FGF19. In some embodiments, the amino acid sequence of the peptide comprises two amino acid substitutions to the RP (amino acids 4-5 of SEQ ID NO:190) amino acid sequence in the Loop-8 region of FGF19. In certain embodiments, the amino acid substitution to the RP (amino acids 4-5 of SEQ ID NO:190) amino acid sequence in the Loop-8 region of FGF19 is an Arg (R) to Leu (L) substitution. In other embodiments, the substitution to the RP (amino acids 4-5 of SEQ ID NO:190) amino acid sequence in the Loop-8 region of FGF19 is a Pro (P) to Glu (E) substitution. In some embodiments, the substitutions to the RP (amino acids 4-5 of SEQ ID NO:190) amino acid sequence in the Loop-8 region of FGF19 is an Arg (R) to Leu (L) substitution and a Pro (P) to Glu (E) substitution. In specific embodiments, the foregoing substitution(s) in the Loop-8 region of FGF19 is in the corresponding FGF19 sequence thereof in a variant peptide provided herein. That is, said substitutions within a corresponding FGF19 sequence (e.g., EIRPD (amino acids 2-6 of SEQ ID NO:190), IRP or RP) of a peptide variant provided herein is also contemplated.

Methods and uses provided herein can be practiced using a peptide or chimeric sequence, as set forth herein. For example, a sequence that includes or consists of any peptide sequence set forth herein as M1-M98, M101 to M160, or M200 to M207, or SEQ ID NOs:1 to 98, or 101 to 135, or 138 to 212. In other embodiments, the peptide sequence includes or consists of any sequence set forth in Table 1. In yet other embodiments, the peptide sequence that includes or consists of any sequence set forth in the Sequence Listing herein.

In still additional embodiments, the chimeric peptide or peptide sequence is included in a pharmaceutical composition, which in turn can be used for practicing the invention methods and uses. That is, in certain embodiments, the treatment peptide is provided as a pharmaceutical compositions. Such compositions can include combinations of inactive or other active ingredients. In one embodiment, treatment peptide is provided as a pharmaceutical composition comprising the treatment peptide and a pharmaceutically acceptable carrier. In one embodiment, a composition, such as a pharmaceutical composition includes chimeric peptide sequence or peptide sequence and an agent that improves bile acid homeostasis.

Non-limiting exemplary bile acid-related or associated disorders treatable according to the methods and uses provided herein include: cholestasis, including, for example diseases of intrahepatic cholestasis (e.g., primary biliary cirrhosis (PBC), primary familial intrahepatic cholestasis (PFIC) (e.g., progressive PFIC), primary sclerosing choangitis (PSC), pregnancy intrahepatic cholestasis (PIC), neonatal cholestasis, and drug-induced cholestasis (e.g., estrogen)), and diseases of extrahepatic cholestasis (e.g., bile duct compression from tumor, bile duct blockade by gall stones); bile acid malabsorption and other disorders involving the distal small intestine, including ileal resection, inflammatory bowel diseases (e.g., Crohn's disease and ulcerative colitis), short bowel syndrome, disorders impairing absorption of bile acids not otherwise characterized (idiopathic)) leading to diarrhea (e.g., bile acid diarrhea (BAD)) and GI symptoms, and GI, liver, and/or biliary cancers (e.g., colon cancer and hepatocellular cancer); and/or bile acid synthesis abnormalities, such as those contributing to non-alcoholic steatohepatitis (NASH), cirrhosis and portal hypertension; e.g., in mammals, such as humans. Additional bile acid-related or associated disorders include metabolic syndrome; a lipid or glucose disorder; cholesterol or triglyceride metabolism; type 2 diabetes.

In one particular embodiment, the bile acid-related or associated disorder is bile acid malabsorption. In another particular embodiment, the bile acid-related or associated disorder is diarrhea. In another particular embodiment, the bile acid-related or associated disorder is bile acid diarrhea. In a still further particular embodiment, the bile acid-related or associated disorder is cholestasis. In one embodiment, the cholestasis is intrahepatic cholestasis. In another embodiment, the cholestasis is extrahepatic cholestasis. In another, further particular embodiment, the bile acid-related or associated disorder is an error in bile acid synthesis. In another, further particular embodiment, the bile acid-related or associated disorder is bile acid malabsorption. In another, further particular embodiment, the bile acid-related or associated disorder is primary billiary cirrhosis (PBC). In other particular embodiments, the bile acid-related or associated disorder is primary sclerosing cholangitis. In another embodiment, the bile acid-related or associated disorder is PFIC (e.g., progressive PFIC). In other particular embodiments, the bile acid-related or associated disorder is NASH.

Methods and uses provided herein for treating a subject are applicable for prophylaxis to prevent or reduce the likelihood of a disorder in a subject, such as a bile acid-related or associated disorder. Accordingly, methods and uses provided herein for treating a subject having, or at risk of developing, a bile acid-related or associated disorder can be practiced prior to, substantially contemporaneously with, or following administration or application of another agent useful for the treatment or prevention of a bile acid-related or associated disorder, and/or can be supplemented with other forms of therapy.

4. DETAILED DESCRIPTION

4.1 Methods of Identifying a Subject for Treatment, Predicting and/or Monitoring Response to Treatment, and Treating Bile Acid-Related or Associated Disorders Based, in part, on the finding that detectable change in C4 levels are observed in subjects with bile acid-related or associated disorders who are responsive to a treatment peptide provided herein, e.g., in Section 4.2 below, the levels of C4 may be used for identifying a subject having a bile acid-related or associated disorder for the treatment by a treatment peptide provided herein, and used for predicting the responsiveness of a subject having or suspected of having a bile acid-related or associated disorder to a treatment peptide provided herein.

In one aspect, provided herein is a method of identifying a subject having or suspected of having a bile acid-related or associated disorder who is likely to be responsive to a treatment peptide, comprising: (a) administering the treatment peptide to a subject having a bile acid-related or associated disorder; (b) obtaining a test sample from the subject; (c) determining the level of C4 in the test sample; and (d) identifying the subject as being likely to be responsive to the treatment peptide if the level of C4 in the test sample of the subject decreases as compared to a reference level of C4. In certain embodiments, the method further comprises administering a therapeutically effective amount of the treatment peptide to the subject identified to be likely to be responsive to the treatment peptide.

In another aspect, provided herein is a method of predicting the responsiveness of a subject having or suspected of having a bile acid-related or associated disorder to a treatment peptide, comprising: (a) administering the treatment peptide to a subject having a bile acid-related or associated disorder; (b) obtaining a test sample from the subject; (c) determining the level of C4 in the test sample; and (d) identifying the subject as being likely to be responsive to a treatment of the bile acid-related or associated disorder with the treatment peptide if the level of C4 in the test sample decreases as compared to a reference level of C4. In certain embodiments, the method further comprises administering a therapeutically effective amount of the treatment peptide to the subject identified to be likely to be responsive to the treatment peptide.

In another aspect, provided herein is a method of monitoring the efficacy of a treatment of a bile acid-related or associated disorder in a subject with a treatment peptide, comprising: (a) administering the treatment peptide to a subject having a bile acid-related or associated disorder; (b) obtaining a test sample from the subject; (c) determining the level of C4 in the test sample; and (d) comparing the level of C4 in the test sample with a reference level of C4, wherein a decrease in the level in the test sample as compared to the reference level is indicative of the efficacy of the treatment peptide in treating the bile acid-related or associated disorder in the subject.

In some embodiments, the methods provided herein further comprise administering the treatment peptide to the subject identified as being likely to be responsive to a treatment of the bile acid-related or associated disorder with the treatment peptide.

In yet another aspect, provided herein is a method of treating a bile acid-related or associated disorder, comprising: (a) obtaining a test sample from the subject; (b) determining the level of C4 in the test sample; (c) identifying the subject as being likely to be responsive to a treatment peptide if the level of C4 in the test sample of the subject is higher than a reference level of C4; and (d) administering a therapeutically effective amount of the treatment peptide to the subject identified to be likely to be responsive to the treatment peptide.

In some embodiments, the reference provided herein is prepared by using a control sample obtained from the subject prior to administration of the treatment peptide to the subject; and wherein the control sample is from the same source as the test sample. In other embodiments, the reference provided herein is prepared by using a control sample obtained from a subject having a bile acid-related or associated disorder.

In some embodiments, the reference is prepared by using a control sample obtained from a control subject without a bile acid-related or associated disorder. In some embodiments, the level of C4 in the test sample is from 1.5-fold to 10-fold of the reference level of C4.

In some embodiments, the reference is prepared by using a control sample obtained from the subject prior to administration of the treatment peptide to the subject. In certain embodiments, the control sample is from the same source as the test sample. In other embodiments, the reference is prepared by using a control sample obtained from a control subject having a bile acid-related or associated disorder. In some embodiments, the level of C4 in the test sample after administration with the treatment peptide is from 10% to 90% of the reference level of C4.

In certain embodiments of the various methods provided herein, the test sample is blood serum. In other embodiments, the test sample is blood plasma. In some embodiments, the control sample is blood serum. In an embodiment, the control sample is blood plasma.

In some embodiments, C4 level is lowered in the sample after treatment compared to the reference level of C4, and the subject is likely to be responsive to a treatment of the bile acid-related or associated disorder with the treatment peptide if the level of C4 in the test sample is lower than the reference level of C4. In one embodiment, C4 level after treatment with the treatment peptide provided herein is lower the C4 level in the subject prior to the treatment.

In some embodiments, the level of C4 in the test sample after administration with the treatment peptide is less than 90% of the reference level of C4. In some embodiments, the level of C4 in the test sample after administration with the treatment peptide is less than 80% of the reference level of C4. In other embodiments, the level of C4 in the test sample after administration with the treatment peptide is less than 70% of the reference level of C4. In other embodiments, the level of C4 in the test sample after administration with the treatment peptide is less than 60% of the reference level of C4. In other embodiments, the level of C4 in the test sample after administration with the treatment peptide is less than 50% of the reference level of C4. In other embodiments, the level of C4 in the test sample after administration with the treatment peptide is less than 50% of the reference level of C4. In other embodiments, the level of C4 in the test sample after administration with the treatment peptide is less than 40% of the reference level of C4. In other embodiments, the level of C4 in the test sample after administration with the treatment peptide is less than 30% of the reference level of C4. In other embodiments, the level of C4 in the test sample after administration with the treatment peptide is less than 20% of the reference level of C4. In other embodiments, the level of C4 in the test sample after administration with the treatment peptide is less than 10% of the reference level of C4. In some embodiments, the level of C4 in the test sample after administration with the treatment peptide is 10% to 90% of the reference level of C4. In some embodiments, the level of C4 in the test sample after administration with the treatment peptide is 20% to 90% of the reference level of C4. In some embodiments, the level of C4 in the test sample after administration with the treatment peptide is 30% to 90% of the reference level of C4. In some embodiments, the level of C4 in the test sample after administration with the treatment peptide is 40% to 90% of the reference level of C4. In some embodiments, the level of C4 in the test sample after administration with the treatment peptide is 50% to 90% of the reference level of C4. In some embodiments, the level of C4 in the test sample after administration with the treatment peptide is 60% to 90% of the reference level of C4. In some embodiments, the level of C4 in the test sample after administration with the treatment peptide is 70% to 90% of the reference level of C4. In some embodiments, the level of C4 in the test sample after administration with the treatment peptide is 80% to 90% of the reference level of C4.

Once a patient is identified as being likely to be responsive to a treatment peptide provided herein, further administration of a treatment peptide can be performed. Thus, in some embodiments, the methods provided herein further comprises administering the treatment peptide to the subject identified as being likely to be responsive to a treatment of the bile acid-related or associated disorder with the treatment peptide.

In yet another aspect, provided herein is a method of treating a bile acid-related or associated disorder, comprising: (a) obtaining a test sample from the subject; (b) determining the level of C4 in the test sample; (c) identifying the subject as being likely to be responsive to a treatment peptide if the level of C4 in the test sample of the subject is higher than a reference level of C4; and (d) administering a therapeutically effective amount of the treatment peptide to the subject identified to be likely to be responsive to the treatment peptide.

In some embodiments, the reference level of C4 is within a normal range of C4 level in a control subject without a bile acid-related or associated disorder. In some embodiments, the reference level of C4 is from 10 to 20 ng/ml. In other embodiments, the reference level of C4 is from 12 to 18 ng/ml. In some embodiments, the reference level of C4 is from 14 to 17 ng/ml.

In some embodiments, the reference level of C4 is within a normal range of C4 level in the median of a population of control subjects without a bile acid-related or associated disorder. In some embodiments, the median is 10 to 20 ng/ml. In other embodiments, the median is from 12 to 18 ng/ml. In some embodiments, the median is from 14 to 17 ng/ml.

In some embodiments, the reference provided herein is prepared by using a control sample obtained from a subject without a bile acid-related or associated disorder. In some embodiments, when the level of C4 in the sample is higher than the reference level of C4, the subject is identified as being likely to be responsive to a treatment peptide.

In some embodiments, the level of C4 in the test sample is from about 1.5-fold to about 10-fold of the reference level of C4. Exemplary levels of C4 in the test sample include about 1.5-fold, 2.0-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, and 10-fold of the reference level of C4. In some embodiments, the level of C4 in the test sample is from 30 to 1000 ng/ml. In some embodiments, the level of C4 in the test sample is from 30 to 500 ng/ml. In some embodiments, the level of C4 in the test sample is from 30 to 200 ng/ml. In some embodiments, the level of C4 in the test sample is from 30 to 100 ng/ml. In other embodiments, the level of C4 in the test sample is from 40 to 90 ng/ml. In some embodiments, the level of C4 in the test sample is from 50 to 80 ng/ml. In other embodiments, the level of C4 in the test sample is from 60 to 70 ng/ml.

In some embodiments, the level of C4 in the test sample is higher than 30 ng/ml. In other embodiments, the level of C4 in the test sample is higher than 40 ng/ml. In certain embodiments, the level of C4 in the test sample is higher than 50 ng/ml. In some embodiments, the level of C4 in the test sample is higher than 60 ng/ml. In other embodiments, the level of C4 in the test sample is higher than 70 ng/ml. In yet other embodiments, the level of C4 in the test sample is higher than 80 ng/ml. In certain embodiments, the level of C4 in the test sample is higher than 90 ng/ml. In some embodiments, the level of C4 in the test sample is higher than 100 ng/ml.

In some embodiments, after a first treatment with the treatment peptide provided herein, the level of C4 can be measured to determine if further treatment is beneficial. In some embodiments, the level of C4 after the first treatment can be compared to a reference level of C4 that falls within the normal range of C4 in a normal subject without a bile acid-related or associated disorder, and if the level of C4 after the first treatment is still higher than the normal level, further administration of the treatment peptide can be performed.

Thus, in some embodiments, the methods provided herein further comprise administering the treatment peptide to a subject having a bile acid-related or associated disorder prior to the step (a); comparing the level of C4 in the test sample after the administration with the treatment peptide with a reference level of C4, wherein a higher level of C4 in the test sample after the administration than the reference level is indicative that the patient is in need of an additional amount of treatment peptide in treating the bile acid-related or associated disorder in the subject; and administering the additional amount of the treatment peptide to the subject. In some embodiments, the reference is prepared by using a control sample obtained from a control subject without a bile acid-related or associated disorder.

Any method of determining the level of C4 in a sample may be used in the methods provided herein. Exemplary methods are provided elsewhere herein and in the experimental section.

As used herein, the term "bile acid-related disorder," "bile acid-related or associated disorder," and the like, when used in reference to a condition of a subject means a transient or chronic abnormal level of a bile acid (one or more bile acids) present in the subject. The condition can be caused by inhibition, reduction or a delay in bile acid synthesis, metabolism or absorption such that the subject exhibits a bile acid level not typically found in normal subjects.

The term "treat," "treating," or "treatment" refers to alleviating or abrogating a disease, e.g., a bile acid-related or associated disorder, or one or more of the symptoms associated with the disease; or alleviating or eradicating the cause(s) of the disease itself.

Thus, provided herein includes methods of preventing (e.g., in subjects predisposed to having a particular disorder(s)), delaying, slowing or inhibiting progression of, the onset of, or treating (e.g., ameliorating) a bile acid-related or associated disorder relative to an appropriate matched subject of comparable age, gender, race, etc.). Thus, in various embodiments, a method provided herein for, for example, modulating bile acid homeostasis or treating a bile acid-related or associated disorder includes contacting or administering a peptide as set forth herein (e.g., a variant or fusion of FGF19 and/or FGF21 as set forth in Table 1 or the Sequence Listing, for example) in an amount effective to modulate bile acid homeostasis or treat a bile acid-related or associated disorder.

Moreover, provided herein are methods of preventing (e.g., in subjects predisposed to having a particular disorder(s)), slowing or inhibiting the progression of, delaying the onset of, or treating undesirable levels or abnormally low levels of bile acids, all of which, alone or in combination, can lead to, for example, to at a bile acid-related or associated disorder. Such disorders can be due to, for example, genetic predisposition or diet, for example.

The term "subject" refers to an animal. Typically, the animal is a mammal that would benefit from treatment with a peptide sequence provided herein. Particular examples include primates (e.g., humans), dogs, cats, horses, cows, pigs, and sheep.

Subjects include those having a disorder, e.g., a bile acid-related or associated disorder, such as metabolic syndrome; a lipid- or glucose-related disorder; cholesterol or triglyceride metabolism; type 2 diabetes; cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile duct compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension; or subjects that do not have a disorder but may be at risk of developing the disorder. Subjects at risk of developing a bile acid associated or related disorder include, for example, those whose diet may contribute to development of acute or metabolic syndrome; a lipid- or glucose-related disorder; cholesterol or triglyceride metabolism; type 2 diabetes; cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile duct compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension; as well as those which may have a family history or genetic predisposition towards development of a bile acid-related or associated disorder, such as metabolic syndrome; a lipid- or glucose-related disorder; cholesterol or triglyceride metabolism; type 2 diabetes; cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile duct compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension.

The level of C4 can be determined using methods provided herein. In some embodiments, the level of C4 from a subject sample can be increased, for example, by about 5%, about 10%, about 20%, about 30%, about 40%, about 50%, about 60%, about 70%, about 90%, about 100%, about 200%, about 300%, about 500%, about 1,000%, about 5,000% or more of the comparative control level or a reference level. Alternatively, the level of C4 from a subject sample can be decreased, for example, by about 99%, about 95%, about 90%, about 80%, about 70%, about 60%, about 50%, about 40%, about 30%, about 20%, about 10%, about 5%, about 2%, about 1% or less of the comparative control level or a reference level.

The term "level" refers to the amount, accumulation, or concentration of a molecule. The term "level" refers to an absolute amount of a molecule in a sample or to a relative amount of the molecule, determined under steady-state or non-steady-state conditions.

The term "responsiveness" or "responsive" when used in reference to a treatment refer to the degree of effectiveness of the treatment in lessening or decreasing the symptoms of a disease, e.g., a bile acid-related or associated, being treated. For example, the term "increased responsiveness" when used in reference to a treatment of a cell or a subject refers to an increase in the effectiveness in lessening or decreasing the symptoms of the disease when measured using any methods known in the art. In certain embodiments, the increase in the effectiveness is at least about 5%, at least about 10%, at least about 20%, at least about 30%, at least about 40%, or at least about 50%.

The term "likely," or "likelihood" refers to an increase in the probability of an event. The term "likelihood" when used in reference to the effectiveness of a subject response to a treatment of a disease, e.g., a bile acid-related or associated disorder, contemplates an increased probability that the symptoms of the disease will be lessened or decreased.

The term "predict" generally means to determine or tell in advance. When used to "predict" the effectiveness of the treatment of a disease (e.g., a bile acid-related or associated disorder), for example, the term "predict" can mean that the likelihood of the outcome of the treatment can be determined at the outset, before the treatment has begun, or before the treatment period has progressed substantially.

The terms "determining", "measuring", "evaluating", "assessing" and "assaying" are used interchangeably herein to refer to a form of measurement, including determining if an element is present or not. The measurement can be quantitative and/or qualitative determinations. "Assessing the presence of" can include determining the amount of something present, as well as determining whether it is present or absent.

4.2 Treatment Peptides

Provided herein, in certain embodiments, are uses of chimeric and peptide sequences that modulate bile acid homeostasis or treatment modalities that are useful in the treatment and/or prevention of bile acid-related or associated disorders. The invention is based, in part, on the use of variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of a bile acid-related or associated disorder (e.g., PBC). Such variants and fusions (chimeras) of FGF19 and/or FGF21 peptide sequences include sequences that do not substantially increase or induce HCC formation or HCC tumorigenesis and/or do not induce a substantial elevation or increase in lipid profile.

In one embodiment, a chimeric peptide sequence includes or consists of an N-terminal region having at least seven amino acid residues and the N-terminal region having a first amino acid position and a last amino acid position, where the N-terminal region has a DSSPL (SEQ ID NO:121) or DASPH (SEQ ID NO:122) sequence; and a C-terminal region having a portion of FGF19 and the C-terminal region having a first amino acid position and a last amino acid position, where the C-terminal region includes amino acid residues 16-29 of FGF19 (WGDPIRLRHLYTSG; SEQ ID NO:169) and the W residue corresponds to the first amino acid position of the C-terminal region. In particular embodiments, the variant is M70: MRDSSPLVHYGWGDPIRLRHLYTSGPHGLSSCFLRIRADGVVDCARGQSAHSLLEIKAVALR TVAIKGVHSVRYLCMGADGKMQGLLQYSEEDCAFEEEIRPDGYNVYRSEKHRLPVSLSSAK QRQLYKNRGFLPLSHFLPMLPMVPEEPEDLRGHLESDMFSSPLETDS16MDPFGLVTGLEAV RSPSFEK (SEQ ID NO:70). In particular embodiments, the variant is M69:

(SEQ ID NO: 69)
RDSSPLVHYGWGDPIRLRHLYTSGPHGLSSCFLRIRADGVVDCARGQSA

HSLLEIKAVALRTVAIKGVHSVRYLCMGADGKMQGLLQYSEEDCAFEEE

IRPDGYNVYRSEKHRLPVSLSSAKQRQLYKNRGFLPLSHFLPMLPMVPE

EPEDLRGHLESDMFSSPLETDSMDPFGLVTGLEAVRSPSFEK (M69).

In another embodiment, the treatment peptide, comprises: a) an N-terminal region comprising at least seven amino acid residues, the N-terminal region having a first amino acid position and a last amino acid position; and b) a C-terminal region comprising a portion of SEQ ID NO:99 [FGF19], the C-terminal region having a first amino acid position and a last amino acid position, wherein the C-terminal region comprises (i) a first C-terminal region sequence comprising WGDPIRLRHLYTSG (amino acids 16 to 29 of SEQ ID NO:99 [FGF19]), wherein the W residue corresponds to the first amino acid position of the C-terminal region; and (ii) a second C-terminal region sequence comprising

PHGLSSCFLRIRADGVVDCARGQSAHSLLEIKAVALRTVAIKGVHSVRYL

CMGADGKMQGLLQYSEEDCAFEEEIRPDGYNVYRSEKHRLPVSLSSAKQR

QLYKNRGFLPLSHFLPMLPMVPEEPEDLRGHLESDMFSSPLETDSMDPFG

LVTGLEAVRSPSFEK
(amino acid residues 30 to 194 of SEQ ID NO:99
[FGF19]).

In another embodiment, the treatment peptide, comprises: a) an N-terminal region comprising at least seven amino acid residues, the N-terminal region having a first amino acid position and a last amino acid position, wherein the N-terminal region comprises DSSPL (SEQ ID NO:121) or DASPH (SEQ ID NO:122); and b) a C-terminal region comprising a portion of SEQ ID NO:99 [FGF19], the C-terminal region having a first amino acid position and a last amino acid position, wherein the C-terminal region comprises (i) a first C-terminal region sequence comprising WGDPIRLRHLYTSG (amino acids 16 to 29 of SEQ ID NO:99 [FGF19]), wherein the W residue corresponds to the first amino acid position of the C-terminal region; and (ii) a second C-terminal region sequence comprising PHGLSSCFLRIRADGVVDCARGQSAHSLLEIKAVALRTVAIKGVHSVRYLCMGADGKMQGL LQYSEEDCAFEEEIRPDGYNVYRSEKHRLPVSLSSAKQRQLYKNRGFLPLSHFLPMLPMVPE EPEDLRGHLESDMFSSPLETDSMDPFGLVTGLEAVRSPSFEK (amino acid residues 30 to 194 of SEQ ID NO:99 [FGF19]). In certain embodiments, the peptide (i) binds to FGFR4 with an affinity equal to or greater than FGF19 binding affinity for FGFR4; (ii) activates FGFR4 to an extent or amount equal to or greater than FGF19 activates FGFR4; (iii) has at least one of reduced HCC formation; greater glucose lowering activity, less lipid increasing activity, less triglyceride activity, less cholesterol activity, less non-HDL activity or less HDL increasing activity, as compared to FGF19, or as compared to an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19 (SEQ ID NO:99); and/or (iv) has less lean mass reducing activity as compared to FGF21.

In certain embodiments, the second C-terminal region sequence comprises at least one amino acid substitution to the EIRPD (amino acids 2-6 of SEQ ID NO:190) sequence. In some embodiments, the at least one amino acid substitution is to the IRP sequence of the EIRPD (amino acids 2-6 of SEQ ID NO:190) sequence. In some embodiments, the at least one amino acid substitution is to the RP sequence of the EIRPD sequence (amino acids 2-6 of SEQ ID NO:190). In some embodiments, the at least one amino acid substitution is R to L substitution. In other embodiments, the at least one amino acid substitution is P to E substitution. In yet other embodiments, the at least one amino acid substitution is RP to LE substitution.

In some embodiments, the second C-terminal region sequence comprises from 2 to 5 amino acid substitutions, deletions or insertions. In other embodiments, the peptide is less than about 250 amino acids in length.

In one embodiment, the treatment peptide has an amino acid sequence comprising or consisting of MRDSSPLVHYGWGDPIRLRHLYTSGPHGLSSCFLRIRADGVVDCARGQSAHSLLEIKAVALR TVAIKGVHSVRYLCMGADGKMQGLLQYSEEDCAFEEEIRPDGYNVYRSEKHRLPVSLSSAK QRQLYKNRGFLPLSHFLPMLPMVPEEPEDLRGHLESDMFSSPLETDSMDPFGLVTGLEAVRS PSFEK (SEQ ID NO:70). In certain embodiments, the treatment peptide has an amino acid sequence comprising SEQ ID NO:70. In other embodiments, the treatment peptide has an amino acid sequence consisting of SEQ ID NO:70. In some embodiments, the treatment peptide is fused with an immunoglobulin Fc region.

In another embodiment, the treatment peptide has an amino acid sequence comprising or consisting of RDSSPLVHYGWGDPIRLRHLYTSGPHGLSSCFLRIRADGVVDCARGQSAHSLLEIKAVALRT VAIKGVHSVRYLCMGADGKMQGLLQYSEEDCAFEEEIRPDGYNVYRSEKHRLPVSLSSAKQRQLYKNRGFLPLSHFLPMLPMVPEEPEDLRGHLESDMFSSPLETDSMDPFGLVTGLEAVRSP SFEK (SEQ ID NO:69). In certain embodiments, the treatment peptide has an amino acid sequence comprising SEQ ID NO:69. In other embodiments, the treatment peptide has an amino acid sequence consisting of SEQ ID NO:69. In some embodiments, the treatment peptide is fused with an immunoglobulin Fc region.

In another embodiment, the treatment peptide, comprises: a) an N-terminal region comprising at least seven amino acid residues, the N-terminal region having a first amino acid position and a last amino acid position; and b) a C-terminal region comprising a first amino acid position and a last amino acid position, wherein the C-terminal region comprises (i) a first C-terminal region sequence comprising WGDPIRQRHLYTSG (SEQ ID NO:169 with a L7Q substitution), wherein the W residue corresponds to the first amino acid position of the C-terminal region; and (ii) a second C-terminal region sequence comprising (SEQ ID NO: 188)
PHGLSSCFLRIRADGVVDCARGQSAHSLLEIKAVALRTVAIKGVHSVRYL

CMGADGKMQGLLQYSEEDCAFEEEIRPDGYNVYRSEKHRLPVSLSSAKQR

QLYKNRGFLPLSHFLPMLPMVPEEPEDLRGHLESDMFSSPLETDSMDPFG

LVTGLEAVRSPSFEK.

In another embodiment, the treatment peptide, comprises: a) an N-terminal region comprising at least seven amino acid residues, the N-terminal region having a first amino acid position and a last amino acid position, wherein the N-terminal region comprises DSSPL (SEQ ID NO:121), DASPH (SEQ ID NO:122), or DAGPH (amino acids 7 to 11 of SEQ ID NO:99 [FGF19]); and b) a C-terminal region comprising a first amino acid position and a last amino acid position, wherein the C-terminal region comprises (i) a first C-terminal region sequence comprising WGDPIRQRHLYTSG (SEQ ID NO:169 with a L7Q substitution), wherein the W residue corresponds to the first amino acid position of the C-terminal region; and (ii) a second C-terminal region sequence comprising PHGLSSCFLRIRADGVVDCARGQSAHSLLEIKAVALRTVAIKGVHSVRYLCMGADGKMQGL LQYSEEDCAFEEEIRPDGYNVYRSEKHRLPVSLSSAKQRQLYKNRGFLPLSHFLPMLPMVPE EPEDLRGHLESDMFSSPLETDSMDPFGLVTGLEAVRSPSFEK (SEQ ID NO:188). In some embodiments, the peptide (i) binds to FGFR4 with an affinity equal to or greater than FGF19 binding affinity for FGFR4; (ii) activates FGFR4 to an extent or amount equal to or greater than FGF19 activates FGFR4; (iii) has at least one of reduced hepatocellular carcinoma (HCC) formation; greater glucose lowering activity, less lipid increasing activity, less triglyceride activity, less cholesterol activity, less non-HDL activity or less HDL increasing activity, as compared to FGF19, or as compared to an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the FGF19 WGDPI (SEQ ID NO:170) sequence at amino acids 16-20; and/or (iv) has less lean mass reducing activity as compared to FGF21.

In certain embodiments, the second C-terminal region sequence comprises at least one amino acid substitution to the EIRPD (amino acids 2-6 of SEQ ID NO:190) sequence. In some embodiments, the at least one amino acid substitution is to the IRP sequence of the EIRPD (amino acids 2-6 of SEQ ID NO:190) sequence. In some embodiments, the at least one amino acid substitution is to the RP sequence of the EIRPD sequence (amino acids 2-6 of SEQ ID NO:190). In some embodiments, the at least one amino acid substitution is R to L substitution. In other embodiments, the at least one amino acid substitution is P to E substitution. In yet other embodiments, the at least one amino acid substitution is RP to LE substitution.

In some embodiments, the second C-terminal region sequence comprises from 2 to 5 amino acid substitutions, deletions or insertions. In other embodiments, the peptide is less than about 250 amino acids in length.

In another embodiment, a chimeric peptide sequence includes or consists of an N-terminal region having a portion of FGF21 and the N-terminal region having a first amino acid position and a last amino acid position, where the N-terminal region has a GQV sequence and the V residue corresponds to the last amino acid position of the N-terminal region; and a C-terminal region having a portion of FGF19 and the C-terminal region having a first amino acid position and a last amino acid position where the C-terminal region includes amino acid residues 21-29 of FGF19 (RLRHLYTSG; SEQ ID NO: 185) and the R residue corresponds to the first position of the C-terminal region.

In particular aspects, modifications to the Loop-8 region of FGF19 are disclosed herein that possess favorable metabolic parameters without exhibiting substantial tumorigenicity. Herein, FGF19 residues 127-129 are defined as constituting the Loop-8 region, although in the literature the Loop-8 region is sometimes defined as including or consisting of other residues (e.g., residues 125-129). Certain combinations of R127L and P128E substitutions to the FGF19 framework had an unexpectedly positive effect on HCC formation. Even more surprisingly, a combination of R127L and P128E substitutions and a substitution of Gln (Q) for Leu (L) in the FGF19 core region had an even more significant effect on preventing HCC formation.

Accordingly, variants of FGF19 Loop-8 region are included since they can reduce or eliminate substantial, measurable or detectable HCC formation. Furthermore, the effect of reducing HCC formation may be enhanced by modifications to amino acid residues outside of the Loop-8 region (e.g., substitutions of amino acid residues in the core region, such as the region corresponding to amino acids 21-29 of SEQ ID NO:99). In some embodiments, the Loop-8 modified variant comprises a substitution in the FGF19 Loop-8 region corresponding to amino acids 127-129 of SEQ ID NO:99. In certain embodiments, the Loop-8 modified variant comprises a substitution in the FGF19 Loop-8 region corresponding to (i) a R127L substitution, (ii) a P128E substitution, or (iii) a R127L substitution and a P128E substitution.

In certain embodiments, the amino acid sequence of the peptide comprises at least one amino acid substitution in the Loop-8 region of FGF19, or the corresponding FGF19 sequence thereof in a variant peptide provided herein. In certain embodiments, the amino acid sequence of the peptide comprises one amino acid substitution to the EIRPD (amino acids 2-6 of SEQ ID NO:190) amino acid sequence in the Loop-8 region of FGF19. In some embodiments, the amino acid sequence of the peptide comprises two amino acid substitutions to the EIRPD (amino acids 2-6 of SEQ ID NO:190) amino acid sequence in the Loop-8 region of FGF19. In other embodiments, the amino acid sequence of the peptide comprises three amino acid substitutions to the EIRPD (amino acids 2-6 of SEQ ID NO:190) amino acid sequence in the Loop-8 region of FGF19. In certain embodiments, the amino acid sequence of the peptide comprises four amino acid substitutions to the EIRPD (amino acids 2-6 of SEQ ID NO:190) amino acid sequence in the Loop-8 region of FGF19. In some embodiments, the amino acid sequence of the peptide comprises five amino acid substitutions to the EIRPD (amino acids 2-6 of SEQ ID NO:190) amino acid sequence in the Loop-8 region of FGF19. In certain embodiments, the amino acid sequence of the peptide comprises one amino acid substitution to the IRP (amino acids 3-5 of SEQ ID NO:190) amino acid sequence in the Loop-8 region of FGF19. In some embodiments, the amino acid sequence of the peptide comprises two amino acid substitutions to the IRP (amino acids 3-5 of SEQ ID NO:190) amino acid sequence in the Loop-8 region of FGF19. In other embodiments, the amino acid sequence of the peptide comprises three amino acid substitutions to the IRP (amino acids 3-5 of SEQ ID NO:190) amino acid sequence in the Loop-8 region of FGF19. In certain embodiments, the amino acid sequence of the peptide comprises one amino acid substitution to the RP (amino acids 4-5 of SEQ ID NO:190) amino acid sequence in the Loop-8 region of FGF19. In some embodiments, the amino acid sequence of the peptide comprises two amino acid substitutions to the RP (amino acids 4-5 of SEQ ID NO:190) amino acid sequence in the Loop-8 region of FGF19. In certain embodiments, the amino acid substitution to the RP (amino acids 4-5 of SEQ ID NO:190) amino acid sequence in the Loop-8 region of FGF19 is an Arg (R) to Leu (L) substitution. In other embodiments, the substitution to the RP (amino acids 4-5 of SEQ ID NO:190) amino acid sequence in the Loop-8 region of FGF19 is a Pro (P) to Glu (E) substitution. In some embodiments, the substitutions to the RP (amino acids 4-5 of SEQ ID NO:190) amino acid sequence in the Loop-8 region of FGF19 is an Arg (R) to Leu (L) substitution and a Pro (P) to Glu (E) substitution. In specific embodiments, the foregoing substitution(s) in the Loop-8 region of FGF19 is in the corresponding FGF19 sequence thereof in a variant peptide provided herein. That is, said substitutions within a corresponding FGF19 sequence (e.g., EIRPD (amino acids 2-6 of SEQ ID NO:190), IRP or RP) of a peptide variant provided herein is also contemplated.

In some embodiments, the FGF19 variant comprises or further comprises a substitution in the core region corresponding to amino acids 21-29 of SEQ ID NO:99. In certain embodiments, the FGF19 variant comprises or further comprises a substitution in the core region corresponding to a L22Q substitution.

In some embodiments, the Loop-8 modified variant is M70: MRDSSPLVHYGWGDPIRLRHLYTSGPHGLSS-CFLRIRADGVVDCARGQSAHSLLEIKAVALR TVAI-KGVHSVRYLCMGADGKMQGLLQYSEEDCAFEEEI RPDGYNVYRSEKHRLPVSLSSAK QRQLYKNRGFLPLSHFLPMLPMVPEEPEDLRGHL-ESDMFSSPLETDS16MDPFGLVTGLEAV RSPSFEK (SEQ ID NO:70), comprising a substitution in the FGF19 Loop-8 region (underlined). In certain embodiments, the Loop-8 modified M70 variant comprises a substitution in the FGF19 Loop-8 region (underlined) corresponding to (i) a R127L substitution, (ii) a P128E substitution, or (iii) a R127L substitution and a P128E substitution (SEQ. ID NO:204). In certain embodiments, the Loop-8 modified M70 variant further comprises or further comprises a substitution in the FGF19 core region. In some embodiments, the Loop-8 modified M70 variant comprises a L18Q substitution.

In some embodiments, the Loop-8 modified variant is M69: RDSSPLVHYGWGDPIRLRHLYTSGPHGLSSCFL-RIRADGVVDCARGQSAHSLLEIKAVALRT VAI-KGVHSVRYLCMGADGKMQGLLQYSEEDCAFEEE-IRPDGYNVYRSEKHRLPVSLSSAKQ RQLYKNRGFLPLSHFLPMLPMVPEEPEDLRGHL-ESDMFSSPLETDSMDPFGLVTGLEAVRSP SFEK (M69) (SEQ ID NO:69), comprising a substitution in the FGF19 Loop-8 region (underlined). In certain embodiments, the Loop-8 modified M69 variant comprises a substitution in the FGF19 Loop-8 region (underlined) corresponding to (i) a R100L substitution, (ii) a P101E substitution, or (iii) a R100L substitution and a P101E substitution. In certain embodiments, the Loop-8 modified M69 variant further comprises or further comprises a substitution in the FGF19 core region. In some embodiments, the Loop-8 modified M69 variant comprises a L17Q substitution.

In some embodiments, the Loop-8 modified variant comprises a substitution in the FGF19 Loop-8 region corresponding to amino acids 127-129 of SEQ ID NO:3. In certain embodiments, the Loop-8 modified variant comprises a substitution in the FGF19 Loop-8 region corresponding to (i) a R127L substitution, (ii) a P128E substitution, or (iii) a R127L substitution and a P128E substitution. In some embodiments, the FGF19 variant comprises or further comprises a substitution in the core region corresponding to amino acids 21-29 of SEQ ID NO:3. In certain embodiments, the FGF19 variant comprises or further comprises a substitution in the core region corresponding to a L22Q substitution.

In further embodiments, a peptide sequence includes or consists of a FGF19 variant having one or more amino acid substitutions, insertions or deletions compared to a reference or wild type FGF19. In additional embodiments, a peptide sequence includes or consists of a FGF21 sequence variant having one or more amino acid substitutions, insertions or deletions compared to a reference or wild type FGF21. In yet additional embodiments, a peptide sequence includes or consists of a portion of a FGF19 sequence fused to a portion of a FGF21 sequence. In still additional embodiments, a peptide sequence includes or consists of a portion of a FGF19 sequence fused to a portion of a FGF21 sequence, where the FGF19 and/or FGF21 sequence portion(s) have one or more amino acid substitutions, insertions or deletions compared to a reference or wild type FGF19 and/or FGF21. Examples of such sequences are disclosed in PCT Pub. No. WO 2013/006486 and US Pub. No. 2013/0023474, as well as PCT Publ. No. WO 2014/085365, published Jun. 5, 2014. Table 1 and the Sequence Listing also sets forth representative sequences that may be used in the methods provided herein.

In some embodiments, the treatment peptides provided herein include variants and fusions of FGF19 and/or FGF21 peptide sequences. In one embodiment, the treatment peptides include one or more variant or fusion FGF19 and/or FGF21 peptide. In other embodiments, the methods provided herein include contacting or administering to a subject one or more nucleic acid molecules encoding a variant or fusion FGF19 and/or FGF21 peptide sequence (for example, an expression control element in operable linkage with the nucleic acid encoding the peptide sequence, optionally including a vector), in an amount effective for treating a bile acid-related or associated disorder.

A representative reference or wild type FGF19 sequence is set forth as:

(SEQ ID NO: 99)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK.

A representative reference or wild type FGF21 sequence is set forth as: HPIPDSSPLLQFGGQVRQRYLYTD-DAQQTEAHLEIREDGTVGGAADQSPESLLQLKA-LKPGV IQILGVKTSRFLCQRPDGA-LYGSLHFDPEACSFRELLLEDGYNVYQSEAHGLPL-HLPGNKSPH RDPAPRGPARFLPLPGLPPALPEPPGI-LAPQPPDVGSSDPLSMVGPSQGRSPSYAS (SEQ ID NO:100). FGF21 allelic variants include, e.g., M70, M71 and M72.

The terms "peptide," "protein," and "polypeptide" sequence are used interchangeably herein to refer to two or more amino acids, or "residues," including chemical modifications and derivatives of amino acids, covalently linked by an amide bond or equivalent. The amino acids forming all or a part of a peptide may be from among the known 21 naturally occurring amino acids, which are referred to by both their single letter abbreviation or common three-letter abbreviation. In the peptide sequences provided herein, conventional amino acid residues have their conventional meaning. Thus, "Leu" is leucine, "Ile" is isoleucine, "Nle" is norleucine, and so on.

In various particular aspects, a peptide or chimeric sequence provided herein has at the N-terminal region first amino acid position an "M" residue, an "R" residue, a "S" residue, a "H" residue, a "P" residue, a "L" residue or an "D" residue. In various alternative particular aspects, a peptide or chimeric sequence peptide sequence does not have a "M" residue or an "R" residue at the first amino acid position of the N-terminal region.

Also provided herein are subsequences, variants and modified forms of the exemplified peptide sequences (including the FGF19 and FGF21 variants and subsequences listed in the Sequence Listing, or Table 1), so long as the foregoing retains at least a detectable or measureable activity or function. Also, certain exemplified variant peptides, for example, those having all or a portion of FGF21 sequence at the amino-terminus, have an "R" residue positioned at the N-terminus, which can be omitted. Similarly, certain exemplified variant peptides, include an "M" residue positioned at the N-terminus, which can be appended to or further substituted for an omitted residue, such as an "R" residue. More particularly, in various embodiments peptide sequences at the N-terminus include any of: RDSS (SEQ ID NO:115), DSS, MDSS (SEQ ID NO:116) or MRDSS (SEQ ID NO:117). Furthermore, when a "M" residue is adjacent to a "S" residue, the "M" residue may be cleaved such that the "M" residue is deleted from the peptide sequence, whereas when the "M" residue is adjacent to a "D" residue, the "M" residue may not be cleaved. Thus, by way of example, in various embodiments peptide sequences include those with the following residues at the N-terminus: MDSSPL (SEQ ID NO:119), MSDSSPL (SEQ ID NO:120) (cleaved to SDSSPL (SEQ ID NO:112)) and MSSPL (SEQ ID NO:113) (cleaved to SSPL (SEQ ID NO:114)).

Exemplified herein are peptide sequences, distinct from reference FGF19 and FGF21 polypeptides set forth herein, that modulate bile acid homeostasis, in vivo (e.g., Table 1 and the Sequence Listing). Non-limiting particular examples are a peptide sequence with amino-terminal amino acids 1-16 of FGF21 fused to carboxy-terminal amino acids 21-194 of FGF19; a peptide sequence with amino-terminal amino acids 1-147 of FGF19 fused to carboxy-terminal amino acids 147-181 of FGF21; a peptide sequence with amino-terminal amino acids 1-20 of FGF19 fused to carboxy-terminal amino acids 17-181 of FGF21; a peptide sequence with amino-terminal amino acids 1-146 of FGF21 fused to carboxy-terminal amino acids 148-194 of FGF19; and a peptide sequence with amino-terminal amino acids 1-20 of FGF19 fused to internal amino acids 17-146 of FGF21 fused to carboxy-terminal amino acids 148-194 of FGF19.

In yet additional embodiments, a peptide sequence or a chimeric peptide sequence has a WGDPI (SEQ ID NO:170) sequence motif corresponding to the WGDPI (SEQ ID NO:170) sequence of amino acids 16-20 of SEQ ID NO:99 (FGF19); has a substituted, mutated or absent WGDPI (SEQ ID NO:170) sequence motif corresponding to FGF19 WGDPI (SEQ ID NO:170) sequence of amino acids 16-20 of FGF19; has a WGDPI (SEQ ID NO:170) sequence with one or more amino acids substituted, mutated or absent.

Particular peptide sequences provided herein also include sequences distinct from FGF19 and FGF21 (e.g., as set forth herein), and FGF19 variant sequences having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for FGF19 WGDPI (SEQ ID NO:170) sequence at amino acids 16-20. Accordingly, the wild-type FGF19 and FGF21 (e.g., as set forth herein as SEQ ID NOS:99 and 100, respectively) may be excluded sequences, and FGF19 having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19 may also be excluded. This exclusion, however, does not apply to where a sequence has, for example, 3 FGF21 residues fused to FGF19 having, for example, any of GQV, GQV, GDI, or GPI, or 2 FGF21 residues fused to any of WGPI (SEQ ID NO:171), WGDI (SEQ ID NO:173), GDPI (SEQ ID NO:174), WDPI (SEQ ID NO:181), WGDI (SEQ ID NO:182), or WGDP (SEQ ID NO:183).

In yet further embodiments, a peptide sequence or a chimeric peptide sequence has N-terminal region comprises amino acid residues VHYG (SEQ ID NO:101), wherein the N-terminal region comprises amino acid residues DAS-PHVHYG (SEQ ID NO:102), or the N-terminal region comprises amino acid residues DSSPLVHYG (SEQ ID NO:103). More particularly, in one aspect the G corresponds to the last position of the N-terminal region.

In various additional aspects, the N-terminal region comprises amino acid residues DSSPLLQ (SEQ ID NO:104), where the Q residue is the last amino acid position of the N-terminal region, or comprises amino acid residues DSSPLLQFGGQV (SEQ ID NO:105), where the V residue corresponds to the last position of the N-terminal region.

In certain embodiments, an N-terminal region comprises or consists of (or further comprises or consists of): RHPIP (SEQ ID NO:106), where R is the first amino acid position of the N-terminal region; or HPIP (SEQ ID NO:107), where H is the first amino acid position of the N-terminal region; or RPLAF (SEQ ID NO:108), where R is the first amino acid position of the N-terminal region; or PLAF (SEQ ID NO:109), where P is the first amino acid position of the N-terminal region; or R, where R is the first amino acid position of the N-terminal region.

In various other aspects, a peptide or chimeric sequence has: amino acid residues HPIP (SEQ ID NO:107), which are the first 4 amino acid residues of the N-terminal region. In various still further aspects, a peptide or chimeric sequence has: an R residue at the first position of the N-terminal region, or the first position of the N-terminal region is an M residue, or the first and second positions of the N-terminal region is an MR sequence, or the first and second positions of the N-terminal region is an RM sequence, or the first and second positions of the N-terminal region is an RD sequence, or the first and second positions of the N-terminal region is an DS sequence, or the first and second positions of the N-terminal region is an MD sequence, or the first and second positions of the N-terminal region is an MS sequence, or the first through third positions of the N-terminal region is an MDS sequence, or the first through third positions of the N-terminal region is an RDS sequence, or the first through third positions of the N-terminal region is an MSD sequence, or the first through third positions of the N-terminal region is an MSS sequence, or the first through third positions of the N-terminal region is an DSS sequence, or the first through fourth positions of the N-terminal region is an RDSS (SEQ ID NO:115), sequence, or the first through fourth positions of the N-terminal region is an MDSS (SEQ ID NO:116), sequence, or the first through fifth positions of the N-terminal region is an MRDSS (SEQ ID NO:117), sequence, or the first through fifth positions of the N-terminal region is an MSSPL (SEQ ID NO:113) sequence, or the first through sixth positions of the N-terminal region is an MDSSPL (SEQ ID NO:110) sequence, or the first through seventh positions of the N-terminal region is an MSDSSPL (SEQ ID NO:111) sequence.

In further various other embodiments, a peptide or chimeric sequence has an N-terminal region with any one of the following sequences: MDSSPL (SEQ ID NO:110), MSDSSPL (SEQ ID NO:111), SDSSPL (SEQ ID NO:112), MSSPL (SEQ ID NO:113) or SSPL (SEQ ID NO:114).

In certain embodiments, a peptide sequence includes the addition of amino acid residues 30-194 of SEQ ID NO:99 (FGF19) at the C-terminus, resulting in a chimeric polypeptide. In various still additional embodiments, a peptide or chimeric sequence has a residue at the last position of the C-terminal region that corresponds to about residue 194 of SEQ ID NO:99 (FGF19). In still other embodiments, a peptide sequence or a chimeric peptide sequence an addition of amino acid residues 30-194 of SEQ ID NO:99 (FGF19) at the C-terminus, resulting in a chimeric polypeptide having at the last position of the C-terminal region that corresponds to about residue 194 of SEQ ID NO:99 (FGF19). In further other embodiments, a chimeric peptide sequence or peptide sequence comprises all or a portion of a FGF19 sequence (e.g., SEQ ID NO:99), positioned at the C-terminus of the peptide, or where the amino terminal "R" residue is deleted from the peptide.

Methods and uses provided herein can be practiced using a peptide or chimeric sequence, as set forth herein. For example, a sequence that comprises or consists of any peptide sequence set forth herein, e.g., as M1-M98, M101 to M160, or M200 to M207; or SEQ ID NOs:1 to 98, or 101 to 135, or 138 to 212. In other embodiments, the peptide sequence comprises or consists of any sequence set forth in Table 1. In yet other embodiments, the peptide sequence that comprises or consists of any sequence set forth in the Sequence Listing herein.

Particular non-limiting examples of peptide sequences include or consist of all or a part of a sequence variant specified herein as M1-M98 (SEQ ID NOs:1-52, 192, and 54-98, respectively).

More particular non-limiting examples of peptide sequences include or consist of all or a part of a sequence set forth as:

```
                                               (SEQ ID NO: 160)
HPIPDSSPLLQFGGQVRLRHLYTSGPHGLSSCFLRIRADGVVDCARGQSAHSLLEIKAVA

LRTVAIKGVHSVRYLCMGADGKMQGLLQYSEEDCAFEEEIRPDGYNVYRSEKHRLPVS

LSSAKQRQLYKNRGFLPLSHFLPMLPMVPEEPEDLRGHLESDMFSSPLETDSMDPFGLVT

GLEAVRSPSFEK (M5-R)
(FGF21 sequences can also include an "R" residue at the
amino terminus);

(SEQ ID NO: 138 and 161)
DSSPLLQFGGQVRLRHLYTSGPHGLSSCFLRIRADGVVDCARGQSAHSLLEIKAVALRTVAI

KGVHSVRYLCMGADGKMQGLLQYSEEDCAFEEEIRPDGYNVYRSEKHRLPVSLSSAKQRQ

LYKNRGFLPLSHFLPMLPMVPEEPEDLRGHLESDMFSSPLETDSMDPFGLVTGLEAVRSPSFE

K;

(SEQ ID NO: 1 or 139)
RPLAFSDASPHVHYGWGDPIRLRHLYTSGPHGLSSCFLRIRADGVVDCARGQSAHSLLEIKA

VALRTVAIKGVHSVRYLCMGADGKMQGLLQYSEEDCAFEEEIRPDGYNVYRSEKHRLPVSL

SSAKQRQLYKNRGFLPLSHFLPMLPMVPEEPEDLRGHLESDMFSSPLETDSMDPFGLVTGLE

AVRSPSFEK (M1);
```

-continued

```
                                                 (SEQ ID NO: 2 or 140)
RPLAFSDSSPLVHYGWGDPIRLRHLYTSGPHGLSSCFLRIRADGVVDCARGQSAHSLLEIKAV

ALRTVAIKGVHSVRYLCMGADGKMQGLLQYSEEDCAFEEEIRPDGYNVYRSEKHRLPVSLS

SAKQRQLYKNRGFLPLSHFLPMLPMVPEEPEDLRGHLESDMFSSPLETDSMDPFGLVTGLEA

VRSPSFEK (M2);

(SEQ ID NO: 141)
DSSPLVHYGWGDPIRLRHLYTSGPHGLSSCFLRIRADGVVDCARGQSAHSLLEIKAVALRTV

AIKGVHSVRYLCMGADGKMQGLLQYSEEDCAFEEEIRPDGYNVYRSEKHRLPVSLSSAKQR

QLYKNRGFLPLSHFLPMLPMVPEEPEDLRGHLESDMFSSPLETDSMDPFGLVTGLEAVRSPSF

EK;

(SEQ ID NO: 69)
RDSSPLVHYGWGDPIRLRHLYTSGPHGLSSCFLRIRADGVVDCARGQSAHSLLEIKAVALRT

VAIKGVHSVRYLCMGADGKMQGLLQYSEEDCAFEEEIRPDGYNVYRSEKHRLPVSLSSAKQ

RQLYKNRGFLPLSHFLPMLPMVPEEPEDLRGHLESDMFSSPLETDSMDPFGLVTGLEAVRSP

SFEK (M69);

(SEQ ID NO: 52)
RDSSPLLQWGDPIRLRHLYTSGPHGLSSCFLRIRADGVVDCARGQSAHSLLEIKAVALRTVAI

KGVHSVRYLCMGADGKMQGLLQYSEEDCAFEEEIRPDGYNVYRSEKHRLPVSLSSAKQRQ

LYKNRGFLPLSHFLPMLPMVPEEPEDLRGHLESDMFSSPLETDSMDPFGLVTGLEAVRSPSFE

K (M52);

(SEQ ID NO: 5)
RHPIPDSSPLLQFGGQVRLRHLYTSGPHGLSSCFLRIRADGVVDCARGQSAHSLLEIKAVALR

TVAIKGVHSVRYLCMGADGKMQGLLQYSEEDCAFEEEIRPDGYNVYRSEKHRLPVSLSSAK

QRQLYKNRGFLPLSHFLPMLPMVPEEPEDLRGHLESDMFSSPLETDSMDPFGLVTGLEAVRS

PSFEK (M5);

(SEQ ID NO: 160)
HPIPDSSPLLQFGGQVRLRHLYTSGPHGLSSCFLRIRADGVVDCARGQSAHSLLEIKAVALRT

VAIKGVHSVRYLCMGADGKMQGLLQYSEEDCAFEEEIRPDGYNVYRSEKHRLPVSLSSAKQ

RQLYKNRGFLPLSHFLPMLPMVPEEPEDLRGHLESDMFSSPLETDSMDPFGLVTGLEAVRSP

SFEK (M5-R);

(SEQ ID NO: 71)
HPIPDSSPLLQFGGQVRQRYLYTDDAQQTEAHLEIREDGTVGGAADQSPESLLQLKALKPGV

IQILGVKTSRFLCQRPDGALYGSLHFDPEACSFRELLLEDGYNVYQSEAHSLPLHLPGNKSPH

RDPAPRGPARFLPLPGLPPALPEPPGILAPQPPDVGSSDPLSMVGPSQGRSPSYAS (M71);

(SEQ ID NO: 72)
HPIPDSSPLLQFGGQVRQRYLYTDDAQQTEAHLEIREDGTVGGAADQSPESLLQLKALKPGV

IQILGVKTSRFLCQRPDGALYGSLHFDPEACSFRELLLEDGYNVYQSEAHGLPLHLPGNKSPH

RDPAPRGPARFLPLPGLPPAPPEPPGILAPQPPDVGSSDPLSMVGPSQGRSPSYAS (M72);

(SEQ ID NO: 73)
HPIPDSSPLLQFGGQVRQRYLYTDDAQQTEAHLEIREDGTVGGAADQSPESLLQLKALKPGV

IQILGVKTSRFLCQRPDGALYGSLHFDPEACSFRELLLEDGYNVYQSEAHGLPLHLPGNKSPH

RDPAPRGPARFLPLPGLPPALPEPPGILAPQPPDVGSSDPLSMVVQDELQGVGGEGCHMHPE

NCKTLLTDIDRTHTEKPVWDGITGE (M73);
```

```
                                                         (SEQ ID NO: 3)
RPLAFSDAGPHVHYGWGDPIRLRHLYTSGPHGLSSCFLRIRADGVVDCARGQSAHSLLEIKA

VALRTVAIKGVHSVRYLCMGADGKMQGLLQYSEEDCAFEEEILEDGYNVYRSEKHRLPVSL

SSAKQRQLYKNRGFLPLSHFLPMLPMVPEEPEDLRGHLESDMFSSPLETDSMDPFGLVTGLE

AVRSPSFEK (M3);

(SEQ ID NO: 48, 6 or 148)
RDSSPLLQFGGQVRLRHLYTSGPHGLSSCFLRIRADGVVDCARGQSAHSLLEIKAVALRTVAI

KGVHSVRYLCMGADGKMQGLLQYSEEDCAFEEEIRPDGYNVYRSEKHRLPVSLSSAKQRQ

LYKNRGFLPLSHFLPMLPMVPEEPEDLRGHLESDMFSSPLETDSMDPFGLVTGLEAVRSPSFE

K (M48);

(SEQ ID NO: 49, 7 or 149)
RPLAFSDSSPLLQFGGQVRLRHLYTSGPHGLSSCFLRIRADGVVDCARGQSAHSLLEIKAVAL

RTVAIKGVHSVRYLCMGADGKMQGLLQYSEEDCAFEEEIRPDGYNVYRSEKHRLPVSLSSA

KQRQLYKNRGFLPLSHFLPMLPMVPEEPEDLRGHLESDMFSSPLETDSMDPFGLVTGLEAVR

SPSFEK (M49);

(SEQ ID NO: 50)
RHPIPDSSPLLQFGDQVRLRHLYTSGPHGLSSCFLRIRADGVVDCARGQSAHSLLEIKAVALR

TVAIKGVHSVRYLCMGADGKMQGLLQYSEEDCAFEEEILEDGYNVYRSEKHRLPVSLSSAK

QRQLYKNRGFLPLSHFLPMLPMVPEEPEDLRGHLESDMFSSPLETDSMDPFGLVTGLEAVRS

PSFEK (M50);

(SEQ ID NO: 51, 36 or 155)
RHPIPDSSPLLQFGGNVRLRHLYTSGPHGLSSCFLRIRADGVVDCARGQSAHSLLEIKAVALR

TVAIKGVHSVRYLCMGADGKMQGLLQYSEEDCAFEEEIRPDGYNVYRSEKHRLPVSLSSAK

QRQLYKNRGFLPLSHFLPMLPMVPEEPEDLRGHLESDMFSSPLETDSMDPFGLVTGLEAVRS

PSFEK (M51);

(SEQ ID NO: 192)
MDSSPLLQWGDPIRLRHLYTSGPHGLSSCFLRIRADGVVDCARGQSAHSLLEIKAVALRTVA

IKGVHSVRYLCMGADGKMQGLLQYSEEDCAFEEEIRPDGYNVYRSEKHRLPVSLSSAKQRQ

LYKNRGFLPLSHFLPMLPMVPEEPEDLRGHLESDMFSSPLETDSMDPFGLVTGLEAVRSPSFE

K (M53);

(SEQ ID NO: 70)
MRDSSPLVHYGWGDPIRLRHLYTSGPHGLSSCFLRIRADGVVDCARGQSAHSLLEIKAVALR

TVAIKGVHSVRYLCMGADGKMQGLLQYSEEDCAFEEEIRPDGYNVYRSEKHRLPVSLSSAK

QRQLYKNRGFLPLSHFLPMLPMVPEEPEDLRGHLESDMFSSPLETDSMDPFGLVTGLEAVRS

PSFEK (M70);

(SEQ ID NO: 193)
RPLAFSDAGPHVHYGWGDPIRLRHLYTSGPHGLSSCFLRIRADGVVDCARGQSAHSLLEIKA

VALRTVAIKGVHSVRYLCMGADGKMQGLLQYSEEDCAFEEEILPDGYNVYRSEKHRLPVSL

SSAKQRQLYKNRGFLPLSHFLPMLPMVPEEPEDLRGHLESDMFSSPLETDSMDPFGLVTGLE

AVRSPSFEK (M139);

(SEQ ID NO: 194)
RPLAFSDAGPHVHYGWGDPIRLRHLYTSGPHGLSSCFLRIRADGVVDCARGQSAHSLLEIKA

VALRTVAIKGVHSVRYLCMGADGKMQGLLQYSEEDCAFEEEIREDGYNVYRSEKHRLPVSL

SSAKQRQLYKNRGFLPLSHFLPMLPMVPEEPEDLRGHLESDMFSSPLETDSMDPFGLVTGLE

AVRSPSFEK (M140);
```

-continued

```
                                             (SEQ ID NO: 195)
RPLAFSDAGPHVHYGWGDPIRLRHLYTSGPHGLSSCFLRIRADGVVDCARGQSAHSLLEIKA

VALRTVAIKGVHSVRYLCMGADGKMQGLLQYSEEDCAFEEEILCDGYNVYRSEKHRLPVSL

SSAKQRQLYKNRGFLPLSHFLPMLPMVPEEPEDLRGHLESDMFSSPLETDSMDPFGLVTGLE

AVRSPSFEK (M141);
or
                                             (SEQ ID NO: 196)
RPLAFSDAGPHVHYGWGDPIRQRHLYTSGPHGLSSCFLRIRADGVVDCARGQSAHSLLEIKA

VALRTVAIKGVHSVRYLCMGADGKMQGLLQYSEEDCAFEEEILEDGYNVYRSEKHRLPVSL

SSAKQRQLYKNRGFLPLSHFLPMLPMVPEEPEDLRGHLESDMFSSPLETDSMDPFGLVTGLE

AVRSPSFEK (M160);
``` or a subsequence or fragment thereof of any of the foregoing peptide sequences. In certain embodiments of any of the foregoing peptide sequences, the N-terminal R residue (R residue at the N-terminums) is deleted.

In various further particular embodiments, a peptide sequence includes or consists of:

```
                                             (SEQ ID NO: 160)
HPIPDSSPLLQFGGQVRLRHLYTSGPHGLSSCFLRIRADGVVDCARGQSA

HSLLEIKAVALRTVAIKGVHSVRYLCMGADGKMQGLLQYSEEDCAFEEEI

RPDGYNVYRSEKHRLPVSLSSAKQRQLYKNRGFLPLSHFLPMLPMVPEEP

EDLRGHLESDMFSSPLETDSMDPFGLVTGLEAVRSPSFEK;

(SEQ ID NO: 138 or 161)
DSSPLLQFGGQVRLRHLYTSGPHGLSSCFLRIRADGVVDCARGQSAHSLL

EIKAVALRTVAIKGVHSVRYLCMGADGKMQGLLQYSEEDCAFEEEIRPDG

YNVYRSEKHRLPVSLSSAKQRQLYKNRGFLPLSHFLPMLPMVPEEPEDLR

GHLESDMFSSPLETDSMDPFGLVTGLEAVRSPSFEK;

(SEQ ID NO: 1 or 139)
RPLAFSDASPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK;

(SEQ ID NO: 2 or 140)
RPLAFSDSSPLVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK;
or
                                             (SEQ ID NO: 141)
DSSPLVHYGWGDPIRLRHLYTSGPHGLSSCFLRIRADGVVDCARGQSAHS

LLEIKAVALRTVAIKGVHSVRYLCMGADGKMQGLLQYSEEDCAFEEEIRP

DGYNVYRSEKHRLPVSLSSAKQRQLYKNRGFLPLSHFLPMLPMVPEEPED

LRGHLESDMFSSPLETDSMDPFGLVTGLEAVRSPSFEK;
``` or a subsequence or fragment thereof of any of the foregoing peptide sequences. In certain embodiments of any of the foregoing peptide sequences, the N-terminal R residue is deleted.

Additional particular non-limiting examples of peptide sequences, having at the N-terminus, a peptide sequence including or consisting of all or a part of any of:

```
                        (amino acids 1-25 of SEQ ID NO: 160)
HPIPDSSPLLQFGGQVRLRHLYTSG (M5-R);

(amino acids 2-22 of SEQ ID NO: 6)
DSSPLLQFGGQVRLRHLYTSG (M6) (M6-R);

(amino acids 1-27 of SEQ ID NO: 7)
RPLAFSDSSPLLQFGGQVRLRHLYTSG (M7);

(amino acids 2-26 of SEQ ID NO: 8)
HPIPDSSPLLQWGDPIRLRHLYTSG (M8-R);

(amino acids 2-28 of SEQ ID NO: 9)
HPIPDSSPLLQFGWGDPIRLRHLYTSG (M9-R);

(amino acids 2-28 of SEQ ID NO: 10)
HPIPDSSPHVHYGWGDPIRLRHLYTSG (M10-R);

(amino acids 1-27 of SEQ ID NO: 11)
RPLAFSDAGPLLQWGDPIRLRHLYTSG (M11);

(amino acids 1-29 of SEQ ID NO: 12)
RPLAFSDAGPLLQFGWGDPIRLRHLYTSG (M12);

(amino acids 1-27 of SEQ ID NO: 13)
RPLAFSDAGPLLQFGGQVRLRHLYTSG (M13);

(amino acids 2-26 of SEQ ID NO: 14)
HPIPDSSPHVHYGGQVRLRHLYTSG (M14-R);

(amino acids 1-27 of SEQ ID NO: 15)
RPLAFSDAGPHVHYGGQVRLRHLYTSG (M15);

(amino acids 1-27 of SEQ ID NO: 16)
RPLAFSDAGPHVHWGDPIRLRHLYTSG (M16);

(amino acids 1-27 of SEQ ID NO: 17)
RPLAFSDAGPHVGWGDPIRLRHLYTSG (M17);

(amino acids 1-27 of SEQ ID NO: 18)
RPLAFSDAGPHYGWGDPIRLRHLYTSG (M18);

(amino acids 1-27 of SEQ ID NO: 19)
RPLAFSDAGPVYGWGDPIRLRHLYTSG (M19);

(amino acids 1-27 of SEQ ID NO: 20)
RPLAFSDAGPVHGWGDPIRLRHLYTSG (M20);

(amino acids 1-27 of SEQ ID NO: 21)
RPLAFSDAGPVHYWGDPIRLRHLYTSG (M21);

(amino acids 1-27 of SEQ ID NO: 22)
RPLAFSDAGPHVHGWGDPIRLRHLYTSG (M22);
```

(amino acids 1-27 of SEQ ID NO: 23)
RPLAFSDAGPHHGWGDPIRLRHLYTSG (M23);

(amino acids 1-27 of SEQ ID NO: 24)
RPLAFSDAGPHHYWGDPIRLRHLYTSG (M24);

(amino acids 1-27 of SEQ ID NO: 25)
RPLAFSDAGPHVYWGDPIRLRHLYTSG (M25);

(amino acids 1-27 of SEQ ID NO: 26)
RPLAFSDSSPLVHWGDPIRLRHLYTSG (M26);

(amino acids 1-27 of SEQ ID NO: 27)
RPLAFSDSSPHVHWGDPIRLRHLYTSG (M27);

(amino acids 1-26 of SEQ ID NO: 28)
RPLAFSDAGPHVWGDPIRLRHLYTSG (M28);

(amino acids 1-28 of SEQ ID NO: 29)
RPLAFSDAGPHVHYWGDPIRLRHLYTSG (M29);

(amino acids 1-29 of SEQ ID NO: 30)
RPLAFSDAGPHVHYAWGDPIRLRHLYTSG (M30);

(amino acids 1-26 of SEQ ID NO: 31)
RHPIPDSSPLLQFGAQVRLRHLYTSG (M31);

(amino acids 1-26 of SEQ ID NO: 32)
RHPIPDSSPLLQFGDQVRLRHLYTSG (M32);

(amino acids 1-26 of SEQ ID NO: 33)
RHPIPDSSPLLQFGPQVRLRHLYTSG (M33);

(amino acids 1-26 of SEQ ID NO: 34)
RHPIPDSSPLLQFGGAVRLRHLYTSG (M34);

(amino acids 1-26 of SEQ ID NO: 35)
RHPIPDSSPLLQFGGEVRLRHLYTSG (M35);

(amino acids 1-26 of SEQ ID NO: 36)
RHPIPDSSPLLQFGGNVRLRHLYTSG (M36);

(amino acids 1-26 of SEQ ID NO: 37)
RHPIPDSSPLLQFGGQARLRHLYTSG (M37);

(amino acids 1-26 of SEQ ID NO: 38)
RHPIPDSSPLLQFGGQIRLRHLYTSG (M38);

(amino acids 1-26 of SEQ ID NO: 39)
RHPIPDSSPLLQFGGQTRLRHLYTSG (M39);

(amino acids 1-28 of SEQ ID NO: 40)
RHPIPDSSPLLQFGWGQPVRLRHLYTSG (M40);

(amino acids 2-24 of SEQ ID NO: 74)
DAGPHVHYGWGDPIRLRHLYTSG (M74-R);

(amino acids 2-19 of SEQ ID NO: 75)
VHYGWGDPIRLRHLYTSG (M75-R);

(amino acids 2-10 of SEQ ID NO: 77)
RLRHLYTSG (M77-R);

(amino acids 1-28 of SEQ ID NO: 9)
RHPIPDSSPLLQFGWGDPIRLRHLYTSG (M9);

(amino acids 1-26 of SEQ ID NO: 8)
RHPIPDSSPLLQWGDPIRLRHLYTSG (M8);

(amino acids 1-29 of SEQ ID NO: 12)
RPLAFSDAGPLLQFGWGDPIRLRHLYTSG (M12);

(amino acids 1-28 of SEQ ID NO: 10)
RHPIPDSSPHVHYGWGDPIRLRHLYTSG (M10);

(amino acids 1-27 of SEQ ID NO: 13)
RPLAFSDAGPLLQFGGQVRLRHLYTSG (M13);

(amino acids 1-26 of SEQ ID NO: 14)
RHPIPDSSPHVHYGGQVRLRHLYTSG (M14);

(amino acids 1-27 of SEQ ID NO: 43)
RPLAFSDAGPHVHYGGDIRLRHLYTSG (M43);
or (amino acids 1-22 of SEQ ID NO: 6)
RDSSPLLQFGGQVRLRHLYTSG (M6);

and for any of the foregoing peptide sequences the amino terminal R residue may be deleted.

In certain embodiments, the peptide comprises or consists of any of:

(amino acids 1-25 of SEQ ID NO: 160)
HPIPDSSPLLQFGGQVRLRHLYTSG (M5-R);

(amino acids 2-22 of SEQ ID NO: 6)
DSSPLLQFGGQVRLRHLYTSG (M6-R);

(amino acids 1-27 of SEQ ID NO: 7)
RPLAFSDSSPLLQFGGQVRLRHLYTSG (M7);

(amino acids 2-26 of SEQ ID NO: 8)
HPIPDSSPLLQWGDPIRLRHLYTSG (M8-R);

(amino acids 2-28 of SEQ ID NO: 9)
HPIPDSSPLLQFGWGDPIRLRHLYTSG (M9-R);

(amino acids 2-28 of SEQ ID NO: 10)
HPIPDSSPHVHYGWGDPIRLRHLYTSG (M10-R);

(amino acids 1-27 of SEQ ID NO: 11)
RPLAFSDAGPLLQWGDPIRLRHLYTSG (M11);

(amino acids 1-29 of SEQ ID NO: 12)
RPLAFSDAGPLLQFGWGDPIRLRHLYTSG (M12);

(amino acids 1-27 of SEQ ID NO: 13)
RPLAFSDAGPLLQFGGQVRLRHLYTSG (M13);

(amino acids 2-26 of SEQ ID NO: 14)
HPIPDSSPHVHYGGQVRLRHLYTSG (M14-R);

(amino acids 1-27 of SEQ ID NO: 15)
RPLAFSDAGPHVHYGGQVRLRHLYTSG (M15);

(amino acids 1-27 of SEQ ID NO: 16)
RPLAFSDAGPHVHWGDPIRLRHLYTSG (M16);

(amino acids 1-27 of SEQ ID NO: 17)
RPLAFSDAGPHVGWGDPIRLRHLYTSG (M17);

(amino acids 1-27 of SEQ ID NO: 18)
RPLAFSDAGPHYGWGDPIRLRHLYTSG (M18);

(amino acids 1-27 of SEQ ID NO: 19)
RPLAFSDAGPVYGWGDPIRLRHLYTSG (M19);

(amino acids 1-27 of SEQ ID NO: 20)
RPLAFSDAGPVHGWGDPIRLRHLYTSG (M20);

(amino acids 1-27 of SEQ ID NO: 21)
RPLAFSDAGPVHYWGDPIRLRHLYTSG (M21);

(amino acids 1-27 of SEQ ID NO: 22)
RPLAFSDAGPHVHGWDPIRLRHLYTSG (M22);

(amino acids 1-27 of SEQ ID NO: 23)
RPLAFSDAGPHHGWGDPIRLRHLYTSG (M23);

(amino acids 1-27 of SEQ ID NO: 24)
RPLAFSDAGPHHYWGDPIRLRHLYTSG (M24);

(amino acids 1-27 of SEQ ID NO: 25)
RPLAFSDAGPHVYWGDPIRLRHLYTSG (M25);

(amino acids 1-27 of SEQ ID NO: 26)
RPLAFSDSSPLVHWGDPIRLRHLYTSG (M26);

```
            (amino acids 1-27 of SEQ ID NO: 27)
RPLAFSDSSPHVHWGDPIRLRHLYTSG (M27);

(amino acids 1-26 of SEQ ID NO: 28)
RPLAFSDAGPHVWGDPIRLRHLYTSG (M28);

(amino acids 1-28 of SEQ ID NO: 29)
RPLAFSDAGPHVHYWGDPIRLRHLYTSG (M29);

(amino acids 1-29 of SEQ ID NO: 30)
RPLAFSDAGPHVHYAWGDPIRLRHLYTSG (M30);

(amino acids 1-26 of SEQ ID NO: 31)
RHPIPDSSPLLQFGAQVRLRHLYTSG (M31);

(amino acids 1-26 of SEQ ID NO: 32)
RHPIPDSSPLLQFGDQVRLRHLYTSG (M32);

(amino acids 1-26 of SEQ ID NO: 33)
RHPIPDSSPLLQFGPQVRLRHLYTSG (M33);

(amino acids 1-26 of SEQ ID NO: 34)
RHPIPDSSPLLQFGGAVRLRHLYTSG (M34);

(amino acids 1-26 of SEQ ID NO: 35)
RHPIPDSSPLLQFGGEVRLRHLYTSG (M35);

(amino acids 1-26 of SEQ ID NO: 36)
RHPIPDSSPLLQFGGNVRLRHLYTSG (M36);

(amino acids 1-26 of SEQ ID NO: 37)
RHPIPDSSPLLQFGGQARLRHLYTSG (M37);

(amino acids 1-26 of SEQ ID NO: 38)
RHPIPDSSPLLQFGGQIRLRHLYTSG (M38);

(amino acids 1-26 of SEQ ID NO: 39)
RHPIPDSSPLLQFGGQTRLRHLYTSG (M39);

(amino acids 1-28 of SEQ ID NO: 40)
RHPIPDSSPLLQFGWGQPVRLRHLYTSG (M40);

(amino acids 2-24 of SEQ ID NO: 74)
DAGPHVYGWGDPIRLRHLYTSG (M74-R);

(amino acids 2-19 of SEQ ID NO: 75)
VHYGWGDPIRLRHLYTSG (M75-R);

(amino acids 2-10 of SEQ ID NO: 77)
RLRHLYTSG (M77-R);

(amino acids 1-28 of SEQ ID NO: 9)
RHPIPDSSPLLQFGWGDPIRLRHLYTSG (M9);

(amino acids 1-26 of SEQ ID NO: 8)
RHPIPDSSPLLQWGDPIRLRHLYTSG (M8);

(amino acids 1-29 of SEQ ID NO: 12)
RPLAFSDAGPLLQFGWGDPIRLRHLYTSG (M12);

(amino acids 1-28 of SEQ ID NO: 10)
RHPIPDSSPHVHYGWGDPIRLRHLYTSG (M10);

(amino acids 1-27 of SEQ ID NO: 13)
RPLAFSDAGPLLQFGGQVRLRHLYTSG (M13);

(amino acids 1-26 of SEQ ID NO: 14)
RHPIPDSSPHVHYGGQVRLRHLYTSG (M14);

amino acids 1-27 of SEQ ID NO: 43)
RPLAFSDAGPHVHYGGDIRLRHLYTSG (M43);
or (amino acids 1-22 of SEQ ID NO: 6)
RDSSPLLQFGGQVRLRHLYTSG (M6).
```

In some embodiments, the peptide comprise one of the foregoing sequences. In another embodiment, the peptide consists of one of the foregoing sequences. In some embodiments, the peptide comprises a C-terminal region comprising a portion of SEQ ID NO:99 (FGF19), the C-terminal region having a first amino acid position and a last amino acid position, wherein the C-terminal region comprises amino acid residues 16-29 of SEQ ID NO:99 (FGF19), WGDPIRLRHLYTSG (SEQ ID NO:169), wherein the W residue corresponds to the first amino acid position of the C-terminal region.

In a specific embodiment, a peptide sequence comprises or consists of: MRDSSPLVHYGWGDPIRLRHLYTSGPHGLSSCFLRIRADGVVDCARGQSAHSLLEIKAV ALRTVAIKGVHSVRYLCMGAD-GKMQGLLQYSEEDCAFEEEIRPDGYNVYRSEKHRLPVSLSSAKQRQLYKNRGFLPLSHFLPMLPMV-PEEPEDLRGHLESDMFSSPLETDSMDPFGLV TGLEAVRSPSFEK (M70) (SEQ ID NO:70), or a subsequence or fragment thereof.

In another embodiment, a peptide sequence comprises or consists of: RDSSPLVHYGWGDPIRLRHLYTSGPHGLSSCFLRIRADGVVDCARGQSAHSLLEIKAVA LRTVAIKGVHSVRYLCMGAD-GKMQGLLQYSEEDCAFEEEIRPDGYNVYRSEKHRLPVS LSSAKQRQLYKNRGFLPLSHFLPMLPMVPEEPED-LRGHLESDMFSSPLETDSMDPFGLVT GLEAVRSPSFEK (M69) (SEQ ID NO:69), or a subsequence or fragment thereof.

In other embodiments, the peptide comprises or consists of: RDSSPLVHYGWGDPIRLRHLYTSGPHGLSSCFLRIRADGVVDCARGQSAHSLLEIKAVA LRTVAIKGVHSVRYLCMGADGKMQGLLQYSEEDCAFEEEILEDGYNVYRSEKHRLPVS LSSAKQRQLYKNRGFLPLSHFLPMLPMVPEEPEDLRGHLESDMFSSPLETDSMDPFGLVT GLEAVRSPSFEK (M200) (SEQ ID NO:197); or a subsequence or fragment thereof. In one embodiment, the N-terminal R residue is deleted.

In some embodiments, the peptide comprises or consists of: RPLAFSDSSPLVHYGWGDPIRLRHLYTSGPHGLSSCFLRIRADGVVDCARGQS AHSLLEIKAVALRTVAIKGVHSVRYLCMGADGKMQGLLQYSEEDCAFEEEILEDGYNV YRSEKHRLPVSLSSAKQRQLYKNRGFLPLSHFLPMLP-MVPEEPEDLRGHLESDMFSSPLE TDSMDPFGLVTGLEAVRSPSFEK (M201) (SEQ ID NO:198); or a subsequence or fragment thereof. In one embodiment, the N-terminal R residue is deleted.

In certain embodiments, the peptide comprises or consists of: RPLAFSDASPHVHYGWGDPIRLRHLYTSGPHGLSSCFLRIRADGVVDCARGQ SAHSLLEIKAVALRTVAIKGVHSVRYLCMGAD-GKMQGLLQYSEEDCAFEEEILEDGYN VYRSEKHRLPVSLSSAKQRQLYKNRGFLPLSHFLPMLPMVPEEPEDLRGHLESDMFSSPL ETDSMDPFGLVTGLEAVRSPSFEK (M202) (SEQ ID NO:199); or a subsequence or fragment thereof. In one embodiment, the N-terminal R residue is deleted.

In other embodiments, the peptide comprises or consists of: RDSSPLLQWGDPIRLRHLYTSGPHGLSSCFLRIRADGVVDCARGQSAHSLLEI KAVALRTVAIKGVHSVRYLCMGADGKMQGLLQYSEEDCAFEEEILEDGYNVYRSEKHR LPVSLSSAKQRQLYKNRGFLPLSHFLPMLPMVPEEPEDLRGHLESDMFSSPLETDSMDPF GLVTGLEAVR- SPSFEK (M203) (SEQ ID NO:200); or a subsequence or fragment thereof. In one embodiment, the N-terminal R residue is deleted.

In some embodiments, the peptide comprises or consists of: RHPIPDSSPLLQFGDQVRLRHLYTSGPHGLSSCFL-RIRADGVVDCARGQSAHS LLEIKAVALRTVAI-KGVHSVRYLCMGADGKMQGLLQYSEEDCAFEEE-ILEDGYNVYRS EKHRLPVSLS-SAKQRQLYKNRGFLPLSHFLPMLPMVPEEPEDL-RGHLESDMFSSPLETDS MDPFGLVTGLEAVRSPSFEK (M204) (SEQ ID NO:201); or a subsequence or fragment thereof. In one embodiment, the N-terminal R residue is deleted.

In certain embodiments, the peptide comprises or consists of: RDSSPLLQFGGQVRLRHLYTSGPHGLSSCFLRI-RADGVVDCARGQSAHSLLEI KAVALRTVAI-KGVHSVRYLCMGADGKMQGLLQYSEEDCAFEEE-ILEDGYNVYRSEKHR LPVSLS-SAKQRQLYKNRGFLPLSHFLPMLPMVPEEPED-LRGHLESDMFSSPLETDSMDPF GLVTGLEAVRSPS-FEK (M205) (SEQ ID NO:202); or a subsequence or fragment thereof. In one embodiment, the N-terminal R residue is deleted.

In some embodiments, the peptide comprises or consists of: RHPIPDSSPLLQFGGQVRLRHLYTSGPHGLSSCFL-RIRADGVVDCARGQSAHS LLEIKAVALRTVAI-KGVHSVRYLCMGADGKMQGLLQYSEEDCAFEEE-ILEDGYNVYRS EKHRLPVSLSSAKQRQLYKNRGFLPLS-HFLPMLPMVPEEPEDLRGHLESDMFSSPLETDS MDPFGLVTGLEAVRSPSFEK (M206) (SEQ ID NO:203); or a subsequence or fragment thereof. In one embodiment, the N-terminal R residue is deleted.

In other embodiments, the peptide comprises or consists of: MRDSSPLVHYGWGDPIRLRHLYTSGPHGLSSCFL-RIRADGVVDCARGQSAHS LLEIKAVALRTVAI-KGVHSVRYLCMGADGKMQGLLQYSEEDCAFEEE-ILEDGYNVYRS EKHRLPVSLS-SAKQRQLYKNRGFLPLSHFLPMLPMVPEEPEDL-RGHLESDMFSSPLETDS MDPFGLVTGLEAVRSPSFEK (M207) (SEQ ID NO:204); or a subsequence or fragment thereof.

In some embodiments, the peptide is a variant peptide designated M139. In some embodiments, the peptide comprises an amino acid sequence set forth in SEQ ID NO:193. In other embodiments, the peptide consists of an amino acid sequence set forth in SEQ ID NO:193. In some embodiments, the peptide is a variant peptide designated M140. In some embodiments, the peptide comprises an amino acid sequence set forth in SEQ ID NO:194. In other embodiments, the peptide consists of an amino acid sequence set forth in SEQ ID NO:194. In some embodiments, the peptide is a variant peptide designated M141. In some embodiments, the peptide comprises an amino acid sequence set forth in SEQ ID NO:195. In other embodiments, the peptide consists of an amino acid sequence set forth in SEQ ID NO:195. In some embodiments, the peptide is a variant peptide designated M160. In some embodiments, the peptide comprises an amino acid sequence set forth in SEQ ID NO:196. In other embodiments, the peptide consists of an amino acid sequence set forth in SEQ ID NO:196. In some embodiments, the peptide is a variant peptide designated M200. In some embodiments, the peptide comprises an amino acid sequence set forth in SEQ ID NO:197. In other embodiments, the peptide consists of an amino acid sequence set forth in SEQ ID NO:197. In some embodiments, the peptide is a variant peptide designated M201. In some embodiments, the peptide comprises an amino acid sequence set forth in SEQ ID NO:198. In other embodiments, the peptide consists of an amino acid sequence set forth in SEQ ID NO:198. In other embodiments, the peptide is a variant peptide designated M202. In some embodiments, the peptide comprises an amino acid sequence set forth in SEQ ID NO:199. In other embodiments, the peptide consists of an amino acid sequence set forth in SEQ ID NO:199. In certain embodiments, the peptide is a variant peptide designated M203. In some embodiments, the peptide comprises an amino acid sequence set forth in SEQ ID NO:200. In other embodiments, the peptide consists of an amino acid sequence set forth in SEQ ID NO:200. In some embodiments, the peptide is a variant peptide designated M204. In some embodiments, the peptide comprises an amino acid sequence set forth in SEQ ID NO:201. In other embodiments, the peptide consists of an amino acid sequence set forth in SEQ ID NO:201. In another embodiment, the peptide is a variant peptide designated M205. In some embodiments, the peptide comprises an amino acid sequence set forth in SEQ ID NO:202. In other embodiments, the peptide consists of an amino acid sequence set forth in SEQ ID NO:202. In other embodiments, the peptide is a variant peptide designated M206. In some embodiments, the peptide comprises an amino acid sequence set forth in SEQ ID NO:203. In other embodiments, the peptide consists of an amino acid sequence set forth in SEQ ID NO:203. In yet other embodiments, the peptide is a variant peptide designated M207. In some embodiments, the peptide comprises an amino acid sequence set forth in SEQ ID NO:204. In other embodiments, the peptide consists of an amino acid sequence set forth in SEQ ID NO:204.

Peptide sequences provided herein additionally include those with reduced or absent induction or formation of HCC compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. Peptide sequences provided herein also include those with greater glucose lowering activity compared to FGF19, or a FGF19 variant sequence having any of GQV, GDI, WGPI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. Peptide sequences provided herein moreover include those with less lipid (e.g., triglyceride, cholesterol, non-HDL or HDL) increasing activity compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19.

Peptide or chimeric sequences provided herein can be of any suitable length. In particular embodiments, the N-terminal or C-terminal region of the peptide or chimeric sequence is from about 20 to about 200 amino acid residues in length. Typically, the number of amino acids or residues in a peptide sequence provided herein will total less than about 250 (e.g., amino acids or mimetics thereof). In various particular embodiments, the number of residues comprise from about 20 up to about 200 residues (e.g., amino acids or mimetics thereof). In additional embodiments, the number of residues comprise from about 50 up to about 200 residues (e.g., amino acids or mimetics thereof). In further embodiments, the number of residues comprise from about 100 up to about 195 residues (e.g., amino acids or mimetics thereof) in length.

In further particular embodiments, a chimeric peptide sequence or peptide sequence has at least one amino acid deletion. In other particular aspects, a peptide or chimeric sequence has 1, 2, 3, 4, 5, 6, 7, 8, 9, 10, 11, 12, 13, 14, 15, 16, 17, 18, 19, 20 or more amino acid deletions from the amino terminus, the carboxy-terminus or internally. In further particular embodiments, a peptide or chimeric sequence has an N-terminal region, or a C-terminal region that comprises or consists of an amino acid sequence of about 5 to 10, 10 to 20, 20 to 30, 30 to 40, 40 to 50, 50 to 60, 60 to 70, 70 to 80, 80 to 90, 90 to 100 or more amino acids. In additional more particular embodiments, a peptide or chimeric sequence has a FGF19 sequence portion, or a FGF21 sequence portion that comprises or consists of an amino acid sequence of about 5 to 10, 10 to 20, 20 to 30, 30 to 40, 40 to 50, 50 to 60, 60 to 70, 70 to 80, 80 to 90, 90 to 100 or more amino acids of FGF19 or FGF21.

In various further embodiments, a peptide or chimeric sequence has an amino acid substitution, an addition, insertion or is a subsequence that has at least one amino acid deleted. Such amino acid substitutions, additions, insertions and deletions of a peptide sequence can be 1, 2, 3, 4, 5, 6, 7, 8, 9, 10 or more amino acid residues (10-20, 20-30, 30-40, 40-50, etc.), for example, at the N- or C-terminus, or internal. For example, a subsequence that has 1, 2, 3, 4, 5, 6, 7, 8, 9, 10, 11, 12, 13, 14, 15, 16, 17, 18, 19, 20 or more amino acid deletions from the amino terminus, the carboxy-terminus or internally. In a particular embodiment, the amino acid substitution, or deletion is at any of amino acid positions 8-20 of FGF19 (AGPHVHYGWGDPI) (SEQ ID NO:187).

Amino acids or residues can be linked by amide or by non-natural and non-amide chemical bonds including, for example, those formed with glutaraldehyde, N-hydroxysuccinimide esters, bifunctional maleimides, or N, N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, NY). Thus, when a peptide provided herein includes a portion of a FGF19 sequence and a portion of a FGF21 sequence, the two portions need not be joined to each other by an amide bond, but can be joined by any other chemical moiety or conjugated together via a linker moiety.

In further additional various embodiments, a peptide or chimeric sequence includes one or more L-amino acids, D-amino acids, non-naturally occurring amino acids, or amino acid mimetic, derivative or analogue. In still further various embodiments, a peptide or chimeric sequence has an N-terminal region, or a C-terminal region, or a FGF19 sequence portion, or a FGF21 sequence portion, joined by a linker or spacer.

In some embodiments, the treatment peptides provided herein also include subsequences, variants and modified forms of the exemplified peptide sequences (including the FGF19 and FGF21 variants and subsequences listed in Table 1 and Sequence Listing), so long as the foregoing retains at least a detectable or measureable activity or function. For example, certain exemplified variant peptides have FGF19 C-terminal sequence, PHGLSSCFLRIRADGVVD-CARGQSAHSLLEIKAVALRTVAIKGVHSVRYL-CMGADGKMQGL LQYSEEDCAFEEEIRPDGYN-VYRSEKHRLPVSLSSAKQRQLYKNRGFLPLSHFLP-MLPMVPE EPEDLRGHLESDMFSSPLETDSMDPFGLVTGLEAVR-SPSFEK (SEQ ID NO:188) at the C-terminal portion, e.g., following the "TSG" amino acid residues of the variant.

Also, certain exemplified variant peptides, for example, those having all or a portion of FGF21 sequence at the amino-terminus, have an "R" residue positioned at the N-terminus, which can be omitted. Similarly, certain exemplified variant peptides, include an "M" residue positioned at the N-terminus, which can be appended to or further substituted for an omitted residue, such as an "R" residue. More particularly, in various embodiments peptide sequences at the N-terminus include any of: RDSS (SEQ ID NO:115), DSS, MDSS (SEQ ID NO:116) or MRDSS (SEQ ID NO:117).

Furthermore, in cells when a "M" residue is adjacent to a "S" residue, the "M" residue may be cleaved such that the "M" residue is deleted from the peptide sequence, whereas when the "M" residue is adjacent to a "D" residue, the "M" residue may not be cleaved. Thus, by way of example, in various embodiments peptide sequences include those with the following residues at the N-terminus: MDSSPL (SEQ ID NO:119), MSDSSPL (SEQ ID NO:120) (cleaved to SDSSPL (SEQ ID NO:112)) and MSSPL (SEQ ID NO:113) (cleaved to SSPL (SEQ ID NO:114)).

Accordingly, in some embodiments, the "peptide," "polypeptide," and "protein" sequences provided herein include subsequences, variants and modified forms of the FGF19 and FGF21 variants and subsequences listed in Table 1 and Sequence Listing, and the FGF19/FGF21 fusions and chimeras listed in Table 1 and Sequence Listing, so long as the subsequence, variant or modified form (e.g., fusion or chimera) retains at least a detectable activity or function, e.g., modulates bile acid homeostasis.

As used herein, the term "modify" and grammatical variations thereof, means that the composition deviates relative to a reference composition, such as a peptide sequence. Such modified peptide sequences, nucleic acids and other compositions may have greater or less activity or function, or have a distinct function or activity compared with a reference unmodified peptide sequence, nucleic acid, or other composition, or may have a property desirable in a protein formulated for therapy (e.g. serum half-life), to elicit antibody for use in a detection assay, and/or for protein purification. For example, a peptide sequence provided herein can be modified to increase serum half-life, to increase in vitro and/or in vivo stability of the protein, etc.

Particular examples of such subsequences, variants and modified forms of the peptide sequences exemplified herein (e.g., a peptide sequence listed in the Sequence Listing or Table 1) include substitutions, deletions and/or insertions/additions of one or more amino acids, to or from the amino-terminus, the carboxy-terminus or internally. One example is a substitution of an amino acid residue for another amino acid residue within the peptide sequence. Another is a deletion of one or more amino acid residues from the peptide sequence, or an insertion or addition of one or more amino acid residues into the peptide sequence.

The number of residues substituted, deleted or inserted/added are one or more amino acids (e.g., 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more) of a peptide sequence. Thus, a FGF19 or FGF21 sequence can have few or many amino acids substituted, deleted or inserted/added (e.g., 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more). In addition, a FGF19 amino acid sequence can include or consist of an amino acid sequence of about 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more amino acids from FGF21; or a FGF21 amino acid or sequence can include or consist of an amino acid sequence of about 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more amino acids from FGF19.

Specific examples of substitutions include substituting a D residue for an L-residue. Accordingly, although residues are listed in the L-isomer configuration, D-amino acids at any particular or all positions of the peptide sequences provided herein are included, unless a D-isomer leads to a sequence that has no detectable or measurable function.

Additional specific examples are non-conservative and conservative substitutions. A "conservative substitution" is a replacement of one amino acid by a biologically, chemically or structurally similar residue. Biologically similar means that the substitution is compatible with a biological activity, e.g., activity that improves PBC and/or the manifestations thereof. Structurally similar means that the amino acids have side chains with similar length, such as alanine, glycine and serine, or having similar size, or the structure of a first, second or additional peptide sequence is maintained. Chemical similarity means that the residues have the same charge or are both hydrophilic and hydrophobic. Particular examples include the substitution of one hydrophobic residue, such as isoleucine, valine, leucine or methionine, for another, or the substitution of one polar residue for another, such as the substitution of arginine for lysine, glutamic for aspartic acids, or glutamine for asparagine, serine for threonine, etc. Routine assays can be used to determine whether a subsequence, variant or modified form has activity, e.g., activity that improves PBC and/or the manifestations thereof.

Particular examples of subsequences, variants and modified forms of the peptide sequences exemplified herein have 50%-60%, 60%-70%, 70%-75%, 75%-80%, 80%-85%, 85%-90%, 90%-95%, or 96%, 97%, 98%, or 99% identity to a reference peptide sequence. The term "identity" and "homology" and grammatical variations thereof mean that two or more referenced entities are the same. Thus, where two amino acid sequences are identical, they have the identical amino acid sequence. "Areas, regions or domains of identity" mean that a portion of two or more referenced entities are the same. Thus, where two amino acid sequences are identical or homologous over one or more sequence regions, they share identity in those regions.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., J. Mol. Biol. 215:403 (1990), publicly available through NCBI) has exemplary search parameters as follows: Mismatch −2; gap open 5; gap extension 2. For peptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., Proc. Natl. Acad. Sci. USA 85:2444 (1988); Pearson, Methods Mol Biol. 132:185 (2000); and Smith et al., J. Mol. Biol. 147:195 (1981)). Programs for quantitating protein structural similarity using Delaunay-based topological mapping have also been developed (Bostick et al., Biochem Biophys Res Commun. 304:320 (2003)).

In the peptide sequences, including subsequences, variants and modified forms of the peptide sequences exemplified herein, an "amino acid" or "residue" includes conventional alpha-amino acids as well as beta-amino acids; alpha, alpha disubstituted amino acids; and N-substituted amino acids, wherein at least one side chain is an amino acid side chain moiety as defined herein. An "amino acid" further includes N-alkyl alpha-amino acids, wherein the N-terminus amino group has a $C_1$ to $C_6$ linear or branched alkyl substituent. The term "amino acid" therefore includes stereoisomers and modifications of naturally occurring protein amino acids, non-protein amino acids, post-translationally modified amino acids (e.g., by glycosylation, phosphorylation, ester or amide cleavage, etc.), enzymatically modified or synthesized amino acids, derivatized amino acids, constructs or structures designed to mimic amino acids, amino acids with a side chain moiety modified, derivatized from naturally occurring moieties, or synthetic, or not naturally occurring, etc. Modified and unusual amino acids are included in the peptide sequences provided herein (see, for example, in *Synthetic Peptides: A User's Guide*; Hruby et al., Biochem. J. 268:249 (1990); and Toniolo C., Int. J. Peptide Protein Res. 35:287 (1990)).

In addition, protecting and modifying groups of amino acids are included. The term "amino acid side chain moiety" as used herein includes any side chain of any amino acid, as the term "amino acid" is defined herein. This therefore includes the side chain moiety in naturally occurring amino acids. It further includes side chain moieties in modified naturally occurring amino acids as set forth herein and known to one of skill in the art, such as side chain moieties in stereoisomers and modifications of naturally occurring protein amino acids, non-protein amino acids, post-translationally modified amino acids, enzymatically modified or synthesized amino acids, derivatized amino acids, constructs or structures designed to mimic amino acids, etc. For example, the side chain moiety of any amino acid disclosed herein or known to one of skill in the art is included within the definition.

A "derivative of an amino acid side chain moiety" is included within the definition of an amino acid side chain moiety. Non-limiting examples of derivatized amino acid side chain moieties include, for example: (a) adding one or more saturated or unsaturated carbon atoms to an existing alkyl, aryl, or aralkyl chain; (b) substituting a carbon in the side chain with another atom, such as oxygen or nitrogen; (c) adding a terminal group to a carbon atom of the side chain, including methyl (—CH$_3$), methoxy (—OCH$_3$), nitro (—NO$_2$), hydroxyl (—OH), or cyano (—C≡N); (d) for side chain moieties including a hydroxy, thiol or amino groups, adding a suitable hydroxy, thiol or amino protecting group; or (e) for side chain moieties including a ring structure, adding one or more ring substituents, including hydroxyl, halogen, alkyl, or aryl groups attached directly or through, e.g., an ether linkage. For amino groups, suitable protecting groups are known to the skilled artisan. Provided such derivatization provides a desired activity in the final peptide sequence (e.g., activity that improves PBC and/or the manifestations thereof).

An "amino acid side chain moiety" includes all such derivatization, and particular non-limiting examples include: gamma-amino butyric acid, 12-amino dodecanoic acid, alpha-aminoisobutyric acid, 6-amino hexanoic acid, 4-(aminomethyl)-cyclohexane carboxylic acid, 8-amino octanoic acid, biphenylalanine, Boc-t-butoxycarbonyl, benzyl, benzoyl, citrulline, diaminobutyric acid, pyrrollysine, diaminopropionic acid, 3,3-diphenylalanine, orthonine, citrulline, 1,3-dihydro-2H-isoindolecarboxylic acid, ethyl, Fmoc-fluorenylmethoxycarbonyl, heptanoyl (CH$_3$—(CH$_2$)$_5$—C(=O)—), hexanoyl (CH$_3$—(CH$_2$)$_4$—C(=O)—), homoarginine, homocysteine, homolysine, homophenylalanine, homoserine, methyl, methionine sulfoxide, methionine sulfone, norvaline (NVA), phenylglycine, propyl, isopropyl, sarcosine (SAR), tert-butylalanine, and benzyloxycarbonyl.

A single amino acid, including stereoisomers and modifications of naturally occurring protein amino acids, non-protein amino acids, post-translationally modified amino acids, enzymatically-synthesized amino acids, non-naturally occurring amino acids including derivatized amino acids, an alpha, alpha disubstituted amino acid derived from any of the foregoing (i.e., an alpha, alpha disubstituted amino acid, wherein at least one side chain is the same as that of the residue from which it is derived), a beta-amino acid derived from any of the foregoing (i.e., a beta-amino acid which, other than for the presence of a beta-carbon, is the same as the residue from which it is derived) etc., including all of the foregoing can be referred to herein as a "residue." Suitable substituents, in addition to the side chain moiety of the alpha-amino acid, include C$_1$ to C$_6$ linear or branched alkyl. Aib is an example of an alpha, alpha disubstituted amino acid. While alpha, alpha disubstituted amino acids can be referred to using conventional L- and D-isomeric references, it is to be understood that such references are for convenience, and that where the substituents at the alpha-position are different, such amino acid can interchangeably be referred to as an alpha, alpha disubstituted amino acid derived from the L- or D-isomer, as appropriate, of a residue with the designated amino acid side chain moiety. Thus (S)-2-Amino-2-methyl-hexanoic acid can be referred to as either an alpha, alpha disubstituted amino acid derived from L-Nle (norleucine) or as an alpha, alpha disubstituted amino acid derived from D-Ala. Similarly, Aib can be referred to as an alpha, alpha disubstituted amino acid derived from Ala. Whenever an alpha, alpha disubstituted amino acid is provided, it is to be understood as including all (R) and (S) configurations thereof.

An "N-substituted amino acid" includes any amino acid wherein an amino acid side chain moiety is covalently bonded to the backbone amino group, optionally where there are no substituents other than H in the alpha-carbon position. Sarcosine is an example of an N-substituted amino acid. By way of example, sarcosine can be referred to as an N-substituted amino acid derivative of Ala, in that the amino acid side chain moiety of sarcosine and Ala is the same, i.e., methyl.

In certain embodiments, covalent modifications of the peptide sequences, including subsequences, variants and modified forms of the peptide sequences exemplified herein are provided. An exemplary type of covalent modification includes reacting targeted amino acid residues with an organic derivatizing agent that is capable of reacting with selected side chains or the N- or C-terminal residues of the peptide. Derivatization with bifunctional agents is useful, for instance, for cross-linking peptide to a water-insoluble support matrix or surface for use in the method for purifying anti-peptide antibodies, and vice-versa. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, amidation of any C-terminal carboxyl group, etc.

Exemplified peptide sequences, and subsequences, variants and modified forms of the peptide sequences exemplified herein can also include alterations of the backbone for stability, derivatives, and peptidomimetics. The term "peptidomimetic" includes a molecule that is a mimic of a residue (referred to as a "mimetic"), including but not limited to piperazine core molecules, keto-piperazine core molecules and diazepine core molecules. Unless otherwise specified, an amino acid mimetic of a peptide sequence provided herein includes both a carboxyl group and amino group, and a group corresponding to an amino acid side chain, or in the case of a mimetic of Glycine, no side chain other than hydrogen.

By way of example, these would include compounds that mimic the sterics, surface charge distribution, polarity, etc. of a naturally occurring amino acid, but need not be an amino acid, which would impart stability in the biological system. For example, Proline may be substituted by other lactams or lactones of suitable size and substitution; Leucine may be substituted by an alkyl ketone, N-substituted amide, as well as variations in amino acid side chain length using alkyl, alkenyl or other substituents, others may be apparent to the skilled artisan. The essential element of making such substitutions is to provide a molecule of roughly the same size and charge and configuration as the residue used to design the molecule. Refinement of these modifications will be made by analyzing the compounds in a functional (e.g., glucose lowering) or other assay, and comparing the structure-activity relationship. Such methods are within the scope of the skilled artisan working in medicinal chemistry and drug development.

The term "bind," or "binding," when used in reference to a peptide sequence, means that the peptide sequence interacts at the molecular level. Specific and selective binding can be distinguished from non-specific binding using assays known in the art (e.g., competition binding, immunoprecipitation, ELISA, flow cytometry, Western blotting).

Peptides and peptidomimetics can be produced and isolated using methods known in the art. Peptides can be synthesized, in whole or in part, using chemical methods (see, e.g., Caruthers (1980). Nucleic Acids Res. Symp. Ser. 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge Science 269:202 (1995); Merrifield, Methods Enzymol. 289:3 (1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, Nucleic Acids Res. 25:3440 (1997); Frenkel, Free Radic. Biol. Med. 19:373 (1995); and Blommers, Biochemistry 33:7886 (1994)). Peptide sequence variations, derivatives, substitutions and modifications can also be made using methods such as oligonucleotide-mediated (site-directed) mutagenesis, alanine scanning, and PCR-based mutagenesis. Site-directed mutagenesis (Carter et al., Nucl. Acids Res., 13:4331 (1986); Zoller et al., Nucl. Acids Res. 10:6487 (1987)), cassette mutagenesis (Wells et al, Gene 34:315 (1985)), restriction selection mutagenesis (Wells et al, Philos. Trans. R. Soc. London SerA 317:415 (1986)) and other techniques can be performed on cloned DNA to produce peptide sequences, variants, fusions and chimeras provided herein, and variations, derivatives, substitutions and modifications thereof.

A "synthesized" or "manufactured" peptide sequence is a peptide made by any method involving manipulation by the hand of man. Such methods include, but are not limited to, the aforementioned, such as chemical synthesis, recombinant DNA technology, biochemical or enzymatic fragmentation of larger molecules, and combinations of the foregoing.

Peptide sequences provided herein including subsequences, sequence variants and modified forms of the exemplified peptide sequences (e.g., sequences listed in the Sequence Listing or Table 1), can also be modified to form a chimeric molecule. In certain embodiments, provided herein are peptide sequences that include a heterologous domain. Such domains can be added to the amino-terminus or at the carboxyl-terminus of the peptide sequence. Heterologous domains can also be positioned within the peptide sequence, and/or alternatively flanked by FGF19 and/or FGF21 derived amino acid sequences.

The term "peptide" also includes dimers or multimers (oligomers) of peptides. In certain embodiments, dimers or multimers (oligomers) of the exemplified peptide sequences are provided herein, as well as subsequences, variants and modified forms of the exemplified peptide sequences, including sequences listed in the Sequence Listing or Table 1.

In certain embodiments, a peptide sequence (e.g., a treatment peptide) provided herein comprises an amino acid sequence set forth in Table 1. In other embodiments, a peptide sequence provided herein consists of an amino acid sequence set forth in Table 1.

TABLE 1

| SEQ ID NO. | Amino Acid Sequence |
|---|---|
| 1. | RPLAFSDASPHVHYGWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 2. | RPLAFSDSSPLVHYGWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 3. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEILEDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 4. | RPLAFSDAGPHVHYAWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 5. | RHPIPDSSPLLQFGGQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 6. | RDSSPLLQFGGQVRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKH RLPVSLSSAKQRQLYKNRGFLPLSHFLPMLPMVPEEPEDLRGHLESDMFSSPLETD SMDPFGLVTGLEAVRSPSFEK |

TABLE 1-continued

| SEQ ID NO. | Amino Acid Sequence |
|---|---|
| 7. | RPLAFSDSSPLLQFGGQVRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 8. | RHPIPDSSPLLQWGDPIRLRHLYTSGPHGLSSCFLRIRADGVVDCARGQSAHSLLEI<br>KAVALRTVAIKGVHSVRYLCMGADGKMQGLLQYSEEDCAFEEEIRPDGYNVYRS<br>EKHRLPVSLSSAKQRQLYKNRGFLPLSHFLPMLPMVPEEPEDLRGHLESDMFSSPL<br>ETDSMDPFGLVTGLEAVRSPSFEK |
| 9. | RHPIPDSSPLLQFGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 10. | RHPIPDSSPHVHYGWGDPIRLRHLYTSGPHGLSSCFLRIRADGVVDCARGQSAHSL<br>LEIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 11. | RPLAFSDAGPLLQWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 12. | RPLAFSDAGPLLQFGWGDPIRLRHLYTSGPHGLSSCFLRIRADGVVDCARGQSAHS<br>LLEIKAVALRTVAIKGVHSVRYLCMGADGKMQGLLQYSEEDCAFEEEIRPDGYNV<br>YRSEKHRLPVSLSSAKQRQLYKNRGFLPLSHFLPMLPMVPEEPEDLRGHLESDMFS<br>SPLETDSMDPFGLVTGLEAVRSPSFEK |
| 13. | RPLAFSDAGPLLQFGGQVRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 14. | RHPIPDSSPHVHYGGQVRLRHLYTSGPHGLSSCFLRIRADGVVDCARGQSAHSLLE<br>IKAVALRTVAIKGVHSVRYLCMGADGKMQGLLQYSEEDCAFEEEIRPDGYNVYRS<br>EKHRLPVSLSSAKQRQLYKNRGFLPLSHFLPMLPMVPEEPEDLRGHLESDMFSSPL<br>ETDSMDPFGLVTGLEAVRSPSFEK |
| 15. | RPLAFSDAGPHVHYGGQVRLRHLYTSGPHGLSSCFLRIRADGVVDCARGQSAHSL<br>LEIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 16. | RPLAFSDAGPHVHWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 17. | RPLAFSDAGPHVGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 18. | RPLAFSDAGPHYGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 19. | RPLAFSDAGPVYGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 20. | RPLAFSDAGPVHGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 21. | RPLAFSDAGPVHYWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |

TABLE 1-continued

| SEQ ID NO. | Amino Acid Sequence |
|---|---|
| 22. | RPLAFSDAGPHVHGWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 23. | RPLAFSDAGPHHGWGDPIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 24. | RPLAFSDAGPHHYWGDPIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 25. | RPLAFSDAGPHVYWGDPIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 26. | RPLAFSDSSPLVHWGDPIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 27. | RPLAFSDSSPHVHWGDPIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 28. | RPLAFSDAGPHVWGDPIRLRHLYTSGPHGLSSCFLRIRADGVVDCARGQSAHSLLE IKAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 29. | RPLAFSDAGPHVHYWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 30. | RPLAFSDAGPHVHYAWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 31. | RHPIPDSSPLLQFGAQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 32. | RHPIPDSSPLLQFGDQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 33. | RHPIPDSSPLLQFGPQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 34. | RHPIPDSSPLLQFGGAVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 35. | RHPIPDSSPLLQFGGEVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 36. | RHPIPDSSPLLQFGGNVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |

TABLE 1-continued

| SEQ ID NO. | Amino Acid Sequence |
|---|---|
| 37. | RHPIPDSSPLLQFGGQARLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 38. | RHPIPDSSPLLQFGGQIRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 39. | RHPIPDSSPLLQFGGQTRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 40. | RHPIPDSSPLLQFGWGQPVRLRHLYTSGPHGLSSCFLRIRADGVVDCARGQSAHSL LEIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 41. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSHFLPMLPEPPGILAPQPPDVGSSDPL SMVGPSQGRSPSYAS |
| 42. | HPIPDSSPLLQFGGQVRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPEPPGILAPQPPDVGSSDPLSMVGP SQGRSPSYAS |
| 43. | RPLAFSDAGPHVHYGGDIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 44. | RPLAFSDAGPHVHYGWGDPIRQRYLYTDDAQQTEAHLEIREDGTVGGAADQSPES LLQLKALKPGVIQILGVKTSRFLCQRPDGALYGSLHFDPEACSFRELLLEDGYNVY QSEAHGLPLHLPGNKSPHRDPAPRGPARFLPLPGLPPALPEPPGILAPQPPDVGSSDP LSMVGPSQGRSPSYAS |
| 45. | HPIPDSSPLLQFGGQVRQRYLYTDDAQQTEAHLEIREDGTVGGAADQSPESLLQLK ALKPGVIQILGVKTSRFLCQRPDGALYGSLHFDPEACSFRELLLEDGYNVYQSEAH GLPLHLPGNKSPHRDPAPRGPARFLPLPGLPPALPMVPEEPEDLRGHLESDMFSSPL ETDSMDPFGLVTGLEAVRSPSFEK |
| 46. | RPLAFSDAGPHVHYGWGDPIRQRYLYTDDAQQTEAHLEIREDGTVGGAADQSPES LLQLKALKPGVIQILGVKTSRFLCQRPDGALYGSLHFDPEACSFRELLLEDGYNVY QSEAHGLPLHLPGNKSPHRDPAPRGPARFLPLPGLPPALPEPPGILAPQPPDVGSSDP LSMVGPSQGRSPSYASPMVPEEPEDLRGHLESDMFSSPLETDSMDPFGLVTGLEAV RSPSFEK |
| 47. | HPIPDSSPLLQWGDPIRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 48. | RDSSPLLQFGGQVRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKH RLPVSLSSAKQRQLYKNRGFLPLSHFLPMLPMVPEEPEDLRGHLESDMFSSPLETD SMDPFGLVTGLEAVRSPSFEK |
| 49. | RPLAFSDSSPLLQFGGQVRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 50. | RHPIPDSSPLLQFGDQVRLRHLYTSGPHGLSSCFLRIRADGVVDCARGQSAHSLLEI KAVALRTVAIKGVHSVRYLCMGADGKMQGLLQYSEEDCAFEEEILEDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 51. | RHPIPDSSPLLQFGGNVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |

TABLE 1-continued

| SEQ ID NO. | Amino Acid Sequence |
|---|---|
| 52. | RDSSPLLQWGDPIRLRHLYTSGPHGLSSCFLRIRADGVVDCARGQSAHSLLEIKAV<br>ALRTVAIKGVHSVRYLCMGADGKMQGLLQYSEEDCAFEEEIRPDGYNVYRSEKH<br>RLPVSLSSAKQRQLYKNRGFLPLSHFLPMLPMVPEEPEDLRGHLESDMFSSPLETD<br>SMDPFGLVTGLEAVRSPSFEK |
| 53. | MDSSPLVHYGWGDPIRLRHLYTSGPHGLSSCFLRIRADGVVDCARGQSAHSLLEIK<br>AVALRTVAIKGVHSVRYLCMGADGKMQGLLQYSEEDCAFEEEIRPDGYNVYRSE<br>KHRLPVSLSSAKQRQLYKNRGFLPLSHFLPMLPMVPEEPEDLRGHLESDMFSSPLE<br>TDSMDPFGLVTGLEAVRSPSFEK |
| 54. | RPLAFSDAGPLLQWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 55. | RPLAFSDAGPHYGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 56. | RPLAFSDAGPVYGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 57. | RPLAFSDAGPVHGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 58. | RPLAFSDAGPVHYWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 59. | RPLAFSDAGPHHGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 60. | RPLAFSDAGPHHYWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 61. | RPLAFSDAGPHVGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 62. | RPLAFSDAGPHVYWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 63. | RPLAFSDAGPHVHWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 64. | RPLAFSDSSPLVHWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 65. | RPLAFSDSSPHVHWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |
| 66. | RPLAFSDAGPHLQWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDGYNVY<br>RSEKHRLPVSLSSAKQRQLYKNRGFLPLSHFLPMLPMVPEEPEDLRGHLESDMFSS<br>PLETDSMDPFGLVTGLEAVRSPSFEK |

TABLE 1-continued

| SEQ ID NO. | Amino Acid Sequence |
|---|---|
| 67. | RPLAFSDAGPHVWGDPIRLRHLYTSGPHGLSSCFLRIRADGVVDCARGQSAHSLLE IKAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 68. | RPLAFSDAGPHVHYWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 69. | RDSSPLVHYGWGDPIRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 70. | MRDSSPLVHYGWGDPIRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 71. | HPIPDSSPLLQFGGQVRQRYLYTDDAQQTEAHLEIREDGTVGGAADQSPESLLQLK ALKPGVIQILGVKTSRFLCQRPDGALYGSLHFDPEACSFRELLLEDGYNVYQSEAH SLPLHLPGNKSPHRDPAPRGPARFLPLPGLPPALPEPPGILAPQPPDVGSSDPLSMVG PSQGRSPSYAS |
| 72. | HPIPDSSPLLQFGGQVRQRYLYTDDAQQTEAHLEIREDGTVGGAADQSPESLLQLK ALKPGVIQILGVKTSRFLCQRPDGALYGSLHFDPEACSFRELLLEDGYNVYQSEAH GLPLHLPGNKSPHRDPAPRGPARFLPLPGLPPAPPEPPGILAPQPPDVGSSDPLSMV GPSQGRSPSYAS |
| 73. | HPIPDSSPLLQFGGQVRQRYLYTDDAQQTEAHLEIREDGTVGGAADQSPESLLQLK ALKPGVIQILGVKTSRFLCQRPDGALYGSLHFDPEACSFRELLLEDGYNVYQSEAH GLPLHLPGNKSPHRDPAPRGPARFLPLPGLPPALPEPPGILAPQPPDVGSSDPLSMV VQDELQGVGGEGCHMHPENCKTLLTDIDRTHTEKPVWDGITGE |
| 74. | RDAGPHVHYGWGDPIRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 75. | RVHYGWGDPIRLRHLYTSGPHGLSSCFLRIRADGVVDCARGQSAHSLLEIKAVAL RTVAIKGVHSVRYLCMGADGKMQGLLQYSEEDCAFEEEIRPDGYNVYRSEKHRL PVSLSSAKQRQLYKNRGFLPLSHFLPMLPMVPEEPEDLRGHLESDMFSSPLETDSM DPFGLVTGLEAVRSPSFEK |
| 76. | RGDPIRLRHLYTSGPHGLSSCFLRIRADGVVDCARGQSAHSLLEIKAVALRTVAIK GVHSVRYLCMGADGKMQGLLQYSEEDCAFEEEIRPDGYNVYRSEKHRLPVSLSSA KQRQLYKNRGFLPLSHFLPMLPMVPEEPEDLRGHLESDMFSSPLETDSMDPFGLVT GLEAVRSPSFEK |
| 77. | RRLRHLYTSGPHGLSSCFLRIRADGVVDCARGQSAHSLLEIKAVALRTVAIKGVHS VRYLCMGADGKMQGLLQYSEEDCAFEEEIRPDGYNVYRSEKHRLPVSLSSAKQR QLYKNRGFLPLSHFLPMLPMVPEEPEDLRGHLESDMFSSPLETDSMDPFGLVTGLE AVRSPSFEK |
| 78. | RAGPHVHYGWGDPIRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 79. | RGPHVHYGWGDPIRLRHLYTSGPHGLSSCFLRIRADGVVDCARGQSAHSLLEIKA VALRTVAIKGVHSVRYLCMGADGKMQGLLQYSEEDCAFEEEIRPDGYNVYRSEK HRLPVSLSSAKQRQLYKNRGFLPLSHFLPMLPMVPEEPEDLRGHLESDMFSSPLET DSMDPFGLVTGLEAVRSPSFEK |
| 80. | RPHVHYGWGDPIRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKH RLPVSLSSAKQRQLYKNRGFLPLSHFLPMLPMVPEEPEDLRGHLESDMFSSPLETD SMDPFGLVTGLEAVRSPSFEK |
| 81. | RHVHYGWGDPIRLRHLYTSGPHGLSSCFLRIRADGVVDCARGQSAHSLLEIKAVA LRTVAIKGVHSVRYLCMGADGKMQGLLQYSEEDCAFEEEIRPDGYNVYRSEKHR LPVSLSSAKQRQLYKNRGFLPLSHFLPMLPMVPEEPEDLRGHLESDMFSSPLETDS MDPFGLVTGLEAVRSPSFEK |

TABLE 1-continued

| SEQ ID NO. | Amino Acid Sequence |
|---|---|
| 82. | RPLAFSAAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 83. | RPLAFSDAAPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 84. | RPLAFSDAGAHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 85. | RPLAFSDAGPHVHYGAGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 86. | RPLAFSDAGPHVHYGWGAPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 87. | RPLAFSDAGPHVHYGWGDAICARGQSAHSLLEIKAVALRTVAIKGVHSVRYLCM GADGKMQGLLQYSEEDCAFEEEIRPDGYNVYRSEKHRLPVSLSSAKQRQLYKNRG FLPLSHFLPMLPMVPEEPEDLRGHLESDMFSSPLETDSMDPFGLVTGLEAVRSPSFE K |
| 88. | RPLAFSDAGPHVHYGWGDPIRLRHLYTSGPAGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLAHFLPMLPMVPEEPEDLRGHLESDM FSSPLETDSMDPFGLVTGLEAVRSPSFEK |
| 89. | RPLAFSDAGPHVHYGWGDPIRLRHLYTSGPAGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLSAFLPMLPMVPEEPEDLRGHLESDMF SSPLETDSMDPFGLVTGLEAVRSPSFEK |
| 90. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAAQAQLYKNRGFLPLSHFLPMLPMVPEEPEDLRGHLESDM FSSPLETDSMDPFGLVTGLEAVRSPSFEK |
| 91. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAAQRQLYKNRGFLPLAHFLPMLPMVPEEPEDLRGHLESDM FSSPLETDSMDPFGLVTGLEAVRSPSFEK |
| 92. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAAQRQLYKNRGFLPLSAFLPMLPMVPEEPEDLRGHLESDMF SSPLETDSMDPFGLVTGLEAVRSPSFEK |
| 93. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQAQLYKNRGFLPLAHFLPMLPMVPEEPEDLRGHLESDM FSSPLETDSMDPFGLVTGLEAVRSPSFEK |
| 94. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAKQRQLYKNRGFLPLAAFLPMLPMVPEEPEDLRGHLESDM FSSPLETDSMDPFGLVTGLEAVRSPSFEK |
| 95. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAAQRQLYKNRGFLPLSAFLPMLPMVPEEPEDLRGHLESDMF SSPLETDSMDPFGLVTGLEAVRSPSFEK |
| 96. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAAQAQLYKNRGFLPLAHFLPMLPMVPEEPEDLRGHLESDM FSSPLETDSMDPFGLVTGLEAVRSPSFEK |

TABLE 1-continued

| SEQ ID NO. | Amino Acid Sequence |
|---|---|
| 97. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAAQAQLYKNRGFLPLSAFLPMLPMVPEEPEDLRGHLESDM FSSPLETDSMDPFGLVTGLEAVRSPSFEK |
| 98. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIRPDGYN VYRSEKHRLPVSLSSAAQAQLYKNRGFLPLAAFLPMLPMVPEEPEDLRGHLESDM FSSPLETDSMDPFGLVTGLEAVRSPSFEK |
| 138. | DSSPLLQFGGQVRLRHLYTSGPHGLSSCFLRIRADGVVDCARGQSAHSLLEIKAVA LRTVAIKGVHSVRYLCMGADGKMQGLLQYSEEDCAFEEEIRPDGYNVYRSEKHR LPVSLSSAKQRQLYKNRGFLPLSHFLPMLPMVPEEPEDLRGHLESDMFSSPLETDS MDPFGLVTGLEAVRSPSFEK |
| 139. | RPLAFSDASPHVHYGWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 140. | RPLAFSDSSPLVHYGWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 141. | DSSPLVHYGWGDPIRLRHLYTSGPHGLSSCFLRIRADGVVDCARGQSAHSLLEIKA VALRTVAIKGVHSVRYLCMGADGKMQGLLQYSEEDCAFEEEIRPDGYNVYRSEK HRLPVSLSSAKQRQLYKNRGFLPLSHFLPMLPMVPEEPEDLRGHLESDMFSSPLET DSMDPFGLVTGLEAVRSPSFEK |
| 142. | RHPIPDSSPLLQFGWGDPIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 143. | RHPIPDSSPLLQWGDPIRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 144. | RPLAFSDAGPLLQFGWGDPIRLRHLYTSGPHGLSSCFLRIRADGVVDCARGQSAHS LLEIKAVALRTVAIKGVHSVRYLCMGADGKMQGLLQYSEEDCAFEEEIRPDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 145. | RHPIPDSSPHVHYGWGDPIRLRHLYTSGPHGLSSCFLRIRADGVVDCARGQSAHSL LEIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 146. | RPLAFSDAGPLLQFGGQVRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 147. | RHPIPDSSPHVHYGGQVRLRHLYTSGPHGLSSCFLRIRADGVVDCARGQSAHSLLE IKAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 148. | RDSSPLLQFGGQVRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKH RLPVSLSSAKQRQLYKNRGFLPLSHFLPMLPMVPEEPEDLRGHLESDMFSSPLETD SMDPFGLVTGLEAVRSPSFEK |
| 149. | RPLAFSDSSPLLQFGGQVRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 150. | RHPIPDSSPLLQFGAQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |

TABLE 1-continued

| SEQ ID NO. | Amino Acid Sequence |
|---|---|
| 151. | RHPIPDSSPLLQFGDQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 152. | RHPIPDSSPLLQFGPQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 153. | RHPIPDSSPLLQFGGAVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 154. | RHPIPDSSPLLQFGGEVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 155. | RHPIPDSSPLLQFGGNVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 156. | RHPIPDSSPLLQFGGQARLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 157. | RHPIPDSSPLLQFGGQIRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 158. | RHPIPDSSPLLQFGGQTRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 159. | RHPIPDSSPLLQFGWGQPVRLRHLYTSGPHGLSSCFLRIRADGVVDCARGQSAHSL LEIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 160. | HPIPDSSPLLQFGGQVRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 161. | DSSPLLQFGGQVRLRHLYTSGPHGLSSCFLRIRADGVVDCARGQSAHSLLEIKAVA LRTVAIKGVHSVRYLCMGADGKMQGLLQYSEEDCAFEEEIRPDGYNVYRSEKHR LPVSLSSAKQRQLYKNRGFLPLSHFLPMLPMVPEEPEDLRGHLESDMFSSPLETDS MDPFGLVTGLEAVRSPSFEK |
| 162. | HPIPDSSPLLQWGDPIRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 163. | HPIPDSSPLLQFGWGDPIRLRHLYTSGPHGLSSCFLRIRADGVVDCARGQSAHSLLE IKAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 164. | HPIPDSSPHVHYGWGDPIRLRHLYTSGPHGLSSCFLRIRADGVVDCARGQSAHSLL EIKAVALRTVAIKGVHSVRYLCMGADGKMQGLLQYSEEDCAFEEEIRPDGYNVY RSEKHRLPVSLSSAKQRQLYKNRGFLPLSHFLPMLPMVPEEPEDLRGHLESDMFSS PLETDSMDPFGLVTGLEAVRSPSFEK |
| 165. | HPIPDSSPHVHYGGQVRLRHLYTSGPHGLSSCFLRIRADGVVDCARGQSAHSLLEI KAVALRTVAIKGVHSVRYLCMGADGKMQGLLQYSEEDCAFEEEIRPDGYNVYRS EKHRLPVSLSSAKQRQLYKNRGFLPLSHFLPMLPMVPEEPEDLRGHLESDMFSSPL ETDSMDPFGLVTGLEAVRSPSFEK |

TABLE 1-continued

| SEQ ID NO. | Amino Acid Sequence |
|---|---|
| 166. | DAGPHVHYGWGDPIRLRHLYTSGPHGLSSCFLRIRADGVVDCARGQSAHSLLEIK AVALRTVAIKGVHSVRYLCMGADGKMQGLLQYSEEDCAFEEEIRPDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 167. | VHYGWGDPIRLRHLYTSGPHGLSSCFLRIRADGVVDCARGQSAHSLLEIKAVALRT VAIKGVHSVRYLCMGADGKMQGLLQYSEEDCAFEEEIRPDGYNVYRSEKHRLPV SLSSAKQRQLYKNRGFLPLSHFLPMLPMVPEEPEDLRGHLESDMFSSPLETDSMDP FGLVTGLEAVRSPSFEK |
| 168. | RLRHLYTSGPHGLSSCFLRIRADGVVDCARGQSAHSLLEIKAVALRTVAIKGVHSV RYLCMGADGKMQGLLQYSEEDCAFEEEIRPDGYNVYRSEKHRLPVSLSSAKQRQL YKNRGFLPLSHFLPMLPMVPEEPEDLRGHLESDMFSSPLETDSMDPFGLVTGLEAV RSPSFEK |
| 188. | PHGLSSCFLRIRADGVVDCARGQSAHSLLEIKAVALRTVAIKGVHSVRYLCMGAD GKMQGLLQYSEEDCAFEEEIRPDGYNVYRSEKHRLPVSLSSAKQRQLYKNRGFLP LSHFLPMLPMVPEEPEDLRGHLESDMFSSPLETDSMDPFGLVTGLEAVRSPSFEK |
| 192. | MDSSPLLQWGDPIRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKH RLPVSLSSAKQRQLYKNRGFLPLSHFLPMLPMVPEEPEDLRGHLESDMFSSPLETD SMDPFGLVTGLEAVRSPSFEK |
| 193. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEILPDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 194. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEIREDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 195. | RPLAFSDAGPHVHYGWGDPIRLRHLYTSGPHGLSSCFLRIRADGVVDCARGQSAH SLLEIKAVALRTVAIKGVHSVRYLCMGADGKMQGLLQYSEEDCAFEEEILCDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 196. | RPLAFSDAGPHVHYGWGDPIRQRHLYTSGPHGLSSCFLRIRADGVVDCARGQSAH SLLEIKAVALRTVAIKGVHSVRYLCMGADGKMQGLLQYSEEDCAFEEEILEDGYN VYRSEKHRLPVSLSSAKQRQLYKNRGFLPLSHFLPMLPMVPEEPEDLRGHLESDMF SSPLETDSMDPFGLVTGLEAVRSPSFEK |
| 197. | RDSSPLVHYGWGDPIRLRHLYTSGPHGLSSCFLRIRADGVVDCARGQSAHSLLEIK AVALRTVAIKGVHSVRYLCMGADGKMQGLLQYSEEDCAFEEEILEDGYNVYRSE KHRLPVSLSSAKQRQLYKNRGFLPLSHFLPMLPMVPEEPEDLRGHLESDMFSSPLE TDSMDPFGLVTGLEAVRSPSFEK |
| 198. | RPLAFSDSSPLVHYGWGDPIRLRHLYTSGPHGLSSCFLRIRADGVVDCARGQSAHS LLEIKAVALRTVAIKGVHSVRYLCMGADGKMQGLLQYSEEDCAFEEEILEDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 199. | RPLAFSDASPHVHYGWGDPIRLRHLYTSGPHGLSSCFLRIRADGVVDCARGQSAHS LLEIKAVALRTVAIKGVHSVRYLCMGADGKMQGLLQYSEEDCAFEEEILEDGYNV YRSEKHRLPVSLSSAKQRQLYKNRGFLPLSHFLPMLPMVPEEPEDLRGHLESDMFS SPLETDSMDPFGLVTGLEAVRSPSFEK |
| 200. | RDSSPLLQWGDPIRLRHLYTSGPHGLSSCFLRIRADGVVDCARGQSAHSLLEIKAV ALRTVAIKGVHSVRYLCMGADGKMQGLLQYSEEDCAFEEEILEDGYNVYRSEKH RLPVSLSSAKQRQLYKNRGFLPLSHFLPMLPMVPEEPEDLRGHLESDMFSSPLETD SMDPFGLVTGLEAVRSPSFEK |
| 201. | RHPIPDSSPLLQFGDQVRLRHLYTSGPHGLSSCFLRIRADGVVDCARGQSAHSLLEI KAVALRTVAIKGVHSVRYLCMGADGKMQGLLQYSEEDCAFEEEILEDGYNVYRS EKHRLPVSLSSAKQRQLYKNRGFLPLSHFLPMLPMVPEEPEDLRGHLESDMFSSPL ETDSMDPFGLVTGLEAVRSPSFEK |
| 202. | RDSSPLLQFGGQVRLRHLYTSGPHGLSSCFLRIRADGVVDCARGQSAHSLLEIKAV ALRTVAIKGVHSVRYLCMGADGKMQGLLQYSEEDCAFEEEILEDGYNVYRSEKH RLPVSLSSAKQRQLYKNRGFLPLSHFLPMLPMVPEEPEDLRGHLESDMFSSPLETD SMDPFGLVTGLEAVRSPSFEK |
| 203. | RHPIPDSSPLLQFGGQVRLRHLYTSGPHGLSSCFLRIRADGVVDCARGQSAHSLLEI KAVALRTVAIKGVHSVRYLCMGADGKMQGLLQYSEEDCAFEEEILEDGYNVYRS |

TABLE 1-continued

| SEQ ID NO. | Amino Acid Sequence |
|---|---|
| | EKHRLPVSLSSAKQRQLYKNRGFLPLSHFLPMLPMVPEEPEDLRGHLESDMFSSPL<br>ETDSMDPFGLVTGLEAVRSPSFEK |
| 204. | MRDSSPLVHYGWGDPIRLRHLYTSGPHGLSSCFLRIRADGVVDCARGQSAHSLLEI<br>KAVALRTVAIKGVHSVRYLCMGADGKMQGLLQYSEEDCAFEEEILEDGYNVYRS<br>EKHRLPVSLSSAKQRQLYKNRGFLPLSHFLPMLPMVPEEPEDLRGHLESDMFSSPL<br>ETDSMDPFGLVTGLEAVRSPSFEK |

In one embodiment, the peptide sequence comprises an amino acid sequence set forth in SEQ ID NO:1. In another embodiment, the peptide sequence comprises an amino acid sequence set forth in SEQ ID NO:2. In other embodiments, the peptide sequence comprises an amino acid sequence set forth in SEQ ID NO:3. In one embodiment, the peptide sequence comprises an amino acid sequence set forth in SEQ ID NO:4. In another embodiment, the peptide sequence comprises an amino acid sequence set forth in SEQ ID NO:5. In other embodiments, the peptide sequence comprises an amino acid sequence set forth in SEQ ID NO:6. In one embodiment, the peptide sequence comprises an amino acid sequence set forth in SEQ ID NO:7. In another embodiment, the peptide sequence comprises an amino acid sequence set forth in SEQ ID NO:8. In other embodiments, the peptide sequence comprises an amino acid sequence set forth in SEQ ID NO:9. In one embodiment, the peptide sequence comprises an amino acid sequence set forth in SEQ ID NO:10. In another embodiment, the peptide sequence comprises an amino acid sequence set forth in SEQ ID NO:11. In other embodiments, the peptide sequence comprises an amino acid sequence set forth in SEQ ID NO:12. In one embodiment, the peptide sequence comprises an amino acid sequence set forth in SEQ ID NO:13. In another embodiment, the peptide sequence comprises an amino acid sequence set forth in SEQ ID NO:14. In other embodiments, the peptide sequence comprises an amino acid sequence set forth in SEQ ID NO:15. In one embodiment, the peptide sequence comprises an amino acid sequence set forth in SEQ ID NO:16. In another embodiment, the peptide sequence comprises an amino acid sequence set forth in SEQ ID NO:17. In other embodiments, the peptide sequence comprises an amino acid sequence set forth in SEQ ID NO:18. In one embodiment, the peptide sequence comprises an amino acid sequence set forth in SEQ ID NO:19. In another embodiment, the peptide sequence comprises an amino acid sequence set forth in SEQ ID NO:20. In other embodiments, the peptide sequence comprises an amino acid sequence set forth in SEQ ID NO:21. In one embodiment, the peptide sequence comprises an amino acid sequence set forth in SEQ ID NO:22. In another embodiment, the peptide sequence comprises an amino acid sequence set forth in SEQ ID NO:23. In other embodiments, the peptide sequence comprises an amino acid sequence set forth in SEQ ID NO:24. In one embodiment, the peptide sequence comprises an amino acid sequence set forth in SEQ ID NO:25. In another embodiment, the peptide sequence comprises an amino acid sequence set forth in SEQ ID NO:26. In other embodiments, the peptide sequence comprises an amino acid sequence set forth in SEQ ID NO:27. In one embodiment, the peptide sequence comprises an amino acid sequence set forth in SEQ ID NO:28. In another embodiment, the peptide sequence comprises an amino acid sequence set forth in SEQ ID NO:29. In other embodiments, the peptide sequence comprises an amino acid sequence set forth in SEQ ID NO:30. In one embodiment, the peptide sequence comprises an amino acid sequence set forth in SEQ ID NO:31. In another embodiment, the peptide sequence comprises an amino acid sequence set forth in SEQ ID NO:32. In other embodiments, the peptide sequence comprises an amino acid sequence set forth in SEQ ID NO:33. In one embodiment, the peptide sequence comprises an amino acid sequence set forth in SEQ ID NO:34. In another embodiment, the peptide sequence comprises an amino acid sequence set forth in SEQ ID NO:35. In other embodiments, the peptide sequence comprises an amino acid sequence set forth in SEQ ID NO:36. In one embodiment, the peptide sequence comprises an amino acid sequence set forth in SEQ ID NO:37. In another embodiment, the peptide sequence comprises an amino acid sequence set forth in SEQ ID NO:38. In other embodiments, the peptide sequence comprises an amino acid sequence set forth in SEQ ID NO:39. In one embodiment, the peptide sequence comprises an amino acid sequence set forth in SEQ ID NO:40. In another embodiment, the peptide sequence comprises an amino acid sequence set forth in SEQ ID NO:41. In other embodiments, the peptide sequence comprises an amino acid sequence set forth in SEQ ID NO:42. In one embodiment, the peptide sequence comprises an amino acid sequence set forth in SEQ ID NO:43. In another embodiment, the peptide sequence comprises an amino acid sequence set forth in SEQ ID NO:44. In other embodiments, the peptide sequence comprises an amino acid sequence set forth in SEQ ID NO:45. In one embodiment, the peptide sequence comprises an amino acid sequence set forth in SEQ ID NO:46. In another embodiment, the peptide sequence comprises an amino acid sequence set forth in SEQ ID NO:47. In other embodiments, the peptide sequence comprises an amino acid sequence set forth in SEQ ID NO:48. In one embodiment, the peptide sequence comprises an amino acid sequence set forth in SEQ ID NO:49. In another embodiment, the peptide sequence comprises an amino acid sequence set forth in SEQ ID NO:50. In other embodiments, the peptide sequence comprises an amino acid sequence set forth in SEQ ID NO:51. In one embodiment, the peptide sequence comprises an amino acid sequence set forth in SEQ ID NO:52. In another embodiment, the peptide sequence comprises an amino acid sequence set forth in SEQ ID NO:53. In other embodiments, the peptide sequence comprises an amino acid sequence set forth in SEQ ID NO:54. In one embodiment, the peptide sequence comprises an amino acid sequence set forth in SEQ ID NO:55. In another embodiment, the peptide sequence comprises an amino acid sequence set forth in SEQ ID NO:56. In other embodiments, the peptide sequence comprises an amino acid sequence set forth in SEQ ID NO:57. In one embodiment, the peptide sequence comprises an amino acid sequence set forth in SEQ ID NO:58. In another embodiment, the peptide sequence comprises an amino acid sequence set forth in SEQ ID NO:59. In other embodiments, the peptide sequence comprises an amino acid sequence set forth in SEQ ID NO:60. In one embodiment, the peptide sequence comprises an amino acid sequence set forth in SEQ ID NO:61. In another embodiment, the peptide sequence comprises an amino acid sequence set forth in SEQ ID NO:62. In other embodiments, the peptide sequence comprises an amino acid sequence set forth in SEQ ID NO:63. In one embodiment, the peptide sequence comprises an amino acid sequence set forth in SEQ ID NO:64. In another embodiment, the peptide sequence comprises an amino acid sequence set forth in SEQ ID NO:65. In other embodiments, the peptide sequence comprises an amino acid sequence set forth in SEQ ID NO:66. In one embodiment, the peptide sequence comprises an amino acid sequence set forth in SEQ ID NO:67. In another embodiment, the peptide sequence comprises an amino acid sequence set forth in SEQ ID NO:68. In other embodiments, the peptide sequence comprises an amino acid sequence set forth in SEQ ID NO:69. In one embodiment, the peptide sequence comprises an amino acid sequence set forth in SEQ ID NO:70. In another embodiment, the peptide sequence comprises an amino acid sequence set forth in SEQ ID NO:71. In other embodiments, the peptide sequence comprises an amino acid sequence set forth in SEQ ID NO:72. In one embodiment, the peptide sequence comprises an amino acid sequence set forth in SEQ ID NO:73. In another embodiment, the peptide sequence comprises an amino acid sequence set forth in SEQ ID NO:74. In other embodiments, the peptide sequence comprises an amino acid sequence set forth in SEQ ID NO:75. In one embodiment, the peptide sequence comprises an amino acid sequence set forth in SEQ ID NO:76. In another embodiment, the peptide sequence comprises an amino acid sequence set forth in SEQ ID NO:77. In other embodiments, the peptide sequence comprises an amino acid sequence set forth in SEQ ID NO:78. In one embodiment, the peptide sequence comprises an amino acid sequence set forth in SEQ ID NO:79. In another embodiment, the peptide sequence comprises an amino acid sequence set forth in SEQ ID NO:80. In other embodiments, the peptide sequence comprises an amino acid sequence set forth in SEQ ID NO:81. In one embodiment, the peptide sequence comprises an amino acid sequence set forth in SEQ ID NO:82. In another embodiment, the peptide sequence comprises an amino acid sequence set forth in SEQ ID NO:83. In other embodiments, the peptide sequence comprises an amino acid sequence set forth in SEQ ID NO:84. In one embodiment, the peptide sequence comprises an amino acid sequence set forth in SEQ ID NO:85. In another embodiment, the peptide sequence comprises an amino acid sequence set forth in SEQ ID NO:86. In other embodiments, the peptide sequence comprises an amino acid sequence set forth in SEQ ID NO:87. In one embodiment, the peptide sequence comprises an amino acid sequence set forth in SEQ ID NO:88. In another embodiment, the peptide sequence comprises an amino acid sequence set forth in SEQ ID NO:89. In other embodiments, the peptide sequence comprises an amino acid sequence set forth in SEQ ID NO:90. In one embodiment, the peptide sequence comprises an amino acid sequence set forth in SEQ ID NO:91. In another embodiment, the peptide sequence comprises an amino acid sequence set forth in SEQ ID NO:92. In other embodiments, the peptide sequence comprises an amino acid sequence set forth in SEQ ID NO:93. In one embodiment, the peptide sequence comprises an amino acid sequence set forth in SEQ ID NO:94. In another embodiment, the peptide sequence comprises an amino acid sequence set forth in SEQ ID NO:95. In other embodiments, the peptide sequence comprises an amino acid sequence set forth in SEQ ID NO:96. In one embodiment, the peptide sequence comprises an amino acid sequence set forth in SEQ ID NO:97. In another embodiment, the peptide sequence comprises an amino acid sequence set forth in SEQ ID NO:98. In other embodiments, the peptide sequence comprises an amino acid sequence set forth in SEQ ID NO:138. In one embodiment, the peptide sequence comprises an amino acid sequence set forth in SEQ ID NO:139. In another embodiment, the peptide sequence comprises an amino acid sequence set forth in SEQ ID NO:140. In other embodiments, the peptide sequence comprises an amino acid sequence set forth in SEQ ID NO:141. In one embodiment, the peptide sequence comprises an amino acid sequence set forth in SEQ ID NO:142. In another embodiment, the peptide sequence comprises an amino acid sequence set forth in SEQ ID NO:143. In other embodiments, the peptide sequence comprises an amino acid sequence set forth in SEQ ID NO:144. In one embodiment, the peptide sequence comprises an amino acid sequence set forth in SEQ ID NO:145. In another embodiment, the peptide sequence comprises an amino acid sequence set forth in SEQ ID NO:146. In other embodiments, the peptide sequence comprises an amino acid sequence set forth in SEQ ID NO:147. In one embodiment, the peptide sequence comprises an amino acid sequence set forth in SEQ ID NO:148. In another embodiment, the peptide sequence comprises an amino acid sequence set forth in SEQ ID NO:149. In other embodiments, the peptide sequence comprises an amino acid sequence set forth in SEQ ID NO:150. In one embodiment, the peptide sequence comprises an amino acid sequence set forth in SEQ ID NO:151. In another embodiment, the peptide sequence comprises an amino acid sequence set forth in SEQ ID NO:152. In other embodiments, the peptide sequence comprises an amino acid sequence set forth in SEQ ID NO:153. In one embodiment, the peptide sequence comprises an amino acid sequence set forth in SEQ ID NO:154. In another embodiment, the peptide sequence comprises an amino acid sequence set forth in SEQ ID NO:155. In other embodiments, the peptide sequence comprises an amino acid sequence set forth in SEQ ID NO:156. In one embodiment, the peptide sequence comprises an amino acid sequence set forth in SEQ ID NO:157. In another embodiment, the peptide sequence comprises an amino acid sequence set forth in SEQ ID NO:158. In other embodiments, the peptide sequence comprises an amino acid sequence set forth in SEQ ID NO:159. In one embodiment, the peptide sequence comprises an amino acid sequence set forth in SEQ ID NO:160. In another embodiment, the peptide sequence comprises an amino acid sequence set forth in SEQ ID NO:161. In other embodiments, the peptide sequence comprises an amino acid sequence set forth in SEQ ID NO:162. In one embodiment, the peptide sequence comprises an amino acid sequence set forth in SEQ ID NO:163. In another embodiment, the peptide sequence comprises an amino acid sequence set forth in SEQ ID NO:164. In other embodiments, the peptide sequence comprises an amino acid sequence set forth in SEQ ID NO:165. In one embodiment, the peptide sequence comprises an amino acid sequence set forth in SEQ ID NO:166. In another embodiment, the peptide sequence comprises an amino acid sequence set forth in SEQ ID NO:167. In other embodiments, the peptide sequence comprises an amino acid sequence set forth in SEQ ID NO:168. In another embodiment, the peptide sequence comprises an amino acid sequence set forth in SEQ ID NO:192. In other embodiments, the peptide sequence comprises an amino acid sequence set forth in SEQ ID NO:193. In one embodiment, the peptide sequence comprises an amino acid sequence set forth in SEQ ID NO:194. In another embodiment, the peptide sequence comprises an amino acid sequence set forth in SEQ ID NO:195. In other embodiments, the peptide sequence comprises an amino acid sequence set forth in SEQ ID NO:196. In one embodiment, the peptide sequence comprises an amino acid sequence set forth in SEQ ID NO:197. In another embodiment, the peptide sequence comprises an amino acid sequence set forth in SEQ ID NO:198. In other embodiments, the peptide sequence comprises an amino acid sequence set forth in SEQ ID NO:199. In one embodiment, the peptide sequence comprises an amino acid sequence set forth in SEQ ID NO:200. In another embodiment, the peptide sequence comprises an amino acid sequence set forth in SEQ ID NO:201. In other embodiments, the peptide sequence comprises an amino acid sequence set forth in SEQ ID NO:202. In one embodiment, the peptide sequence comprises an amino acid sequence set forth in SEQ ID NO:203. In another embodiment, the peptide sequence comprises an amino acid sequence set forth in SEQ ID NO:204. In certain embodiments of the various peptide sequences provided herein, the R residue at the N-terminus is deleted.

In yet other embodiments, the peptide sequence consists of an amino acid sequence set forth in SEQ ID NO:1. In another embodiment, the peptide sequence consists of an amino acid sequence set forth in SEQ ID NO:2. In other embodiments, the peptide sequence consists of an amino acid sequence set forth in SEQ ID NO:3. In one embodiment, the peptide sequence consists of an amino acid sequence set forth in SEQ ID NO:4. In another embodiment, the peptide sequence consists of an amino acid sequence set forth in SEQ ID NO: 5. In other embodiments, the peptide sequence consists of an amino acid sequence set forth in SEQ ID NO:6. In one embodiment, the peptide sequence consists of an amino acid sequence set forth in SEQ ID NO:7. In another embodiment, the peptide sequence consists of an amino acid sequence set forth in SEQ ID NO:8. In other embodiments, the peptide sequence consists of an amino acid sequence set forth in SEQ ID NO:9. In one embodiment, the peptide sequence consists of an amino acid sequence set forth in SEQ ID NO:10. In another embodiment, the peptide sequence consists of an amino acid sequence set forth in SEQ ID NO:11. In other embodiments, the peptide sequence consists of an amino acid sequence set forth in SEQ ID NO:12. In one embodiment, the peptide sequence consists of an amino acid sequence set forth in SEQ ID NO:13. In another embodiment, the peptide sequence consists of an amino acid sequence set forth in SEQ ID NO:14. In other embodiments, the peptide sequence consists of an amino acid sequence set forth in SEQ ID NO:15. In one embodiment, the peptide sequence consists of an amino acid sequence set forth in SEQ ID NO:16. In another embodiment, the peptide sequence consists of an amino acid sequence set forth in SEQ ID NO:17. In other embodiments, the peptide sequence consists of an amino acid sequence set forth in SEQ ID NO:18. In one embodiment, the peptide sequence consists of an amino acid sequence set forth in SEQ ID NO:19. In another embodiment, the peptide sequence consists of an amino acid sequence set forth in SEQ ID NO:20. In other embodiments, the peptide sequence consists of an amino acid sequence set forth in SEQ ID NO:21. In one embodiment, the peptide sequence consists of an amino acid sequence set forth in SEQ ID NO:22. In another embodiment, the peptide sequence consists of an amino acid sequence set forth in SEQ ID NO:23. In other embodiments, the peptide sequence consists of an amino acid sequence set forth in SEQ ID NO:24. In one embodiment, the peptide sequence consists of an amino acid sequence set forth in SEQ ID NO:25. In another embodiment, the peptide sequence consists of an amino acid sequence set forth in SEQ ID NO:26. In other embodiments, the peptide sequence consists of an amino acid sequence set forth in SEQ ID NO:27. In one embodiment, the peptide sequence consists of an amino acid sequence set forth in SEQ ID NO:28. In another embodiment, the peptide sequence consists of an amino acid sequence set forth in SEQ ID NO:29. In other embodiments, the peptide sequence consists of an amino acid sequence set forth in SEQ ID NO:30. In one embodiment, the peptide sequence consists of an amino acid sequence set forth in SEQ ID NO:31. In another embodiment, the peptide sequence consists of an amino acid sequence set forth in SEQ ID NO:32. In other embodiments, the peptide sequence consists of an amino acid sequence set forth in SEQ ID NO:33. In one embodiment, the peptide sequence consists of an amino acid sequence set forth in SEQ ID NO:34. In another embodiment, the peptide sequence consists of an amino acid sequence set forth in SEQ ID NO:35. In other embodiments, the peptide sequence consists of an amino acid sequence set forth in SEQ ID NO:36. In one embodiment, the peptide sequence consists of an amino acid sequence set forth in SEQ ID NO:37. In another embodiment, the peptide sequence consists of an amino acid sequence set forth in SEQ ID NO:38. In other embodiments, the peptide sequence consists of an amino acid sequence set forth in SEQ ID NO:39. In one embodiment, the peptide sequence consists of an amino acid sequence set forth in SEQ ID NO:40. In another embodiment, the peptide sequence consists of an amino acid sequence set forth in SEQ ID NO:41. In other embodiments, the peptide sequence consists of an amino acid sequence set forth in SEQ ID NO:42. In one embodiment, the peptide sequence consists of an amino acid sequence set forth in SEQ ID NO:43. In another embodiment, the peptide sequence consists of an amino acid sequence set forth in SEQ ID NO:44. In other embodiments, the peptide sequence consists of an amino acid sequence set forth in SEQ ID NO:45. In one embodiment, the peptide sequence consists of an amino acid sequence set forth in SEQ ID NO:46. In another embodiment, the peptide sequence consists of an amino acid sequence set forth in SEQ ID NO:47. In other embodiments, the peptide sequence consists of an amino acid sequence set forth in SEQ ID NO:48. In one embodiment, the peptide sequence consists of an amino acid sequence set forth in SEQ ID NO:49. In another embodiment, the peptide sequence consists of an amino acid sequence set forth in SEQ ID NO:50. In other embodiments, the peptide sequence consists of an amino acid sequence set forth in SEQ ID NO: 51. In one embodiment, the peptide sequence consists of an amino acid sequence set forth in SEQ ID NO:52. In another embodiment, the peptide sequence consists of an amino acid sequence set forth in SEQ ID NO:53. In other embodiments, the peptide sequence consists of an amino acid sequence set forth in SEQ ID NO:54. In one embodiment, the peptide sequence consists of an amino acid sequence set forth in SEQ ID NO:55. In another embodiment, the peptide sequence consists of an amino acid sequence set forth in SEQ ID NO:56. In other embodiments, the peptide sequence consists of an amino acid sequence set forth in SEQ ID NO:57. In one embodiment, the peptide sequence consists of an amino acid sequence set forth in SEQ ID NO:58. In another embodiment, the peptide sequence consists of an amino acid sequence set forth in SEQ ID NO:59. In other embodiments, the peptide sequence consists of an amino acid sequence set forth in SEQ ID NO:60. In one embodiment, the peptide sequence consists of an amino acid sequence set forth in SEQ ID NO:61. In another embodiment, the peptide sequence consists of an amino acid sequence set forth in SEQ ID NO:62. In other embodiments, the peptide sequence consists of an amino acid sequence set forth in SEQ ID NO:63. In one embodiment, the peptide sequence consists of an amino acid sequence set forth in SEQ ID NO:64. In another embodiment, the peptide sequence consists of an amino acid sequence set forth in SEQ ID NO:65. In other embodiments, the peptide sequence consists of an amino acid sequence set forth in SEQ ID NO:66. In one embodiment, the peptide sequence consists of an amino acid sequence set forth in SEQ ID NO:67. In another embodiment, the peptide sequence consists of an amino acid sequence set forth in SEQ ID NO:68. In other embodiments, the peptide sequence consists of an amino acid sequence set forth in SEQ ID NO:69. In one embodiment, the peptide sequence consists of an amino acid sequence set forth in SEQ ID NO:70. In another embodiment, the peptide sequence consists of an amino acid sequence set forth in SEQ ID NO:71. In other embodiments, the peptide sequence consists of an amino acid sequence set forth in SEQ ID NO:72. In one embodiment, the peptide sequence consists of an amino acid sequence set forth in SEQ ID NO:73. In another embodiment, the peptide sequence consists of an amino acid sequence set forth in SEQ ID NO:74. In other embodiments, the peptide sequence consists of an amino acid sequence set forth in SEQ ID NO:75. In one embodiment, the peptide sequence consists of an amino acid sequence set forth in SEQ ID NO:76. In another embodiment, the peptide sequence consists of an amino acid sequence set forth in SEQ ID NO:77. In other embodiments, the peptide sequence consists of an amino acid sequence set forth in SEQ ID NO:78. In one embodiment, the peptide sequence consists of an amino acid sequence set forth in SEQ ID NO:79. In another embodiment, the peptide sequence consists of an amino acid sequence set forth in SEQ ID NO:80. In other embodiments, the peptide sequence consists of an amino acid sequence set forth in SEQ ID NO:81. In one embodiment, the peptide sequence consists of an amino acid sequence set forth in SEQ ID NO:82. In another embodiment, the peptide sequence consists of an amino acid sequence set forth in SEQ ID NO:83. In other embodiments, the peptide sequence consists of an amino acid sequence set forth in SEQ ID NO:84. In one embodiment, the peptide sequence consists of an amino acid sequence set forth in SEQ ID NO:85. In another embodiment, the peptide sequence consists of an amino acid sequence set forth in SEQ ID NO:86. In other embodiments, the peptide sequence consists of an amino acid sequence set forth in SEQ ID NO: 87. In one embodiment, the peptide sequence consists of an amino acid sequence set forth in SEQ ID NO:88. In another embodiment, the peptide sequence consists of an amino acid sequence set forth in SEQ ID NO:89. In other embodiments, the peptide sequence consists of an amino acid sequence set forth in SEQ ID NO:90. In one embodiment, the peptide sequence consists of an amino acid sequence set forth in SEQ ID NO:91. In another embodiment, the peptide sequence consists of an amino acid sequence set forth in SEQ ID NO:92. In other embodiments, the peptide sequence consists of an amino acid sequence set forth in SEQ ID NO:93. In one embodiment, the peptide sequence consists of an amino acid sequence set forth in SEQ ID NO:94. In another embodiment, the peptide sequence consists of an amino acid sequence set forth in SEQ ID NO:95. In other embodiments, the peptide sequence consists of an amino acid sequence set forth in SEQ ID NO:96. In one embodiment, the peptide sequence consists of an amino acid sequence set forth in SEQ ID NO:97. In another embodiment, the peptide sequence consists of an amino acid sequence set forth in SEQ ID NO:98. In other embodiments, the peptide sequence consists of an amino acid sequence set forth in SEQ ID NO:138. In one embodiment, the peptide sequence consists of an amino acid sequence set forth in SEQ ID NO:139. In another embodiment, the peptide sequence consists of an amino acid sequence set forth in SEQ ID NO:140. In other embodiments, the peptide sequence consists of an amino acid sequence set forth in SEQ ID NO:141. In one embodiment, the peptide sequence consists of an amino acid sequence set forth in SEQ ID NO:142. In another embodiment, the peptide sequence consists of an amino acid sequence set forth in SEQ ID NO:143. In other embodiments, the peptide sequence consists of an amino acid sequence set forth in SEQ ID NO:144. In one embodiment, the peptide sequence consists of an amino acid sequence set forth in SEQ ID NO:145. In another embodiment, the peptide sequence consists of an amino acid sequence set forth in SEQ ID NO:146. In other embodiments, the peptide sequence consists of an amino acid sequence set forth in SEQ ID NO:147. In one embodiment, the peptide sequence consists of an amino acid sequence set forth in SEQ ID NO:148. In another embodiment, the peptide sequence consists of an amino acid sequence set forth in SEQ ID NO:149. In other embodiments, the peptide sequence consists of an amino acid sequence set forth in SEQ ID NO:150. In one embodiment, the peptide sequence consists of an amino acid sequence set forth in SEQ ID NO:151. In another embodiment, the peptide sequence consists of an amino acid sequence set forth in SEQ ID NO:152. In other embodiments, the peptide sequence consists of an amino acid sequence set forth in SEQ ID NO:153. In one embodiment, the peptide sequence consists of an amino acid sequence set forth in SEQ ID NO:154. In another embodiment, the peptide sequence consists of an amino acid sequence set forth in SEQ ID NO:155. In other embodiments, the peptide sequence consists of an amino acid sequence set forth in SEQ ID NO:156. In one embodiment, the peptide sequence consists of an amino acid sequence set forth in SEQ ID NO:157. In another embodiment, the peptide sequence consists of an amino acid sequence set forth in SEQ ID NO:158. In other embodiments, the peptide sequence consists of an amino acid sequence set forth in SEQ ID NO:159. In one embodiment, the peptide sequence consists of an amino acid sequence set forth in SEQ ID NO:160. In another embodiment, the peptide sequence consists of an amino acid sequence set forth in SEQ ID NO:161. In other embodiments, the peptide sequence consists of an amino acid sequence set forth in SEQ ID NO:162. In one embodiment, the peptide sequence consists of an amino acid sequence set forth in SEQ ID NO:163. In another embodiment, the peptide sequence consists of an amino acid sequence set forth in SEQ ID NO:164. In other embodiments, the peptide sequence consists of an amino acid sequence set forth in SEQ ID NO:165. In one embodiment, the peptide sequence consists of an amino acid sequence set forth in SEQ ID NO:166. In another embodiment, the peptide sequence consists of an amino acid sequence set forth in SEQ ID NO:167. In other embodiments, the peptide sequence consists of an amino acid sequence set forth in SEQ ID NO:168. In another embodiment, the peptide sequence consists of an amino acid sequence set forth in SEQ ID NO:192. In other embodiments, the peptide sequence consists of an amino acid sequence set forth in SEQ ID NO:193. In one embodiment, the peptide sequence consists of an amino acid sequence set forth in SEQ ID NO:194. In another embodiment, the peptide sequence consists of an amino acid sequence set forth in SEQ ID NO:195. In other embodiments, the peptide sequence consists of an amino acid sequence set forth in SEQ ID NO:196. In one embodiment, the peptide sequence consists of an amino acid sequence set forth in SEQ ID NO:197. In another embodiment, the peptide sequence consists of an amino acid sequence set forth in SEQ ID NO:198. In other embodiments, the peptide sequence consists of an amino acid sequence set forth in SEQ ID NO:199. In one embodiment, the peptide sequence consists of an amino acid sequence set forth in SEQ ID NO:200. In another embodiment, the peptide sequence consists of an amino acid sequence set forth in SEQ ID NO:201. In other embodiments, the peptide sequence consists of an amino acid sequence set forth in SEQ ID NO:202. In one embodiment, the peptide sequence consists of an amino acid sequence set forth in SEQ ID NO:203. In another embodiment, the peptide sequence consists of an amino acid sequence set forth in SEQ ID NO:204. In certain embodiments of the various peptide sequences provided herein, the R residue at the N-terminus is deleted.

4.3 Particular Modifications to Enhance Peptide Function

It is frequently beneficial, and sometimes imperative, to improve one of more physical properties of the treatment modalities disclosed herein and/or the manner in which they are administered. Improvements of physical properties include, for example, modulating immunogenicity; methods of increasing solubility, bioavailability, serum half-life, and/or therapeutic half-life; and/or modulating biological activity. Certain modifications may also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of is one particular modification contemplated herein, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

4.3.1 Pegylation

The clinical effectiveness of protein therapeutics is often limited by short plasma half-life and susceptibility to protease degradation. Studies of various therapeutic proteins (e.g., filgrastim) have shown that such difficulties may be overcome by, for example, conjugating or linking the protein to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity. In addition to the beneficial effects of pegylation on pharmacokinetic parameters, pegylation itself may enhance activity.

PEGS suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGS are contemplated by the present disclosure. A molecular weight of the PEG used in embodiments provided herein is not restricted to any particular range, and examples are set forth elsewhere herein; by way of example, certain embodiments have molecular weights between 5 kDa and 20 kDa, while other embodiments have molecular weights between 4 kDa and 10 kDa.

In other embodiments, provided herein are compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Cation exchange chromatography may be used to separate conjugates, and a fraction is then identified which contains the conjugate having, for example, the desired number of PEGS attached, purified free from unmodified protein sequences and from conjugates having other numbers of PEGS attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

General pegylation strategies known in the art can be applied herein. PEG may be bound to a polypeptide provided herein via a terminal reactive group (a "spacer" or "linker") which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences provided herein to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments, the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263.

In some embodiments, also provided herein are uses of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., XTEN technology; Amunix; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

4.3.2 Glycosylation

As used herein, "glycosylation" is meant to broadly refer to the enzymatic process by which glycans are attached to proteins, lipids or other organic molecules. The use of the term "glycosylation" herein is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment comprises the generation and use of N-glycosylation variants.

The polypeptide sequences provided herein may optionally be altered through changes at the nucleic acid level, particularly by mutating the nucleic acid encoding the polypeptide at preselected bases such that codons are generated that will translate into the desired amino acids.

4.3.3 Polysialylation

In certain embodiments, also provided herein is the use of polysialylation, the conjugation of polypeptides to the naturally occurring, biodegradable α-(2→8) linked polysialic acid ("PSA") in order to improve the polypeptides' stability and in vivo pharmacokinetics.

Albumin Fusion:

Additional suitable components and molecules for conjugation include albumins such as human serum albumin (HSA), cyno serum albumin, and bovine serum albumin (BSA).

In some embodiments, albumin is conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701).

In the HSA-drug molecule conjugates embodiments provided herein, various forms of albumin may be used, such as albumin secretion pre-sequences and variants thereof, fragments and variants thereof, and HSA variants. Such forms generally possess one or more desired albumin activities. In additional embodiments, fusion proteins are provided herein comprising a polypeptide drug molecule fused directly or indirectly to albumin, an albumin fragment, an albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

As alluded to above, fusion of albumin to one or more polypeptides provided herein can, for example, be achieved by genetic manipulation, such that the nucleic acid coding for HSA, or a fragment thereof, is joined to the nucleic acid coding for the one or more polypeptide sequences.

4.3.4 Alternative Albumin Binding Strategies

Several albumin-binding strategies have been developed as alternatives to direct fusion and may be used with the agents described herein. By way of example, in certain embodiments, provided herein is albumin binding through a conjugated fatty acid chain (acylation) and fusion proteins which comprise an albumin binding domain (ABD) polypeptide sequence and the sequence of one or more of the polypeptides described herein.

Conjugation with Other Molecules: Additional suitable components and molecules for conjugation include, for example, thyroglobulin; tetanus toxoid; Diphtheria toxoid; polyamino acids such as poly(D-lysine:D-glutamic acid); VP6 polypeptides of rotaviruses; influenza virus hemagglutinin, influenza virus nucleoprotein; Keyhole Limpet Hemocyanin (KLH); and hepatitis B virus core protein and surface antigen; or any combination of the foregoing.

Thus, in certain embodiments, conjugation of one or more additional components or molecules at the N- and/or C-terminus of a polypeptide sequence, such as another polypeptide (e.g., a polypeptide having an amino acid sequence heterologous to the subject polypeptide), or a carrier molecule is also contemplated. Thus, an exemplary polypeptide sequence can be provided as a conjugate with another component or molecule.

A polypeptide may also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide provided herein.

Fc-Fusion Molecules:

In certain embodiments, the amino- or carboxyl-terminus of a polypeptide sequence provided herein is fused with an immunoglobulin Fc region to form a fusion conjugate (or fusion molecule). In a specific embodiment, the immunoglobuling Fc region is a human Fc region. Fusion conjugates have been shown to increase the systemic half-life of biopharmaceuticals, and thus the biopharmaceutical product may require less frequent administration. In certain embodiments, the half-life is increased as compared to the same polypeptide that is not fused to an immunoglobuling Fc region.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

In some embodiments, provided herein is a fusion of M70 to a human antibody Fc fragment. In some embodiments, provided herein is a fusion of M69 to a human antibody Fc fragment. Such fusions can be useful in the treatment of bile acid related disorders and other metabolic disorders provided herein. In some embodiments, the Fc-fusion of M70 has a longer half-life. In specific embodiments, the longer half-life of the Fc-fusion of M70 is as compared to M70 that is not an Fc-fusion. In some embodiments, the Fc-fusion of M69 has a longer half-life. In specific embodiments, the longer half life of the Fc-fusion of M69 is as compared to M69 that is not an Fc-fusion. Such a long half-life makes these fusions suitable for once weekly, or less frequent dosing.

In some embodiments, the Fc-fusion comprises a linker. Exemplary flexible linkers include glycine polymers $(G)_n$, glycine-serine polymers, glycine-alanine polymers, alanine-serine polymers, and other flexible linkers. In certain embodiments, the linker is $(G)_4S$ (SEQ ID NO:206). In some embodiments, the linker is $((G)_4S)_n$ (SEQ ID NO:207), where n is an integer of at least one. In some embodiments, the linker is $((G)_4S)_2$ (SEQ ID NO:208). Glycine and glycine-serine polymers are relatively unstructured, and therefore may serve as a neutral tether between components. In some embodiments, the glycine-serine polymer is $(GS)_n$, where n is an integer of at least one. In some embodiments, the glycine-serine polymer is $GSGGS_n$(SEQ ID NO:129), where n is an integer of at least one. In some embodiments, the glycine-serine polymer is $GGGS_n$ (SEQ ID NO:130), where n is an integer of at least one. In certain embodiments, the linker comprises an additional G residue at the N' terminus of SEQ ID NO:130. In one embodiment, the linker is GGSG (SEQ ID NO:131). In one embodiment, the linker is GGSGG (SEQ ID NO:132). In one embodiment, the linker is GSGSG (SEQ ID NO:133). In one embodiment, the linker is GSGGG (SEQ ID NO:134). In one embodiment, the linker is GGGSG (SEQ ID NO:189). In one embodiment, the linker is GSSSG (SEQ ID NO:135).

4.3.5 Purification

Additional suitable components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from 3 to 5.5, such as at pH ~4.5. The content of the fractions obtained by cation exchange chromatography may be identified by molecular weight using conventional methods, for example, mass spectroscopy, SDS-PAGE, or other known methods for separating molecular entities by molecular weight. A fraction is then identified which contains the conjugate having the desired number of PEGs attached, purified free from unmodified protein sequences and from conjugates having other numbers of PEGS attached.

4.3.6 Other Modifications

In certain embodiments, also provided herein is the use of other modifications, currently known or developed in the future, to improve one or more properties. Examples include hesylation, various aspects of which are described in, for example, U.S. Patent Appln. Nos. 2007/0134197 and 2006/0258607, and fusion molecules comprising SUMO as a fusion tag (LifeSensors, Inc.; Malvern, Pa.).

In still other embodiments, a peptide sequence provided herein is linked to a chemical agent (e.g., an immunotoxin or chemotherapeutic agent), including, but are not limited to, a cytotoxic agent, including taxol, cytochalasin B, gramicidin D, mitomycin, etoposide, tenoposide, vincristine, vinblastine, colchicin, doxorubicin, daunorubicin, and analogs or homologs thereof. Other chemical agents include, for example, antimetabolites (e.g., methotrexate, 6-mercaptopurine, 6-thioguanine, cytarabine, 5-fluorouracil decarbazine); alkylating agents (e.g., mechlorethamine, carmustine and lomustine, cyclophosphamide, busulfan, dibromomannitol, streptozotocin, mitomycin C, and cisplatin); antibiotics (e.g., bleomycin); and anti-mitotic agents (e.g., vincristine and vinblastine). Cytotoxins can be conjugated to a peptide provided herein using linker technology known in the art and described herein.

Further suitable components and molecules for conjugation include those suitable for detection in an assay. Particular non-limiting examples include detectable labels, such as a radioisotope (e.g., $^{125}I$; $^{35}S$, $^{32}P$, $^{33}P$), an enzyme which generates a detectable product (e.g., luciferase, β-galactosidase, horse radish peroxidase and alkaline phosphatase), a fluorescent protein, a chromogenic protein, dye (e.g., fluorescein isothiocyanate); fluorescence emitting metals (e.g., $^{152}Eu$); chemiluminescent compounds (e.g., luminol and acridinium salts); bioluminescent compounds (e.g., luciferin); and fluorescent proteins. Indirect labels include labeled or detectable antibodies that bind to a peptide sequence, where the antibody may be detected.

In certain embodiments, a peptide sequence provided herein is conjugated to a radioactive isotope to generate a cytotoxic radiopharmaceutical (radioimmunoconjugates)

useful as a diagnostic or therapeutic agent. Examples of such radioactive isotopes include, but are not limited to, iodine$^{131}$, indium$^{111}$, yttrium$^{90}$ and lutetium$^{177}$. Methods for preparing radioimmunoconjugates are known to the skilled artisan. Examples of radioimmunoconjugates that are commercially available include ibritumomab, tiuxetan, and tositumomab.

Linkers:

Linkers and their use have been described above. Any of the foregoing components and molecules used to modify the polypeptide sequences provided herein may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Exemplary flexible linkers include glycine polymers $(G)_n$, glycine-serine polymers (for example, $(GS)_n$, $GSGGS_n$ (SEQ ID NO:129) and $GGGS_n$ (SEQ ID NO:130), where n is an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:131), GGSGG (SEQ ID NO:132), GSGSG (SEQ ID NO:133), GSGGG (SEQ ID NO:134), GGGSG (SEQ ID NO:189), and GSSSG (SEQ ID NO:135). In certain embodiments, the linker is $(G)_4S$ (SEQ ID NO:206). In some embodiments, the linker is $((G)_4S)_n)$ (SEQ ID NO:207), where n is an integer of at least one. In some embodiments, the linker is $((G)_4S)_2)$ (SEQ ID NO:208). In some embodiments, the glycine-serine polymer is $(GS)_n$, where n is an integer of at least one. In some embodiments, the glycine-serine polymer is $GSGGS_n$ (SEQ ID NO:129), where n is an integer of at least one. In some embodiments, the glycine-serine polymer is $GGGS_n$ (SEQ ID NO:130), where n is an integer of at least one. In certain embodiments, the linker comprises an additional G residue at the N' terminus of SEQ ID NO:130. In one embodiment, the linker is GGSG (SEQ ID NO:131). In one embodiment, the linker is GGSGG (SEQ ID NO:132). In one embodiment, the linker is GSGSG (SEQ ID NO:133). In one embodiment, the linker is GSGGG (SEQ ID NO:134). In one embodiment, the linker is GGGSG (SEQ ID NO:189). In one embodiment, the linker is GSSSG (SEQ ID NO:135).

In various embodiments, a peptide or chimeric sequence has a function or activity greater or less than a comparison sequence. In further particular embodiments, chimeric peptide sequences and peptide sequences have particular functions or activities. In one embodiment, a chimeric peptide sequence or peptide sequence maintains or increases a FGFR4-mediated activity. In additional aspects, a chimeric peptide sequence or peptide sequence binds to FGFR4 or activates FGFR4, or does not detectably bind to FGFR4 or activate FGFR4, or binds to FGFR4 with an affinity less than, comparable to, equal to, or greater than FGF19 binding affinity for FGFR4, or activates FGFR4 to an extent or amount less than, comparable to, equal to, or greater than FGF19 activates FGFR4. In some embodiments, a chimeric peptide sequence or peptide sequence provided herein activates FGFR4 to an extent or amount less than the extent or amount that FGF19 activates FGFR4. In some embodiments, a chimeric peptide sequence or peptide sequence provided herein activates FGFR4 to an extent or amount comparable to, or equal to, the extent or amount that FGF19 activates FGFR4. In some embodiments, a chimeric peptide sequence or peptide sequence provided herein activates FGFR4 to an extent or amount greater than the extent or amount that FGF19 activates FGFR4.

Peptide sequences provided herein, including the FGF19 and FGF21 variants and subsequences and the FGF19/FGF21 fusions and chimeras listed in Table 1 and Sequence Listing, as well as subsequences, sequence variants and modified forms of the sequences listed in Table 1 and Sequence Listing have one or more activities as set forth herein. One example of an activity is modulating bile acid homeostasis. Another example of an activity is reduced stimulation or formation of HCC, for example, as compared to FGF19. An additional example of an activity is lower or reduced lipid (e.g., triglyceride, cholesterol, non-HDL) or HDL increasing activity, for example, as compared to FGF21. A further example of an activity is a lower or reduced lean muscle mass reducing activity, for example, as compared to FGF21. Yet another example of an activity is binding to FGFR4, or activating FGFR4, for example, peptide sequences that bind to FGFR4 with an affinity comparable to, equal to, or greater than FGF19 binding affinity for FGFR4; and peptide sequences that activate FGFR4 to an extent or amount comparable to, equal to, or greater than FGF19 activates FGFR4. Still further examples of activities include treating a bile acid-related or associated disorder.

In one embodiment, a chimeric peptide sequence or peptide sequence provided herein maintains a FGFR4 mediated activity. In one embodiment, a chimeric peptide sequence or peptide sequence provided herein increases a FGFR4 mediated activity. In some embodiments, a chimeric peptide sequence or peptide sequence provided herein binds to FGFR4 with an affinity less than FGF19 binding affinity for FGFR4. In some embodiments, a chimeric peptide sequence or peptide sequence provided herein binds to FGFR4 with an affinity comparable to, or equal to, FGF19 binding affinity for FGFR4. In some embodiments, a chimeric peptide sequence or peptide sequence provided herein binds to FGFR4 with an affinity greater than FGF19 binding affinity for FGFR4. In some embodiments, a chimeric peptide sequence or peptide sequence provided herein does not detectably bind to FGFR4.

In further aspects, a chimeric peptide sequence or peptide sequence has reduced HCC formation compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; or has greater glucose lowering activity compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; has less lipid increasing activity compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; or has less triglyceride, cholesterol, non-HDL or HDL increasing activity compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; or the peptide sequence has less lean mass reducing activity compared to FGF21. Such functions and activities can be ascertained in vitro or in vivo, for example, in a db/db mouse.

In one embodiment, a peptide or chimeric sequence has a function or activity greater or less than a comparison sequence. In some embodiments, the comparison sequence is FGF19. In another embodiment, the comparison sequence is FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. In one embodiment, a peptide or chimeric peptide sequence provided herein has greater glucose lowering activity compared to a comparison sequence. In another embodiment, a peptide or chimeric peptide sequence provided herein has less lipid increasing activity compared to a comparison sequence. In other embodiment, a peptide or chimeric peptide sequence provided herein has lower or reduced lipid (e.g., triglyceride, cholesterol, non-HDL) activity compared to a comparison sequence. In other embodiments, a peptide or chimeric peptide sequence provided herein has more HDL increasing activity as compared to a comparison sequence. In other embodiment, a peptide or chimeric peptide sequence provided herein has less lean mass reducing activity compared to a comparison sequence or FGF21.

More particularly, peptide sequences provided herein, including the FGF19 and FGF21 variants and subsequences and the FGF19/FGF21 fusions and chimeras listed in Table 1 and Sequence Listing, as well as subsequences, variants and modified forms of the sequences listed in Table 1 and Sequence Listing include those with the following activities: peptide sequences modulating bile acid homeostasis or treating a bile acid-related or associated disorder while having reduced HCC formation compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; peptide sequences having greater bile acid modulating activity compared to FGF19, or FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; peptide sequences having less lipid increasing activity (e.g., less triglyceride, cholesterol, non-HDL) or more HDL increasing activity compared to FGF19, or a FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; and peptide sequences having less lean mass reducing activity as compared to FGF21.

More particularly, peptide sequences provided herein, including the FGF19 and FGF21 variants and subsequences and the FGF19/FGF21 fusions and chimeras listed in Table 1 and Sequence Listing, as well as subsequences, variants and modified forms of the sequences listed in Table 1 and the Sequence Listing include those with the following activities: peptide sequences that modulate bile acid homeostasis; peptide sequences that treat a bile acid-related or associated disorder, peptide sequences that bind to FGFR4, or activate FGFR4, such as peptide sequences that bind to FGFR4 with an affinity comparable to, equal to, or greater than FGF19 binding affinity for FGFR4; peptide sequences that activate FGFR4 to an extent or amount comparable to, equal to, or greater than FGF19 activates FGFR4; peptide sequences that down-regulate or reduce aldo-keto reductase gene expression, for example, compared to FGF19; and peptide sequences that up-regulate or increase solute carrier family 1, member 2 (Slc1a2) gene expression as compared to FGF21.

As disclosed herein, variants include various N-terminal modifications and/or truncations of FGF19, including variants in which there has been a substitution of one or several N-terminal FGF19 amino acids with amino acids from FGF21. Such variants include variants having glucose lowering activity, as well as a favorable lipid profile and are not measurably or detectably tumorigenic.

Activities such as, for example, modulation of bile acid homeostasis, glucose lowering activity, analysis of a bile acid-related or associated disorder, HCC formation or tumorigenesis, lipid increasing activity, or lean mass reducing activity can be ascertained in an animal, such as a db/db mouse. Measurement of binding to FGFR4 or activation of FGFR4 can be ascertained by assays disclosed herein or known to the skilled artisan.

4.4 Nucleic Acid Molecules

Also provided are nucleic acid molecules encoding peptide sequences provided herein, including subsequences, sequence variants and modified forms of the sequences listed in the Sequence Listing (and in PCT Pub. No. WO 2013/006486 and US Pub. No. 2013/0023474, as well as PCT Publ. No. WO 2014/085365) or Table 1, and vectors that include nucleic acid encoding the peptides used in the methods described herein. Accordingly, "nucleic acids" include those that encode the exemplified peptide sequences disclosed herein, as well as those encoding functional subsequences, sequence variants and modified forms of the exemplified peptide sequences, so long as the foregoing retain at least detectable or measureable activity or function useful in the treatment or prevention of a bile acid-related or associated disorder (e.g., PBC).

Nucleic acid, which can also be referred to herein as a gene, polynucleotide, nucleotide sequence, primer, oligonucleotide or probe, refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA and cDNA. RNA nucleic acid can be spliced or unspliced mRNA, rRNA, tRNA or antisense. Nucleic acids include naturally occurring, synthetic, as well as nucleotide analogs and derivatives.

As a result of the degeneracy of the genetic code, the nucleic acid molecules provided herein include sequences degenerate with respect to nucleic acid molecules encoding the peptide sequences useful in the methods provided herein. Thus, degenerate nucleic acid sequences encoding peptide sequences, including subsequences, variants and modified forms of the peptide sequences exemplified herein (e.g., in the Sequence Listing or Table 1), are provided. The term "complementary," when used in reference to a nucleic acid sequence, means the referenced regions are 100% complementary, i.e., exhibit 100% base pairing with no mismatches.

Nucleic acid can be produced using any of a variety of known standard cloning and chemical synthesis methods, and can be altered intentionally by site-directed mutagenesis or other recombinant techniques known to one skilled in the art. Purity of polynucleotides can be determined through, for example, sequencing, gel electrophoresis, and UV spectrometry.

Nucleic acids may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically, expression control elements are juxtaposed at the 5' or the 3' ends of the genes but can also be intronic.

Expression control elements include elements that activate transcription constitutively, that are inducible (i.e., require an external signal or stimuli for activation), or derepressible (i.e., require a signal to turn transcription off; when the signal is no longer present, transcription is activated or "derepressed"). Also included in the expression cassettes provided herein are control elements sufficient to render gene expression controllable for specific cell types or tissues (i.e., tissue-specific control elements). Typically, such elements are located upstream or downstream (i.e., 5' or 3') of the coding sequence. Promoters are generally positioned 5' of the coding sequence. Promoters, produced by recombinant DNA or synthetic techniques, can be used to provide for transcription of the polynucleotides provided herein. A "promoter" typically means a minimal sequence element sufficient to direct transcription.

Nucleic acids may be inserted into a plasmid for transformation into a host cell and for subsequent expression and/or genetic manipulation. A plasmid is a nucleic acid that can be stably propagated in a host cell; plasmids may optionally contain expression control elements in order to drive expression of the nucleic acid. For purposes of this invention, a vector is synonymous with a plasmid. Plasmids and vectors generally contain at least an origin of replication for propagation in a cell and a promoter. Plasmids and vectors may also include an expression control element for expression in a host cell, and are therefore useful for expression and/or genetic manipulation of nucleic acids encoding peptide sequences, expressing peptide sequences in host cells and organisms, or producing peptide sequences, for example.

As used herein, the term "transgene" means a polynucleotide that has been introduced into a cell or organism by artifice. For example, in a cell having a transgene, the transgene has been introduced by genetic manipulation or "transformation" of the cell. A cell or progeny thereof into which the transgene has been introduced is referred to as a "transformed cell" or "transformant." Typically, the transgene is included in progeny of the transformant or becomes a part of the organism that develops from the cell. Transgenes may be inserted into the chromosomal DNA or maintained as a self-replicating plasmid, YAC, minichromosome, or the like.

Bacterial system promoters include T7 and inducible promoters such as pL of bacteriophage λ, plac, ptrp, ptac (ptrp-lac hybrid promoter) and tetracycline-responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a peptide sequence in appropriate host cells.

As methods and uses provided herein include in vivo delivery, expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054), CMV vectors (U.S. Pat. No. 5,561,063) and parvovirus, rotavirus, Norwalk virus and lentiviral vectors (see, e.g., U.S. Pat. No. 6,013,516). Vectors include those that deliver genes to cells of the intestinal tract, including the stem cells (Croyle et al., Gene Ther. 5:645 (1998); S. J. Henning, Adv. Drug Deliv. Rev. 17:341 (1997), U.S. Pat. Nos. 5,821,235 and 6,110,456). Many of these vectors have been approved for human studies.

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. Methods in Enzymology, 153:516 (1987), eds. Wu & Grossman; Bitter Methods in Enzymology, 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is co-transfected into a host cell with a first vector containing a nucleic acid encoding a peptide sequence. Selection systems include, but are not limited to, herpes simplex virus thymidine kinase gene (Wigler et al., Cell 11:223 (1977)), hypoxanthine-guanine phosphoribosyltransferase gene (Szybalska et al., Proc. Natl. Acad. Sci. USA 48:2026 (1962)), and adenine phosphoribosyltransferase (Lowy et al., Cell 22:817 (1980)) genes that can be employed in tk-, hgprt- or aprt-cells, respectively. Additionally, antimetabolite resistance can be used as the basis of selection for dhfr, which confers resistance to methotrexate (O'Hare et al., Proc. Natl. Acad. Sci. USA 78:1527 (1981)); the gpt gene, which confers resistance to mycophenolic acid (Mulligan et al., Proc. Natl. Acad. Sci. USA 78:2072 (1981)); neomycin gene, which confers resistance to aminoglycoside G-418 (Colberre-Garapin et al, J. Mol. Biol. 150:1(1981)); puromycin; and hygromycin gene, which confers resistance to hygromycin (Santerre et al., Gene 30:147 (1984)). Additional selectable genes include trpB, which allows cells to utilize indole in place of tryptophan; hisD, which allows cells to utilize histinol in place of histidine (Hartman et al., Proc. Natl. Acad. Sci. USA 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

4.5 Cell Lines and Animal Models

In certain embodiments, also provided is a transformed cell(s) (in vitro, ex vivo and in vivo) and host cells that produce a variant or fusion of FGF19 and/or FGF21 as set forth herein, where expression of the variant or fusion of FGF19 and/or FGF21 is conferred by a nucleic acid encoding the variant or fusion of FGF19 and/or FGF21. As used herein, a "transformed" or "host" cell is a cell into which a nucleic acid is introduced that can be propagated and/or transcribed for expression of an encoded peptide sequence. The term also includes any progeny or subclones of the host cell. Transformed and host cells that express peptide sequences provided herein typically include a nucleic acid that encodes the peptide sequence. In one embodiment, a transformed or host cell is a prokaryotic cell. In another embodiment, a transformed or host cell is a eukaryotic cell. In various aspects, the eukaryotic cell is a yeast or mammalian (e.g., human, primate, etc.) cell.

Transformed and host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for transient or stable propagation or expression.

For gene therapy uses and methods, a transformed cell can be in a subject. A cell in a subject can be transformed with a nucleic acid that encodes a peptide sequence as set forth herein in vivo. Alternatively, a cell can be transformed in vitro with a transgene or polynucleotide, and then transplanted into a tissue of subject in order to effect treatment. Alternatively, a primary cell isolate or an established cell line can be transformed with a transgene or polynucleotide that encodes a variant of FGF19 and/or FGF21 or a fusion/chimeric sequence (or variant) thereof, such as a chimeric peptide sequence including all or a portion of FGF19, or including all or a portion of FGF21, and then optionally transplanted into a tissue of a subject.

Non-limiting target cells for expression of peptide sequences, particularly for expression in vivo, include pancreas cells (islet cells), muscle cells, mucosal cells and endocrine cells. Such endocrine cells can provide inducible production (secretion) of a variant of FGF19 and/or FGF21, or a fusion/chimeric sequence (or variant) thereof, such as a chimeric peptide sequence including all or a portion of FGF19, or including all or a portion of FGF21. Additional cells to transform include stem cells or other multipotent or pluripotent cells, for example, progenitor cells that differentiate into the various pancreas cells (islet cells), muscle cells, mucosal cells and endocrine cells. Targeting stem cells provides longer term expression of peptide sequences provided herein.

As used herein, the term "cultured," when used in reference to a cell, means that the cell is grown in vitro. A particular example of such a cell is a cell isolated from a subject, and grown or adapted for growth in tissue culture. Another example is a cell genetically manipulated in vitro, and transplanted back into the same or a different subject.

The term "isolated," when used in reference to a cell, means a cell that is separated from its naturally occurring in vivo environment. "Cultured" and "isolated" cells may be manipulated by the hand of man, such as genetically transformed. These terms include any progeny of the cells, including progeny cells that may not be identical to the parental cell due to mutations that occur during cell division. The terms do not include an entire human being.

Nucleic acids encoding peptide sequences provided herein can be introduced for stable expression into cells of a whole organism. Such organisms, including non-human transgenic animals, are useful for studying the effect of peptide expression in a whole animal and therapeutic benefit. For example, as disclosed herein, production of a variant of FGF19 and/or FGF21 or a fusion/chimeric sequence (or variant) thereof, such as a chimeric peptide sequence including all or a portion of FGF19, or including all or a portion of FGF21 as set forth herein, in mice.

Mice strains that develop or are susceptible to developing a particular disease (e.g., diabetes, degenerative disorders, cancer, etc.) are also useful for introducing therapeutic proteins as described herein in order to study the effect of therapeutic protein expression in the disease-susceptible mouse. Transgenic and genetic animal models that are susceptible to particular disease or physiological conditions, such as streptozotocin (STZ)-induced diabetic (STZ) mice, are appropriate targets for expressing variants of FGF19 and/or FGF21, fusions/chimeric sequences (or variant) thereof, such as a chimeric peptide sequence including all or a portion of FGF19, or including all or a portion of FGF21, as set forth herein. Thus, in certain embodiments, there are provided non-human transgenic animals that produce a variant of FGF19 and/or FGF21, or a fusion/chimeric sequence (or variant) thereof, such as a chimeric peptide sequence including all or a portion of FGF19, or including all or a portion of FGF21, the production of which is not naturally occurring in the animal which is conferred by a transgene present in somatic or germ cells of the animal.

The term "transgenic animal" refers to an animal whose somatic or germ line cells bear genetic information received, directly or indirectly, by deliberate genetic manipulation at the subcellular level, such as by microinjection or infection with recombinant virus. The term "transgenic" further includes cells or tissues (i.e., "transgenic cell," "transgenic tissue") obtained from a transgenic animal genetically manipulated as described herein. In the present context, a "transgenic animal" does not encompass animals produced by classical crossbreeding or in vitro fertilization, but rather denotes animals in which one or more cells receive a nucleic acid molecule. Transgenic animals provided herein can be either heterozygous or homozygous with respect to the transgene. Methods for producing transgenic animals, including mice, sheep, pigs and frogs, are well known in the art (see, e.g., U.S. Pat. Nos. 5,721,367, 5,695,977, 5,650, 298, and 5,614,396) and, as such, are additionally included.

Peptide sequences, nucleic acids encoding peptide sequences, vectors and transformed host cells expressing peptide sequences include isolated and purified forms. The term "isolated," when used as a modifier of a composition provided herein, means that the composition is separated, substantially, completely, or at least in part, from one or more components in an environment. Generally, compositions that exist in nature, when isolated, are substantially free of one or more materials with which they normally associate with in nature, for example, one or more protein, nucleic acid, lipid, carbohydrate or cell membrane. The term "isolated" does not exclude alternative physical forms of the composition, such as variants, modifications or derivatized forms, fusions and chimeras, multimers/oligomers, etc., or forms expressed in host cells. The term "isolated" also does not exclude forms (e.g., pharmaceutical compositions, combination compositions, etc.) in which there are combinations therein, any one of which is produced by the hand of man.

An "isolated" composition can also be "purified" when free of some, a substantial number of, or most or all of one or more other materials, such as a contaminant or an undesired substance or material.

As used herein, the term "recombinant," when used as a modifier of peptide sequences, nucleic acids encoding peptide sequences, etc., means that the compositions have been manipulated (i.e., engineered) in a fashion that generally does not occur in nature (e.g., in vitro). A particular example of a recombinant peptide would be where a peptide sequence provided herein is expressed by a cell transfected with a nucleic acid encoding the peptide sequence. A particular example of a recombinant nucleic acid would be a nucleic acid (e.g., genomic or cDNA) encoding a peptide sequence cloned into a plasmid, with or without 5', 3' or intron regions that the gene is normally contiguous within the genome of the organism. Another example of a recombinant peptide or nucleic acid is a hybrid or fusion sequence, such as a chimeric peptide sequence comprising a portion of FGF19 and a portion of FGF21.

In accordance with the methods provided herein, there are provided compositions and mixtures of peptide sequences, including subsequences, variants and modified forms of the exemplified peptide sequences (including the FGF19 and FGF21 variants and subsequences listed in Table 1 and the Sequence Listing, and the FGF19/FGF21 fusions and chimeras listed in Table 1 and the Sequence Listing). In one embodiment, a mixture includes one or more peptide sequences and a pharmaceutically acceptable carrier or excipient. In another embodiment, a mixture includes one or more peptide sequences and an adjunct drug or therapeutic agent, such as a bile acid homeostasis modulating or anti-diabetic, or glucose lowering, drug or therapeutic agent. Combinations, such as one or more peptide sequences in a pharmaceutically acceptable carrier or excipient, with one or more of a bile acid homeostasis modulating or a treatment for a bile acid-related or associated disorder, or anti-diabetic, or glucose lowering drug or therapeutic agent are also provided. Such combinations of peptide sequence provided herein with another drug or agent, such as a bile acid homeostasis modulating or acid related disorder treating, or glucose lowering drug or therapeutic agent, for example are useful in accordance with the methods and uses provided herein, for example, for treatment of a subject.

Combinations also include incorporation of peptide sequences or nucleic acids provided herein into particles or a polymeric substances, such as polyesters, carbohydrates, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers; entrapment in microcapsules prepared by coacervation techniques or by interfacial polymerization, for example, by the use of hydroxymethylcellulose or gelatin-microcapsules, or poly (methylmethacrolate) microcapsules, respectively; incorporation in colloid drug delivery and dispersion systems such as macromolecule complexes, nano-capsules, microspheres, beads, and lipid-based systems (e.g., N-fatty acyl groups such as N-lauroyl, N-oleoyl, fatty amines such as dodecyl amine, oleoyl amine, etc., see U.S. Pat. No. 6,638,513), including oil-in-water emulsions, micelles, mixed micelles, and liposomes, for example.

The peptides provided herein including subsequences, variants and modified forms of the exemplified peptide sequences (including the FGF19 and FGF21 variants and subsequences listed in Table 1 and the Sequence Listing, and the FGF19/FGF21 fusions and chimeras listed in Table 1 and the Sequence Listing) as set forth herein can be used to modulate glucose metabolism and facilitate transport of glucose from the blood to key metabolic organs such as muscle, liver and fat. Such peptide sequences can be produced in amounts sufficient or effective to restore glucose tolerance and/or to improve or provide normal glucose homeostasis.

4.6 Bile Acid-Related or Associated Disorders and the Treatment or Prevention Thereof As used herein, the phrases "bile acid-related disorder," "bile acid-related or associated disorder," and the like, when used in reference to a condition of a subject, means a disruption of bile acid homeostasis, which may manifest itself as, for example, an acute, transient or chronic abnormal level of a bile acid or one or more bile acids. The condition can be caused by inhibition, reduction or a delay in bile acid synthesis, metabolism or absorption such that the subject exhibits a bile acid level not typically found in normal subjects.

Also provided herein are in vitro, ex vivo and in vivo (e.g., on or in a subject) methods and uses. Such methods and uses can be practiced with any of the peptide sequences set forth herein. In various embodiments, the methods include administering a peptide sequence, such as a FGF19 or FGF21 variant, fusion or chimera disclosed herein (e.g., in the Sequence Listing or Table 1), or a subsequence, a variant or modified form of a FGF19 or FGF21 variant, fusion or chimera disclosed herein (e.g., the Sequence Listing or Table 1), to a subject in an amount effective for treating a bile acid-related or associated disorder.

In certain embodiments, the peptide is administered in combination with an additional therapeutic agent(s) and/or treatment modalities (e.g., an agent useful in the treatment and/or prevention of PBC). The additional therapeutic agent(s) can be administered before, with, or following administration of the peptides described herein.

Also provided here are methods of preventing (e.g., in subjects predisposed to having a particular disorder(s)), delaying, slowing or inhibiting progression of, the onset of, or treating (e.g., ameliorating) a bile acid-related or associated disorder relative to an appropriate matched subject of comparable age, gender, race, etc.). Thus, in various embodiments, a method provided herein for, for example, modulating bile acid homeostasis or treating a bile acid-related or associated disorder includes contacting or administering one or more peptides provided herein (e.g., a variant or fusion of FGF19 and/or FGF21 as set forth in the Sequence Listing or Table 1) in an amount effective to modulate bile acid homeostasis or treat a bile acid-related or associated disorder. In certain embodiments the method further comprises contacting or administering at least one additional therapeutic agent or treatment modality that is useful in the treatment or prevention of a bile acid-related or associated disorder (e.g., PBC).

The term "subject" refers to an animal. Typically, the animal is a mammal that would benefit from treatment with a peptide sequence provided herein. Particular examples include primates (e.g., humans), dogs, cats, horses, cows, pigs, and sheep.

Subjects include those having a disorder, e.g., a bile acid-related or associated disorder, such as cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile duct compression from tumor, bile duct blockade by gall stones); bile acid malabsorption and other disorders involving the distal small intestine, including ileal resection, inflammatory bowel diseases (e.g., Crohn's disease and ulcerative colitis), short bowel syndrome, disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension; or subjects that do not have a disorder but may be at risk of developing the disorder.

Additional bile acid-related or associated disorders that may be treated or prevented with the peptide sequences provided herein include metabolic syndrome, a lipid or glucose disorder, cholesterol or triglyceride metabolism, diabetes (e.g., type 2 diabetes), other hyperglycemic-related disorders, including kidney damage (e.g., tubule damage or nephropathy), liver degeneration, eye damage (e.g., diabetic retinopathy or cataracts), and diabetic foot disorders, and dyslipidemias and their sequelae such as, for example, atherosclerosis, coronary artery disease, cerebrovascular disorders and the like.

Other conditions which may be associated with metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension (including portal hypertension (defined as a hepatic venous pressure gradient (HVPG) greater than 5 mm Hg), cardiovascular disease, stroke and heart failure; Disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; Disorders of cell cycle or cell differentiation processes such as adipose cell tumors, lipomatous carcinomas including, for example, liposarcomas, solid tumors, and neoplasms; Neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; Skin and dermatological disorders and/or disorders of wound healing processes, including erythemato-squamous dermatoses; and Other Disorders such as syndrome X, osteoarthritis, and acute respiratory distress syndrome.

Treatment of a bile acid-related or associated disorder (e.g., NASH) may have the benefit of alleviating or abolishing a disorder secondary thereto. By way of example, a subject suffering from NASH may also have depression or anxiety due to NASH; thus, treating the subject's NASH may also indirectly treat the depression or anxiety. The use of the therapies disclosed herein to target such secondary disorders is also contemplated in certain embodiments.

In particular embodiments, the subject has or is at risk of having PBC. In other particular embodiments, the subject has or is at risk of having NASH.

Subjects at risk of developing a bile acid-related or associated disorder (such as the disorders described above) include, for example, those who may have a family history or genetic predisposition toward such disorder, as well those whose diet may contribute to development of such disorders.

As disclosed herein, treatment methods include contacting or administering a peptide as set forth herein (e.g., a variant or fusion of FGF19 and/or FGF21 as set forth in the Sequence Listing or Table 1) in an amount effective to achieve a desired outcome or result in a subject. A treatment that results in a desired outcome or result includes decreasing, reducing or preventing the severity or frequency of one or more symptoms of the condition in the subject, e.g., an improvement in the subject's condition or a "beneficial effect" or "therapeutic effect." Therefore, treatment can decrease or reduce or prevent the severity or frequency of one or more symptoms of the disorder, stabilize or inhibit progression or worsening of the disorder, and in some instances, reverse the disorder, transiently (e.g., for 1-6, 6-12, or 12-24 hours), for medium term (e.g., 1-6, 6-12, 12-24 or 24-48 days) or long term (e.g., for 1-6, 6-12, 12-24, 24-48 weeks, or greater than 24-48 weeks). Thus, in the case of a bile acid-related or associated disorder, treatment can lower or reduce one or more symptoms or effects of the bile acid-related or associated disorders described above.

In certain embodiments, the various methods provided herein further include contacting or administering one or more additional agents or therapeutic modalities useful in the treatment or prevention of a bile acid-related or associated disorder, such as those agents or therapeutic modalities described herein, in an amount effective to achieve a desired outcome or result in a subject.

An "effective amount" or a "sufficient amount" for use and/or for treating a subject refers to an amount that provides, in single or multiple doses, alone, or in combination with one or more other agents, treatments, protocols, or therapeutic regimens, a detectable response of any duration of time (transient, medium or long term), a desired outcome in or an objective or subjective benefit to a subject of any measurable or detectable degree or for any duration of time (e.g., for hours, days, months, years, in remission or cured). Such amounts typically are effective to ameliorate a disorder, or one, multiple or all adverse symptoms, consequences or complications of the disorder, to a measurable extent, although reducing or inhibiting a progression or worsening of the disorder, is considered a satisfactory outcome.

As used herein, the term "ameliorate" means an improvement in the subject's disorder, a reduction in the severity of the disorder, or an inhibition of progression or worsening of the disorder (e.g., stabilizing the disorder). In the case of a bile acid-related or associated disorder such as those described above, including cholestasis (e.g., PBC), disorders impairing absorption of bile acids leading to diarrhea (e.g., BAD) and bile acid synthesis abnormalities (e.g., NASH), an improvement can be a lowering or a reduction in one or more symptoms or effects of the disorder.

A therapeutic benefit or improvement therefore need not be complete ablation of any one, most or all symptoms, complications, consequences or underlying causes associated with the disorder or disease. Thus, a satisfactory endpoint is achieved when there is a transient, medium or long term, incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of the disorder or disease, over a duration of time (hours, days, weeks, months, etc.).

Thus, in the case of a disorder treatable by a peptide sequence provided herein, either alone or in combination with an additional agent, the amount of the peptide (and optionally the additional agent) sufficient to ameliorate a disorder will depend on the type, severity and extent, or duration of the disorder, the therapeutic effect or outcome desired, and can be readily ascertained by the skilled artisan. Appropriate amounts will also depend upon the individual subject (e.g., the bioavailability within the subject, gender, age, etc.). For example, a transient, or partial, restoration of normal bile acid homeostasis in a subject can reduce the dosage amount or frequency of the peptides and agents described herein in order to treat the bile acid-related or associated disorders described previously even though complete freedom from treatment has not resulted. An effective amount can be ascertained, for example, by measuring one or more relevant physiological effects.

Methods and uses provided herein for treating a subject are applicable for prophylaxis to prevent or reduce the likelihood of a disorder in a subject, such as a bile acid-related or associated disorder. Accordingly, methods and uses provided herein for treating a subject having, or at risk of developing, a bile acid-related or associated disorder can be practiced prior to, substantially contemporaneously with, or following administration or application of another agent useful for the treatment or prevention of a bile acid-related or associated disorder, and/or can be supplemented with other forms of therapy. Supplementary therapies include other glucose lowering treatments, such as insulin, an insulin sensitivity enhancer and other drug treatments, a change in diet (low sugar, fats, etc.), weight loss surgery—(reducing stomach volume by gastric bypass, gastrectomy), gastric banding, gastric balloon, gastric sleeve, etc. For example, a method or use provided herein for treating a hyperglycemic or insulin resistance disorder can be used in combination with drugs or other pharmaceutical compositions that lower glucose or increase insulin sensitivity in a subject.

In still further embodiments, the at least one additional agent effective in modulating bile acid homeostasis or treating a bile acid-related or associated disorder is: a glucocorticoid; CDCA; UDCA; insulin, an insulin secretagogues, an insulin mimetic, a sulfonylurea and a meglitinide; a biguanide; an alpha-glucosidase inhibitors; a DPP-IV inhibitor, GLP-1, a GLP-1 agonists and a GLP-1 analog; a DPP-IV-resistant analogue; a PPAR gamma agonist, a dual-acting PPAR agonist, a pan-acting PPAR agonist; a PTP1B inhibitor; an SGLT inhibitor; an RXR agonist; a glycogen synthase kinase-3 inhibitor; an immune modulator; a beta-3 adrenergic receptor agonist; an 1 lbeta-HSD1 inhibitor; amylin and an amylin analogue; a bile acid sequestrant; or an SGLT-2 inhibitor.

In certain embodiments, the at least one additional agent effective in modulating bile acid homeostasis or treating a bile acid-related or associated disorder, such as PBC is UDCA, an FXR agonist, OCA, an ASBT inhibitor, an autoimmune agent, an anti-IL-12 agent, an anti-CD80 agent, an anti-CD20 agent, a CXCL10 neutralizing antibody, a ligand for CXCR3, a fibrate, fish oil, colchicine, methotrexate, azathioprine, cyclosporine, or an anti-retroviral therapy. In particular embodiments, the at least one additional agent effective in modulating PBC is UDCA, OCA, an ASBT inhibitor, an anti-IL-12 agent, an anti-CD20 agent, or a fibrate.

In some embodiments, the chimeric peptide sequence or a peptide sequence described herein, either alone or in combination with at least one additional therapeutic agent or treatment modality, is assessed to ensure that it does not cause untoward adverse effects in the subject. In a particular aspect, the combination of a chimeric peptide sequence or a peptide sequence described herein and at least one additional therapeutic agent or treatment modality is assessed to ensure that it does not induce HCC in the subject. Such assessments may be performed before initiation of therapy (e.g., in a dose escalation study), during therapy, (e.g., by evaluating a marker correlating with HCC activity), or subsequent to termination of therapy (e.g., by performing a liver biopsy). In some aspects, the assessment is performed in a suitable test environment (e.g., a validated animal model). One of ordinary skill in the art is familiar with additional means for ensuring that any combination therapy described herein is suitable for the particular subject, or a subject population representative of the particular subject, taking into consideration all relevant factors including, for example, the severity of the subject's bile acid-related or associated disorder (e.g., PBC) and the other medications be taken by the subject.

4.6.1 PBC and Therapy with Agents Effective in the Treatment or Prevention Thereof Primary biliary cirrhosis (PBC), the most common cholestatic liver disease, is a progressive hepatic disease that primarily results from autoimmune destruction of the bile ducts that transport bile acids out of the liver. As the disease progresses, persistent toxic build-up of bile acids causes progressive liver damage marked by chronic inflammation and fibrosis. Because patients with PBC have an increased risk of HCC, therapy with the variants of FGF19 peptide sequences, fusions of FGF19 and/or FGF21 peptide sequences and variants of fusions (chimeras) of FGF19 and/or FGF21 peptide sequences described herein is of particular import, as such sequences do not induce, or do not substantially increase, HCC formation or HCC tumorigenesis.

Although patients with PBC are often asymptomatic at the time of initial diagnosis, most present, or subsequently develop, one or more of the following: pruritus; fatigue; jaundice; xanthoma; disorders associated with an extrahepatic autoimmune disorder (e.g., Sjögren's Syndrome and rheumatoid arthritis); and complications that result from cirrhosis or portal hypertension (e.g., ascites, esophageal varices and hepatic encephalopathy).

While a definitive cause of PBC has not been identified, most research suggests that it is an autoimmune disorder. There appears to be a genetic predisposition, and genetic studies have indicated that part of the IL-12 signaling cascade, including IL-12A and I-12RB2 polymorphisms, is important in the etiology of the disease.

There is no definitive means of diagnosing PBC; rather, assessment of a number of factors is generally required. Moreover, diagnosis of PBC requires that other conditions with similar symptoms (e.g., autoimmune hepatitis and primary sclerosing cholangitis) by ruled out; by way of example, abdominal ultrasound or CT scan is usually performed to rule out blockage of the bile ducts.

Diagnostic blood tests include deranged liver function tests (gamma-glutamyl transferase and alkaline phosphatase) and the presence of particular antibodies (antimitochondrial antibody (AMA) an antinuclear antibody (ANA)). Antinuclear antibodies are believed to be prognostic indicators of PBC. When other tests and procedures are indicative of PBC, a liver biopsy is frequently performed to confirm disease. Endoscopic retrograde cholangiopancreatography (ERCP), an endoscopic evaluation of the bile duct, may also be employed to confirm disease.

PBC is classified into four stages marking the progression of disease. Stage 1 (Portal Stage) is characterized by portal inflammation and mild bile duct damage; Stage 2 (Periportal Stage) is characterized by enlarged triads, periportal fibrosis or inflammation; Stage 3 (Septal Stage) is characterized by active and/or passive fibrous septa; and Stage 4 (Biliary Cirrhosis) is characterized by the presence of hepatic nodules. Liver biopsy is required to determine the stage of disease.

Serum bilirubin is an indicator of PBC progression and prognosis. Patients with a serum bilirubin level of 2-6 mg/dL have a mean survival time of 4.1 years, patients with a serum bilirubin level of 6-10 mg/dL have a mean survival time of 2.1 years, and patients with a serum bilirubin level above 10 mg/dL have a mean survival time of 1.4 years. Liver transplantation is an option in advanced cases of PBC, although the recurrence rate may be as high as 18% at 5 years, and up to 30% at 10 years.

Although disease progression may be slowed, pharmaceutical intervention with currently used therapies is neither curative nor effective in all patient populations. In order to improve the therapeutic outcome of pharmacological therapy, one aspect pertains to the use of one or more current therapies in combination with variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of PBC and associated diseases, disorders and conditions. The most commonly used and/or promising agents for combination therapy are set forth hereafter, although it is to be understood that these agents are illustrative, and not exclusionary.

PBC treatment most frequently involves the bile acid ursodeoxycholic acid (Urosdiol, UDCA). UDCA therapy is helpful in reducing the cholestasis and improving the liver function tests in PBC patients; however, it does not demonstrably improve symptoms and has a questionable impact on prognosis. UDCA has been shown to reduce mortality, adverse events and the need for transplantation in PBC. Although UDCA is considered the first-line therapy, approximately one-third of patients may be non-responsive and remain at risk of progressive liver disease and are candidates for alternative or additive therapy.

There are several alternative and adjuvant therapies, some of which are currently in clinical development, that can be used in combination with variants of FGF19 peptide sequences, fusions of FGF19 and/or FGF21 peptide sequences and variants of fusions (chimeras) of FGF19 and/or FGF21 peptide sequences provided herein having one or more activities associated with the treatment and/or prevention of PBC and associated diseases, disorders and conditions.

Farnesoid-X-receptor agonists represent a promising class of agents that may be used in combination therapy. One of the primary functions of agonists of FXR, a nuclear receptor expressed at high levels in the liver and intestine, is the suppression of cholesterol 7α hydroxylase-1 (CYP7A1), the rate-limiting enzyme in the synthesis of bile acids from cholesterol. Obeticholic acid (OCA; Intercept Pharmaceuticals, NY) is a bile acid analog and FXR agonist derived from the primary human bile acid chenodeoxycholic acid, or CDCA. OCA is currently being evaluated for patients having an inadequate therapeutic response to ursodiol or who are unable to tolerate ursodiol.

Inhibitors of the apical sodium-dependent bile acid transporter (ASBT) represent another class of agents that may be used in combination with the variants of FGF19 peptide sequences, fusions of FGF19 and/or FGF21 peptide sequences and variants of fusions (chimeras) of FGF19 and/or FGF21 peptide sequences described herein for the treatment and/or prevention of PBC and associated diseases. ASBT, a member of the sodium/bile-salt co-transport family coded by gene SLC10A2, is currently thought to be the primary mechanism for bile acid reabsorption in the intestine. Examples of ABST inhibitors include LUM001 and SC-435, both of which are being developed by Lumena Pharmaceuticals (San Diego, Calif.).

Bile acid sequestrants also find use in the treatment of PBC. Cholestyramine and colestipol are the best known bile acid sequestrants. However, their use is sometimes limited because they are only available in powder form and are not tolerated by many patients, often because of the poor texture and taste of the resin powder. The bile acid sequestrant colesevelam is available in tablet form and is often better tolerated. All bile acid sequestrants are capable of binding other compounds, including the fat-soluble vitamins A, D, E and K, and deficiencies of these vitamins many necessitate supplementation. Importantly, the PBC patient population inherently has poor lipid-dependent absorption of vitamins A, D, E and K, and thus patients taking bile acid sequestrants are at particular risk for deficiency of those vitamins.

Agents associated with immune and inflammatory function are candidates for combination therapy with the variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of PBC and associated diseases, disorders and conditions.

The interleukin IL-12 is linked with autoimmunity. Data indicate that the IL-12 signaling pathway plays a key role in the effector mechanisms that lead to biliary destruction. Targeting the p40 subunit of IL-12 has also been shown to ameliorate experimental immune-mediated cholangiopathy. Thus, anti-IL-12 agents (e.g., monoclonal Ab inhibitors) provide a promising treatment. Furthermore, because polymorphisms in CD80 have been identified as conferring an increased susceptibility to PBC, blockade of co-stimulation between T cells and antigen-presenting cells through CD80 by use of an anti-CD80 agent could represent an important therapeutic approach for the treatment of PBC. In addition, improvement in IgM titre and an increase in intrahepatic regulatory T-cell number using the anti-CD20 antibody rituximab (RITUXAN) have shown promise.

The immune-mediated destruction of small-sized bile ducts in PBC is predominantly cell-mediated, characterized by Th1 cells, CD8+ T cells, NK cells and NKT cells which express CXCR3. Therefore, neutralizing antibodies to CXCL10, a ligand for CXCR3, may offer the possibility to interfere with one of the key inflammatory processes and contribute to immune-mediated biliary destruction in PBC. Similarly, blockade of co-stimulatory signals between T cells expressing CD28 and antigen-presenting cells expressing CD80 (e.g. cholangiocytes, antibody-secreting B cells) might represent an important approach for the treatment of autoimmune diseases.

The variants of FGF19 peptide sequences, fusions of FGF19 and/or FGF21 peptide sequences and variants of fusions (chimeras) of FGF19 and/or FGF21 peptide sequences described herein can be used alone or in combination with other agents for the treatment and/or prevention of those bile acid-related or associated disorders referenced herein that have an immune and/or inflammatory component, including, but not limited to, PBC and associated diseases, disorders and conditions. Examples of such other agents include, for example, non-steroidal anti-inflammatory drugs (NSAID); steroids; cytokine suppressive anti-inflammatory drug(s) (CSAIDs); antibodies to, or antagonists of, other human cytokines or growth factors (e.g., IL-2, IL-6, or PDGF); TNF antagonists (e.g., agents such as REMICADE, p75TNFRIgG (ENBREL) or p55TNFR1gG (LENERCEPT)); interferon-β1a (AVONEX); interferon-β1b (BETASERON); and immune checkpoint inhibitors, including PD1 (associated agents include the antibodies nivolumab and lambrolizumab), PDL1, BTLA, CTLA4 (associated agents include the fully humanized CTLA4 monoclonal antibody ipilimumab (YERVOY), TIM3, LAGS, and A2aR.

Fibrates have been shown to improve various aspects of PBC, including liver function tests, both as monotherapy and in combination with UDCA non-responders. In certain embodiments, a fibrate is a member selected from the group of bezafibrate (BEZALIP), ciprofibrate (MODALIM), gemfibrozil (LOPID), clofibrate, and fenofibrate (TRICOR). Fish oil has exhibited similar benefits.

In PBC patients demonstrating certain characteristics of hepatitis on biopsy, corticosteroids such as budesonide may improve liver histology and biochemistry, particularly when used in combination with UDCA. Colchicine has been shown to improve liver function tests (e.g., AST and ALP) and represents another alternative treatment for PBC.

Though not an exhaustive list, other drugs that have shown promise include methotrexate as an immunomodulatory treatment, azathioprine, cyclosporine, and certain agents used in anti-retroviral therapy (e.g., combivir).

Various treatments exist for the sequelae associated with PBC. For example, itching can be relieved by the bile acid sequestrant cholestyramine, or alternatively naltrexone and rifampicin. The fatigue associated with PBC may effectively be treated with modafinil (Provigil; Teva (formerly Cephalon)) without damaging the liver. As patients with PBC have increased risk of developing osteoporosis and esophageal varices compared to the general population (and others with liver disease), screening and treatment of these complications is an important part of the management of PBC. Variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of PBC and associated diseases, disorders and conditions, as provided herein, either alone or in combination with other agents, offer novel, promising alternatives to the management of such sequelae. 4.6.2 NASH and NAFLD and Therapy with Agents Effective in the Treatment or Prevention Thereof Non-alcoholic steatohepatitis (NASH), considered part of a spectrum of non-alcoholic fatty liver diseases (NAFLD), causes inflammation and accumulation of fat and fibrous tissue in the liver. Although the exact cause of NASH is unknown, risk factors include central obesity, type-2 diabetes mellitus, insulin resistance (IR) and dyslipidemia; combinations of the foregoing are frequently described as the metabolic syndrome. In addition, certain drugs have been linked to NASH, including tamoxifen, amiodarone and steroids (e.g., prednisone and hydrocortisone). Non-alcoholic fatty liver disease is the most common cause of chronic liver disease in the United States, and the estimated prevalence of NAFLD is 20-30% and for NASH it is estimated at 3.5-5%. (See, e.g., Abrams, G. A., et al., Hepatology, 2004. 40(2):475-83; Moreira, R. K., Arch Pathol Lab Med, 2007. 131(11):1728-34).

NASH frequently presents with no overt symptoms, complicating its diagnosis. Liver function tests generally begin the diagnostic process, with levels of AST (aspartate aminotransferase) and ALT (alanine aminotransferase) elevated in about 90% percent of individuals with NASH. Other blood tests are often used for ruling out other causes of liver disease, such as hepatitis. Imaging tests (e.g., ultrasound, CT scan, or MRI) may reveal fat accumulation in the liver but frequently cannot differentiate NASH from other causes of liver disease that have a similar appearance. A liver biopsy is required to confirm NASH.

The prognosis for individuals suffering from NASH is difficult to predict, although features in the liver biopsy can be helpful. The most serious complication of NASH is cirrhosis, which occurs when the liver becomes severely scarred. It has been reported that between 8 and 26 percent of individuals with NASH develop cirrhosis, and it is predicted that NASH will be the leading indication for liver transplantation by 2020.

At the present time, treatment of NASH focuses primarily on pharmacological and non-pharmacological management of those medical conditions associated with it, including hyperlipidemia, diabetes and obesity. Although not curative, pharmacological intervention of NASH itself includes treatment with vitamin E, pioglitazone, metformin, statins, omega-3 fatty acids, and ursodeoxycholic acid (UDCA (ursodiol)). Other agents being evaluated, currently approved for different indications, include losartan and telisartan, exenatide, GLP-1 agonists, DPP IV inhibitors, and carbamazepine.

In view of the deficiencies of the aforementioned current therapies, therapy with agents having distinct mechanisms of action offers a promising new avenue for the treatment and prevention of NASH and NAFLD. Addressing such deficiencies is contemplated, for example, by using the variants of FGF19 peptide sequences, fusions of FGF19 and/or FGF21 peptide sequences and variants of fusions (chimeras) of FGF19 and/or FGF21 peptide sequences as taught herein. In certain embodiments, the peptides are used in combination with other therapeutic agents and/or treatment modalities. Also provided herein is the prophylactic and/or therapeutic use of these variants of FGF19 peptide sequences, fusions of FGF19 and/or FGF21 peptide sequences and variants of fusions (chimeras) of FGF19 and/or FGF21 peptide sequences, either alone or in combination with therapies developed in the future, for the treatment or prevention of NASH and NAFLD.

4.6.3 Therapy for the Treatment or Prevention of Other Bile Acid-Related Disorders and Associated Diseases, Disorders and Conditions Also provided herein is the use of variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of other bile acid-related disorders and associated diseases, disorders and conditions besides PBC. In certain embodiments, the peptides are used in combination with other therapeutic agents and/or treatment modalities.

By way of example, patients with bile acid diarrhea secondary to Crohn's ileitis will be helped with glucocorticoid treatment. Microscopic colitis is also helped by steroids. In patients with a short-bowel syndrome (a bile acid deficiency occurs in the proximal intestine that leads to impaired micellar solubilization), cholylsarcosine (cholyl-N-methylglycine), a synthetic bile acid analogue, has been shown to increase lipid absorption.

Administration of the primary bile acid chenodeoxycholic Acid (CDCA) has been shown to decrease biliary cholesterol secretion and gradual dissolution of gallstones. Because CDCA is slightly hepatotoxic, it was gradually replaced by UDCA. Despite the efficacy and safety of UDCA administration for cholesterol gallstone dissolution, it is not frequently used today because of the success of laparoscopic cholecystectomy, which provides a rapid cure for symptomatic disease. Medical therapy, in contrast, requires months of therapy, does not always dissolve stones, and is followed by gradual recurrence in some patients.

Bile acid replacement is used in inborn errors of bile acid biosynthesis, usually with a mixture of CDCA or UDCA and cholic acid, to suppress the synthesis of cytotoxic bile acid precursors and restore the input of primary bile acids into the enterohepatic circulation.

In addition to the agents and therapeutic modalities set forth above, combination therapy with numerous additional agents (and classes thereof) is also contemplated, including. but not limited to, 1) insulin e.g., bolus and basal analogs), insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA and ITCA 650 (an osmotic pump inserted subcutaneously that delivers an exenatide analog over a 12-month period; Intarcia, Boston, Mass.)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, RXR agonists, glycogen synthase kinase-3 inhibitors, immune modulators, beta-3 adrenergic receptor agonists, 11beta-HSD1 inhibitors, and amylin analogues.

Other exemplary agents that can be used, in certain embodiments, in combination with the peptides and methods provided herein include dipeptidyl peptidase-4 (DPP-4) inhibitors, bromocriptine formulations (e.g. and bile acid sequestrants (e.g., colesevelam), and SGLT-2 inhibitors. Appetite suppression drugs are also well known and can be used in combination with the compositions and methods provided herein. Supplementary therapies can be administered prior to, contemporaneously with or following methods and uses provided herein 4.7 Dosing and Administration Peptide sequences provided herein including subsequences, sequence variants and modified forms of the exemplified peptide sequences (e.g., sequences listed in the Sequence Listing or Table 1), may be formulated in a unit dose or unit dosage form. In a particular embodiment, a peptide sequence is in an amount effective to treat a subject in need of treatment, e.g., due to abnormal or aberrant bile acid homeostasis, such as metabolic syndrome; a lipid- or glucose-related disorder; cholesterol or triglyceride metabolism; type 2 diabetes; cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile duct compression from tumor, bile duct blockage by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension. Exemplary unit doses range from about 25-250, 250-500, 500-1000, 1000-2500 or 2500-5000, 5000-25,000, 25,000-50,000 ng; from about 25-250, 250-500, 500-1000, 1000-2500 or 2500-5000, 5000-25,000, 25,000-50,000 mg; and from about 25-250, 250-500, 500-1000, 1000-2500 or 2500-5000, 5000-25,000, 25,000-50,000 mg.

Peptide sequences provided herein including subsequences, sequence variants and modified forms of the exemplified peptide sequences (e.g., sequences listed in the Sequence Listing or Table 1) can be administered to provide the intended effect as a single dose or multiple dosages, for example, in an effective or sufficient amount. Exemplary doses range from about 25-250, 250-500, 500-1000, 1000-2500 or 2500-5000, 5000-25,000, 25,000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 25,000-50,000 mg/kg. Single or multiple doses can be administered, for example, multiple times per day, on consecutive days, alternating days, weekly or intermittently (e.g., twice per week, once every 1, 2, 3, 4, 5, 6, 7 or 8 weeks, or once every 2, 3, 4, 5 or 6 months).

Peptide sequences provided herein including subsequences, variants and modified forms of the exemplified peptide sequences (e.g., sequences listed in the Sequence Listing or Table 1) can be administered and methods may be practiced via systemic, regional or local administration, by any route. For example, a peptide sequence can be administered parenterally (e.g., subcutaneously, intravenously, intramuscularly, or intraperitoneally), orally (e.g., ingestion, buccal, or sublingual), inhalation, intradermally, intracavity, intracranially, transdermally (topical), transmucosally or rectally. Peptide sequences provided herein including subsequences, variants and modified forms of the exemplified peptide sequences (e.g., sequences listed in the Sequence Listing or Table 1) and methods provided herein including pharmaceutical compositions can be administered via a (micro)encapsulated delivery system or packaged into an implant for administration.

A particular non-limiting example of parenteral (e.g., subcutaneous) administration entails the use of Intarcia's subcutaneous delivery system (Intarcia Therapeutics, Inc.; Hayward, Calif.). The system comprises a miniature osmotic pump that delivers a consistent amount of a therapeutic agent over a desired period of time. In addition to maintaining drug levels within an appropriate therapeutic range, the system can be used with formulations that maintain the stability of proteinaceous therapeutic agents at human body temperature for extended periods of time.

Another non-limiting example of parenteral administration entails the use of DUROS®-type implantable osmotic pumps (from, e.g., DURECT Corp.). The DUROS® system can be used for therapies requiring systemic or site-specific administration of a drug. To deliver drugs systemically, the DUROS® system is placed just under the skin, for example in the upper arm, in an outpatient procedure that is completed in just a few minutes using local anesthetic. To deliver a drug to a specific site, miniaturized catheter technology can be used. The catheter can be attached to the DUROS® system to direct the flow of a drug to the target organ, tissue or synthetic medical structure, such as a graft. Site-specific delivery enables a therapeutic concentration of a drug to be administered to the desired target without exposing the entire body to a similar concentration. The precision, size and performance of the DUROS® system will allow for continuous site-specific delivery to a variety of precise locations within the body.

Yet another non-limiting example of parenteral administration entails the use of an on-body delivery system (e.g., the Neulasta® Delivery Kit by Amgen). This on-body delivery system includes an on-body injector, which is a small, lightweight, injection system applied on the same day as a doctor visit (such as the day of chemotherapy). It is designed to deliver a dose of the therapeutic agent the next day, or in the near future of the doctor visit, so that the patient does not need to return to the doctor's office to receive the injection.

4.8 Compositions

Also provided herein are "pharmaceutical compositions," which include a peptide sequence (or sequences) provided herein, including subsequences, variants and modified forms of the exemplified peptide sequences (e.g., sequences listed in the Sequence Listing or Table 1), and one or more pharmaceutically acceptable or physiologically acceptable diluents, carriers or excipients; in combination with, or separate from, one or more additional agents for the treatment of a bile acid-related disease, disorder or condition, or a composition comprising such one or more additional agents and one or more pharmaceutically acceptable or physiologically acceptable diluents, carriers or excipients. In particular embodiments, a peptide sequence or sequences and an additional agent(s) are present in a therapeutically acceptable amount. The pharmaceutical compositions may be used in accordance with the methods and uses provided herein. Thus, for example, the pharmaceutical compositions can be administered ex vivo or in vivo to a subject in order to practice treatment methods and uses provided herein. Pharmaceutical compositions provided herein can be formulated to be compatible with the intended method or route of administration; exemplary routes of administration are set forth herein.

In some aspects, the pharmaceutical compositions may further comprise other therapeutically active agents or compounds disclosed herein (e.g., bile acid stabilizing agents or drugs) or known to the skilled artisan which can be used in the treatment or prevention of various bile acid diseases and disorders as set forth herein. As set forth above, the additional therapeutically active agents or compounds may be present in a separate pharmaceutical composition(s). Exemplary dosing parameters and regimens are described herein.

Pharmaceutical compositions typically comprise a therapeutically effective amount of at least one of the peptide sequences provided herein, including subsequences, variants and modified forms of the exemplified peptide sequences (e.g., sequences listed in the Sequence Listing or Table 1) and/or one or more additional agents described herein, and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms used herein. Typical buffers include, but are not limited to pharmaceutically acceptable weak acids, weak bases, or mixtures thereof. Buffer components also include water soluble materials such as phosphoric acid, tartaric acids, lactic acid, succinic acid, citric acid, acetic acid, ascorbic acid, aspartic acid, glutamic acid, and salts thereof.

A primary solvent in a vehicle may be either aqueous or non-aqueous in nature. In addition, the vehicle may contain other pharmaceutically acceptable excipients for modifying or maintaining the pH, osmolarity, viscosity, sterility or stability of the pharmaceutical composition. In certain embodiments, the pharmaceutically acceptable vehicle is an aqueous buffer. In other embodiments, a vehicle comprises, for example, sodium chloride and/or sodium citrate.

Pharmaceutical compositions provided herein may contain still other pharmaceutically-acceptable formulation agents for modifying or maintaining the rate of release of a peptide and/or an additional agent, as described herein. Such formulation agents include those substances known to artisans skilled in preparing sustained-release formulations. For further reference pertaining to pharmaceutically and physiologically acceptable formulation agents, see, for example, *Remington's Pharmaceutical Sciences,* 18th Ed. (1990, Mack Publishing Co., Easton, Pa. 18042) pages 1435-1712, *The Merck Index,* 12th Ed. (1996, Merck Publishing Group, Whitehouse, N.J.); and *Pharmaceutical Principles of Solid Dosage Forms* (1993, Technonic Publishing Co., Inc., Lancaster, Pa.). Additional pharmaceutical compositions appropriate for administration are known in the art and are applicable in the methods and compositions provided herein.

A pharmaceutical composition may be stored in a sterile vial as a solution, suspension, gel, emulsion, solid, or dehydrated or lyophilized powder. Such compositions may be stored either in a ready to use form, a lyophilized form requiring reconstitution prior to use, a liquid form requiring dilution prior to use, or other acceptable form. In some embodiments, a pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver peptides and the other agents described herein, including implants (e.g., implantable pumps) and catheter systems, both of which are known to the skilled artisan. Depot injections, which are generally administered subcutaneously or intramuscularly, may also be utilized to release peptides and/or other agents described herein over a defined period of time. Depot injections are usually either solid- or oil-based and generally comprise at least one of the formulation components set forth herein. The skilled artisan is familiar with possible formulations and uses of depot injections. In certain embodiments, the use of Nano Precision Medical's depot delivery technology (Nano Precision Medical; Emeryville, Calif.) is contemplated. The technology utilizes a titania nanotube membrane that produces zero-order release rates of macromolecules, such as protein and peptide therapeutics. The biocompatible membrane is housed in a small, subcutaneous implant that provides long-term (e.g., up to one year), constant-rate delivery of therapeutic macromolecules. The technology is currently being evaluated, e.g., for the delivery of GLP-1 agonists for the treatment of Type II diabetes.

A pharmaceutical composition can be formulated to be compatible with its intended route of administration. Thus, pharmaceutical compositions include carriers, diluents, or excipients suitable for administration by routes including parenteral (e.g., subcutaneous (s.c.), intravenous, intramuscular, or intraperitoneal), intradermal, oral (e.g., ingestion), inhalation, intracavity, intracranial, and transdermal (topical).

Pharmaceutical compositions may be in the form of a sterile injectable aqueous or oleagenous suspension. This suspension may be formulated using suitable dispersing or wetting agents and suspending agents disclosed herein or known to the skilled artisan. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

Pharmaceutical compositions may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions. Such compositions may contain one or more agents such as sweetening agents, flavoring agents, coloring agents and preserving agents in order to provide pharmaceutically elegant and palatable preparations. Tablets containing a peptide provided herein may be in admixture with non-toxic pharmaceutically acceptable excipients suitable for the manufacture of tablets. These excipients include, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

Tablets, capsules and the like suitable for oral administration may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by addition of water provide the active ingredient in admixture with a dispersing or wetting agent, suspending agent and one or more preservatives. Suitable dispersing or wetting agents and suspending agents are exemplified herein.

Pharmaceutical compositions provided herein may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Pharmaceutical compositions can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed. Prolonged absorption of injectable pharmaceutical compositions can be achieved by including an agent that delays absorption, for example, aluminum monostearate or gelatin. Prevention of the action of microorganisms can be achieved by various antibacterial and antifungal agents, for example, parabens, chlorobutanol, phenol, ascorbic acid, thimerosal, and the like.

Also provided herein are peptides and/or one or more additional agents described herein in the form of suppositories for rectal administration. The suppositories can be prepared by mixing a peptide and/or one or more additional agents described herein with a suitable non-irritating excipient which is solid at ordinary temperatures but liquid at the rectal temperature and will therefore melt in the rectum to release the drug. Such materials include, but are not limited to, cocoa butter and polyethylene glycols.

4.9 Methods of Identifying Modulators of Bile Acid-Related or Associated Disorders Also provided herein are methods of identifying a peptide (or a subsequence, variant or modified form as set forth herein) that modulates bile acid homeostasis without having substantial HCC activity. In one embodiment, a method includes: providing a candidate peptide sequence; administering the candidate peptide sequence to a test animal; measuring bile acid levels of the animal after administration of the candidate peptide sequence, to determine if the candidate peptide sequence favorably modulates bile acid homeostasis; and analyzing the candidate peptide sequence for induction of HCC in the animal, or expression of a marker correlating with HCC activity. A candidate peptide that modulates bile acid homeostasis but does not have substantial HCC activity thereby identifies a peptide sequence that modulates bile acid homeostasis without substantial HCC activity.

The terms "assaying" and "measuring" and grammatical variations thereof are used interchangeably herein and refer to either qualitative or quantitative determinations, or both qualitative and quantitative determinations. When the terms are used in reference to detection, any means of assessing the relative amount is contemplated, including the various methods set forth herein and known in the art. For example, bile acids and precursors, such as 7 alpha-hydroxy-4-cholesten-3-one, can be assayed or measured in a sample (e.g., serum) from a subject. Another non-limiting examples is a two reaction method (Randox Laboratories, Ltd.) using serum or heparinized plasma. In the first reaction bile acids are oxidized by 3-α-hydroxysteroid dehydrogenase with the subsequent reduction of Thio-NAD to Thio-NADH. In the second reaction, oxidized bile acids are reduced by the same enzyme with the subsequent oxidation of NADH to NAD.

The rate of formation of Thio-NADH is determined by measuring the specific absorbance change at 405 nm.

Risk factors for HCC, the most common type of liver cancer, include type 2 diabetes (probably exacerbated by obesity). The risk of HCC in type 2 diabetics is greater (from ~2.5 to ~7 times the non-diabetic risk) depending on the duration of diabetes and treatment protocol.

Various methodologies can be used in the screening and diagnosis of HCC and are well known to the skilled artisan. Indicators for HCC include detection of a tumor maker such as elevated alpha-fetoprotein (AFP) or des-gamma carboxy-prothrombin (DCP) levels. A number of different scanning and imaging techniques are also helpful, including ultrasound, CT scans and MRI. In certain embodiments, evaluation of whether a peptide (e.g., a candidate peptide) exhibits evidence of inducing HCC may be determined in vivo by, for example, quantifying HCC nodule formation in an animal model, such as db/db mice, administered a peptide, compared to HCC nodule formation by wild type FGF19. Macroscopically, liver cancer may be nodular, where the tumor nodules (which are round-to-oval, grey or green, well circumscribed but not encapsulated) appear as either one large mass or multiple smaller masses. Alternatively, HCC may be present as an infiltrative tumor which is diffuse and poorly circumscribed and frequently infiltrates the portal veins.

Pathological assessment of hepatic tissue samples is generally performed after the results of one or more of the aforementioned techniques indicate the likely presence of HCC. Thus, methods provided herein may further include assessing a hepatic tissue sample from an in vivo animal model (e.g., a db/db mouse) useful in HCC studies in order to determine whether a peptide sequence exhibits evidence of inducing HCC. By microscopic assessment, a pathologist can determine whether one of the four general architectural and cytological types (patterns) of HCC are present (i.e., fibrolamellar, pseudoglandular (adenoid), pleomorphic (giant cell) and clear cell).

It is to be understood that the techniques, assays and the like described in this section are applicable to identifying an additional agent described herein having desired properties and/or characteristics. Moreover, the techniques, assays and the like described in this section are applicable to identifying a peptide in combination with an additional agent described herein, for example, a composition comprising a peptide in combination with an additional agent described herein that has at least one favorable characteristic; or a treatment regimen comprising a peptide provided herein in combination with an additional agent described herein that has at least one favorable characteristic.

4.10 Antibodies

Also provided herein is the generation and use of antibodies, and fragments thereof, that bind the peptide sequences provided herein, including subsequences, sequence variants and modified forms of the exemplified peptide sequences (including the peptides listed in the Sequence Listing or Table 1), and/or one or more additional agents as described herein.

As used herein, the terms "antibodies" (Abs) and "immunoglobulins" (Igs) refer to glycoproteins having the same structural characteristics. While antibodies exhibit binding specificity to an antigen, immunoglobulins include both antibodies and other antibody-like molecules which may lack antigen specificity.

The term "antibody" includes intact monoclonal antibodies, polyclonal antibodies, multispecific antibodies (e.g., bispecific antibodies) formed from at least two intact antibodies, and antibody binding fragments including Fab and F(ab)'2, provided that they exhibit the desired biological activity. The basic antibody structural unit comprises a tetramer, and each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. In contrast, the carboxy-terminal portion of each chain defines a constant region primarily responsible for effector function. Human light chains are classified as kappa and lambda light chains, whereas human heavy chains are classified as mu, delta, gamma, alpha, or epsilon, and define the antibody's isotype as IgM, IgD, IgA, and IgE, respectively. Binding fragments are produced by recombinant DNA techniques, or by enzymatic or chemical cleavage of intact antibodies. Binding fragments include Fab, Fab', F(ab')2, Fv, and single-chain antibodies.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Within light and heavy chains, the variable and constant regions are joined by a "J" region of about 12 or more amino acids, with the heavy chain also including a "D" region of about 10 more amino acids. The antibody chains all exhibit the same general structure of relatively conserved framework regions (FR) joined by three hyper-variable regions, also called complementarity-determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

An intact antibody has two binding sites and, except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab' fragments.

As used herein, the term "monoclonal antibody" refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. In contrast to polyclonal antibody preparations which include different antibodies directed against different determinants (epitopes), each monoclonal antibody is directed against a single determinant on the antigen.

A "neutralizing antibody" is an antibody molecule that is able to eliminate or significantly reduce an effector function of a target antigen to which it binds.

Antibody binding fragments may be produced by enzymatic or chemical cleavage of intact antibodies. Digestion of antibodies with the enzyme papain results in two identical antigen-binding fragments, also known as "Fab" fragments, and an "Fc" fragment which has no antigen-binding activity. Digestion of antibodies with the enzyme pepsin results in a F(ab')2 fragment in which the two arms of the antibody molecule remain linked and comprise two-antigen binding sites. The F(ab')$_2$ fragment has the ability to crosslink antigen.

The term "Fab" refers to a fragment of an antibody that comprises the constant domain of the light chain and the CH1 domain of the heavy chain. The term "Fv" when used herein refers to the minimum fragment of an antibody that retains both antigen-recognition and antigen-binding sites. In a two-chain Fv species, this region consists of a dimer of one heavy-chain and one light-chain variable domain in non-covalent association. In a single-chain Fv species, one heavy-chain and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. While the six CDRs, collectively, confer antigen-binding specificity to the antibody, even a single variable domain (or half of an Fv comprising only three CDRs specific for an antigen) has the ability to recognize and bind antigen.

The terms "complementarity determining regions" or "CDRs" refer to parts of immunological receptors that make contact with a specific ligand and determine its specificity. The term "hypervariable region" refers to the amino acid residues of an antibody which are responsible for antigen-binding. The hypervariable region generally comprises amino acid residues from a "complementarity determining region" or "CDR" and/or those residues from a "hypervariable loop".

As used herein, the term "epitope" refers to binding sites for antibodies on protein antigens. Epitopic determinants usually consist of chemically active surface groupings of molecules such as amino acids or sugar side chains, as well as specific three dimensional structural and charge characteristics. An antibody is said to bind an antigen when the dissociation constant is ≤1 µM, such as ≤100 nM or ≤10 nM. An increased equilibrium constant ("$K_D$") means that there is less affinity between the epitope and the antibody, whereas a decreased equilibrium constant means that there is a higher affinity between the epitope and the antibody. An antibody with a $K_D$ of "no more than" a certain amount means that the antibody will bind to the epitope with the given $K_D$ or more strongly. Whereas $K_D$ describes the binding characteristics of an epitope and an antibody, "potency" describes the effectiveness of the antibody itself for a function of the antibody. There is not necessarily a correlation between an equilibrium constant and potency; thus, for example, a relatively low $K_D$ does not automatically mean a high potency.

The term "selectively binds" in reference to an antibody does not mean that the antibody only binds to a single substance, but rather that the $K_D$ of the antibody to a first substance is less than the $K_D$ of the antibody to a second substance. An antibody that exclusively binds to an epitope only binds to that single epitope.

When administered to humans, antibodies that contain rodent (murine or rat) variable and/or constant regions are sometimes associated with, for example, rapid clearance from the body or the generation of an immune response by the body against the antibody. In order to avoid the utilization of rodent-derived antibodies, fully human antibodies can be generated through the introduction of human antibody function into a rodent so that the rodent produces fully human antibodies. Unless specifically identified herein, "human" and "fully human" antibodies can be used interchangeably herein. The term "fully human" can be useful when distinguishing antibodies that are only partially human from those that are completely, or fully human. The skilled artisan is aware of various methods of generating fully human antibodies.

In order to address possible human anti-mouse antibody responses, chimeric or otherwise humanized antibodies can be utilized. Chimeric antibodies have a human constant region and a murine variable region, and, as such, human anti-chimeric antibody responses may be observed in some patients. Therefore, it is advantageous to provide fully human antibodies against multimeric enzymes in order to avoid possible human anti-mouse antibody or human anti-chimeric antibody responses.

Fully human monoclonal antibodies can be prepared, for example, by the generation of hybridoma cell lines by techniques known to the skilled artisan. Other preparation methods involve the use of sequences encoding particular antibodies for transformation of a suitable mammalian host cell, such as a CHO cell. Transformation can be by any known method for introducing polynucleotides into a host cell, including, for example, packaging the polynucleotide in a virus (or into a viral vector) and transducing a host cell with the virus (or vector) or by transfection procedures known in the art. Methods for introducing heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Mammalian cell lines available as hosts for expression are well known in the art and include, but are not limited to CHO cells, HeLa cells, and human hepatocellular carcinoma cells.

Antibodies can be used diagnostically and/or therapeutically. For example, the antibodies can be used as a diagnostic by detecting the level of one or more peptides provided herein in a subject, and either comparing the detected level to standard control level or to a baseline level in a subject determined previously (e.g., prior to any illness). The antibodies can be used as a therapeutic to modulate the activity of one or more peptides provided herein and/or one or more additional agents described herein, thereby having an effect on a condition or disorder.

4.11 Kits

Also provided herein are kits including, but not limited to, peptide sequences provided herein and/or one or more additional agents for the treatment of a bile acid-related or associated disease, disorder or condition, or a composition comprising the foregoing, and one or more pharmaceutically acceptable or physiologically acceptable diluents, carriers or excipients, optionally in further combination with one or more therapeutic agents distinct from those described above, compositions and pharmaceutical compositions thereof, packaged into suitable packaging material. A kit may include a label or packaging insert including a description of the components or instructions for use in vitro, in vivo, or ex vivo, of the components therein. Exemplary instructions include instructions for treatment and/or prevention of a bile acid-related or associated disorder, such as cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile duct compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension, etc.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits provided herein can include labels or inserts. Labels or inserts include "printed matter," e.g., paper or cardboard, separate or affixed to a component, a kit or packing material (e.g., a box), or attached to, for example, an ampule, tube or vial containing a kit component. Labels or inserts can additionally include a computer readable medium, such as a disk (e.g., hard disk, card, memory disk), optical disk such as CD- or DVD-ROM/RAM, DVD, MP3, magnetic tape, or an electrical storage media such as RANI and ROM or hybrids of these such as magnetic/optical storage media, FLASH media or memory type cards. In some embodiments, the instructions recite a method provided herein.

Labels or inserts can include, among other things, identifying information of one or more components therein, dosing parameters, and/or information on the clinical pharmacology of the active ingredient(s), including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimens set forth herein. Exemplary instructions include instructions for treatment or use of a peptide sequence as set forth herein and/or the use of an additional agent or treatment modality useful in treating a bile acid-related or associated disorder, or a disorder of bile acid homeostasis. Kits provided herein therefore can additionally include labels or instructions for practicing any of the methods and uses provided herein, including treatment methods and uses.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse effects could also occur when the subject has, will be, or is currently taking one or more other medications that may be incompatible with the composition, or the subject has, will be, or is currently undergoing another treatment protocol or therapeutic regimen which would be incompatible with the composition and, therefore, instructions could include information regarding such incompatibilities.

Kits provided herein can additionally include other components. Each component of the kit can be enclosed within an individual container and all of the various containers can be within a single package. In certain embodiments, kits are designed for cold storage. Kits provided herein can further be designed to contain peptide sequences provided herein, or that contain nucleic acids encoding peptide sequences. Kits provided herein can also be designed to contain, either separately or in combination with the peptide sequences provided herein, one or more additional agents useful in the treatment or prevention of a bile acid-related or associated disease or disorder. Any cells in the kit can be maintained under appropriate storage conditions until ready to use.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

In case of conflict, the specification, including definitions, will control. As used herein and in the appended claims, the singular forms "a," "an," and "the" include plural referents unless the context clearly dictates otherwise. Thus, for example, reference to "a peptide sequence" or "a treatment," includes a plurality of such sequences, treatments, and so forth. It is further noted that the claims can be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges, unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1000, 1000-2500, 2500-5000, 5000-25,000, or 5000-50,000 includes any numerical value or range within or encompassing such values, e.g., 25, 26, 27, 28, 29 ... 250, 251, 252, 253, 254 ... 500, 501, 502, 503, 504 ..., etc. The use of a series of ranges includes combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

A number of embodiments of the invention have been described. Nevertheless, it will be understood that various modifications may be made without departing from the spirit and scope of the invention. Accordingly, the descriptions in the Experimental section are intended to illustrate but not limit the scope of invention described in the claims.

5. EXPERIMENTAL

The following is a description of various methods and materials used in the studies, and are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present invention. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); s or sec=second(s); min=minute(s); h or hr=hour(s); aa=amino acid(s); kb=kilobase(s); nt=nucleotide(s); pg=picogram; ng=nanogram; µg=microgram; mg=milligram; g=gram; kg=kilogram; pl or pL=picoliter(s); dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; TIW=three times a week; QM=monthly; HPLC=high performance liquid chromatography; BW=body weight; U=unit; ns=not statistically significant; PBS=phosphate-buffered saline; PCR=polymerase chain reaction; NHS=N-Hydroxysuccinimide; HSA=human serum albumin; BSA=bovine serum albumin; DMEM=Dulbeco's Modification of Eagle's Medium; GC=genome copy; EDTA=ethylenediaminetetraacetic acid.

5.1 Materials and Methods

The following general materials and methods can be used.
5.1.1 Standard Molecular Biology Techniques Standard methods in molecular biology are described in the scientific literature (see, e.g., Sambrook and Russell (2001) *Molecular Cloning*, 3$^{rd}$ ed., Cold Spring Harbor Laboratory Press, Cold Spring Harbor, N.Y.; and Ausubel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) *Current Protocols in Protein Science*, Vols. 1-2, John Wiley and Sons, Inc., NY).

Production, purification, and fragmentation of polyclonal and monoclonal antibodies are described (e.g., Harlow and Lane (1999) *Using Antibodies*, Cold Spring Harbor Laboratory Press, Cold Spring Harbor, N.Y.); standard techniques for characterizing ligand/receptor interactions are available (see, e.g., Coligan et al. (2001) *Current Protocols in Immunology*, Vol. 4, John Wiley, Inc., NY); methods for flow cytometry, including fluorescence-activated cell sorting (FACS), are available (see, e.g., Shapiro (2003) *Practical Flow Cytometry*, John Wiley and Sons, Hoboken, N.J.); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, Oreg.; Sigma-Aldrich (2003) Catalogue, St. Louis, Mo.).

5.1.2 Software

Software packages and databases for determining, e.g., antigenic fragments, leader sequences, protein folding, functional domains, glycosylation sites, and sequence alignments, are available (see, e.g., GCG Wisconsin Package™ (Accelrys, Inc., San Diego, Calif.); and DeCypher™ (TimeLogic Corp., Crystal Bay, Nev.).

5.1.3 Animals

Mice can be purchased from The Jackson Laboratory (Bar Harbor, Me.) and used in various models, assays and the like familiar to the skilled artisan. By way of example, db/db mice (The Jackson Laboratory) can be kept in accordance with welfare guidelines under controlled light (12 hr light and 12 hr dark cycle, dark 6:30 pm-6:30 am), temperature (22±4° C.) and humidity (50%±20%) conditions. Mice can have free access to water (autoclaved distilled water) and can be fed ad libitum on a commercial diet (Harlan Laboratories, Indianapolis, Ind., Irradiated 2018 Teklad Global 18% Protein Rodent Diet) containing 17 kcal % fat, 23 kcal % protein and 60 kcal % carbohydrate. All animal studies can be approved by the NGM Institutional Animal Care and Use Committee.

5.1.4 DNA and Amino Acid Sequences cDNA of ORF encoding human FGF19 (*Homo sapiens* FGF19, GenBank Accession No. NM_005117.2) and protein sequence encoded by the cDNA (GenBank Accession No. NP_005108.1) can be used herein.

5.1.5 PCR

FGF19 ORF can be amplified with polymerase chain reaction (PCR) using recombinant DNA (cDNA) prepared from human small intestinal tissue. PCR reagent kits with Phusion® high-fidelity DNA polymerase can be purchased from New England BioLabs (F-530L, Ipswich, Mass.). The following primers can be used:

```
forward PCR primer:
                                        (SEQ ID NO: 136)
5' CCGACTAGTCACCatgcggagcgggtgtgtgg,
``` and

```
reverse PCR primer:
                                        (SEQ ID NO: 137)
5' ATAAGAATGCGGCCGCTTACTTCTCAAAGCTGGGACTCCTC.
```

Amplified DNA fragment can be digested with restriction enzymes Spe I and Not I (the restriction sites are frequently not included in the 5' or 3' PCR primers, respectively) and then ligated with AAV transgene vectors that have been digested with the same restriction enzymes. The vector that can be used for expression can contain a selectable marker and an expression cassette comprising a strong eukaryotic promoter 5' of a site for insertion of the cloned coding sequence, followed by a 3' untranslated region and a bovine growth hormone polyadenylation tail. The expression construct can also be flanked by internal terminal repeats at the 5' and 3' ends.

5.1.6 CYP7A1 Repression Assay in Primary Human Hepatocytes

Primary human hepatocytes can be plated on collagen-coated plates (Becton Dickinson Biosciences) in Williams E media (Invitrogen) supplemented with 100 nM dexamethasone (Sigma) and 0.25 mg/ml MatriGel™ (Becton Dickinson Biosciences). Cells can be treated with FGF19 or variants at 37° C. for 6 hours. CYP7A1 expression can be evaluated in triplicate by quantitative RT-PCR (TaqMane ABI PRISM 7700, Applied Biosystems) and normalized to GAPDH expression.

5.1.7 CYP7A1 In Vivo Repression Assay

Nine-week-old male db/db mice (Jackson Laboratories) can be injected intraperitoneally with recombinant proteins FGF19 or FGF21 at 0.1 mg/kg, 1 mg/kg, and 10 mg/kg. Animals can be euthanized 5 hours post-injection. Livers can be harvested and homogenized in TRIzol® reagent (Invitrogen). Total RNA can be extracted and treated with DNase (Ambion) followed by quantitative RT-PCR analysis and normalized to GAPDH expression.

5.1.8 Production and Purification of AAV

AAV293 cells (which can be obtained from Agilent Technologies, Santa Clara, Calif.) can be cultured in Dulbeco's Modification of Eagle's Medium (DMEM, Mediatech, Inc. Manassas, Va.) supplemented with 10% fetal bovine serum and 1× antibiotic-antimycotic solution (Mediatech, Inc. Manassas, Va.). The cells can be plated at 50% density on day 1 in 150 mm cell culture plates and can be transfected on day 2, using calcium phosphate precipitation method with the following 3 plasmids (20 µg/plate of each): AAV transgene plasmid, pHelper™ plasmids (Agilent Technologies) and AAV2/9 plasmid (Gao et al., J. Virol. 78:6381 (2004)). Forty-eight (48) hours after transfection, the cells can be scraped off the plates, pelleted by centrifugation at 3000×g and resuspended in buffer containing 20 mM Tris pH 8.5, 100 mM NaCl and 1 mM $MgCl_2$. The suspension can be frozen in an alcohol dry ice bath and then thawed in a 37° C. water bath. The freeze and thaw cycles can be repeated three times; Benzonase® (Sigma-aldrich, St. Louis, Mo.) can be added to 50 units/ml; deoxycholate can be added to a final concentration of 0.25%. After incubation at 37° C. for 30 min, cell debris can be pelleted by centrifugation at 5000×g for 20 min. Viral particles in the supernatant can be purified using a gradient comparable to discontinued iodixanal (Sigma-aldrich, St. Louis, Mo.) gradient as previously described (Zolotukhin S. et al (1999) Gene Ther. 6:973). The viral stock can be concentrated using Vivaspin® 20 (MW cutoff 100,000 Dalton, Sartorius Stedim Biotech, Aubagne, France) and re-suspended in phosphate-buffered saline (PBS) with 10% glycerol and stored at −80° C. To determine the viral genome copy number, 2 µl of viral stock can be incubated in 6 µl of solution containing 50 units/ml Benzonase®, 50 mM Tris-HCl pH 7.5, 10 mM MgCl₂ and 10 mM CaCl₂ at 37° C. for 30 minutes.

Afterwards, 15 µl of the solution containing 2 mg/ml of Proteinase K, 0.5% SDS and 25 mM EDTA can be added and the mixture can be incubated for an additional 20 min at 55° C. to release viral DNA. Viral DNA can be cleaned with mini DNeasy® Kit (Qiagen, Valencia, Calif.) and eluted with 40 µl of water. Viral genome copy (GC) can be determined by using quantitative PCR. Viral stock can be diluted with PBS to desirable GC/ml, and viral working solution (200 µl) can be delivered into mice via tail vein injection.

5.1.9 HCC Assay

Liver specimens can be harvested from db/db mice 24 weeks after AAV injection. HCC scores can be recorded as the number of HCC nodules on the surface of the entire liver from variants-injected mice divided by the number of HCC nodules from wild-type FGF19-injected mice.

5.1.10 Serum FGF19/FGF21/Variants Exposure Level Assay

Whole blood (about 50 µl/mouse) from mouse tail snips can be collected into plain capillary tubes (BD Clay Adams SurePrep™, Becton Dickenson and Co. Sparks, Md.). Serum and blood cells can be separated by spinning the tubes in an Autocrit™ Ultra 3 (Becton Dickinson and Co. Sparks, Md.). FGF19, FGF21, and variant exposure levels in serum can be determined using EIA kits (Biovendor) by following the manufacturer's instructions.

5.1.11 FGFR4 Binding and Activity Assays

Solid phase ELISA (binding) and ERK phosphorylation assay can be performed using purified recombinant proteins. FGFR binding assay can be conducted using solid phase ELISA. Briefly, a 96-well plate can be coated with 2 µg/ml anti-hFc antibody and can be incubated with 1 µg/ml FGFR1-hFc or FGFR4-hFc. Binding to FGF19 variants in the presence of 1 µg/ml soluble β-klotho and 20 µg/ml heparin can be detected by biotinylated anti-FGF19 antibodies (0.2 µg/mL), followed by streptavidin-HRP incubation (100 ng/mL). For FGFR4 activation assay, Hep3B cells can be stimulated with FGF19 variants for 10 minutes at 37° C., then can be immediately lysed and assayed for ERK phosphorylation using a commercially available kit from Cis-Bio.

5.1.12 C4 Assays 5.1.12.1 Method 1

Following an overnight fast, a patient's blood can be drawn. Liquid chromatography-tandem mass spectrometry (LCMS/MS) can be used to isolate C4 essentially as provided, e.g., in Vijayvargiya et al. (2013) *Clin. Gastroenterol. Hepatol.* 11:1232-1239; and Camilleri et at (2009) *Neurogastroenterol. Motil.* 21:734-e43.

Briefly, HPLC grade water, acetonitrile and saturated ammonium sulfate can be used to precipitate out proteins and lipids, followed by vortexing and centrifugation. The resulting supernatant can be dried and then reconstituted with 100% methanol, and which can then be injected into a LC-MS/MS system (AB Sciex™ API 5000 MS/MS) that is coupled with an electrospray ionization (ESI) interface on a Cohesive Technologies HPLC System (Thermo Fisher Scientific, Franklin, Mass.) with a Phenomenex® MAX-RP column (150×2.0 mm, 4 µm).

5.1.12.2 Method 2

C4 can be determined using a method essentially as provided in Galman et al. (2003) *J. Lipid Res.* 44:859-866.

5.1.12.2.1 Instrumentation

The HPLC system used can be the Hewlett Packard 1100 series (Hewlett Packard GmbH, Waldbronn, Germany). It consists of a autosampler (G1313A), a column compartment (G1316A), a diode array detector (G1315A), a degasser (G1322A), and a pump (G1312A). The software used can be HP Chemstation® for LC. The column can be a Nova-Pak® C18 steel column, 3.9×300 mm, 4 µm particle size, (part. No. WAT011695, Waters Corp., Milford, Mass.).

Sample preparation columns can be mounted in a Varian CEREX® SPE processor (Varian Inc. Palo Alto, Calif.), to which can be added a removable custom-made 5.5×21.4×8.4 cm stainless steel water-jacketed block heater with 24 positions, hole diameter 1.1 cm. The column heater can be connected to a Lauda E100 water bath (Lauda-Konigshofen, Germany) set to 66° C. in order to obtain 64° C. column temperature. The eluted samples can be evaporated to dryness at 60° C. under a stream of nitrogen using a Techne sample concentrator and a Techne Dry™ block, type DB3D (Techne, Cambridge, UK).

5.1.12.2.2 Chemicals

Acetonitril, methanol, chloroform, and hexane can be HPLC grade (LiChrosolv®, Merck, Darmstadt, Germany). Pyridin and chlorotrimethylsilane can be purchased from Merck and hexamethyldisilazane can be purchased from Pierce (Rockford, Ill.).

5.1.12.2.3 Human Blood Samples

Human blood serum and plasma can be obtained from a patient, and then aliquoted and stored at 4° C., −20° C., −85° C., or in liquid nitrogen.

5.1.12.2.4 Optimization of Conditions for Solid-Phase Extraction of Serum and Plasma Samples For the solid-phase extraction of C4, different columns can be tested. Columns with C2, C4, C6, C8, and C18 as a functional group can give a pure C4 peak, whereas columns with phenyl or cyanopropyl sorbents can result in a highly contaminated end product. To reduce ionic and polar secondary interaction, an end-capped C8 column can be used. The optimal temperature for sample workup can be tested from 60.0° C. to 70.0° C. C4 can have the highest binding capacity at a column temperature of 64.0° C. (internal temperature, monitored using a thermistor); whereas other temperatures can give lower concentrations of C4. Different elution conditions can also be tested using various mixtures of hexane and chloroform (95:5, 90:10, 80:20, 70:30, 60:40, 50:50, 40:60, and 30:70; v/v). Low levels of contaminants can be obtained, for example, using hexane-chloroform at the proportion 95:5 (v/v).

5.1.12.2.5 Specific Procedure for Solid-Phase Extraction of Serum and Plasma Samples Blood serum (1 ml from humans) can be diluted with 1 ml of saline (plasma with 2 ml of saline), and 10 µl internal standard C4 in H₂O can be added. A 0.8 ml serum aliquot from each individual can be used. C8 Isolute® SPE columns (500 mg, 3 ml, International Sorbent Technology Ltd, Hengoed, UK) can be prewashed with 2×2 ml pure methanol and with 2×2 ml of water. Columns can then mounted in the Varian CEREX® SPE processor equipped with a block heater and heated to 64° C. (internal temperature). The samples can be sonicated in water for 15 min. and incubated at 37° C. for 15 min. prior to loading onto the preheated columns. The samples can be allowed to reside on the columns for 5 min. to attain 64° C. Column stoppers can then be removed and samples can be passed through the columns, which can subsequently be washed with 64° C. water. The heating block can be removed, and columns can be washed with 2×2 ml 65% methanol at room temperature.

Prior to elution with 2×2 ml of hexane-chloroform (95:5, v/v), columns can be dried by a stream of nitrogen applied for 30 s. The eluted product can be evaporated to dryness at 60° C. under a stream of nitrogen and dissolved in 100 µl acetonitrile; 50 µl of this is then injected into the HPLC system.

5.1.12.2.6 HPLC Assay

As a mobile phase, acetonitrile-water (95:5, v/v) can be used at a flow rate of 1 ml/min. The wavelength and column temperature can be 241 nm and 20° C., respectively. C4 can be quantitated from the areas of the respective peaks using the known amount of internal standard.

In the examples that follow, wild-type FGF19, wild-type FGF21, variants of FGF19 peptide sequences, fusions of FGF19 and/or FGF21 peptide sequences, and variants of fusions (chimeras) of FGF19 (for purposes of the Experimental section, collectively "Invention Peptides") can be used to illustrate the procedures, methodologies and the like useful in evaluating other Invention Peptides, as well as in evaluating the one or more additional agents or therapeutic modalities having a desired effect on one or more bile acid-related or associated diseases, disorders or conditions (for purposes of the Experimental section, "Additional Agents") useful in combination with the Invention Peptides.

5.2 Example 1

Through assessment of wild-type FGF19 and FGF21, this example illustrates how the peptides (e.g., M70) provided herein can be evaluated for inhibition of CYP7A1 expression.

Briefly, at time 0 db/db mice can be dosed intraperitoneally with either recombinant FGF19 (0.1 mg/kg; 1 mg/kg; 10 mg/kg) or recombinant FGF21 (0.1 mg/kg; 1 mg/kg; 10 mg/kg). Five hours after dosing, livers can be harvested, RNA extracted, and CYP7A1 expression determined by real-time PCR (QPCR) using GADPH as a normalization control. In each group of mice containing the desired number of animals (e.g., n=3), CYP7A1 expression values for the various FGF19 and FGF21 concentrations can be compared to mice dosed with PBS vehicle control.

5.3 Example 2

Using the assays described above (e.g., in vitro cell-based assay (primary human hepatocyte) and in vivo assay (protein dosing in db/db mice)), repression of CYP7A1 in primary human hepatocytes can be determined for Invention Peptides. Invention Peptides that retain CYP7A1 repression activity can be further evaluated in the HCC assay (or other relevant assay or model) described above to identify variants that can be useful for modulating bile acid metabolism and/or for treating bile acid-related or associated diseases (e.g., PBC, NASH, and bile acid diarrhea) without causing induction of HCC.

5.4 Example 4

The teachings of this example can be used to determine whether administration of Invention Peptides to human patients can result in suppression of 7α-hydroxy-4-cholesten-3-one (C4), a marker of bile acid synthesis.

5.4.1 Study Subjects

Healthy adults in the age range 18-65 years and with normal body weight (body mass index, BMI 20-35) can be enrolled in the study. The study protocol can be approved by the Human Research Ethics Committee in Australia, and written informed consent can be obtained from each subject. For inclusion in the study, each subject can be required to be in good health as determined by no clinically significant findings from medical history, physical exam, 12-lead ECG, clinical laboratory findings, and vital signs at screening. Subjects with a history or clinical manifestation of any significant metabolic, allergic, dermatological, hepatic, renal, hematological, pulmonary, cardiovascular, GI, neurological, or psychiatric disorder can be excluded from enrollment.

5.4.2 Study Design

The study can be a randomized, double-blind, placebo-controlled design. Prescreening of subjects can be performed 7-30 days prior to entry, and baseline evaluations can be performed before treatment. Each subject can be given a SC injection of 3 mg/day in a single bolus dose daily for 7 days of one or more Invention Peptides. Blood samples can be collected into heparinized tubes through an indwelling catheter. Blood samples taken on Day 1 and Day 7 at 4.5 hrs or 24 hrs after administration of one or more Invention Peptides or placebo can be analyzed. Serum levels of C4 can be used to monitor CYP7A1 enzymatic activity (bile acid synthesis). They can be analyzed from individual serum samples after sample extraction followed by high-pressure liquid chromatography (HPLC) as described previously (Galman et al. (2003) J Lipid Res. 2003; 44(4):859-66) and elsewhere herein.

6. SEQUENCE LISTING

The present specification is being filed with a computer readable form (CRF) copy of the Sequence Listing. The CRF entitled 13370-108-999_SEQLIST.txt was created on Jul. 15, 2019 and is 256,354 bytes in size. The CRF also serves as the paper copy of the Sequence Listing, and are thus identical, and is incorporated herein by reference in its entirety.

What is claimed is:

1. A method of selectively treating a subject having or suspected of having a bile acid-related disorder comprising administering to the subject a peptide having an amino acid sequence comprising SEQ ID NO:70, wherein the subject has been determined to be likely to responsive to the peptide according a method comprising:

(a) administering the peptide to the subject;

(b) obtaining a test sample from the subject;

(c) determining the level of 7α-hydroxy-4-cholesten-3-one (C4) in the test sample; and (d) identifying the subject as being likely to be responsive to treatment with the peptide if the level of C4 in the test sample decreases as compared to a reference level of C4, wherein the bile-acid related disorder comprises a metabolic syndrome, a lipid or glucose disorder, cholesterol or triglyceride metabolism, type 2 diabetes, cholestasis, intrahepatic cholestasis, primary biliary cirrhosis (PBC), primary familial intrahepatic cholestasis (PFIC), progressive PFIC, primary sclerosing cholangitis (PSC), pregnancy intrahepatic cholestasis (PIC), neonatal cholestasis, drug induced cholestasis, diseases of extrahepatic cholestasis, bile duct compression from tumor, bile duct blockade by gall stones, bile acid malabsorption, disorders involving the distal small intestine, ileal resection, inflammatory bowel diseases, Crohn's disease, ulcerative colitis, idiopathic disorders impairing absorption of bile acids, diarrhea, bile acid diarrhea (BAD), GI symptoms, GI cancers, liver cancers, biliary cancers, colon cancer, hepatocellular cancer, bile acid synthesis abnormalities, cirrhosis, portal hypertension, or any combination thereof.

2. The method of claim 1, wherein the peptide has an amino acid sequence consisting of SEQ ID NO:70.

3. The method of claim 1, further comprising obtaining the reference level of C4 in a control sample prior to administration of the peptide, and wherein the control sample is from the same source as the test sample.

4. The method of claim 1, further comprising obtaining the reference level of C4 in a control sample from a control subject having the bile-acid related disorder.

5. The method of claim 1, wherein the level of C4 in the test sample obtained after administration with the peptide decreases 10% to 90% as compared to the reference level of C4.

6. The method of claim 1, wherein the level of C4 in the test sample obtained after administration with the peptide decreases 30% to 90% as compared to the reference level of C4.

7. The method of claim 1, wherein the level of C4 in the test sample obtained after administration with the peptide decreases 60% to 90% as compared to the reference level of C4.

8. The method of claim 1, wherein the determining the level of C4 in the test sample utilizes liquid chromatography-tandem mass spectrometry (LCMS/MS).

9. The method of claim 1, wherein the bile-acid related disorder is PFIC.

10. The method of claim 1, wherein the bile-acid related disorder is BAD.

* * * * *

SEQUENCE LISTING

```
<160> NUMBER OF SEQ ID NOS: 208

<210> SEQ ID NO 1
<211> LENGTH: 194
<212> TYPE: PRT
<213> ORGANISM: Homo sapiens

<400> SEQUENCE: 1

Arg Pro Leu Ala Phe Ser Asp Ala Ser Pro His Val His Tyr Gly Trp
1               5                   10                  15
```

```
Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 2
<211> LENGTH: 194
<212> TYPE: PRT
<213> ORGANISM: Homo sapiens

<400> SEQUENCE: 2

Arg Pro Leu Ala Phe Ser Asp Ser Ser Pro Leu Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190
```

Glu Lys

<210> SEQ ID NO 3
<211> LENGTH: 194
<212> TYPE: PRT
<213> ORGANISM: Homo sapiens

<400> SEQUENCE: 3

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Glu Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 4
<211> LENGTH: 194
<212> TYPE: PRT
<213> ORGANISM: Homo sapiens

<400> SEQUENCE: 4

Arg Pro Leu Ala Phe Ser Asp Ala Gly Pro His Val His Tyr Ala Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
            130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 5
<211> LENGTH: 191
<212> TYPE: PRT
<213> ORGANISM: Homo sapiens

<400> SEQUENCE: 5

Arg His Pro Ile Pro Asp Ser Ser Pro Leu Leu Gln Phe Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 6
<211> LENGTH: 187
<212> TYPE: PRT
<213> ORGANISM: Homo sapiens

<400> SEQUENCE: 6

Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
            35                  40                  45

Ser Leu Leu Glu Ile Lys Ala Val Ala Leu Arg Thr Val Ala Ile Lys
50                  55                  60

```
Gly Val His Ser Val Arg Tyr Leu Cys Met Gly Ala Asp Gly Lys Met
 65                  70                  75                  80

Gln Gly Leu Leu Gln Tyr Ser Glu Glu Asp Cys Ala Phe Glu Glu Glu
                 85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
            115                 120                 125

Gly Phe Leu Pro Leu Ser His Phe Leu Pro Met Leu Pro Met Val Pro
            130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
            165                 170                 175

Leu Glu Ala Val Arg Ser Pro Ser Phe Glu Lys
            180                 185
```

<210> SEQ ID NO 7
<211> LENGTH: 192
<212> TYPE: PRT
<213> ORGANISM: Homo sapiens

<400> SEQUENCE: 7

```
Arg Pro Leu Ala Phe Ser Asp Ser Ser Pro Leu Leu Gln Phe Gly Gly
  1               5                  10                  15

Gln Val Arg Leu Arg His Leu Tyr Thr Ser Gly Pro His Gly Leu Ser
                 20                  25                  30

Ser Cys Phe Leu Arg Ile Arg Ala Asp Gly Val Val Asp Cys Ala Arg
             35                  40                  45

Gly Gln Ser Ala His Ser Leu Leu Glu Ile Lys Ala Val Ala Leu Arg
         50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
            165                 170                 175

Gly Leu Val Thr Gly Leu Glu Ala Val Arg Ser Pro Ser Phe Glu Lys
            180                 185                 190
```

<210> SEQ ID NO 8
<211> LENGTH: 191
<212> TYPE: PRT
<213> ORGANISM: Homo sapiens

<400> SEQUENCE: 8

```
Arg His Pro Ile Pro Asp Ser Ser Pro Leu Leu Gln Trp Gly Asp Pro
  1               5                  10                  15
```

```
Ile Arg Leu Arg His Leu Tyr Thr Ser Gly Pro His Gly Leu Ser Ser
             20                  25                  30

Cys Phe Leu Arg Ile Arg Ala Asp Gly Val Val Asp Cys Ala Arg Gly
         35                  40                  45

Gln Ser Ala His Ser Leu Leu Glu Ile Lys Ala Val Ala Leu Arg Thr
     50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 9
<211> LENGTH: 193
<212> TYPE: PRT
<213> ORGANISM: Homo sapiens

<400> SEQUENCE: 9

Arg His Pro Ile Pro Asp Ser Ser Pro Leu Leu Gln Phe Gly Trp Gly
  1               5                  10                  15

Asp Pro Ile Arg Leu Arg His Leu Tyr Thr Ser Gly Pro His Gly Leu
             20                  25                  30

Ser Ser Cys Phe Leu Arg Ile Arg Ala Asp Gly Val Val Asp Cys Ala
         35                  40                  45

Arg Gly Gln Ser Ala His Ser Leu Leu Glu Ile Lys Ala Val Ala Leu
     50                  55                  60

Arg Thr Val Ala Ile Lys Gly Val His Ser Val Arg Tyr Leu Cys Met
 65                  70                  75                  80

Gly Ala Asp Gly Lys Met Gln Gly Leu Leu Gln Tyr Ser Glu Glu Asp
                 85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys
```

<210> SEQ ID NO 10
<211> LENGTH: 193
<212> TYPE: PRT
<213> ORGANISM: Homo sapiens

<400> SEQUENCE: 10

```
Arg His Pro Ile Pro Asp Ser Ser Pro His Val Tyr Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys
```

<210> SEQ ID NO 11
<211> LENGTH: 192
<212> TYPE: PRT
<213> ORGANISM: Homo sapiens

<400> SEQUENCE: 11

```
Arg Pro Leu Ala Phe Ser Asp Ala Gly Pro Leu Leu Gln Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
```

```
                130                 135                 140
Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 12
<211> LENGTH: 194
<212> TYPE: PRT
<213> ORGANISM: Homo sapiens

<400> SEQUENCE: 12

Arg Pro Leu Ala Phe Ser Asp Ala Gly Pro Leu Leu Gln Phe Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 13
<211> LENGTH: 192
<212> TYPE: PRT
<213> ORGANISM: Homo sapiens

<400> SEQUENCE: 13

Arg Pro Leu Ala Phe Ser Asp Ala Gly Pro Leu Leu Gln Phe Gly Gly
1               5                   10                  15

Gln Val Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80
```

```
Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 14
<211> LENGTH: 191
<212> TYPE: PRT
<213> ORGANISM: Homo sapiens

<400> SEQUENCE: 14

Arg His Pro Ile Pro Asp Ser Ser Pro His Val His Tyr Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 15
<211> LENGTH: 192
<212> TYPE: PRT
<213> ORGANISM: Homo sapiens

<400> SEQUENCE: 15

Arg Pro Leu Ala Phe Ser Asp Ala Gly Pro His Val His Tyr Gly Gly
1               5                   10                  15

Gln Val Arg Leu Arg His Leu Tyr Thr Ser Gly Pro His Gly Leu Ser
            20                  25                  30
```

```
Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
 50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 16
<211> LENGTH: 192
<212> TYPE: PRT
<213> ORGANISM: Homo sapiens

<400> SEQUENCE: 16

Arg Pro Leu Ala Phe Ser Asp Ala Gly Pro His Val His Trp Gly Asp
 1               5                  10                  15

Pro Ile Arg Leu Arg His Leu Tyr Thr Ser Gly Pro His Gly Leu Ser
             20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
 50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 17
<211> LENGTH: 192
<212> TYPE: PRT
```

<213> ORGANISM: Homo sapiens

<400> SEQUENCE: 17

Arg Pro Leu Ala Phe Ser Asp Ala Gly Pro His Val Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 18
<211> LENGTH: 192
<212> TYPE: PRT
<213> ORGANISM: Homo sapiens

<400> SEQUENCE: 18

Arg Pro Leu Ala Phe Ser Asp Ala Gly Pro His Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe 165                 170                 175
Gly Leu Val Thr Gly Leu Glu Ala Val Arg Ser Pro Ser Phe Glu Lys
                180                 185                 190

<210> SEQ ID NO 19
<211> LENGTH: 192
<212> TYPE: PRT
<213> ORGANISM: Homo sapiens

<400> SEQUENCE: 19

Arg Pro Leu Ala Phe Ser Asp Ala Gly Pro Val Tyr Gly Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 20
<211> LENGTH: 192
<212> TYPE: PRT
<213> ORGANISM: Homo sapiens

<400> SEQUENCE: 20

Arg Pro Leu Ala Phe Ser Asp Ala Gly Pro Val His Gly Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln

```
                115                 120                 125
Leu Tyr Lys Asn Arg Gly Phe Leu Pro Leu Ser His Phe Leu Pro Met
            130                 135                 140
Leu Pro Met Val Pro Glu Glu Pro Glu Asp Leu Arg Gly His Leu Glu
145                 150                 155                 160
Ser Asp Met Phe Ser Ser Pro Leu Glu Thr Asp Ser Met Asp Pro Phe
                165                 170                 175
Gly Leu Val Thr Gly Leu Glu Ala Val Arg Ser Pro Ser Phe Glu Lys
            180                 185                 190

<210> SEQ ID NO 21
<211> LENGTH: 192
<212> TYPE: PRT
<213> ORGANISM: Homo sapiens

<400> SEQUENCE: 21

Arg Pro Leu Ala Phe Ser Asp Ala Gly Pro Val His Tyr Trp Gly Asp
1               5                   10                  15
Pro Ile Arg Leu Arg His Leu Tyr Thr Ser Gly Pro His Gly Leu Ser
            20                  25                  30
Ser Cys Phe Leu Arg Ile Arg Ala Asp Gly Val Val Asp Cys Ala Arg
        35                  40                  45
Gly Gln Ser Ala His Ser Leu Leu Glu Ile Lys Ala Val Ala Leu Arg
    50                  55                  60
Thr Val Ala Ile Lys Gly Val His Ser Val Arg Tyr Leu Cys Met Gly
65                  70                  75                  80
Ala Asp Gly Lys Met Gln Gly Leu Leu Gln Tyr Ser Glu Glu Asp Cys
                85                  90                  95
Ala Phe Glu Glu Glu Ile Arg Pro Asp Gly Tyr Asn Val Tyr Arg Ser
            100                 105                 110
Glu Lys His Arg Leu Pro Val Ser Leu Ser Ser Ala Lys Gln Arg Gln
        115                 120                 125
Leu Tyr Lys Asn Arg Gly Phe Leu Pro Leu Ser His Phe Leu Pro Met
    130                 135                 140
Leu Pro Met Val Pro Glu Glu Pro Glu Asp Leu Arg Gly His Leu Glu
145                 150                 155                 160
Ser Asp Met Phe Ser Ser Pro Leu Glu Thr Asp Ser Met Asp Pro Phe
                165                 170                 175
Gly Leu Val Thr Gly Leu Glu Ala Val Arg Ser Pro Ser Phe Glu Lys
            180                 185                 190

<210> SEQ ID NO 22
<211> LENGTH: 193
<212> TYPE: PRT
<213> ORGANISM: Homo sapiens

<400> SEQUENCE: 22

Arg Pro Leu Ala Phe Ser Asp Ala Gly Pro His Val His Gly Trp Gly
1               5                   10                  15
Asp Pro Ile Arg Leu Arg His Leu Tyr Thr Ser Gly Pro His Gly Leu
            20                  25                  30
Ser Ser Cys Phe Leu Arg Ile Arg Ala Asp Gly Val Val Asp Cys Ala
        35                  40                  45
Arg Gly Gln Ser Ala His Ser Leu Leu Glu Ile Lys Ala Val Ala Leu
    50                  55                  60
Arg Thr Val Ala Ile Lys Gly Val His Ser Val Arg Tyr Leu Cys Met
```

```
                65                  70                  75                  80
Gly Ala Asp Gly Lys Met Gln Gly Leu Leu Gln Tyr Ser Glu Glu Asp
                    85                  90                  95

Cys Ala Phe Glu Glu Glu Ile Arg Pro Asp Gly Tyr Asn Val Tyr Arg
                100                 105                 110

Ser Glu Lys His Arg Leu Pro Val Ser Leu Ser Ser Ala Lys Gln Arg
                115                 120                 125

Gln Leu Tyr Lys Asn Arg Gly Phe Leu Pro Leu Ser His Phe Leu Pro
            130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 23
<211> LENGTH: 192
<212> TYPE: PRT
<213> ORGANISM: Homo sapiens

<400> SEQUENCE: 23

Arg Pro Leu Ala Phe Ser Asp Ala Gly Pro His His Gly Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                    85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
                115                 120                 125

Leu Tyr Lys Asn Arg Gly Phe Leu Pro Leu Ser His Phe Leu Pro Met
            130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 24
<211> LENGTH: 192
<212> TYPE: PRT
<213> ORGANISM: Homo sapiens

<400> SEQUENCE: 24

Arg Pro Leu Ala Phe Ser Asp Ala Gly Pro His His Tyr Trp Gly Asp
1               5                   10                  15
```

```
Pro Ile Arg Leu Arg His Leu Tyr Thr Ser Gly Pro His Gly Leu Ser
        20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
 65                 70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 25
<211> LENGTH: 192
<212> TYPE: PRT
<213> ORGANISM: Homo sapiens

<400> SEQUENCE: 25

Arg Pro Leu Ala Phe Ser Asp Ala Gly Pro His Val Tyr Trp Gly Asp
 1               5                  10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
 65                 70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

```
<210> SEQ ID NO 26
<211> LENGTH: 192
<212> TYPE: PRT
<213> ORGANISM: Homo sapiens

<400> SEQUENCE: 26

Arg Pro Leu Ala Phe Ser Asp Ser Ser Pro Leu Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 27
<211> LENGTH: 192
<212> TYPE: PRT
<213> ORGANISM: Homo sapiens

<400> SEQUENCE: 27

Arg Pro Leu Ala Phe Ser Asp Ser Ser Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
```

145                 150                 155                 160
Ser Asp Met Phe Ser Ser Pro Leu Glu Thr Asp Ser Met Asp Pro Phe
                            165                 170                 175

Gly Leu Val Thr Gly Leu Glu Ala Val Arg Ser Pro Ser Phe Glu Lys
                180                 185                 190

<210> SEQ ID NO 28
<211> LENGTH: 191
<212> TYPE: PRT
<213> ORGANISM: Homo sapiens

<400> SEQUENCE: 28

Arg Pro Leu Ala Phe Ser Asp Ala Gly Pro His Val Trp Gly Asp Pro
1               5                   10                  15

Ile Arg Leu Arg His Leu Tyr Thr Ser Gly Pro His Gly Leu Ser Ser
                20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 29
<211> LENGTH: 193
<212> TYPE: PRT
<213> ORGANISM: Homo sapiens

<400> SEQUENCE: 29

Arg Pro Leu Ala Phe Ser Asp Ala Gly Pro His Val His Tyr Trp Gly
1               5                   10                  15

Asp Pro Ile Arg Leu Arg His Leu Tyr Thr Ser Gly Pro His Gly Leu
                20                  25                  30

Ser Ser Cys Phe Leu Arg Ile Arg Ala Asp Gly Val Val Asp Cys Ala
            35                  40                  45

Arg Gly Gln Ser Ala His Ser Leu Leu Glu Ile Lys Ala Val Ala Leu
        50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg

```
            100                 105                 110
Ser Glu Lys His Arg Leu Pro Val Ser Leu Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 30
<211> LENGTH: 194
<212> TYPE: PRT
<213> ORGANISM: Homo sapiens

<400> SEQUENCE: 30

Arg Pro Leu Ala Phe Ser Asp Ala Gly Pro His Val His Tyr Ala Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 31
<211> LENGTH: 191
<212> TYPE: PRT
<213> ORGANISM: Homo sapiens

<400> SEQUENCE: 31

Arg His Pro Ile Pro Asp Ser Ser Pro Leu Leu Gln Phe Gly Ala Gln
1               5                   10                  15

Val Arg Leu Arg His Leu Tyr Thr Ser Gly Pro His Gly Leu Ser Ser
            20                  25                  30
```

```
Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 32
<211> LENGTH: 191
<212> TYPE: PRT
<213> ORGANISM: Homo sapiens

<400> SEQUENCE: 32

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
                20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 33
<211> LENGTH: 191
<212> TYPE: PRT
<213> ORGANISM: Homo sapiens
```

<400> SEQUENCE: 33

Arg His Pro Ile Pro Asp Ser Ser Pro Leu Leu Gln Phe Gly Pro Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 34
<211> LENGTH: 191
<212> TYPE: PRT
<213> ORGANISM: Homo sapiens

<400> SEQUENCE: 34

Arg His Pro Ile Pro Asp Ser Ser Pro Leu Leu Gln Phe Gly Gly Ala
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

```
Leu Val Thr Gly Leu Glu Ala Val Arg Ser Pro Ser Phe Glu Lys
        180                 185                 190
```

<210> SEQ ID NO 35
<211> LENGTH: 191
<212> TYPE: PRT
<213> ORGANISM: Homo sapiens

<400> SEQUENCE: 35

```
Arg His Pro Ile Pro Asp Ser Ser Pro Leu Leu Gln Phe Gly Gly Glu
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65              70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 36
<211> LENGTH: 191
<212> TYPE: PRT
<213> ORGANISM: Homo sapiens

<400> SEQUENCE: 36

```
Arg His Pro Ile Pro Asp Ser Ser Pro Leu Leu Gln Phe Gly Gly Asn
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65              70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125
```

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 37
<211> LENGTH: 191
<212> TYPE: PRT
<213> ORGANISM: Homo sapiens

<400> SEQUENCE: 37

Arg His Pro Ile Pro Asp Ser Ser Pro Leu Leu Gln Phe Gly Gly Gln
1               5                   10                  15

Ala Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 38
<211> LENGTH: 191
<212> TYPE: PRT
<213> ORGANISM: Homo sapiens

<400> SEQUENCE: 38

Arg His Pro Ile Pro Asp Ser Ser Pro Leu Leu Gln Phe Gly Gly Gln
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 39
<211> LENGTH: 191
<212> TYPE: PRT
<213> ORGANISM: Homo sapiens

<400> SEQUENCE: 39

Arg His Pro Ile Pro Asp Ser Ser Pro Leu Leu Gln Phe Gly Gly Gln
1               5                   10                  15

Thr Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 40
<211> LENGTH: 193
<212> TYPE: PRT
<213> ORGANISM: Homo sapiens

<400> SEQUENCE: 40

Arg His Pro Ile Pro Asp Ser Ser Pro Leu Leu Gln Phe Gly Trp Gly
1               5                   10                  15

Gln Pro Val Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
 50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 41
<211> LENGTH: 182
<212> TYPE: PRT
<213> ORGANISM: Homo sapiens

<400> SEQUENCE: 41

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 42

```
<211> LENGTH: 178
<212> TYPE: PRT
<213> ORGANISM: Homo sapiens

<400> SEQUENCE: 42

His Pro Ile Pro Asp Ser Ser Pro Leu Leu Gln Phe Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser

<210> SEQ ID NO 43
<211> LENGTH: 192
<212> TYPE: PRT
<213> ORGANISM: Homo sapiens

<400> SEQUENCE: 43

Arg Pro Leu Ala Phe Ser Asp Ala Gly Pro His Val His Tyr Gly Gly
1               5                   10                  15

Asp Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160
```

```
Ser Asp Met Phe Ser Ser Pro Leu Glu Thr Asp Ser Met Asp Pro Phe
            165                 170                 175
Gly Leu Val Thr Gly Leu Glu Ala Val Arg Ser Pro Ser Phe Glu Lys
            180                 185                 190

<210> SEQ ID NO 44
<211> LENGTH: 185
<212> TYPE: PRT
<213> ORGANISM: Homo sapiens

<400> SEQUENCE: 44

Arg Pro Leu Ala Phe Ser Asp Ala Gly Pro His Val His Tyr Gly Trp
1               5                   10                  15
Gly Asp Pro Ile Arg Gln Arg Tyr Leu Tyr Thr Asp Asp Ala Gln Gln
            20                  25                  30
Thr Glu Ala His Leu Glu Ile Arg Glu Asp Gly Thr Val Gly Gly Ala
        35                  40                  45
Ala Asp Gln Ser Pro Glu Ser Leu Leu Gln Leu Lys Ala Leu Lys Pro
    50                  55                  60
Gly Val Ile Gln Ile Leu Gly Val Lys Thr Ser Arg Phe Leu Cys Gln
65                  70                  75                  80
Arg Pro Asp Gly Ala Leu Tyr Gly Ser Leu His Phe Asp Pro Glu Ala
                85                  90                  95
Cys Ser Phe Arg Glu Leu Leu Leu Glu Asp Gly Tyr Asn Val Tyr Gln
            100                 105                 110
Ser Glu Ala His Gly Leu Pro Leu His Leu Pro Gly Asn Lys Ser Pro
        115                 120                 125
His Arg Asp Pro Ala Pro Arg Gly Pro Ala Arg Phe Leu Pro Leu Pro
    130                 135                 140
Gly Leu Pro Pro Ala Leu Pro Glu Pro Pro Gly Ile Leu Ala Pro Gln
145                 150                 155                 160
Pro Pro Asp Val Gly Ser Ser Asp Pro Leu Ser Met Val Gly Pro Ser
                165                 170                 175
Gln Gly Arg Ser Pro Ser Tyr Ala Ser
            180                 185

<210> SEQ ID NO 45
<211> LENGTH: 193
<212> TYPE: PRT
<213> ORGANISM: Homo sapiens

<400> SEQUENCE: 45

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
```

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 46
<211> LENGTH: 232
<212> TYPE: PRT
<213> ORGANISM: Homo sapiens

<400> SEQUENCE: 46

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Ala Gln Gln
            20                  25                  30

Thr Glu Ala His Leu Glu Ile Arg Glu Asp Gly Thr Val Gly Gly Ala
        35                  40                  45

Ala Asp Gln Ser Pro Glu Ser Leu Leu Gln Leu Lys Ala Leu Lys Pro
    50                  55                  60

Gly Val Ile Gln Ile Leu Gly Val Lys Thr Ser Arg Phe Leu Cys Gln
65                  70                  75                  80

Arg Pro Asp Gly Ala Leu Tyr Gly Ser Leu His Phe Asp Pro Glu Ala
                85                  90                  95

Cys Ser Phe Arg Glu Leu Leu Leu Glu Asp Gly Tyr Asn Val Tyr Gln
            100                 105                 110

Ser Glu Ala His Gly Leu Pro Leu His Leu Pro Gly Asn Lys Ser Pro
        115                 120                 125

His Arg Asp Pro Ala Pro Arg Gly Pro Ala Arg Phe Leu Pro Leu Pro
    130                 135                 140

Gly Leu Pro Pro Ala Leu Pro Glu Pro Pro Gly Ile Leu Ala Pro Gln
145                 150                 155                 160

Pro Pro Asp Val Gly Ser Ser Asp Pro Leu Ser Met Val Gly Pro Ser
                165                 170                 175

Gln Gly Arg Ser Pro Ser Tyr Ala Ser Pro Met Val Pro Glu Glu Pro
            180                 185                 190

Glu Asp Leu Arg Gly His Leu Glu Ser Asp Met Phe Ser Ser Pro Leu
        195                 200                 205

Glu Thr Asp Ser Met Asp Pro Phe Gly Leu Val Thr Gly Leu Glu Ala
    210                 215                 220

Val Arg Ser Pro Ser Phe Glu Lys
225                 230

<210> SEQ ID NO 47
<211> LENGTH: 190
<212> TYPE: PRT
<213> ORGANISM: Homo sapiens

<400> SEQUENCE: 47

His Pro Ile Pro Asp Ser Ser Pro Leu Leu Gln Trp Gly Asp Pro Ile

```
                1               5                  10                 15
            Arg Leu Arg His Leu Tyr Thr Ser Gly Pro His Gly Leu Ser Ser Cys
                            20                  25                 30

Phe Leu Arg Ile Arg Ala Asp Gly Val Val Asp Cys Ala Arg Gly Gln
                            35                  40                 45

Ser Ala His Ser Leu Leu Glu Ile Lys Ala Val Ala Leu Arg Thr Val
                50                          55                 60

Ala Ile Lys Gly Val His Ser Val Arg Tyr Leu Cys Met Gly Ala Asp
            65                  70                  75                 80

Gly Lys Met Gln Gly Leu Leu Gln Tyr Ser Glu Glu Asp Cys Ala Phe
                            85                  90                 95

Glu Glu Glu Ile Arg Pro Asp Gly Tyr Asn Val Tyr Arg Ser Glu Lys
                            100                 105                110

His Arg Leu Pro Val Ser Leu Ser Ser Ala Lys Gln Arg Gln Leu Tyr
                            115                 120                125

Lys Asn Arg Gly Phe Leu Pro Leu Ser His Phe Leu Pro Met Leu Pro
                130                         135                140

Met Val Pro Glu Glu Pro Glu Asp Leu Arg Gly His Leu Glu Ser Asp
            145                 150                 155                160

Met Phe Ser Ser Pro Leu Glu Thr Asp Ser Met Asp Pro Phe Gly Leu
                            165                 170                175

Val Thr Gly Leu Glu Ala Val Arg Ser Pro Ser Phe Glu Lys
                            180                 185                190

<210> SEQ ID NO 48
<211> LENGTH: 187
<212> TYPE: PRT
<213> ORGANISM: Homo sapiens

<400> SEQUENCE: 48

Arg Asp Ser Ser Pro Leu Leu Gln Phe Gly Gly Gln Val Arg Leu Arg
            1               5                   10                 15

His Leu Tyr Thr Ser Gly Pro His Gly Leu Ser Ser Cys Phe Leu Arg
                            20                  25                 30

Ile Arg Ala Asp Gly Val Val Asp Cys Ala Arg Gly Gln Ser Ala His
                            35                  40                 45

Ser Leu Leu Glu Ile Lys Ala Val Ala Leu Arg Thr Val Ala Ile Lys
                50                          55                 60

Gly Val His Ser Val Arg Tyr Leu Cys Met Gly Ala Asp Gly Lys Met
            65                  70                  75                 80

Gln Gly Leu Leu Gln Tyr Ser Glu Glu Asp Cys Ala Phe Glu Glu Glu
                            85                  90                 95

Ile Arg Pro Asp Gly Tyr Asn Val Tyr Arg Ser Glu Lys His Arg Leu
                            100                 105                110

Pro Val Ser Leu Ser Ser Ala Lys Gln Arg Gln Leu Tyr Lys Asn Arg
                            115                 120                125

Gly Phe Leu Pro Leu Ser His Phe Leu Pro Met Leu Pro Met Val Pro
                130                         135                140

Glu Glu Pro Glu Asp Leu Arg Gly His Leu Glu Ser Asp Met Phe Ser
            145                 150                 155                160

Ser Pro Leu Glu Thr Asp Ser Met Asp Pro Phe Gly Leu Val Thr Gly
                            165                 170                175

Leu Glu Ala Val Arg Ser Pro Ser Phe Glu Lys
                            180                 185
```

```
<210> SEQ ID NO 49
<211> LENGTH: 192
<212> TYPE: PRT
<213> ORGANISM: Homo sapiens

<400> SEQUENCE: 49

Arg Pro Leu Ala Phe Ser Asp Ser Ser Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 50
<211> LENGTH: 191
<212> TYPE: PRT
<213> ORGANISM: Homo sapiens

<400> SEQUENCE: 50

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Leu Glu Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140
```

Pro Met Val Pro Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 51
<211> LENGTH: 191
<212> TYPE: PRT
<213> ORGANISM: Homo sapiens

<400> SEQUENCE: 51

Arg His Pro Ile Pro Asp Ser Ser Pro Leu Leu Gln Phe Gly Gly Asn
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 52
<211> LENGTH: 187
<212> TYPE: PRT
<213> ORGANISM: Homo sapiens

<400> SEQUENCE: 52

Arg Asp Ser Ser Pro Leu Leu Gln Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

```
Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
        180                 185
```

<210> SEQ ID NO 53
<211> LENGTH: 189
<212> TYPE: PRT
<213> ORGANISM: Homo sapiens

<400> SEQUENCE: 53

```
Met Asp Ser Ser Pro Leu Val His Tyr Gly Trp Gly Asp Pro Ile Arg
1               5                   10                  15

Leu Arg His Leu Tyr Thr Ser Gly Pro His Gly Leu Ser Ser Cys Phe
                20                  25                  30

Leu Arg Ile Arg Ala Asp Gly Val Val Asp Cys Ala Arg Gly Gln Ser
            35                  40                  45

Ala His Ser Leu Leu Glu Ile Lys Ala Val Ala Leu Arg Thr Val Ala
        50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185
```

<210> SEQ ID NO 54
<211> LENGTH: 192
<212> TYPE: PRT
<213> ORGANISM: Homo sapiens

<400> SEQUENCE: 54

```
Arg Pro Leu Ala Phe Ser Asp Ala Gly Pro Leu Leu Gln Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45
```

Gly Gln Ser Ala His Ser Leu Leu Glu Ile Lys Ala Val Ala Leu Arg
            50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
                115                 120                 125

Leu Tyr Lys Asn Arg Gly Phe Leu Pro Leu Ser His Phe Leu Pro Met
130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 55
<211> LENGTH: 192
<212> TYPE: PRT
<213> ORGANISM: Homo sapiens

<400> SEQUENCE: 55

Arg Pro Leu Ala Phe Ser Asp Ala Gly Pro His Tyr Gly Trp Gly Asp
 1               5                  10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
                35                  40                  45

Gly Gln Ser Ala His Ser Leu Leu Glu Ile Lys Ala Val Ala Leu Arg
            50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
                115                 120                 125

Leu Tyr Lys Asn Arg Gly Phe Leu Pro Leu Ser His Phe Leu Pro Met
130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 56
<211> LENGTH: 192
<212> TYPE: PRT
<213> ORGANISM: Homo sapiens

<400> SEQUENCE: 56

Arg Pro Leu Ala Phe Ser Asp Ala Gly Pro Val Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 57
<211> LENGTH: 192
<212> TYPE: PRT
<213> ORGANISM: Homo sapiens

<400> SEQUENCE: 57

Arg Pro Leu Ala Phe Ser Asp Ala Gly Pro Val His Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 58
<211> LENGTH: 192
<212> TYPE: PRT
<213> ORGANISM: Homo sapiens

<400> SEQUENCE: 58

```
Arg Pro Leu Ala Phe Ser Asp Ala Gly Pro Val His Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 59
<211> LENGTH: 192
<212> TYPE: PRT
<213> ORGANISM: Homo sapiens

<400> SEQUENCE: 59

```
Arg Pro Leu Ala Phe Ser Asp Ala Gly Pro His His Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140
```

```
Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 60
<211> LENGTH: 192
<212> TYPE: PRT
<213> ORGANISM: Homo sapiens

<400> SEQUENCE: 60

Arg Pro Leu Ala Phe Ser Asp Ala Gly Pro His His Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 61
<211> LENGTH: 192
<212> TYPE: PRT
<213> ORGANISM: Homo sapiens

<400> SEQUENCE: 61

Arg Pro Leu Ala Phe Ser Asp Ala Gly Pro His Val Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95
```

```
Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 62
<211> LENGTH: 192
<212> TYPE: PRT
<213> ORGANISM: Homo sapiens

<400> SEQUENCE: 62

Arg Pro Leu Ala Phe Ser Asp Ala Gly Pro His Val Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 63
<211> LENGTH: 192
<212> TYPE: PRT
<213> ORGANISM: Homo sapiens

<400> SEQUENCE: 63

Arg Pro Leu Ala Phe Ser Asp Ala Gly Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45
```

```
Gly Gln Ser Ala His Ser Leu Leu Glu Ile Lys Ala Val Ala Leu Arg
         50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 64
<211> LENGTH: 192
<212> TYPE: PRT
<213> ORGANISM: Homo sapiens

<400> SEQUENCE: 64

Arg Pro Leu Ala Phe Ser Asp Ser Ser Pro Leu Val His Trp Gly Asp
 1               5                  10                  15

Pro Ile Arg Leu Arg His Leu Tyr Thr Ser Gly Pro His Gly Leu Ser
             20                  25                  30

Ser Cys Phe Leu Arg Ile Arg Ala Asp Gly Val Val Asp Cys Ala Arg
         35                  40                  45

Gly Gln Ser Ala His Ser Leu Leu Glu Ile Lys Ala Val Ala Leu Arg
         50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 65
<211> LENGTH: 192
<212> TYPE: PRT
<213> ORGANISM: Homo sapiens

<400> SEQUENCE: 65
```

Arg Pro Leu Ala Phe Ser Asp Ser Ser Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 66
<211> LENGTH: 192
<212> TYPE: PRT
<213> ORGANISM: Homo sapiens

<400> SEQUENCE: 66

Arg Pro Leu Ala Phe Ser Asp Ala Gly Pro His Leu Gln Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys 180                 185                 190

<210> SEQ ID NO 67
<211> LENGTH: 191
<212> TYPE: PRT
<213> ORGANISM: Homo sapiens

<400> SEQUENCE: 67

Arg Pro Leu Ala Phe Ser Asp Ala Gly Pro His Val Trp Gly Asp Pro
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 68
<211> LENGTH: 193
<212> TYPE: PRT
<213> ORGANISM: Homo sapiens

<400> SEQUENCE: 68

Arg Pro Leu Ala Phe Ser Asp Ala Gly Pro His Val His Tyr Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro

```
                130                 135                 140
Met Leu Pro Met Val Pro Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 69
<211> LENGTH: 189
<212> TYPE: PRT
<213> ORGANISM: Homo sapiens

<400> SEQUENCE: 69

Arg Asp Ser Ser Pro Leu Val His Tyr Gly Trp Gly Asp Pro Ile Arg
1               5                   10                  15

Leu Arg His Leu Tyr Thr Ser Gly Pro His Gly Leu Ser Ser Cys Phe
                20                  25                  30

Leu Arg Ile Arg Ala Asp Gly Val Val Asp Cys Ala Arg Gly Gln Ser
            35                  40                  45

Ala His Ser Leu Leu Glu Ile Lys Ala Val Ala Leu Arg Thr Val Ala
        50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
            115                 120                 125

Asn Arg Gly Phe Leu Pro Leu Ser His Phe Leu Pro Met Leu Pro Met
        130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
                180                 185

<210> SEQ ID NO 70
<211> LENGTH: 190
<212> TYPE: PRT
<213> ORGANISM: Homo sapiens

<400> SEQUENCE: 70

Met Arg Asp Ser Ser Pro Leu Val His Tyr Gly Trp Gly Asp Pro Ile
1               5                   10                  15

Arg Leu Arg His Leu Tyr Thr Ser Gly Pro His Gly Leu Ser Ser Cys
                20                  25                  30

Phe Leu Arg Ile Arg Ala Asp Gly Val Val Asp Cys Ala Arg Gly Gln
            35                  40                  45

Ser Ala His Ser Leu Leu Glu Ile Lys Ala Val Ala Leu Arg Thr Val
        50                  55                  60

Ala Ile Lys Gly Val His Ser Val Arg Tyr Leu Cys Met Gly Ala Asp
65                  70                  75                  80
```

Gly Lys Met Gln Gly Leu Leu Gln Tyr Ser Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 71
<211> LENGTH: 181
<212> TYPE: PRT
<213> ORGANISM: Homo sapiens

<400> SEQUENCE: 71

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Ser Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 72
<211> LENGTH: 181
<212> TYPE: PRT
<213> ORGANISM: Homo sapiens

<400> SEQUENCE: 72

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

```
Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 73
<211> LENGTH: 212
<212> TYPE: PRT
<213> ORGANISM: Homo sapiens

<400> SEQUENCE: 73

His Pro Ile Pro Asp Ser Ser Pro Leu Leu Gln Phe Gly Gly Gln Val
 1               5                  10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Val Gln Asp Glu Leu Gln Gly
                165                 170                 175

Val Gly Gly Glu Gly Cys His Met His Pro Glu Asn Cys Lys Thr Leu
                180                 185                 190

Leu Thr Asp Ile Asp Arg Thr His Thr Glu Lys Pro Val Trp Asp Gly
            195                 200                 205

Ile Thr Gly Glu
```

<210> SEQ ID NO 74
<211> LENGTH: 189
<212> TYPE: PRT
<213> ORGANISM: Homo sapiens

<400> SEQUENCE: 74

```
Arg Asp Ala Gly Pro His Val His Tyr Gly Trp Gly Asp Pro Ile Arg
1               5                   10                  15

Leu Arg His Leu Tyr Thr Ser Gly Pro His Gly Leu Ser Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
            85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185
```

<210> SEQ ID NO 75
<211> LENGTH: 184
<212> TYPE: PRT
<213> ORGANISM: Homo sapiens

<400> SEQUENCE: 75

```
Arg Val His Tyr Gly Trp Gly Asp Pro Ile Arg Leu Arg His Leu Tyr
1               5                   10                  15

Thr Ser Gly Pro His Gly Leu Ser Ser Cys Phe Leu Arg Ile Arg Ala
            20                  25                  30

Asp Gly Val Val Asp Cys Ala Arg Gly Gln Ser Ala His Ser Leu Leu
        35                  40                  45

Glu Ile Lys Ala Val Ala Leu Arg Thr Val Ala Ile Lys Gly Val His
    50                  55                  60

Ser Val Arg Tyr Leu Cys Met Gly Ala Asp Gly Lys Met Gln Gly Leu
65                  70                  75                  80

Leu Gln Tyr Ser Glu Glu Asp Cys Ala Phe Glu Glu Glu Ile Arg Pro
            85                  90                  95

Asp Gly Tyr Asn Val Tyr Arg Ser Glu Lys His Arg Leu Pro Val Ser
            100                 105                 110

Leu Ser Ser Ala Lys Gln Arg Gln Leu Tyr Lys Asn Arg Gly Phe Leu
        115                 120                 125

Pro Leu Ser His Phe Leu Pro Met Leu Pro Met Val Pro Glu Glu Pro
```

```
                    130                 135                 140
Glu Asp Leu Arg Gly His Leu Glu Ser Asp Met Phe Ser Ser Pro Leu
145                 150                 155                 160

Glu Thr Asp Ser Met Asp Pro Phe Gly Leu Val Thr Gly Leu Glu Ala
                    165                 170                 175

Val Arg Ser Pro Ser Phe Glu Lys
                    180

<210> SEQ ID NO 76
<211> LENGTH: 179
<212> TYPE: PRT
<213> ORGANISM: Homo sapiens

<400> SEQUENCE: 76

Arg Gly Asp Pro Ile Arg Leu Arg His Leu Tyr Thr Ser Gly Pro His
1               5                   10                  15

Gly Leu Ser Ser Cys Phe Leu Arg Ile Arg Ala Asp Gly Val Val Asp
                20                  25                  30

Cys Ala Arg Gly Gln Ser Ala His Ser Leu Leu Glu Ile Lys Ala Val
            35                  40                  45

Ala Leu Arg Thr Val Ala Ile Lys Gly Val His Ser Val Arg Tyr Leu
        50                  55                  60

Cys Met Gly Ala Asp Gly Lys Met Gln Gly Leu Leu Gln Tyr Ser Glu
65                  70                  75                  80

Glu Asp Cys Ala Phe Glu Glu Ile Arg Pro Asp Gly Tyr Asn Val
                85                  90                  95

Tyr Arg Ser Glu Lys His Arg Leu Pro Val Ser Leu Ser Ser Ala Lys
                100                 105                 110

Gln Arg Gln Leu Tyr Lys Asn Arg Gly Phe Leu Pro Leu Ser His Phe
            115                 120                 125

Leu Pro Met Leu Pro Met Val Pro Glu Glu Pro Glu Asp Leu Arg Gly
        130                 135                 140

His Leu Glu Ser Asp Met Phe Ser Ser Pro Leu Glu Thr Asp Ser Met
145                 150                 155                 160

Asp Pro Phe Gly Leu Val Thr Gly Leu Glu Ala Val Arg Ser Pro Ser
                165                 170                 175

Phe Glu Lys

<210> SEQ ID NO 77
<211> LENGTH: 175
<212> TYPE: PRT
<213> ORGANISM: Homo sapiens

<400> SEQUENCE: 77

Arg Arg Leu Arg His Leu Tyr Thr Ser Gly Pro His Gly Leu Ser Ser
1               5                   10                  15

Cys Phe Leu Arg Ile Arg Ala Asp Gly Val Val Asp Cys Ala Arg Gly
                20                  25                  30

Gln Ser Ala His Ser Leu Leu Glu Ile Lys Ala Val Ala Leu Arg Thr
            35                  40                  45

Val Ala Ile Lys Gly Val His Ser Val Arg Tyr Leu Cys Met Gly Ala
        50                  55                  60

Asp Gly Lys Met Gln Gly Leu Leu Gln Tyr Ser Glu Glu Asp Cys Ala
65                  70                  75                  80

Phe Glu Glu Glu Ile Arg Pro Asp Gly Tyr Asn Val Tyr Arg Ser Glu
                85                  90                  95
```

```
Lys His Arg Leu Pro Val Ser Leu Ser Ser Ala Lys Gln Arg Gln Leu
            100                 105                 110

Tyr Lys Asn Arg Gly Phe Leu Pro Leu Ser His Phe Leu Pro Met Leu
            115                 120                 125

Pro Met Val Pro Glu Glu Pro Glu Asp Leu Arg Gly His Leu Glu Ser
130                 135                 140

Asp Met Phe Ser Ser Pro Leu Glu Thr Asp Ser Met Asp Pro Phe Gly
145                 150                 155                 160

Leu Val Thr Gly Leu Glu Ala Val Arg Ser Pro Ser Phe Glu Lys
                165                 170                 175

<210> SEQ ID NO 78
<211> LENGTH: 188
<212> TYPE: PRT
<213> ORGANISM: Homo sapiens

<400> SEQUENCE: 78

Arg Ala Gly Pro His Val His Tyr Gly Trp Gly Asp Pro Ile Arg Leu
1               5                   10                  15

Arg His Leu Tyr Thr Ser Gly Pro His Gly Leu Ser Ser Cys Phe Leu
            20                  25                  30

Arg Ile Arg Ala Asp Gly Val Val Asp Cys Ala Arg Gly Gln Ser Ala
        35                  40                  45

His Ser Leu Leu Glu Ile Lys Ala Val Ala Leu Arg Thr Val Ala Ile
50                  55                  60

Lys Gly Val His Ser Val Arg Tyr Leu Cys Met Gly Ala Asp Gly Lys
65                  70                  75                  80

Met Gln Gly Leu Leu Gln Tyr Ser Glu Glu Asp Cys Ala Phe Glu Glu
                85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
            115                 120                 125

Arg Gly Phe Leu Pro Leu Ser His Phe Leu Pro Met Leu Pro Met Val
130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185

<210> SEQ ID NO 79
<211> LENGTH: 187
<212> TYPE: PRT
<213> ORGANISM: Homo sapiens

<400> SEQUENCE: 79

Arg Gly Pro His Val His Tyr Gly Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
50                  55                  60
```

```
Gly Val His Ser Val Arg Tyr Leu Cys Met Gly Ala Asp Gly Lys Met
 65                  70                  75                  80

Gln Gly Leu Leu Gln Tyr Ser Glu Glu Asp Cys Ala Phe Glu Glu Glu
                 85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 80
<211> LENGTH: 186
<212> TYPE: PRT
<213> ORGANISM: Homo sapiens

<400> SEQUENCE: 80

Arg Pro His Val His Tyr Gly Trp Gly Asp Pro Ile Arg Leu Arg His
1               5                   10                  15

Leu Tyr Thr Ser Gly Pro His Gly Leu Ser Ser Cys Phe Leu Arg Ile
            20                  25                  30

Arg Ala Asp Gly Val Val Asp Cys Ala Arg Gly Gln Ser Ala His Ser
        35                  40                  45

Leu Leu Glu Ile Lys Ala Val Ala Leu Arg Thr Val Ala Ile Lys Gly
    50                  55                  60

Val His Ser Val Arg Tyr Leu Cys Met Gly Ala Asp Gly Lys Met Gln
 65                 70                  75                  80

Gly Leu Leu Gln Tyr Ser Glu Glu Asp Cys Ala Phe Glu Glu Glu Ile
                85                  90                  95

Arg Pro Asp Gly Tyr Asn Val Tyr Arg Ser Glu Lys His Arg Leu Pro
            100                 105                 110

Val Ser Leu Ser Ser Ala Lys Gln Arg Gln Leu Tyr Lys Asn Arg Gly
        115                 120                 125

Phe Leu Pro Leu Ser His Phe Leu Pro Met Leu Pro Met Val Pro Glu
    130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 81
<211> LENGTH: 185
<212> TYPE: PRT
<213> ORGANISM: Homo sapiens

<400> SEQUENCE: 81

Arg His Val His Tyr Gly Trp Gly Asp Pro Ile Arg Leu Arg His Leu
1               5                   10                  15
```

```
Tyr Thr Ser Gly Pro His Gly Leu Ser Ser Cys Phe Leu Arg Ile Arg
            20                  25                  30

Ala Asp Gly Val Val Asp Cys Ala Arg Gly Gln Ser Ala His Ser Leu
            35                  40                  45

Leu Glu Ile Lys Ala Val Ala Leu Arg Thr Val Ala Ile Lys Gly Val
 50                  55                  60

His Ser Val Arg Tyr Leu Cys Met Gly Ala Asp Gly Lys Met Gln Gly
 65                  70                  75                  80

Leu Leu Gln Tyr Ser Glu Glu Asp Cys Ala Phe Glu Glu Glu Ile Arg
                85                  90                  95

Pro Asp Gly Tyr Asn Val Tyr Arg Ser Glu Lys His Arg Leu Pro Val
                100                 105                 110

Ser Leu Ser Ser Ala Lys Gln Arg Gln Leu Tyr Lys Asn Arg Gly Phe
                115                 120                 125

Leu Pro Leu Ser His Phe Leu Pro Met Leu Pro Met Val Pro Glu Glu
 130                 135                 140

Pro Glu Asp Leu Arg Gly His Leu Glu Ser Asp Met Phe Ser Ser Pro
145                 150                 155                 160

Leu Glu Thr Asp Ser Met Asp Pro Phe Gly Leu Val Thr Gly Leu Glu
                165                 170                 175

Ala Val Arg Ser Pro Ser Phe Glu Lys
                180                 185

<210> SEQ ID NO 82
<211> LENGTH: 194
<212> TYPE: PRT
<213> ORGANISM: Homo sapiens

<400> SEQUENCE: 82

Arg Pro Leu Ala Phe Ser Ala Ala Gly Pro His Val His Tyr Gly Trp
 1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
                35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
                115                 120                 125

Arg Gln Leu Tyr Lys Asn Arg Gly Phe Leu Pro Leu Ser His Phe Leu
            130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys
```

<210> SEQ ID NO 83
<211> LENGTH: 194
<212> TYPE: PRT
<213> ORGANISM: Homo sapiens

<400> SEQUENCE: 83

Arg Pro Leu Ala Phe Ser Asp Ala Ala Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 84
<211> LENGTH: 194
<212> TYPE: PRT
<213> ORGANISM: Homo sapiens

<400> SEQUENCE: 84

Arg Pro Leu Ala Phe Ser Asp Ala Gly Ala His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
            130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 85
<211> LENGTH: 194
<212> TYPE: PRT
<213> ORGANISM: Homo sapiens

<400> SEQUENCE: 85

Arg Pro Leu Ala Phe Ser Asp Ala Gly Pro His Val His Tyr Gly Ala
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 86
<211> LENGTH: 194
<212> TYPE: PRT
<213> ORGANISM: Homo sapiens

<400> SEQUENCE: 86

Arg Pro Leu Ala Phe Ser Asp Ala Gly Pro His Val His Tyr Gly Trp
1               5                   10                  15

Gly Ala Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

```
Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 87
<211> LENGTH: 167
<212> TYPE: PRT
<213> ORGANISM: Homo sapiens

<400> SEQUENCE: 87

Arg Pro Leu Ala Phe Ser Asp Ala Gly Pro His Val His Tyr Gly Trp
 1                5                  10                  15

Gly Asp Ala Ile Cys Ala Arg Gly Gln Ser Ala His Ser Leu Leu Glu
                 20                  25                  30

Ile Lys Ala Val Ala Leu Arg Thr Val Ala Ile Lys Gly Val His Ser
             35                  40                  45

Val Arg Tyr Leu Cys Met Gly Ala Asp Gly Lys Met Gln Gly Leu Leu
    50                  55                  60

Gln Tyr Ser Glu Glu Asp Cys Ala Phe Glu Glu Glu Ile Arg Pro Asp
 65                  70                  75                  80

Gly Tyr Asn Val Tyr Arg Ser Glu Lys His Arg Leu Pro Val Ser Leu
                 85                  90                  95

Ser Ser Ala Lys Gln Arg Gln Leu Tyr Lys Asn Arg Gly Phe Leu Pro
            100                 105                 110

Leu Ser His Phe Leu Pro Met Leu Pro Met Val Pro Glu Glu Pro Glu
        115                 120                 125

Asp Leu Arg Gly His Leu Glu Ser Asp Met Phe Ser Ser Pro Leu Glu
    130                 135                 140

Thr Asp Ser Met Asp Pro Phe Gly Leu Val Thr Gly Leu Glu Ala Val
145                 150                 155                 160

Arg Ser Pro Ser Phe Glu Lys
                165

<210> SEQ ID NO 88
<211> LENGTH: 194
<212> TYPE: PRT
<213> ORGANISM: Homo sapiens

<400> SEQUENCE: 88

Arg Pro Leu Ala Phe Ser Asp Ala Gly Pro His Val His Tyr Gly Trp
 1                5                  10                  15
```

```
Gly Asp Pro Ile Arg Leu Arg His Leu Tyr Thr Ser Gly Pro Ala Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Gln Tyr Ser Glu Glu
                85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ala His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 89
<211> LENGTH: 194
<212> TYPE: PRT
<213> ORGANISM: Homo sapiens

<400> SEQUENCE: 89

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro Ala Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Gln Tyr Ser Glu Glu
                85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser Ala Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190
```

Glu Lys

<210> SEQ ID NO 90
<211> LENGTH: 194
<212> TYPE: PRT
<213> ORGANISM: Homo sapiens

<400> SEQUENCE: 90

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 91
<211> LENGTH: 194
<212> TYPE: PRT
<213> ORGANISM: Homo sapiens

<400> SEQUENCE: 91

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

```
Arg Gln Leu Tyr Lys Asn Arg Gly Phe Leu Pro Leu Ala His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 92
<211> LENGTH: 194
<212> TYPE: PRT
<213> ORGANISM: Homo sapiens

<400> SEQUENCE: 92

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Ala Gln
            115                 120                 125

Arg Gln Leu Tyr Lys Asn Arg Gly Phe Leu Pro Leu Ser Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 93
<211> LENGTH: 194
<212> TYPE: PRT
<213> ORGANISM: Homo sapiens

<400> SEQUENCE: 93

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
```

```
                50                  55                  60
Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
                100                 105                 110

Arg Ser Glu Lys His Arg Leu Pro Val Ser Leu Ser Ala Lys Gln
                115                 120                 125

Ala Gln Leu Tyr Lys Asn Arg Gly Phe Leu Pro Leu Ala His Phe Leu
                130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 94
<211> LENGTH: 194
<212> TYPE: PRT
<213> ORGANISM: Homo sapiens

<400> SEQUENCE: 94

Arg Pro Leu Ala Phe Ser Asp Ala Gly Pro His Val His Tyr Gly Trp
 1               5                  10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
                35                  40                  45

Ala Arg Gly Gln Ser Ala His Ser Leu Leu Glu Ile Lys Ala Val Ala
                50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
                100                 105                 110

Arg Ser Glu Lys His Arg Leu Pro Val Ser Leu Ser Ala Lys Gln
                115                 120                 125

Arg Gln Leu Tyr Lys Asn Arg Gly Phe Leu Pro Leu Ala Ala Phe Leu
                130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 95
<211> LENGTH: 194
<212> TYPE: PRT
<213> ORGANISM: Homo sapiens
```

<400> SEQUENCE: 95

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ala Ala Gln
        115                 120                 125

Arg Gln Leu Tyr Lys Asn Arg Gly Phe Leu Pro Leu Ser Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys
```

<210> SEQ ID NO 96
<211> LENGTH: 194
<212> TYPE: PRT
<213> ORGANISM: Homo sapiens

<400> SEQUENCE: 96

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ala His Phe Leu
    130                 135                 140

Pro Met Leu Pro Met Val Pro Glu Glu Pro Glu Asp Leu Arg Gly His
145                 150                 155                 160
```

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 97
<211> LENGTH: 194
<212> TYPE: PRT
<213> ORGANISM: Homo sapiens

<400> SEQUENCE: 97

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ser Ala Phe Leu
    130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 98
<211> LENGTH: 194
<212> TYPE: PRT
<213> ORGANISM: Homo sapiens

<400> SEQUENCE: 98

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

```
Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ala Ala Gln
        115                 120                 125

Ala Gln Leu Tyr Lys Asn Arg Gly Phe Leu Pro Leu Ala Ala Phe Leu
    130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 99
<211> LENGTH: 194
<212> TYPE: PRT
<213> ORGANISM: Homo sapiens

<400> SEQUENCE: 99

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 100
<211> LENGTH: 181
<212> TYPE: PRT
<213> ORGANISM: Homo sapiens

<400> SEQUENCE: 100

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
```

```
                 20                  25                  30

Leu Glu Ile Arg Glu Asp Gly Thr Val Gly Ala Ala Asp Gln Ser
            35                  40                  45

Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 101
<211> LENGTH: 4
<212> TYPE: PRT
<213> ORGANISM: Homo sapiens

<400> SEQUENCE: 101

```
Val His Tyr Gly
1
```

<210> SEQ ID NO 102
<211> LENGTH: 9
<212> TYPE: PRT
<213> ORGANISM: Homo sapiens

<400> SEQUENCE: 102

```
Asp Ala Ser Pro His Val His Tyr Gly
1               5
```

<210> SEQ ID NO 103
<211> LENGTH: 9
<212> TYPE: PRT
<213> ORGANISM: Homo sapiens

<400> SEQUENCE: 103

```
Asp Ser Ser Pro Leu Val His Tyr Gly
1               5
```

<210> SEQ ID NO 104
<211> LENGTH: 7
<212> TYPE: PRT
<213> ORGANISM: Homo sapiens

<400> SEQUENCE: 104

```
Asp Ser Ser Pro Leu Leu Gln
1               5
```

<210> SEQ ID NO 105
<211> LENGTH: 12

```
<212> TYPE: PRT
<213> ORGANISM: Homo sapiens

<400> SEQUENCE: 105

Asp Ser Ser Pro Leu Leu Gln Phe Gly Gly Gln Val
1               5                   10

<210> SEQ ID NO 106
<211> LENGTH: 5
<212> TYPE: PRT
<213> ORGANISM: Homo sapiens

<400> SEQUENCE: 106

Arg His Pro Ile Pro
1               5

<210> SEQ ID NO 107
<211> LENGTH: 4
<212> TYPE: PRT
<213> ORGANISM: Homo sapiens

<400> SEQUENCE: 107

His Pro Ile Pro
1

<210> SEQ ID NO 108
<211> LENGTH: 5
<212> TYPE: PRT
<213> ORGANISM: Homo sapiens

<400> SEQUENCE: 108

Arg Pro Leu Ala Phe
1               5

<210> SEQ ID NO 109
<211> LENGTH: 4
<212> TYPE: PRT
<213> ORGANISM: Homo sapiens

<400> SEQUENCE: 109

Pro Leu Ala Phe
1

<210> SEQ ID NO 110
<211> LENGTH: 6
<212> TYPE: PRT
<213> ORGANISM: Homo sapiens

<400> SEQUENCE: 110

Met Asp Ser Ser Pro Leu
1               5

<210> SEQ ID NO 111
<211> LENGTH: 7
<212> TYPE: PRT
<213> ORGANISM: Homo sapiens

<400> SEQUENCE: 111

Met Ser Asp Ser Ser Pro Leu
1               5

<210> SEQ ID NO 112
<211> LENGTH: 6
<212> TYPE: PRT
<213> ORGANISM: Homo sapiens
```

<400> SEQUENCE: 112

Ser Asp Ser Ser Pro Leu
1               5

<210> SEQ ID NO 113
<211> LENGTH: 5
<212> TYPE: PRT
<213> ORGANISM: Homo sapiens

<400> SEQUENCE: 113

Met Ser Ser Pro Leu
1               5

<210> SEQ ID NO 114
<211> LENGTH: 4
<212> TYPE: PRT
<213> ORGANISM: Homo sapiens

<400> SEQUENCE: 114

Ser Ser Pro Leu
1

<210> SEQ ID NO 115
<211> LENGTH: 4
<212> TYPE: PRT
<213> ORGANISM: Homo sapiens

<400> SEQUENCE: 115

Arg Asp Ser Ser
1

<210> SEQ ID NO 116
<211> LENGTH: 4
<212> TYPE: PRT
<213> ORGANISM: Homo sapiens

<400> SEQUENCE: 116

Met Asp Ser Ser
1

<210> SEQ ID NO 117
<211> LENGTH: 5
<212> TYPE: PRT
<213> ORGANISM: Homo sapiens

<400> SEQUENCE: 117

Met Arg Asp Ser Ser
1               5

<210> SEQ ID NO 118
<211> LENGTH: 5
<212> TYPE: PRT
<213> ORGANISM: Homo sapiens

<400> SEQUENCE: 118

Met Ser Ser Pro Leu
1               5

<210> SEQ ID NO 119
<211> LENGTH: 6
<212> TYPE: PRT
<213> ORGANISM: Homo sapiens

<400> SEQUENCE: 119

Met Asp Ser Ser Pro Leu
1               5

<210> SEQ ID NO 120
<211> LENGTH: 7
<212> TYPE: PRT
<213> ORGANISM: Homo sapiens

<400> SEQUENCE: 120

Met Ser Asp Ser Ser Pro Leu
1               5

<210> SEQ ID NO 121
<211> LENGTH: 5
<212> TYPE: PRT
<213> ORGANISM: Homo sapiens

<400> SEQUENCE: 121

Asp Ser Ser Pro Leu
1               5

<210> SEQ ID NO 122
<211> LENGTH: 5
<212> TYPE: PRT
<213> ORGANISM: Homo sapiens

<400> SEQUENCE: 122

Asp Ala Ser Pro His
1               5

<210> SEQ ID NO 123
<211> LENGTH: 4
<212> TYPE: PRT
<213> ORGANISM: Homo sapiens

<400> SEQUENCE: 123

Arg Asp Ser Ser
1

<210> SEQ ID NO 124
<211> LENGTH: 4
<212> TYPE: PRT
<213> ORGANISM: Homo sapiens

<400> SEQUENCE: 124

Met Asp Ser Ser
1

<210> SEQ ID NO 125
<211> LENGTH: 5
<212> TYPE: PRT
<213> ORGANISM: Homo sapiens

<400> SEQUENCE: 125

Met Arg Asp Ser Ser
1               5

<210> SEQ ID NO 126
<211> LENGTH: 6
<212> TYPE: PRT
<213> ORGANISM: Homo sapiens

<400> SEQUENCE: 126

Met Asp Ser Ser Pro Leu

```
1               5

<210> SEQ ID NO 127
<211> LENGTH: 7
<212> TYPE: PRT
<213> ORGANISM: Homo sapiens

<400> SEQUENCE: 127

Met Ser Asp Ser Ser Pro Leu
1               5

<210> SEQ ID NO 128
<211> LENGTH: 5
<212> TYPE: PRT
<213> ORGANISM: Homo sapiens

<400> SEQUENCE: 128

Met Ser Ser Pro Leu
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 129

Gly Ser Gly Gly Ser
1               5

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Linker
      sequence

<400> SEQUENCE: 130

Gly Gly Gly Ser
1

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Linker
      sequence

<400> SEQUENCE: 131

Gly Gly Ser Gly
1

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 132

Gly Gly Ser Gly Gly
1               5
```

-continued

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 133

Gly Ser Gly Ser Gly
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 134

Gly Ser Gly Gly Gly
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 135

Gly Ser Ser Ser Gly
1               5

<210> SEQ ID NO 136
<211> LENGTH: 32
<212> TYPE: DNA
<213> ORGANISM: Artificial Sequence
<220> FEATURE:
<223> OTHER INFORMATION: Description of Artificial Sequence: Forward
      primer

<400> SEQUENCE: 136
ccgactagtc accatgcgga gcgggtgtgt gg                                32

<210> SEQ ID NO 137
<211> LENGTH: 41
<212> TYPE: DNA
<213> ORGANISM: Artificial Sequence
<220> FEATURE:
<223> OTHER INFORMATION: Description of Artificial Sequence: Reverse
      primer

<400> SEQUENCE: 137
ataagaatgc ggccgcttac ttctcaaagc tgggactcct c                     41

<210> SEQ ID NO 138
<211> LENGTH: 186
<212> TYPE: PRT
<213> ORGANISM: Homo sapiens

<400> SEQUENCE: 138

Asp Ser Ser Pro Leu Leu Gln Phe Gly Gly Gln Val Arg Leu Arg His
1               5                   10                  15

Leu Tyr Thr Ser Gly Pro His Gly Leu Ser Ser Cys Phe Leu Arg Ile
            20                  25                  30

Arg Ala Asp Gly Val Val Asp Cys Ala Arg Gly Gln Ser Ala His Ser
        35                  40                  45

Leu Leu Glu Ile Lys Ala Val Ala Leu Arg Thr Val Ala Ile Lys Gly
    50                  55                  60

Val His Ser Val Arg Tyr Leu Cys Met Gly Ala Asp Gly Lys Met Gln
65                  70                  75                  80

Gly Leu Leu Gln Tyr Ser Glu Glu Asp Cys Ala Phe Glu Glu Glu Ile
                85                  90                  95

Arg Pro Asp Gly Tyr Asn Val Tyr Arg Ser Glu Lys His Arg Leu Pro
            100                 105                 110

Val Ser Leu Ser Ser Ala Lys Gln Arg Gln Leu Tyr Lys Asn Arg Gly
        115                 120                 125

Phe Leu Pro Leu Ser His Phe Leu Pro Met Leu Pro Met Val Pro Glu
    130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 139
<211> LENGTH: 194
<212> TYPE: PRT
<213> ORGANISM: Homo sapiens

<400> SEQUENCE: 139

Arg Pro Leu Ala Phe Ser Asp Ala Ser Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 140
<211> LENGTH: 194
<212> TYPE: PRT
<213> ORGANISM: Homo sapiens

<400> SEQUENCE: 140

```
Arg Pro Leu Ala Phe Ser Asp Ser Ser Pro Leu Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys
```

<210> SEQ ID NO 141
<211> LENGTH: 188
<212> TYPE: PRT
<213> ORGANISM: Homo sapiens

<400> SEQUENCE: 141

```
Asp Ser Ser Pro Leu Val His Tyr Gly Trp Gly Asp Pro Ile Arg Leu
1               5                   10                  15

Arg His Leu Tyr Thr Ser Gly Pro His Gly Leu Ser Ser Cys Phe Leu
                20                  25                  30

Arg Ile Arg Ala Asp Gly Val Val Asp Cys Ala Arg Gly Gln Ser Ala
            35                  40                  45

His Ser Leu Leu Glu Ile Lys Ala Val Ala Leu Arg Thr Val Ala Ile
        50                  55                  60

Lys Gly Val His Ser Val Arg Tyr Leu Cys Met Gly Ala Asp Gly Lys
65                  70                  75                  80

Met Gln Gly Leu Leu Gln Tyr Ser Glu Glu Asp Cys Ala Phe Glu Glu
                85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
        115                 120                 125
```

```
Arg Gly Phe Leu Pro Leu Ser His Phe Leu Pro Met Leu Pro Met Val
    130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185
```

<210> SEQ ID NO 142
<211> LENGTH: 193
<212> TYPE: PRT
<213> ORGANISM: Homo sapiens

<400> SEQUENCE: 142

```
Arg His Pro Ile Pro Asp Ser Ser Pro Leu Leu Gln Phe Gly Trp Gly
1               5                   10                  15

Asp Pro Ile Arg Leu Arg His Leu Tyr Thr Ser Gly Pro His Gly Leu
                20                  25                  30

Ser Ser Cys Phe Leu Arg Ile Arg Ala Asp Gly Val Val Asp Cys Ala
            35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys
```

<210> SEQ ID NO 143
<211> LENGTH: 191
<212> TYPE: PRT
<213> ORGANISM: Homo sapiens

<400> SEQUENCE: 143

```
Arg His Pro Ile Pro Asp Ser Ser Pro Leu Leu Gln Trp Gly Asp Pro
1               5                   10                  15

Ile Arg Leu Arg His Leu Tyr Thr Ser Gly Pro His Gly Leu Ser Ser
                20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
```

```
                65                  70                  75                  80
Asp Gly Lys Met Gln Gly Leu Leu Gln Tyr Ser Glu Glu Asp Cys Ala
                    85                  90                  95

Phe Glu Glu Glu Ile Arg Pro Asp Gly Tyr Asn Val Tyr Arg Ser Glu
                    100                 105                 110

Lys His Arg Leu Pro Val Ser Leu Ser Ser Ala Lys Gln Arg Gln Leu
                    115                 120                 125

Tyr Lys Asn Arg Gly Phe Leu Pro Leu Ser His Phe Leu Pro Met Leu
                    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                    165                 170                 175

Leu Val Thr Gly Leu Glu Ala Val Arg Ser Pro Ser Phe Glu Lys
                    180                 185                 190

<210> SEQ ID NO 144
<211> LENGTH: 194
<212> TYPE: PRT
<213> ORGANISM: Homo sapiens

<400> SEQUENCE: 144

Arg Pro Leu Ala Phe Ser Asp Ala Gly Pro Leu Leu Gln Phe Gly Trp
1               5                   10                  15

Gly Asp Pro Ile Arg Leu Arg His Leu Tyr Thr Ser Gly Pro His Gly
                    20                  25                  30

Leu Ser Ser Cys Phe Leu Arg Ile Arg Ala Asp Gly Val Val Asp Cys
                35                  40                  45

Ala Arg Gly Gln Ser Ala His Ser Leu Leu Glu Ile Lys Ala Val Ala
            50                  55                  60

Leu Arg Thr Val Ala Ile Lys Gly Val His Ser Val Arg Tyr Leu Cys
65              70                  75                  80

Met Gly Ala Asp Gly Lys Met Gln Gly Leu Leu Gln Tyr Ser Glu Glu
                    85                  90                  95

Asp Cys Ala Phe Glu Glu Glu Ile Arg Pro Asp Gly Tyr Asn Val Tyr
                    100                 105                 110

Arg Ser Glu Lys His Arg Leu Pro Val Ser Leu Ser Ser Ala Lys Gln
                    115                 120                 125

Arg Gln Leu Tyr Lys Asn Arg Gly Phe Leu Pro Leu Ser His Phe Leu
                130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                    165                 170                 175

Pro Phe Gly Leu Val Thr Gly Leu Glu Ala Val Arg Ser Pro Ser Phe
                    180                 185                 190

Glu Lys

<210> SEQ ID NO 145
<211> LENGTH: 193
<212> TYPE: PRT
<213> ORGANISM: Homo sapiens

<400> SEQUENCE: 145

Arg His Pro Ile Pro Asp Ser Ser Pro His Val His Tyr Gly Trp Gly
1               5                   10                  15
```

Asp Pro Ile Arg Leu Arg His Leu Tyr Thr Ser Gly Pro His Gly Leu
           20                  25                  30

Ser Ser Cys Phe Leu Arg Ile Arg Ala Asp Gly Val Val Asp Cys Ala
       35                  40                  45

Arg Gly Gln Ser Ala His Ser Leu Leu Glu Ile Lys Ala Val Ala Leu
   50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
               85                  90                  95

Cys Ala Phe Glu Glu Glu Ile Arg Pro Asp Gly Tyr Asn Val Tyr Arg
           100                 105                 110

Ser Glu Lys His Arg Leu Pro Val Ser Leu Ser Ser Ala Lys Gln Arg
       115                 120                 125

Gln Leu Tyr Lys Asn Arg Gly Phe Leu Pro Leu Ser His Phe Leu Pro
   130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
               165                 170                 175

Phe Gly Leu Val Thr Gly Leu Glu Ala Val Arg Ser Pro Ser Phe Glu
           180                 185                 190

Lys

<210> SEQ ID NO 146
<211> LENGTH: 192
<212> TYPE: PRT
<213> ORGANISM: Homo sapiens

<400> SEQUENCE: 146

Arg Pro Leu Ala Phe Ser Asp Ala Gly Pro Leu Leu Gln Phe Gly Gly
1               5                   10                  15

Gln Val Arg Leu Arg His Leu Tyr Thr Ser Gly Pro His Gly Leu Ser
           20                  25                  30

Ser Cys Phe Leu Arg Ile Arg Ala Asp Gly Val Val Asp Cys Ala Arg
       35                  40                  45

Gly Gln Ser Ala His Ser Leu Leu Glu Ile Lys Ala Val Ala Leu Arg
   50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
               85                  90                  95

Ala Phe Glu Glu Glu Ile Arg Pro Asp Gly Tyr Asn Val Tyr Arg Ser
           100                 105                 110

Glu Lys His Arg Leu Pro Val Ser Leu Ser Ser Ala Lys Gln Arg Gln
       115                 120                 125

Leu Tyr Lys Asn Arg Gly Phe Leu Pro Leu Ser His Phe Leu Pro Met
   130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
               165                 170                 175

Gly Leu Val Thr Gly Leu Glu Ala Val Arg Ser Pro Ser Phe Glu Lys
           180                 185                 190

<210> SEQ ID NO 147
<211> LENGTH: 191
<212> TYPE: PRT
<213> ORGANISM: Homo sapiens

<400> SEQUENCE: 147

```
Arg His Pro Ile Pro Asp Ser Ser Pro His Val His Tyr Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 148
<211> LENGTH: 187
<212> TYPE: PRT
<213> ORGANISM: Homo sapiens

<400> SEQUENCE: 148

```
Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140
```

```
Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
            165                 170                 175

Leu Glu Ala Val Arg Ser Pro Ser Phe Glu Lys
        180                 185
```

<210> SEQ ID NO 149
<211> LENGTH: 192
<212> TYPE: PRT
<213> ORGANISM: Homo sapiens

<400> SEQUENCE: 149

```
Arg Pro Leu Ala Phe Ser Asp Ser Ser Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 150
<211> LENGTH: 191
<212> TYPE: PRT
<213> ORGANISM: Homo sapiens

<400> SEQUENCE: 150

```
Arg His Pro Ile Pro Asp Ser Ser Pro Leu Leu Gln Phe Gly Ala Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95
```

```
Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190
```

<210> SEQ ID NO 151
<211> LENGTH: 191
<212> TYPE: PRT
<213> ORGANISM: Homo sapiens

<400> SEQUENCE: 151

```
Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190
```

<210> SEQ ID NO 152
<211> LENGTH: 191
<212> TYPE: PRT
<213> ORGANISM: Homo sapiens

<400> SEQUENCE: 152

```
Arg His Pro Ile Pro Asp Ser Ser Pro Leu Leu Gln Phe Gly Pro Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45
```

```
Gln Ser Ala His Ser Leu Leu Glu Ile Lys Ala Val Ala Leu Arg Thr
     50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 153
<211> LENGTH: 191
<212> TYPE: PRT
<213> ORGANISM: Homo sapiens

<400> SEQUENCE: 153

Arg His Pro Ile Pro Asp Ser Ser Pro Leu Leu Gln Phe Gly Gly Ala
  1               5                  10                  15

Val Arg Leu Arg His Leu Tyr Thr Ser Gly Pro His Gly Leu Ser Ser
                 20                  25                  30

Cys Phe Leu Arg Ile Arg Ala Asp Gly Val Val Asp Cys Ala Arg Gly
             35                  40                  45

Gln Ser Ala His Ser Leu Leu Glu Ile Lys Ala Val Ala Leu Arg Thr
     50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 154
<211> LENGTH: 191
<212> TYPE: PRT
<213> ORGANISM: Homo sapiens

<400> SEQUENCE: 154
```

```
Arg His Pro Ile Pro Asp Ser Ser Pro Leu Leu Gln Phe Gly Gly Glu
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65              70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 155
<211> LENGTH: 191
<212> TYPE: PRT
<213> ORGANISM: Homo sapiens

<400> SEQUENCE: 155

Arg His Pro Ile Pro Asp Ser Ser Pro Leu Leu Gln Phe Gly Gly Asn
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65              70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
```

180             185             190

<210> SEQ ID NO 156
<211> LENGTH: 191
<212> TYPE: PRT
<213> ORGANISM: Homo sapiens

<400> SEQUENCE: 156

Arg His Pro Ile Pro Asp Ser Ser Pro Leu Leu Gln Phe Gly Gly Gln
1               5                   10                  15

Ala Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 157
<211> LENGTH: 191
<212> TYPE: PRT
<213> ORGANISM: Homo sapiens

<400> SEQUENCE: 157

Arg His Pro Ile Pro Asp Ser Ser Pro Leu Leu Gln Phe Gly Gly Gln
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu

```
            130                 135                 140
Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 158
<211> LENGTH: 191
<212> TYPE: PRT
<213> ORGANISM: Homo sapiens

<400> SEQUENCE: 158

```
Arg His Pro Ile Pro Asp Ser Ser Pro Leu Leu Gln Phe Gly Gly Gln
1               5                   10                  15

Thr Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 159
<211> LENGTH: 193
<212> TYPE: PRT
<213> ORGANISM: Homo sapiens

<400> SEQUENCE: 159

```
Arg His Pro Ile Pro Asp Ser Ser Pro Leu Leu Gln Phe Gly Trp Gly
1               5                   10                  15

Gln Pro Val Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
```

Cys Ala Phe Glu Glu Ile Arg Pro Asp Gly Tyr Asn Val Tyr Arg
                100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
        130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 160
<211> LENGTH: 190
<212> TYPE: PRT
<213> ORGANISM: Homo sapiens

<400> SEQUENCE: 160

His Pro Ile Pro Asp Ser Ser Pro Leu Leu Gln Phe Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 161
<211> LENGTH: 186
<212> TYPE: PRT
<213> ORGANISM: Homo sapiens

<400> SEQUENCE: 161

Asp Ser Ser Pro Leu Leu Gln Phe Gly Gly Gln Val Arg Leu Arg His
1               5                   10                  15

Leu Tyr Thr Ser Gly Pro His Gly Leu Ser Ser Cys Phe Leu Arg Ile
            20                  25                  30

Arg Ala Asp Gly Val Asp Cys Ala Arg Gly Gln Ser Ala His Ser
    35                  40                  45

Leu Leu Glu Ile Lys Ala Val Ala Leu Arg Thr Val Ala Ile Lys Gly
 50                  55                  60

Val His Ser Val Arg Tyr Leu Cys Met Gly Ala Asp Gly Lys Met Gln
 65                  70                  75                  80

Gly Leu Leu Gln Tyr Ser Glu Glu Asp Cys Ala Phe Glu Glu Ile
                85                  90                  95

Arg Pro Asp Gly Tyr Asn Val Tyr Arg Ser Glu Lys His Arg Leu Pro
                100                 105                 110

Val Ser Leu Ser Ser Ala Lys Gln Arg Gln Leu Tyr Lys Asn Arg Gly
            115                 120                 125

Phe Leu Pro Leu Ser His Phe Leu Pro Met Leu Pro Met Val Pro Glu
130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 162
<211> LENGTH: 190
<212> TYPE: PRT
<213> ORGANISM: Homo sapiens

<400> SEQUENCE: 162

His Pro Ile Pro Asp Ser Ser Pro Leu Leu Gln Trp Gly Asp Pro Ile
 1               5                  10                  15

Arg Leu Arg His Leu Tyr Thr Ser Gly Pro His Gly Leu Ser Ser Cys
                20                  25                  30

Phe Leu Arg Ile Arg Ala Asp Gly Val Val Asp Cys Ala Arg Gly Gln
            35                  40                  45

Ser Ala His Ser Leu Leu Glu Ile Lys Ala Val Ala Leu Arg Thr Val
 50                  55                  60

Ala Ile Lys Gly Val His Ser Val Arg Tyr Leu Cys Met Gly Ala Asp
 65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
                100                 105                 110

His Arg Leu Pro Val Ser Leu Ser Ser Ala Lys Gln Arg Gln Leu Tyr
            115                 120                 125

Lys Asn Arg Gly Phe Leu Pro Leu Ser His Phe Leu Pro Met Leu Pro
130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 163
<211> LENGTH: 192
<212> TYPE: PRT

<213> ORGANISM: Homo sapiens

<400> SEQUENCE: 163

```
His Pro Ile Pro Asp Ser Ser Pro Leu Leu Gln Phe Gly Trp Gly Asp
1               5                   10                  15
Pro Ile Arg Leu Arg His Leu Tyr Thr Ser Gly Pro His Gly Leu Ser
            20                  25                  30
Ser Cys Phe Leu Arg Ile Arg Ala Asp Gly Val Val Asp Cys Ala Arg
        35                  40                  45
Gly Gln Ser Ala His Ser Leu Leu Glu Ile Lys Ala Val Ala Leu Arg
    50                  55                  60
Thr Val Ala Ile Lys Gly Val His Ser Val Arg Tyr Leu Cys Met Gly
65                  70                  75                  80
Ala Asp Gly Lys Met Gln Gly Leu Leu Gln Tyr Ser Glu Glu Asp Cys
                85                  90                  95
Ala Phe Glu Glu Glu Ile Arg Pro Asp Gly Tyr Asn Val Tyr Arg Ser
            100                 105                 110
Glu Lys His Arg Leu Pro Val Ser Leu Ser Ser Ala Lys Gln Arg Gln
        115                 120                 125
Leu Tyr Lys Asn Arg Gly Phe Leu Pro Leu Ser His Phe Leu Pro Met
    130                 135                 140
Leu Pro Met Val Pro Glu Glu Pro Glu Asp Leu Arg Gly His Leu Glu
145                 150                 155                 160
Ser Asp Met Phe Ser Ser Pro Leu Glu Thr Asp Ser Met Asp Pro Phe
                165                 170                 175
Gly Leu Val Thr Gly Leu Glu Ala Val Arg Ser Pro Ser Phe Glu Lys
            180                 185                 190
```

<210> SEQ ID NO 164
<211> LENGTH: 192
<212> TYPE: PRT
<213> ORGANISM: Homo sapiens

<400> SEQUENCE: 164

```
His Pro Ile Pro Asp Ser Ser Pro His Val His Tyr Gly Trp Gly Asp
1               5                   10                  15
Pro Ile Arg Leu Arg His Leu Tyr Thr Ser Gly Pro His Gly Leu Ser
            20                  25                  30
Ser Cys Phe Leu Arg Ile Arg Ala Asp Gly Val Val Asp Cys Ala Arg
        35                  40                  45
Gly Gln Ser Ala His Ser Leu Leu Glu Ile Lys Ala Val Ala Leu Arg
    50                  55                  60
Thr Val Ala Ile Lys Gly Val His Ser Val Arg Tyr Leu Cys Met Gly
65                  70                  75                  80
Ala Asp Gly Lys Met Gln Gly Leu Leu Gln Tyr Ser Glu Glu Asp Cys
                85                  90                  95
Ala Phe Glu Glu Glu Ile Arg Pro Asp Gly Tyr Asn Val Tyr Arg Ser
            100                 105                 110
Glu Lys His Arg Leu Pro Val Ser Leu Ser Ser Ala Lys Gln Arg Gln
        115                 120                 125
Leu Tyr Lys Asn Arg Gly Phe Leu Pro Leu Ser His Phe Leu Pro Met
    130                 135                 140
Leu Pro Met Val Pro Glu Glu Pro Glu Asp Leu Arg Gly His Leu Glu
145                 150                 155                 160
Ser Asp Met Phe Ser Ser Pro Leu Glu Thr Asp Ser Met Asp Pro Phe
```

```
                165                 170                 175
Gly Leu Val Thr Gly Leu Glu Ala Val Arg Ser Pro Ser Phe Glu Lys
            180                 185                 190

<210> SEQ ID NO 165
<211> LENGTH: 190
<212> TYPE: PRT
<213> ORGANISM: Homo sapiens

<400> SEQUENCE: 165

His Pro Ile Pro Asp Ser Ser Pro His Val His Tyr Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 166
<211> LENGTH: 188
<212> TYPE: PRT
<213> ORGANISM: Homo sapiens

<400> SEQUENCE: 166

Asp Ala Gly Pro His Val His Tyr Gly Trp Gly Asp Pro Ile Arg Leu
1               5                   10                  15

Arg His Leu Tyr Thr Ser Gly Pro His Gly Leu Ser Ser Cys Phe Leu
            20                  25                  30

Arg Ile Arg Ala Asp Gly Val Val Asp Cys Ala Arg Gly Gln Ser Ala
        35                  40                  45

His Ser Leu Leu Glu Ile Lys Ala Val Ala Leu Arg Thr Val Ala Ile
    50                  55                  60

Lys Gly Val His Ser Val Arg Tyr Leu Cys Met Gly Ala Asp Gly Lys
65                  70                  75                  80

Met Gln Gly Leu Leu Gln Tyr Ser Glu Glu Asp Cys Ala Phe Glu Glu
                85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
```

```
            115                 120                 125
Arg Gly Phe Leu Pro Leu Ser His Phe Leu Pro Met Leu Pro Met Val
        130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
        180                 185

<210> SEQ ID NO 167
<211> LENGTH: 183
<212> TYPE: PRT
<213> ORGANISM: Homo sapiens

<400> SEQUENCE: 167

Val His Tyr Gly Trp Gly Asp Pro Ile Arg Leu Arg His Leu Tyr Thr
1               5                   10                  15

Ser Gly Pro His Gly Leu Ser Ser Cys Phe Leu Arg Ile Arg Ala Asp
                20                  25                  30

Gly Val Val Asp Cys Ala Arg Gly Gln Ser Ala His Ser Leu Leu Glu
            35                  40                  45

Ile Lys Ala Val Ala Leu Arg Thr Val Ala Ile Lys Gly Val His Ser
        50                  55                  60

Val Arg Tyr Leu Cys Met Gly Ala Asp Gly Lys Met Gln Gly Leu Leu
65                  70                  75                  80

Gln Tyr Ser Glu Glu Asp Cys Ala Phe Glu Glu Ile Arg Pro Asp
                85                  90                  95

Gly Tyr Asn Val Tyr Arg Ser Glu Lys His Arg Leu Pro Val Ser Leu
                100                 105                 110

Ser Ser Ala Lys Gln Arg Gln Leu Tyr Lys Asn Arg Gly Phe Leu Pro
            115                 120                 125

Leu Ser His Phe Leu Pro Met Leu Pro Met Val Pro Glu Glu Pro Glu
        130                 135                 140

Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
            180

<210> SEQ ID NO 168
<211> LENGTH: 174
<212> TYPE: PRT
<213> ORGANISM: Homo sapiens

<400> SEQUENCE: 168

Arg Leu Arg His Leu Tyr Thr Ser Gly Pro His Gly Leu Ser Ser Cys
1               5                   10                  15

Phe Leu Arg Ile Arg Ala Asp Gly Val Val Asp Cys Ala Arg Gly Gln
                20                  25                  30

Ser Ala His Ser Leu Leu Glu Ile Lys Ala Val Ala Leu Arg Thr Val
            35                  40                  45

Ala Ile Lys Gly Val His Ser Val Arg Tyr Leu Cys Met Gly Ala Asp
        50                  55                  60

Gly Lys Met Gln Gly Leu Leu Gln Tyr Ser Glu Glu Asp Cys Ala Phe
```

```
                65                  70                  75                  80
Glu Glu Glu Ile Arg Pro Asp Gly Tyr Asn Val Tyr Arg Ser Glu Lys
                    85                  90                  95

His Arg Leu Pro Val Ser Leu Ser Ser Ala Lys Gln Arg Gln Leu Tyr
                100                 105                 110

Lys Asn Arg Gly Phe Leu Pro Leu Ser His Phe Leu Pro Met Leu Pro
            115                 120                 125

Met Val Pro Glu Glu Pro Glu Asp Leu Arg Gly His Leu Glu Ser Asp
        130                 135                 140

Met Phe Ser Ser Pro Leu Glu Thr Asp Ser Met Asp Pro Phe Gly Leu
145                 150                 155                 160

Val Thr Gly Leu Glu Ala Val Arg Ser Pro Ser Phe Glu Lys
                165                 170

<210> SEQ ID NO 169
<211> LENGTH: 14
<212> TYPE: PRT
<213> ORGANISM: Artificial Sequence
<220> FEATURE:
<223> OTHER INFORMATION: Synthetic peptide

<400> SEQUENCE: 169

Trp Gly Asp Pro Ile Arg Leu Arg His Leu Tyr Thr Ser Gly
1               5                   10

<210> SEQ ID NO 170
<211> LENGTH: 5
<212> TYPE: PRT
<213> ORGANISM: Artificial Sequence
<220> FEATURE:
<223> OTHER INFORMATION: Synthetic peptide

<400> SEQUENCE: 170

Trp Gly Asp Pro Ile
1               5

<210> SEQ ID NO 171
<211> LENGTH: 4
<212> TYPE: PRT
<213> ORGANISM: Artificial Sequence
<220> FEATURE:
<223> OTHER INFORMATION: Synthetic peptide

<400> SEQUENCE: 171

Trp Gly Pro Ile
1

<210> SEQ ID NO 172
<211> LENGTH: 5
<212> TYPE: PRT
<213> ORGANISM: Artificial Sequence
<220> FEATURE:
<223> OTHER INFORMATION: Synthetic peptide

<400> SEQUENCE: 172

Trp Gly Asp Pro Val
1               5

<210> SEQ ID NO 173
<211> LENGTH: 4
<212> TYPE: PRT
<213> ORGANISM: Artificial Sequence
<220> FEATURE:
<223> OTHER INFORMATION: Synthetic peptide
```

<400> SEQUENCE: 173

Trp Gly Asp Ile
1

<210> SEQ ID NO 174
<211> LENGTH: 4
<212> TYPE: PRT
<213> ORGANISM: Artificial Sequence
<220> FEATURE:
<223> OTHER INFORMATION: Synthetic peptide

<400> SEQUENCE: 174

Gly Asp Pro Ile
1

<210> SEQ ID NO 175
<211> LENGTH: 5
<212> TYPE: PRT
<213> ORGANISM: Artificial Sequence
<220> FEATURE:
<223> OTHER INFORMATION: Synthetic peptide

<400> SEQUENCE: 175

Trp Gly Gln Pro Ile
1               5

<210> SEQ ID NO 176
<211> LENGTH: 5
<212> TYPE: PRT
<213> ORGANISM: Artificial Sequence
<220> FEATURE:
<223> OTHER INFORMATION: Synthetic peptide

<400> SEQUENCE: 176

Trp Gly Ala Pro Ile
1               5

<210> SEQ ID NO 177
<211> LENGTH: 5
<212> TYPE: PRT
<213> ORGANISM: Artificial Sequence
<220> FEATURE:
<223> OTHER INFORMATION: Synthetic peptide

<400> SEQUENCE: 177

Ala Gly Asp Pro Ile
1               5

<210> SEQ ID NO 178
<211> LENGTH: 5
<212> TYPE: PRT
<213> ORGANISM: Artificial Sequence
<220> FEATURE:
<223> OTHER INFORMATION: Synthetic peptide

<400> SEQUENCE: 178

Trp Ala Asp Pro Ile
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic peptide

```
<400> SEQUENCE: 179

Trp Gly Asp Ala Ile
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic peptide

<400> SEQUENCE: 180

Trp Gly Asp Pro Ala
1               5

<210> SEQ ID NO 181
<211> LENGTH: 4
<212> TYPE: PRT
<213> ORGANISM: Artificial Sequence
<220> FEATURE:
<223> OTHER INFORMATION: Synthetic peptide

<400> SEQUENCE: 181

Trp Asp Pro Ile
1

<210> SEQ ID NO 182
<211> LENGTH: 4
<212> TYPE: PRT
<213> ORGANISM: Artificial Sequence
<220> FEATURE:
<223> OTHER INFORMATION: Synthetic peptide

<400> SEQUENCE: 182

Trp Gly Asp Ile
1

<210> SEQ ID NO 183
<211> LENGTH: 4
<212> TYPE: PRT
<213> ORGANISM: Artificial Sequence
<220> FEATURE:
<223> OTHER INFORMATION: Synthetic peptide

<400> SEQUENCE: 183

Trp Gly Asp Pro
1

<210> SEQ ID NO 184
<211> LENGTH: 5
<212> TYPE: PRT
<213> ORGANISM: Artificial Sequence
<220> FEATURE:
<223> OTHER INFORMATION: Synthetic peptide

<400> SEQUENCE: 184

Phe Gly Asp Pro Ile
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic peptide

<400> SEQUENCE: 185
```

```
Arg Leu Arg His Leu Tyr Thr Ser Gly
1               5
```

<210> SEQ ID NO 186
<211> LENGTH: 9
<212> TYPE: PRT
<213> ORGANISM: Artificial Sequence
<220> FEATURE:
<223> OTHER INFORMATION: core sequence

<400> SEQUENCE: 186

```
Arg Gln Arg Tyr Leu Tyr Thr Asp Asp
1               5
```

<210> SEQ ID NO 187
<211> LENGTH: 13
<212> TYPE: PRT
<213> ORGANISM: Artificial Sequence
<220> FEATURE:
<223> OTHER INFORMATION: Synthetic peptide

<400> SEQUENCE: 187

```
Ala Gly Pro His Val His Tyr Gly Trp Gly Asp Pro Ile
1               5                   10
```

<210> SEQ ID NO 188
<211> LENGTH: 165
<212> TYPE: PRT
<213> ORGANISM: Homo sapiens
<220> FEATURE:
<223> OTHER INFORMATION: FGF19 C-terminal sequence

<400> SEQUENCE: 188

```
Pro His Gly Leu Ser Ser Cys Phe Leu Arg Ile Arg Ala Asp Gly Val
1               5                   10                  15

Val Asp Cys Ala Arg Gly Gln Ser Ala His Ser Leu Leu Glu Ile Lys
            20                  25                  30

Ala Val Ala Leu Arg Thr Val Ala Ile Lys Gly Val His Ser Val Arg
        35                  40                  45

Tyr Leu Cys Met Gly Ala Asp Gly Lys Met Gln Gly Leu Leu Gln Tyr
    50                  55                  60

Ser Glu Glu Asp Cys Ala Phe Glu Glu Ile Arg Pro Asp Gly Tyr
65                  70                  75                  80

Asn Val Tyr Arg Ser Glu Lys His Arg Leu Pro Val Ser Leu Ser Ser
                85                  90                  95

Ala Lys Gln Arg Gln Leu Tyr Lys Asn Arg Gly Phe Leu Pro Leu Ser
            100                 105                 110

His Phe Leu Pro Met Leu Pro Met Val Pro Glu Glu Pro Glu Asp Leu
        115                 120                 125

Arg Gly His Leu Glu Ser Asp Met Phe Ser Ser Pro Leu Glu Thr Asp
    130                 135                 140

Ser Met Asp Pro Phe Gly Leu Val Thr Gly Leu Glu Ala Val Arg Ser
145                 150                 155                 160

Pro Ser Phe Glu Lys
                165
```

<210> SEQ ID NO 189
<211> LENGTH: 5
<212> TYPE: PRT
<213> ORGANISM: Artificial Sequence
<220> FEATURE:

<223> OTHER INFORMATION: Linker sequence

<400> SEQUENCE: 189

Gly Gly Gly Ser Gly
1               5

<210> SEQ ID NO 190
<211> LENGTH: 11
<212> TYPE: PRT
<213> ORGANISM: Homo sapiens
<220> FEATURE:
<223> OTHER INFORMATION: Sheet-8/Loop-8/Sheet-9 region of FGF19

<400> SEQUENCE: 190

Glu Glu Ile Arg Pro Asp Gly Tyr Asn Val Tyr
1               5                   10

<210> SEQ ID NO 191
<211> LENGTH: 11
<212> TYPE: PRT
<213> ORGANISM: Homo sapiens
<220> FEATURE:
<223> OTHER INFORMATION: Sheet-8/Loop-8/Sheet-9 region of FGF21

<400> SEQUENCE: 191

Glu Leu Leu Leu Glu Asp Gly Tyr Asn Val Tyr
1               5                   10

<210> SEQ ID NO 192
<211> LENGTH: 187
<212> TYPE: PRT
<213> ORGANISM: Artificial Sequence
<220> FEATURE:
<223> OTHER INFORMATION: M53 sequence

<400> SEQUENCE: 192

Met Asp Ser Ser Pro Leu Leu Gln Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 193
<211> LENGTH: 194
<212> TYPE: PRT
<213> ORGANISM: Artificial Sequence
<220> FEATURE:
<223> OTHER INFORMATION: M139 sequence

<400> SEQUENCE: 193

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys
```

<210> SEQ ID NO 194
<211> LENGTH: 194
<212> TYPE: PRT
<213> ORGANISM: Artificial Sequence
<220> FEATURE:
<223> OTHER INFORMATION: M140 sequence

<400> SEQUENCE: 194

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Glu Asp Gly Tyr Asn Val Tyr
            100                 105                 110
```

Arg Ser Glu Lys His Arg Leu Pro Val Ser Leu Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
            165                 170                 175

Pro Phe Gly Leu Val Thr Gly Leu Glu Ala Val Arg Ser Pro Ser Phe
            180                 185                 190

Glu Lys

<210> SEQ ID NO 195
<211> LENGTH: 194
<212> TYPE: PRT
<213> ORGANISM: Artificial Sequence
<220> FEATURE:
<223> OTHER INFORMATION: M141 sequence

<400> SEQUENCE: 195

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
            85                  90                  95

Asp Cys Ala Phe Glu Glu Glu Ile Leu Cys Asp Gly Tyr Asn Val Tyr
            100                 105                 110

Arg Ser Glu Lys His Arg Leu Pro Val Ser Leu Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
            165                 170                 175

Pro Phe Gly Leu Val Thr Gly Leu Glu Ala Val Arg Ser Pro Ser Phe
            180                 185                 190

Glu Lys

<210> SEQ ID NO 196
<211> LENGTH: 194
<212> TYPE: PRT
<213> ORGANISM: Artificial Sequence
<220> FEATURE:
<223> OTHER INFORMATION: M160 sequence

<400> SEQUENCE: 196

Arg Pro Leu Ala Phe Ser Asp Ala Gly Pro His Val His Tyr Gly Trp
1               5                   10                  15

Gly Asp Pro Ile Arg Gln Arg His Leu Tyr Thr Ser Gly Pro His Gly

```
                20                  25                  30
Leu Ser Ser Cys Phe Leu Arg Ile Arg Ala Asp Gly Val Asp Cys
            35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Leu Glu Asp Gly Tyr Asn Val Tyr
                100                 105                 110

Arg Ser Glu Lys His Arg Leu Pro Val Ser Leu Ser Ser Ala Lys Gln
                115                 120                 125

Arg Gln Leu Tyr Lys Asn Arg Gly Phe Leu Pro Leu Ser His Phe Leu
            130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 197
<211> LENGTH: 189
<212> TYPE: PRT
<213> ORGANISM: Artificial Sequence
<220> FEATURE:
<223> OTHER INFORMATION: M200 Sequence

<400> SEQUENCE: 197

Arg Asp Ser Ser Pro Leu Val His Tyr Gly Trp Gly Asp Pro Ile Arg
 1               5                  10                  15

Leu Arg His Leu Tyr Thr Ser Gly Pro His Gly Leu Ser Ser Cys Phe
                20                  25                  30

Leu Arg Ile Arg Ala Asp Gly Val Asp Cys Ala Arg Gly Gln Ser
            35                  40                  45

Ala His Ser Leu Leu Glu Ile Lys Ala Val Ala Leu Arg Thr Val Ala
 50                  55                  60

Ile Lys Gly Val His Ser Val Arg Tyr Leu Cys Met Gly Ala Asp Gly
 65                  70                  75                  80

Lys Met Gln Gly Leu Leu Gln Tyr Ser Glu Glu Asp Cys Ala Phe Glu
                 85                  90                  95

Glu Glu Ile Leu Glu Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
                115                 120                 125

Asn Arg Gly Phe Leu Pro Leu Ser His Phe Leu Pro Met Leu Pro Met
            130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185
```

<210> SEQ ID NO 198
<211> LENGTH: 194
<212> TYPE: PRT
<213> ORGANISM: Artificial Sequence
<220> FEATURE:
<223> OTHER INFORMATION: M201 Sequence

<400> SEQUENCE: 198

```
Arg Pro Leu Ala Phe Ser Asp Ser Ser Pro Leu Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Glu Asp Gly Tyr Asn Val Tyr
            100                 105                 110

Arg Ser Glu Lys His Arg Leu Pro Val Ser Leu Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys
```

<210> SEQ ID NO 199
<211> LENGTH: 194
<212> TYPE: PRT
<213> ORGANISM: Artificial Sequence
<220> FEATURE:
<223> OTHER INFORMATION: M202 Sequence

<400> SEQUENCE: 199

```
Arg Pro Leu Ala Phe Ser Asp Ala Ser Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Glu Asp Gly Tyr Asn Val Tyr
            100                 105                 110
```

```
Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 200
<211> LENGTH: 187
<212> TYPE: PRT
<213> ORGANISM: Artificial Sequence
<220> FEATURE:
<223> OTHER INFORMATION: M203 Sequence

<400> SEQUENCE: 200

Arg Asp Ser Ser Pro Leu Leu Gln Trp Gly Asp Pro Ile Arg Leu Arg
1               5                   10                  15

His Leu Tyr Thr Ser Gly Pro His Gly Leu Ser Ser Cys Phe Leu Arg
                20                  25                  30

Ile Arg Ala Asp Gly Val Val Asp Cys Ala Arg Gly Gln Ser Ala His
                35                  40                  45

Ser Leu Leu Glu Ile Lys Ala Val Ala Leu Arg Thr Val Ala Ile Lys
        50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Leu Glu Asp Gly Tyr Asn Val Tyr Arg Ser Glu Lys His Arg Leu
                100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
        130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
                180                 185

<210> SEQ ID NO 201
<211> LENGTH: 191
<212> TYPE: PRT
<213> ORGANISM: Artificial Sequence
<220> FEATURE:
<223> OTHER INFORMATION: M204 Sequence

<400> SEQUENCE: 201

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
                20                  25                  30
```

Cys Phe Leu Arg Ile Arg Ala Asp Gly Val Val Asp Cys Ala Arg Gly
                35                  40                  45

Gln Ser Ala His Ser Leu Leu Glu Ile Lys Ala Val Ala Leu Arg Thr
 50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Leu Glu Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 202
<211> LENGTH: 187
<212> TYPE: PRT
<213> ORGANISM: Artificial Sequence
<220> FEATURE:
<223> OTHER INFORMATION: M205 Sequence

<400> SEQUENCE: 202

Arg Asp Ser Ser Pro Leu Leu Gln Phe Gly Gly Gln Val Arg Leu Arg
 1                5                  10                  15

His Leu Tyr Thr Ser Gly Pro His Gly Leu Ser Ser Cys Phe Leu Arg
                 20                  25                  30

Ile Arg Ala Asp Gly Val Val Asp Cys Ala Arg Gly Gln Ser Ala His
            35                  40                  45

Ser Leu Leu Glu Ile Lys Ala Val Ala Leu Arg Thr Val Ala Ile Lys
 50                  55                  60

Gly Val His Ser Val Arg Tyr Leu Cys Met Gly Ala Asp Gly Lys Met
 65                  70                  75                  80

Gln Gly Leu Leu Gln Tyr Ser Glu Glu Asp Cys Ala Phe Glu Glu Glu
                 85                  90                  95

Ile Leu Glu Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
            115                 120                 125

Gly Phe Leu Pro Leu Ser His Phe Leu Pro Met Leu Pro Met Val Pro
            130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 203

```
<211> LENGTH: 191
<212> TYPE: PRT
<213> ORGANISM: Artificial Sequence
<220> FEATURE:
<223> OTHER INFORMATION: M206 Sequence

<400> SEQUENCE: 203

Arg His Pro Ile Pro Asp Ser Ser Pro Leu Leu Gln Phe Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Leu Glu Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 204
<211> LENGTH: 190
<212> TYPE: PRT
<213> ORGANISM: Artificial Sequence
<220> FEATURE:
<223> OTHER INFORMATION: M207 Sequence

<400> SEQUENCE: 204

Met Arg Asp Ser Ser Pro Leu Val His Tyr Gly Trp Gly Asp Pro Ile
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Leu Glu Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
```

```
            130                 135                 140
Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
                180                 185                 190

<210> SEQ ID NO 205
<211> LENGTH: 11
<212> TYPE: PRT
<213> ORGANISM: Artificial Sequence
<220> FEATURE:
<223> OTHER INFORMATION: Modified Sheet-8/Loop-8/Sheet-9 region of FGF19

<400> SEQUENCE: 205

Glu Glu Ile Leu Glu Asp Gly Tyr Asn Val Tyr
1               5                   10

<210> SEQ ID NO 206
<211> LENGTH: 5
<212> TYPE: PRT
<213> ORGANISM: Artificial Sequence
<220> FEATURE:
<223> OTHER INFORMATION: Flexible linker sequence

<400> SEQUENCE: 206

Gly Gly Gly Gly Ser
1               5

<210> SEQ ID NO 207
<211> LENGTH: 5
<212> TYPE: PRT
<213> ORGANISM: Artificial Sequence
<220> FEATURE:
<223> OTHER INFORMATION: Flexible linker sequence
<220> FEATURE:
<221> NAME/KEY: REPEAT
<222> LOCATION: (1)..(5)
<223> OTHER INFORMATION: "GGGGS" can be repeated 1 to n times

<400> SEQUENCE: 207

Gly Gly Gly Gly Ser
1               5

<210> SEQ ID NO 208
<211> LENGTH: 10
<212> TYPE: PRT
<213> ORGANISM: Artificial Sequence
<220> FEATURE:
<223> OTHER INFORMATION: Flexible linker sequence

<400> SEQUENCE: 208

Gly Gly Gly Gly Ser Gly Gly Gly Gly Ser
1               5                   10
```